(12) United States Patent
Zuo et al.

(10) Patent No.: US 12,318,391 B2
(45) Date of Patent: Jun. 3, 2025

(54) METHODS AND COMPOSITIONS FOR THE PREVENTION AND TREATMENT OF HEARING LOSS

(71) Applicant: St. Jude Children's Research Hospital, Memphis, TN (US)

(72) Inventors: Jian Zuo, Omaha, NE (US); Tal Teitz, Omaha, NE (US); Fang Jie, Memphis, TN (US); Goktug Asli, Memphis, TN (US); Chen Taosheng, Germantown, TN (US); Min Jaeki, Memphis, TN (US); R Kiplin Guy, Memphis, TN (US)

(73) Assignee: St. Jude Children's Research Hospital, Inc.

( * ) Notice: Subject to any disclaimer, the term of this patent is extended or adjusted under 35 U.S.C. 154(b) by 368 days.

(21) Appl. No.: 17/862,656

(22) Filed: Jul. 12, 2022

(65) Prior Publication Data
US 2023/0000881 A1 Jan. 5, 2023

Related U.S. Application Data

(60) Division of application No. 16/707,991, filed on Dec. 9, 2019, now Pat. No. 11,446,308, which is a (Continued)

(51) Int. Cl.
*A61K 31/404* (2006.01)
*A61K 31/4015* (2006.01)
(Continued)

(52) U.S. Cl.
CPC .......... *A61K 31/55* (2013.01); *A61K 31/4015* (2013.01); *A61K 31/404* (2013.01); (Continued)

(58) Field of Classification Search
CPC .................. A61K 31/55; A61P 27/16
See application file for complete search history.

(56) References Cited

U.S. PATENT DOCUMENTS

| 5,543,158 A | 8/1996 | Gref et al. |
| 7,132,406 B2 | 11/2006 | Kil et al. |
| (Continued) | | |

FOREIGN PATENT DOCUMENTS

| WO | 1994029469 A2 | 12/1994 |
| WO | 1997000957 A1 | 1/1997 |
| (Continued) | | |

OTHER PUBLICATIONS

Helms et al. (1998) Progenitors of dorsal commissural interneurons are defined by MATH1 expression, Development vol. 125, 919-928.
(Continued)

*Primary Examiner* — Craig D Ricci
*Assistant Examiner* — Janet L Coppins
(74) *Attorney, Agent, or Firm* — Susan Fentress; Veritay Group, IP

(57) ABSTRACT

In one aspect, pharmaceutical compositions comprising a CDK2 inhibitor and one or more of at least one agent known to treat a hearing impairment and at least one agent known to prevent a hearing impairment, and methods of treating and/or preventing hearing impairments or disorders using the compositions are disclosed. This abstract is intended as a scanning tool for purposes of searching in the particular art and is not intended to be limiting of the present invention.

6 Claims, 17 Drawing Sheets

Related U.S. Application Data continuation of application No. 15/580,224, filed as application No. PCT/US2016/038384 on Jun. 20, 2016, now abandoned.

(60) Provisional application No. 62/181,755, filed on Jun. 18, 2015.

(51) Int. Cl.

| | | |
|---|---|---|
| *A61K 31/4155* | (2006.01) | |
| *A61K 31/454* | (2006.01) | |
| *A61K 31/506* | (2006.01) | |
| *A61K 31/519* | (2006.01) | |
| *A61K 31/52* | (2006.01) | |
| *A61K 31/55* | (2006.01) | |
| *A61P 27/16* | (2006.01) | |

(52) U.S. Cl.
CPC ........ *A61K 31/4155* (2013.01); *A61K 31/454* (2013.01); *A61K 31/506* (2013.01); *A61K 31/519* (2013.01); *A61K 31/52* (2013.01); *A61P 27/16* (2018.01)

(56) References Cited

U.S. PATENT DOCUMENTS

| | | | |
|---|---|---|---|
| 7,206,639 | B2 | 4/2007 | Jacobsen et al. |
| 7,232,814 | B2 | 6/2007 | Meijer et al. |
| 7,470,673 | B2 | 12/2008 | Zoghbi et al. |
| 7,612,196 | B2 | 11/2009 | Khvorova et al. |
| 7,741,303 | B2 | 6/2010 | Kil et al. |
| 8,188,131 | B2 | 5/2012 | Edge et al. |
| 9,572,815 | B2 | 2/2017 | Zuo et al. |
| 2003/0004351 | A1 | 1/2003 | Davis et al. |
| 2003/0181439 | A1 | 9/2003 | Meijer et al. |
| 2003/0203482 | A1 | 10/2003 | Kil et al. |
| 2004/0237127 | A1 | 11/2004 | Zoghbi et al. |
| 2006/0002852 | A1 | 1/2006 | Saltzman et al. |
| 2006/0030837 | A1 | 2/2006 | McKenna et al. |
| 2006/0148829 | A1 | 7/2006 | Meijer et al. |
| 2006/0222652 | A1 | 10/2006 | Sebbel et al. |
| 2006/0251677 | A1 | 11/2006 | Bachmann et al. |
| 2007/0093878 | A1 | 4/2007 | Edge et al. |
| 2008/0145441 | A1 | 6/2008 | Penades et al. |
| 2009/0028910 | A1 | 1/2009 | DeSimone et al. |
| 2009/0226525 | A1 | 9/2009 | Rios et al. |
| 2009/0232780 | A1 | 9/2009 | Edge et al. |
| 2011/0304574 | A1 | 12/2011 | Harrison |
| 2011/0305674 | A1* | 12/2011 | Edge .................... A61K 35/30 424/93.7 |
| 2012/0328580 | A1 | 12/2012 | Edge et al. |
| 2013/0085112 | A1 | 4/2013 | Collard et al. |
| 2013/0210145 | A1 | 8/2013 | Edge |
| 2014/0029927 | A1 | 1/2014 | Leblanc et al. |
| 2014/0371213 | A1 | 12/2014 | Berdini et al. |
| 2016/0030445 | A1 | 2/2016 | Zuo et al. |
| 2017/0189477 | A1 | 7/2017 | Zuo et al. |

FOREIGN PATENT DOCUMENTS

| | | |
|---|---|---|
| WO | 2006117212 A2 | 11/2006 |
| WO | 2009006999 A1 | 1/2009 |
| WO | 2009010298 A3 | 6/2009 |
| WO | 2009051837 A3 | 7/2009 |
| WO | 2010047839 A1 | 4/2010 |
| WO | 2013071415 A1 | 5/2013 |
| WO | 2014145205 A3 | 12/2014 |
| WO | 2016205806 A1 | 12/2016 |

OTHER PUBLICATIONS

Herbst, et al. (2009) Multiplexing a High-Throughput Liability Assay to Leverage Efficiencies, Assay and Drug Development Technologies, vol. 7, 294-303.

Huangfu D, et al. (2008) Induction of pluripotent stem cells by defined factors is greatly improved by small-molecule compounds. Nat Biotechnol vol. 26, 795-797.

Huch, M., et al. (2013) Lgr5+ liver stem cells, hepatic organoids and regenerative medicine, Regen. Med. vol. 8, No. 4, 385-387.

Hudspeth AJ (2000) Hearing and deafness. Neurobiology of Diseases, vol. 7: 511-514.

Ieda M, et al. (2010) Direct reprogramming of fibroblasts into functional cardiomyocytes by defined factors. Cell, vol. 142, 375-386.

International Preliminary Report on Patentability was mailed on Dec. 19, 2017 by the International Searching Authority for Application No. PCT/US2016/038384, filed Jun. 20, 2016, and published as WO 2016/205806 on Dec. 22, 2016 (Applicant—St. Jude Children's Research Hospital) (5 pages).

International Preliminary Report on Patentability was mailed on Sep. 15, 2015 by the International Searching Authority for Application No. PCT/US201 4/029927, filed Mar. 15, 2014, and published as WO 2014/145205 on Sep. 18, 2014 (Applicant—St. Jude Children's Research Hospital) (9 pages).

International Search Report and Written Opinion were mailed on Oct. 17, 2014 by the International Searching Authority for Application No. PCT/US2014/029927, filed Mar. 15, 2014, and published as WO 2014/145205 on Sep. 18, 2014 (Applicant—St. Jude Children's Research Hospital) (13 pages).

International Search Report and Written Opinion were mailed on Sep. 13, 2016 by the International Searching Authority for Application No. PCT/US2016/038384, filed Jun. 20, 2016, and published as WO 2016/205806 on Dec. 22, 2016 (Applicant—St. Jude Children's Research Hospital) (6 pages).

Isaka et al. (1999) Short Communication Ectopic expression of the bHLH gene Math1 disturbs neural development, European Journal of Neuroscience. vol. 11, 2582-2588.

Izumikawa M, et al. (2005) Auditory hair cell replacement and hearing improvement by Aton1 gene therapy in deaf mammals. Nat Med vol. 11, 271-276.

Jahan I, et al (2013) Beyond generalized hair cells: Molecular cues for hair cell types. Hear Res. vol. 297, 30-41.

Jarman, A. P., et al. (1993) atonal Is a Proneural Gene That Directs Chordotonal Organ Formation in the *Drosophila* Peripheral Nervous System, Cell, vol. 73, 1307-1321.

Jayasena, C.S., et al. (2008) Notch signaling augments the canonical Wnt pathway to specify the size of the otic placode, Development vol. 135, 2251-2261.

Jin, E. J., et al. (2001) Wnt and BMP Signaling Govern Lineage Segregation of Melanocytes in the Avian Embryo, Developmental Biology, vol. 233, 22-37.

Kamezis, A. N., et al. (2001) Loss of p27Kip1 enhances the transplantation efficiency of hepatocytes transferred into diseased livers, Journal of Clinical Investigation vol. 108, No. 3, 383-390.

Kang SH, et al (2010) NG2+ Cns glial progenitors remain committed to the oligodendrocyte lineage in postnatal life and following neurodegeneration, Neuron, vol. 68, No. 4, 668-681.

Kanzaki S, et al. (2006) p27(Kip1) deficiency causes organ of Cortipathology and hearing loss. Hear Res vol. 214, 28-36.

Kawamoto, K., et al. (2003) Math1 Gene Transfer Generates New Cochlear Hair Cells in Mature Guinea Pigs In Vivo, Journal of Neuroscience vol. 23, No. 11, 4395-4400.

Kelley, M. W. (2007) Cellular commitment and differentiation in the organ of Corti, Int. J. Dev. Bioi. vol. 51, 571-583.

Kelly MC, et al (2012) Aton' directs the formation of sensory mosaics and induces cell proliferation in the postnatal mammalian cochlea in vivo, Journal of Neuroscience vol. 32: 6699-6710.

Kiernan, A. E. (2013) Notch signaling during cell fate determination in the inner ear, Seminar in Cell Developmental Biology, vol. 24, 470-479.

Kiernan, A. E., et al. (2005) The Notch ligands DLL1 and JAG2 act synergistically to regulate hair cell development in the mammalian inner ear, Development vol. 132, 4353-4362.

Kiernan, A. E., et al. (2006) The Notch Ligand JAG1 Is Required for Sensory Progenitor Development in the Mammalian Inner Ear, PloS Genetics. vol. 2, Issue 1, 27-38.

(56) References Cited

OTHER PUBLICATIONS

Kiernan, A. E., et, al. (2001) The Notch ligand Jagged1 is required for inner ear sensory development, PNAS U.S.A. vol. 98, No. 7, 3873-3878.
Kim K, et al. (2010) Epigenetic memory in induced pluripotent stem cells, Nature vol. 467: 285-290.
Klisch TJ, et al. (2011) In vivo Atoh1 targetome reveals how a proneural transcription factor regulates cerebellar development. PNAS USA, vol. 108: 3288-3293.
Korrapati, S., et al. (2013) Notch Signaling Limits Supporting Cell Plasticity in the Hair Cell-Damaged Early Postnatal Murine Cochlea, PLoS One vol. 8, Issue 8, €73276, 1-12.
Kunick, C., et al. (2005) Structure-Aided Optimization of Kinase Inhibitors Derived from Alsterpaullone, ChemBioChem vol. 6, 541-549.
Kwon, C., et al. (2011) Notch post-translationally regulates B-catenin protein in stem and progenitor cells, Nature Cell Bioilogy vol. 13, No. 10, 1244-1251.
Lanford, P. J., et al. (1999) Notch signalling pathway mediates hair cell development in mammalian cochlea, Nature Genetics vol. 21, 289-292.
Layman WS, et al. (2013) Epigenetic alterations by NuRD and PRC2 in the neonatal mouse cochlea, Hearing Research, vol. 304:167-78.
Lee, Y. S., et al. (2006) A morphogenetic wave of p27Kip1 transcription directs cell cycle exit during organ of Corti development, Development vol. 133, 2817-2826.
Leonardi, et al. (2010) Modulation of Pantothenate Kinase 3 Activity by Small Molecules that interact with the substrate/allosteic Regulatory Domain, Chemistry & Biology, vol. 17, 892-902.
Leost, M., et al. (2000) Paullones are potent inhibitors of glycogen synthase kinase-3β and cyclin-dependent kinase 5/o25, European Journal of Biochemistry vol. 267, 5983-5994.
Li et al. (2004) Stem cells as therapy for hearing loss Trends in Molecular Medicine vol. 10, No. 7, SD {309-315.
Li H, Collado M, Villasante A, Matheu A, Lynch Cu, et al. (2012) p27(Kip1) directly represses Sox2 during embryonic stem cell differentiation. Cell Stem Cell vol. 11, 845-852.
Li, H., et al. (2003) Pluripotent stem cells from the adult mouse inner ear, Nature Medicine vol. 9, No. 10, 1293-1299.
Liberman MC, et al (2006) Deletion of SLC19A2, the high affinity thiamine transporter, causes selective inner hair cell loss and an auditory neuropathy phenotype, JARO, vol. 7: 211-217.
Lin, et al. (2008) Cyclin-dependent Kinase 2 Negatively Regulates Human Pregnane X Receptor-CH mediated CYP3A4 Gene Expression in HepG2 Liver Carcinoma Cells, J. Biological Chem, vol. 283, No. 45, 30650-30657.
Liu Z, et al. (2012) Age-dependent in vivo conversion of mouse cochlear pillar and Deiters' cells to immature hair cells by Atoh1 ectopic expression, Journal of Neuroscience vol. 32, 6600-6610.
Liu Z, et al. (2012) Regulation of p27Kip1 by Sox2 maintains quiescence of inner pillar cells in the murine auditory sensory epithelium. Journal of Neuroscience, vol. 32, No. 31, 10530-10540.
Liu, J., et al. (2001) Siah-1 Mediates a Novel B-Catenin Degradation Pathway Linking p53 to the Adenomatous Polyposis Coli Protein, Molecular Cell vol. 7, 927-936.
Liu, Z., et al. (2012) Age-dependent in vivo conversion of mouse cochlear pillar and Deiters' cells CL to immature hair cells by Atoh1 ectopic expression, Journal of Neuroscience vol. 32, No. 19, 6600-6610.
Liu, Z., et al. (2014) In Vivo Generation of Immature Inner Hair Cells in Neonatal Mouse Cochleae by Ectopic Atoh1 Expression, PloS One vol. 9, Issue 2, e89377, 1-12.
Lou §, et al (2013) Runx1 Controls Terminal Morphology and Mechanosensitivity of VGLUT3-expressing C-Mechanoreceptors, Journal of Neuroscience vol. 33: 870-882.
Lowenheim, H., et al. (1999) Gene disruption of p27(Kip1) allows cell proliferation in the postnatal and adult organ of corti, PNAS USA vol. 96, 4084-4088.

Maas et al. (2013) p27Kip1 Knockdown Induces Proliferation in the Organ of Corti in Culture after Efficient shRNA Lentiviral Transduction, JARO, vol. 14, 495-508.
Mangi, A. A., et al. (2003) Mesenchymal stem cells modified with Akt prevent remodeling and restore performance of infarcted hearts, Nature Medicine, vol. 9, No. 9, 1195-1201.
Mantela, J., et al. (2005) The retinoblastoma gene pathway regulates the postmitotic state of hair cells of the mouse inner ear, Development vol. 132, 2377-2388.
Marro S, et al. (2011) Direct lineage conversion of terminally differentiated hepatocytes to functional neurons, Cell Stem Cell, vol. 9: 374-382.
Masuda M, et al. (2011) Regulation of POU4F3 gene expression in hair cells by 5' DNA in mice. Neuroscience vol. 197: 48-64.
Masuda M, et al. (2012) TFE2 and GATA3 enhance induction of POU4F3 and myosin VIIa positive cells in nonsensory cochlear epithelium by ATOH1, Developmental Biology, vol. 372: 68-80.
Medema, J.P., and Vermeulen, L. (2011) Microenvironmental regulation of stem cells in intestinal homeostasis and cancer, Nature, vol. 474, 318-326.
Mellado Lagarde MM, et al. (2013) Selective ablation of pillar and deiters' cells severely affects cochlear postnatal development and hearing in mice. Journal of Neuroscience vol. 33: 1564-1576.
Menchon, C., et al., (2011) The cell cycle inhibitor p27KiP1 controls self-renewal and pluripotency Cx of human embryonic stem cells by regulating the cell cycle, Brachyury and Twist, Cell Cycle vol. 109, 1435-1447.
Minoda R, et al. (2007) Manipulating cell cycle regulation in the mature cochlea. Hearing Research vol. 232: 44-51.
Mizutari K, et al. (201 3) Notch inhibition induces cochlear hair cell regeneration and recovery of hearing after acoustic trauma. Neuron vol. 77: 58-69.
Mori T, et al. (2006) Inducible gene deletion in astroglia and radial glia—a valuable tool for functional and lineage analysis. Glia vol. 54: 21-34.
Munnamalai, V. et al. (2013) Wnt Signaling during Cochlear Development, Semin. Cell Dev. Bioi. vol. 24, 480-489.
Nakano Y, et al. (2012) A Mutation in the Srrm4 gene causes alternative splicing defects and deafness in the Bronx waltzer mouse. PLoS Genetics vol. 8 Issue 10, €1002966, 1-17.
Niles, R. M., et al. (2006) Resveratrol is rapidly metabolized in athymic (nu/nu) mice and does not inhibit human melanoma xenograft tumor growth , Journal of Nutrition vol. 136, 2542-2546.
Oesterle EC (2012) Changes in the adult vertebrate auditory sensory epithelium after trauma. Hear Res. vol. 27, 91-98.
Oesterle EC, et al. (2008) Sox2 and JAGGED' expression in normal and drug damaged adult mouse inner ear. JARO vol. 9: 65-89.
Oesterle EC, et al. (2011) p27(Kip1) is required to maintain proliferative quiescence in the adult cochlea and pituitary, Cell Cycle vol. 10: 1237-1248.
Ohyama, T., et al. (2006) Wnt signals mediate a fate decision between otic placode and epidermis, Development vol. 133, 865-875.
Ohyama, T., et al. (2007) The first steps towards hearing: mechanisms of otic placode induction, Int. J. Dev. Bioi. vol. 51, 463-472.
Ono K, et al. (2009) Silencing p27 reverses post-mitotic state of supporting cells in neonatal mouse cochleae. Mol Cell Neurosci. vol. 42: 391-398.
P. Paolicelli et al. (2010) Surface-modified PLGA-based Nanoparticles that can Efficiently Associate and Deliver Virus-like Particles, Nanomedicine, vol. 5, No. 6, 843-853.
Pan N, et al (2010) Notch signaling is required for the generation of hair cells and supporting cells in the mammalian inner ear, PNAS, vol. 107, No. 36, 15798-15803.
Pan N, et al. (2012) A novel Atoh1 "self-terminating" mouse model reveals the necessity of proper Atoht1 level and duration for hair cell differentiation and viability. PLoS One vol. 7, Issue 1 €30358, 1-12.
Papp B, Plath K (2011) Reprogramming to pluripotency: stepwise resetting of the epigenetic landscape. Cell Res vol. 21, 486-501.
Pellegata, N. S., et al. (2006) Proceedings of the National Academy of Sciences of the United States of America 103, 15558-15563.
Pietrocola, F., et al. (2012) Pro-autophagic polyphenols reduce the acetylation of cytoplasmic proteins, Cell Cycle vol. 11, 3851-3860.

(56) References Cited

OTHER PUBLICATIONS

Polyak, K., et al. (1994) Cloning of p27kip1, a Cyclin-Dependent Kinase Inhibitor and a Potential Mediator of Extracellular Antimitogenic Signals, Cell, vol. 78, 59-66.
Rabbani, F., et al. (2007) Prognostic significance of p27Kip1 expression in bladder cancer, BJU International, vol. 100, 259-263.
Ramskold D, et al. (2012) Full-length mRNA-Seq from single-cell levels of RNA and individual circulating tumor cells. Nat Biotechnol vol. 30, 777-782.
Rask-Andersen, H., et al. (2005) Regeneration of human auditory nerve. In vitro/in video demonstration of neural progenitor cells in adult human and guinea pig spiral ganglion, Hearing Research, vol. 203, 180-191.
Riccomagno, M. M., et al. (2005) Wnt-dependent regulation of inner ear morphogenesis is balanced by the opposing and supporting roles of Shh, Genes & Development, vol. 19, 1612-1623.
Ryals BM, Rubel EW (1988) Hair cell regeneration after acoustic trauma in adult Coturnix quail, Science, vol. 240: 1774-1776.
Sage C, et al. (2006) Essential role of retinoblastoma protein in mammalian hair cell development and hearing. PNAS USA, vol. 103, No. 19, 7345-7350.
Salt and Plontke (2005) Local inner-ear drug delivery and pharmacokinetics, Drug Discovery Today, vol. 10, No. 19, 1299-1306.
Sato, T. and Clevers, H. (2013) Growing Self-Organizing Mini-Guts from a Single Intestinal Stem Cell: Mechanism and Applications, Science, vol. 340, 1190-1194.
Sato, T., et al. (2009) Single Lgr5 stem cells build crypt-villus structures in vitro without a mesenchymal niche, Nature, vol. 459, 262-265.
Savary E, et al. (2007) Distinct population of hair cell progenitors can be isolated from the postnatal mouse cochlea using side population analysis. Stem Cells, vol. 25, 332-339.
Shi F, Kempfle JS, Edge AS (2012) Wnht-responsive Lgr5-expressing stem cells are hair cell progenitors in the cochlea, J Neurosci, vol. 32, 9639-9648.
Shi, F., et al. (2010) b-Catenin Up-regulates Atoh1 Expression in Neural Progenitor Cells by Interaction with an Atoh1 3' Enhancer, J. Biol. Chem. vol. 285, 392-400.
Sinkkonen ST, et al. (2011) Intrinsic regenerative potential of murine cochlear supporting cells. Scientific Reports, vol. 1, No. 26, 1-8.
Slingerland, J., and Pagano, M. (2000) Regulation of the Cdk Inhibitor p27 and Its Deregulation in Cancer, Journal of cellular physiology vol. 183, 10-17.
So HS, etal. (2005) Protective effect of T-type calcium channel blocker flunarizine on cisplatin-induced death of auditory cells. Hearing Research, vol. 204: 127-139.
Stevens, C. B., et al. (2003) Forced activation of Wnt signaling alters morphogenesis and sensory organ identity in the chicken inner ear, Dev. Bioi., vol. 261, 149-164.
Takebayashi, S., et al. (2007) Multiple roles of Notch signaling in cochlear development, Dev. Bioi., vol. 307, 165-178.
Taylor RR,et al. (2012) Defining the cellular environment in the organ of Corti following extensive hair cell loss: a basis for future sensory cell replacement in the Cochlea. PLoS One vol. 7, Issue 1: €30577, 1-21.
Tian, H., et al. (2011) A reserve stem cell population in small intestine renders Lgr5-positive cells dispensable, Nature, vol. 478, 255-259.
Trapp, J., et al. (2006) Adenosine Mimetics as Inhibitors of NAD+-Dependent Histone Deacetylases, from Kinase to Sirtuin Inhibition, J. Med. Chem. vol. 49, 7307-7316.
Vierbuchen T, et al. (2010) Direct conversion of fibroblasts to functional neurons by defined factors. Nature vol. 463, 1035-1041.
Vrijens, et al. (2013) Identification of Small Molecule Activators of BMP Signaling, PLoS One, vol. 8, Issue 3, e59045, 1-10.
Walters and Zuo (2013) Postnatal development, maturation and aging in the mouse cochlea and their effects on hair cell regeneration, Hearing Res. vol. 297, 68-33.
Walters B, Zuo J. (2015) A Sox10 rtTA/+ Mouse Line Allows for Inducible Gene Expression in the Auditory and Balance Organs of the Inner Ear, JARO, vol. 16, No. 3, 331-45.
Wang CA, et al. (2012) SIX1 induces lymphangiogenesis and metastasis via upregulation of VEGF-C in mouse models of breast cancer, J Clin Invest. vol. 122: 1895-1906.
Wang, et al. (2007) SIRT2 deacetylates FOXO3a in response to oxidative stress and caloric restriction, Aging Cell, vol. 6, 505-514.
Warchol ME, et al (1996) Regenerative proliferation in organ cultures of the avian cochlea: ET identification of the initial progenitors and determination of the latency of the proliferative response. Journal of Neuroscience, vol. 16 No. 17, 5466-5477.
Weber T, et al. (2008) Rapid cell-cycle reentry and cell death after acute inactivation of the retinoblastoma gene product in postnatal cochlear hair cells. PNAS, vol. 105, No. 2, 781-785.
Weddell TD, et al. (2011) Prestin links extrinsic tuning to neural excitation in the mammalian cochlea. Current Biology vol. 21, No. 18, R682-R683.
White PM, et al (2006) Mammalian cochlear supporting cells can divide and trans-differentiate into hair cells. Nature, vol. 441, 984-987.
Woods, et al., (2004) Math1 regulates development of the sensory epithelium in the mammalian cochlea, Nature Neuroscience, vol. 7, No. 12, 1310-1318.
Xiang M, et al. (1997) Essential role of POU-domain factor Brn-3c in auditory and vestibular hair cell development. PNS USA vol. 94, 9445-9450.
Yamamoto, N., et al. (2006) Inhibition of Notch/RBP-J signaling induces hair cell formation in neonate mouse cochleas, J.Mol. Med., vol. 84, 37-45.
Yamashita T, etal. (2012) Normal Hearing Sensitivity at Low-to-Middle Frequencies with 34% Prestin-Charge Density, PLoS One vol. 7, Issue 9, €45453, 1-10.
Yan, K. S., et al. (2012) The intestinal stem cell markers Bmi1 and Lgr5 identify two functionally distinct populations, PNAS U.S. A. vol. 109, No. 2, 466-471.
Yang J, et al. (2012) Functional features of trans-differentiated hair cells mediated by Atoh1 reveals a primordial mechanism. J Neurosci vol. 32, No. 11, 3712-3725.
Yoon, M. K., et al. (2012) Cell cycle regulation by the intrinsically disordered proteins p21 and p27, Biochemical Society Transactions, vol. 40, 981-988.
Yu, Y., et al. (2010) In Vivo Proliferation of Postmitotic Cochlear Supporting Cells by Acute Ablation of the Retinoblastoma Protein in Neonatal Mice J. Neurosci. vol. 30, No. 17, 5927-5936.
Zaharevitz et al, Cancer Research (1999), vol. 59 (Jun. 1), pp. 2566-2569. (Year: 1999).
Zhang, S., et al., (2013) FOXO3a/p27kip1 Expression and Essential Role After Acute Spinal Cord Injury in Adult Rat, Journal of Cellular Biochemistry vol. 114, 354-365.
Zheng JL, et al. (2000) Overexpression of Math' induces robust production of extra hair cells in postnatal rat inner ears, Nature Neuroscience vol. 3, No. 6, 580-586.
Zheng, J. L., et al. (2000) Hes1 is a negative regulator of inner ear hair cell differentiation, Development vol. 127, 4551-4560.
Zilberstein Y, et al. (2012) Inner hair cells are not required for survival of spiral ganglion neurons in the adult cochlea. J Neurosci vol. 32, No. 2, 405-410.
Zine, A., et al. (2001) Hes1 and Hes5 Activities Are Required for the Normal Development of the Hair Cells in the Mammalian Inner Ear, J. Neurosci. vol. 21, No. 13, 4712-4720.
Zuo J, et al. (1999) Visualization of alpha9 acetylcholine receptor expression in hair cells of transgenic mice containing a modified bacterial artificial chromosome, PNAS USA, vol. 96, No. 24, 14100-14105.
Adler HJ, Raphael Y (1996) New hair cells arise from supporting cell conversion in the acoustically damaged chick inner ear. Neuroscience letters vol. 205, 17-20.
Ahmed M, Wong EY, Sun J, Xu J, Wang F, et al. (2012) Eya1-Six1 interaction is sufficient to induce hair cell fate in the cochlea by activating Atoh1 expression in cooperation with Sox2. Dev Cell vol. 22, 377-390.

(56) References Cited

OTHER PUBLICATIONS

Akazawa, C., et al. (1995) A Mammalian Helix-Loop-Helix Factor Structurally Related to the Product of *Drosophila proneural* Gene atonal Is a Positive Transcriptional Regulator Expressed inthe Developing Nervous System, J. Bioi. Chem. 270, 8730-8738.

Aletsee et al. (2001) The Disintegrin Kistrin Inhibits Neurite Extension from Spiral Ganglion Explants Cultured on Laminin, Audiology Neuro-Otology. vol. 6, 57-65.

Anderson et al. "Imidazoles: Sar and Development of a Potent Class oof cyclin-dependent Kinase inhibitors", (2008), 18: 5487-5492.

Baird RA, Steyger PS, Schuff NR (1996) Mitotic and nonmitotic hair cell regeneration in the bullfrog vestibular otolith organs, Annals of the New York Academy of Sciences 781: 59-70.

Ben-Arie et al. (2000) Functional conservation of atonal and Math1 in the CNS and PNS, Development 127, 1039.

Ben-Arie, N., et al. (1996) Evolutionary conservation of sequence and expression of the bHLH protein Atonal suggests a conserved role in neurogenesis, Human Molecular Genetics, vol. 5, No. 9, 1207-1216.

Berminghan, et al. (1999) Math1: An Essential Gene for the Generation of Inner Ear Hair Cells, Science, vol. 284, 1837-1841.

Bertagnolli, M. M., et al. (2009) p27Kip1 in Stage III Colon Cancer: Implications for Outcome following Adjuvant Chemotherapy in Cancer and Leukemia Group B Protocol 89803, Clinical cancer research : an official journal of the American Association for Cancer Research vol. 15, No. 6, 2116-2122.

Bisht, M. and Bist, S. Indian J. Otolaryngol Head Neck Surg (2011), vol. 63(3), pp. 255-259. (Year: 2011).

Boros et al. (1986) Expression vectors based on the rac fusion promoter, Gene., vol. 42, 97-100.

Bottini, C., et al. (2009) p27Kip1 is inactivated in human colorectal cancer by cytoplasmic localization associated with activation of Akt/PKB, International Journal of Oncology vol. 34, 69-77.

Brigande & Heller (2009) Quo vadis, hair cell regeneration?, Nature Neuroscience, vol. 12, No. 6, 679-685.

Brooker, R., et al. (2006) Notch ligands with contrasting functions: Jagged' and Delta in the mouse inner ear, Development vol. 133, 1277-1286.

Brors, D., et al. (2003) EphA4 provides repulsive signals to developing cochlear ganglion neurites mediated through ephrin-B2 and -B3, Journal of Comparative Neurology vol. 462, 90-100.

Cafaro, et al. (2007) Atoh1 Expression Defines Activated Progenitors and Differentiating Hair Cells During Avian Hair Cell Regeneration, Dev. Dyn. vol. 236, 156-170.

Caiazzo M, et al. (2011) Direct generation of functional dopaminergic neurons from mouse and human fibroblasts. Nature vol. 476, 224-227.

Cariou, S., et al. (2000) Down-regulation of p21 WAF1yCIP1 or p27Kip1 abrogates antiestrogen-mediated cell cycle arrest in human breast cancer cells, PNAS USA, vol. 97, No. 16, 9042-9046.

Carmon, K. S., et al. (2011) R-spondins function as ligands of the orphan receptors LGR4 and LGRS5 to regulate Wnt/&-catenin signaling, PNAS, U.S.A. vol. 108, No. 28, 11452-11457.

Chai R, et al. (2012) Wnt signaling induces proliferation of sensory precursors in the postnatal mouse cochlea, PNAS U.S.A., vol. 109: 8167-8172.

Chai, R., et al. (2011) Dynamic Expression of Lgr5, a Wnt Target Gene, in the Developing and Mature Mouse Cochlea, JARO, vol. 12, 455-469.

Chang, B. L., et al. (2004) A Polymorphism in the CDKN1B Gene Is Associated with Increased Risk of Hereditary Prostate Cancer, Cancer Research vol. 64, 1997-1999.

Chellappa R, et al. (2008) Barhl1 regulatory sequences required for cell-specific gene expression and autoregulation in the inner ear and central nervous system. Mol Cell Biol vol. 28, 1905-1914.

Chen P, Segil N (1999) p27(Kip1) links cell proliferation to morphogenesis in the developing organ of Corti. Development vol. 126, 1581-1590.

Chen, et al. (2002) The role of Math' in inner ear development: Uncoupling the establishment of the sensory primordium from hair cell fate determination, Development vol. 129, 2495-2505.

Chu, I. M., et al. (2008) The Cdk inhibitor p27 in human cancer: prognostic potential and relevance to anticancer therapy, Nature reviews. Cancer vol. 8, 253-267.

Corwin JT, Cotanche DA (1988) Regeneration of sensory hair cells after acoustic trauma. Science vol. 240, 1772-1774.

Cox B.C., et al.(2012) Conditional gene expression in the mouse inner ear using Cre-loxP, JARO AC Ivol. 13, 295-322.

Cox, et al., (2014) Spontaneous hair cell regeneration in the neonatal mouse cochlea in vivo. Development, vol. 141, 817-829.

Daudet, N., et al. (2002) Expression of members of Wnt and Frizzled gene families in the postnatal rat cochlea, Brain Res. Mol. Brain Res. vol. 105, 98-107.

Diao F, White BH (2012) A novel approach for directing transgene expression in *Drosophila*: T2A-AE | Gai4 in-frame fusion. Genetics vol. 190: 1139-1144.

Doerflinger, N.H., et al. (2003) Inducible Site-Specific Recombination in Myelinating Cells, Genesis AF vol. 35, 63-72.

Doetzlhofer A, White P, Lee YS, Groves A, Segil N (2006) Prospective identification and AG purification of hair cell and supporting cell progenitors from the embryonic cochlea. Brain Res vol. 1091, 282-288.

Elbashir, W., et al. (2001) RNA interference is mediated by 21- and 22-nucleotide RNAs, Genes & Development vol. 15, 188-200.

Fekete, et al. (1998) Hair Cells and Supporting Cells Share a Common Progenitor in the Avian Inner Ear, J. Neurosci. vol. 18, No. 19, 7811-7821.

Fire, A., et al. (1998) Potent and specific genetic interference by double-stranded RNA in Caenorhabditis elegans, Nature vol. 391, 806-811.

Flanagan, J. G., et al. (1999) A cytosine analog that confers enhanced potency to antisense oligonucleotides, PNAS USA vol. 96, 3513-3518.

Fujioka M, et al (2011) Generating mouse models of degenerative diseases using Cre/los-mediated in vivo mosaic cell ablation. J Clin Invest vol. 121, 2462-2469.

Gao J, Wu X, Zuo J (2004) Targeting hearing genes in mice, Brain Res Mol Brain Res vol. 132, 192-207.

Garcia, M. I., et al. (2009) LGR5 deficiency deregulates Wnt signaling and leads to precocious Paneth cell differentiation in the fetal intestine, Developmental Biology, vol. 331, 58-67.

Gillespie, L. N., et al. (2001) LIF is more potent than BDNF in promoting neurite outgrowth of AO mammalian auditory neurons in vitro, Neuro Report vol. 12, No. 2, 275-279.

Golub JS, Tong L, Ngyuen TB, Hume CR, Palmiter RD, et al. (2012) Hair cell replacement in adult mouse utricles after targeted ablation of hair cells with diphtheria toxin. J Neurosci vol. 32, 15093-15105.

Gomez-Casati ME, Murtie J, Taylor B, Corfas G (2010) Cell-specific inducible gene recombination AQ in postnatal inner ear supporting cells and glia, JARO vol. 11, 19-26.

Gross J, et al.(2011) Expression analysis of prestin and selected transcription factors in newborn rats. Cell Mol Neurobiol vol. 31, 1089-1101.

Gubbels, et al. (2008) Functional auditory hair cells produced in the mammalian cochlea by in utero gene transfer, Nature vol. 455, 537-541.

Harada, N., et al. (1999) Intestinal polyposis in mice with dominant stable muttion of the p-catenin gene, The EMBO Journal, vol. 18, No. 21, 5931-5942.

Hashimshony T, et al (2012) CEL-Seq;: single-cell RNA-Seq by multiplexed linear amplification. AU |cell Rep vol. 2, 666-673.

Hayward, et al. (2005) Notch modulates Wht signalling by associating with Armadillo/beta-catenin and regulating its transcriptional activity, Development vol. 132, 1819-1830.

He DZ, et al. (2010) Changes in plasma membrane structure and electromotile properties in prestin deficient outer hair cells, Cytoskeleton vol. 67, 43-55.

* cited by examiner

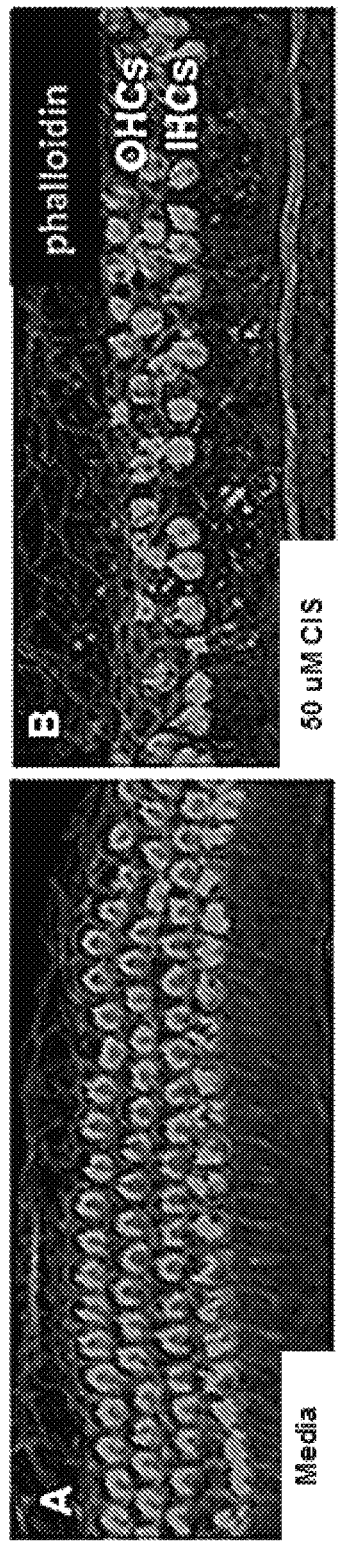
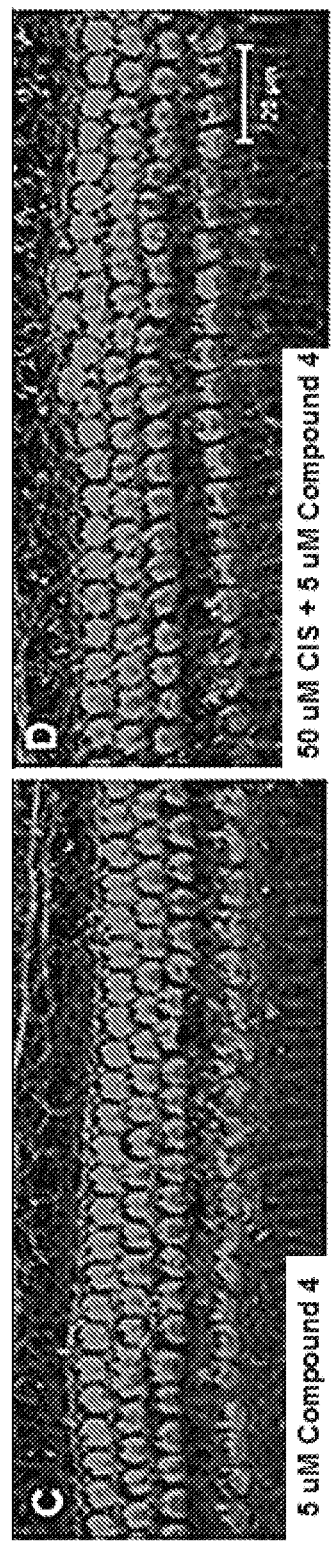
FIG. 3A  FIG. 3B  FIG. 3C  FIG. 3D

METHODS AND COMPOSITIONS FOR THE PREVENTION AND TREATMENT OF HEARING LOSS

CROSS-REFERENCE TO RELATED APPLICATIONS

This application is a continuation of U.S. application Ser. No. 15/580,224, filed on Dec. 6, 2017, which is a national stage filing under 35 U.S.C § 371 of International Application No. PCT/US2016/038384, filed on Jun. 20, 2016, which claims the benefit of U.S. Provisional Application No. 62/181,755, filed on Jun. 18, 2015, the contents of which are incorporated herein by reference in their entireties.

STATEMENT REGARDING FEDERALLY SPONSORED RESEARCH

This invention was made with U.S. Government support under grant numbers N00014-09-V-1014, N00014-12-V-0191, N00014-12-V-0775, and N00014-16-V-2315 awarded by the Office of Naval Research (ONR), and grant numbers DC006471, DC013879, DC015010, and CA021765 awarded by the National Institutes of Health (NIH). The government has certain rights in the invention.

BACKGROUND

Noise-induced hearing loss (NIHL) is the most common sensorineural hearing impairment. The World Health Organization recently reported that more than a billion teens and young adults worldwide are at risk of NIHL caused by loud music (http://www.cnn.com/2015/03/06/health/hearing-loss-loud-music/index.html). Acute or chronic acoustic overexposure has put more than 40 million U.S. workers at risk of permanent hearing loss (Kopke et al. (2007) *Hear. Res.* 226: 114-125). NIHL is also prevalent in military settings, costing more than $2 billion per year in veterans (VA) compensation.

Noise trauma results in two types of hearing loss, depending on intensity and duration: permanent or temporary threshold shift (PTS or TTS). Persons can recover from TTS within 24-48 hrs, whereas PTS is irreversible. Mechanistically, acoustic overexposure causes hearing loss through overproduction of reactive oxygen species (ROS), mitochondrial injury, lipid peroxidation, glutathione (GSH) depletion, reperfusion injury, excessive glutamate release, and/or loss of hair cells and neurons through programmed cell death (PCD, apoptosis) and inflammatory pathways (Kopke et al. (2007) *Hear. Res.* 226: 114-125). Many of these cellular pathways overlap with those involved in hearing loss caused by cisplatin chemotherapy, antibiotics, and age (Mukherj ea et al. (2011) *Expert Opin. Drug Discov.* 6: 491-505; Schacht et al. (2012)*Anat Rec. (Hoboken)* 295: 1837-1850; Vu et al. (2013) *PLoS One* 8: e54794. However, it is not known which pathways, established or novel, are key to the prevention of NIHL and other forms of ototoxicity, such as cisplatin-induced or chemotherapy-induced hearing loss, antibiotic-induced hearing loss, and age-related hearing loss.

Cisplatin is known to exhibit toxic effects on hair cells of the inner ear. Indeed, high frequency hearing loss (>8 kHZ) has been reported to be as high as 90% in children undergoing cisplatin therapy (Allen et al. (1998) *Otolaryngol Head Neck Surg* 118: 584-588). Other clinically important and commonly used drugs also have documented ototoxic effects, including loop diuretics (Greenberg (2000) *Am. J. Med. Sci.* 319:10-24), antimalarial sesquiterpene lactone endoperoxides (e.g., artemesinins) (Toovey and Jamieson (2004) *Trans. R. Soc. Trop. Med. Hyg.* 98: 261-267), antimalarial quinines (Claessen et al. (1998) *Trop. Med. Int. Health* 3: 482-489), salicylates (Matz (1990) *Ann. Otol. Rhinol. Laryngol.* Suppl. 148: 39-41), and interferon polypeptides (Formann et al. (2004) *Am. J. Gastroenterol.* 99: 873-877).

Moreover, ototoxicity to the vestibular system, which includes the vestibule and semicircular canal, manifests as balance and orientation-related disorders. These disorders include, but are not limited to, induced or spontaneous vertigo, dysequilibrium, increased susceptibility to motion sickness, nausea, vomiting, ataxia, labyrinthitis, oscillopsia, nystagmus, syncope, lightheadedness, dizziness, increased falling, difficulty walking at night, Meniere's disease, and difficulty in visual tracking and processing.

Extensive research in recent years has sought to identify small molecules that can protect against hearing loss. Those tested can be classified into three different groups based on their main cellular function: 1) antioxidants and ROS scavengers, 2) anti-inflammatory drugs, and 3) apoptosis inhibitors. Many candidate compounds are currently in pre-clinical and clinical trials; most are related to antioxidants, vitamins, and glutathione metabolism, although their effectiveness remains unclear.

Despite the promising protective effects of N-acetylcysteine (NAC) in preclinical and clinical safety studies, it has shown no protection against NIHL in several clinical trials (Kopke et al. (2007) *Hear. Res.* 226: 114-125; Tieu and Campbell (2013) *Otolaryngology* 3:130). D-methionine has shown protective effects against NIHL but remains to be tested in clinical trials (Muller and Barr-Gillespie (2015) *Nat. Rev. Drug Discov.* 14: 346-365; Oishi and Schacht (2011) *Expert Opin. Emerg. Drugs* 16: 235-245). Similarly, Ebelsen (SPI-1005), a seleno-organic compound with antioxidant activity through glutathione peroxidase-like action, has been tested against TTS in noise-induced excitotoxicity studies but remains unproven in clinical trials (See "Sound Pharmaceuticals Inc. successfully completes its first Phase 2 clinical trial with SPI-1005" (Nov. 5, 2013); Lynch and Kil (2005) *Drug Discov. Today* 10: 1291-1298). To date, no drugs are FDA-approved for protection against NIHL and traumatic brain injury (TBI)-associated hearing loss. Thus, there remains a need for compositions and methods of preventing and treating hearing loss.

SUMMARY

In accordance with the purpose(s) of the invention, as embodied and broadly described herein, the invention, in one aspect, relates to compositions and methods for use in the prevention and treatment of a hearing impairment.

Disclosed are methods of treating hearing impairment, the methods comprising administering to a subject diagnosed with a need for treatment of hearing impairment a therapeutically effective amount of a cyclin-dependent kinase 2 (CDK2) inhibitor, or a pharmaceutically acceptable salt thereof.

Also disclosed are methods of preventing hearing impairment, the methods comprising administering to a subject a CDK2 inhibitor in an amount of from about 0.001 µM to about $1.0 \times 10^4$ µM at least once every three weeks, or a pharmaceutically acceptable salt thereof.

Also disclosed are pharmaceutical compositions comprising a CDK2 inhibitor, or a pharmaceutically acceptable salt thereof; and one or more of: (a) at least one agent known to treat hearing impairment, or a pharmaceutically acceptable salt thereof; and (b) at least one agent known to prevent hearing impairment, or a pharmaceutically acceptable salt thereof; and a pharmaceutically acceptable carrier.

Also disclosed are pharmaceutical compositions comprising a CDK2 inhibitor, wherein the CDK2 inhibitor is not a paullone derivative, or a pharmaceutically acceptable salt thereof; and one or more of: at least one agent known to treat hearing impairment, or a pharmaceutically acceptable salt thereof; and at least one agent known to prevent hearing impairment, or a pharmaceutically acceptable salt thereof; and a pharmaceutically acceptable carrier.

Also disclosed are methods for making compounds and for making compounds for use in pharmaceutical compositions. Also disclosed are the products of said methods.

Also disclosed are methods of preparing a pharmaceutical composition, the method comprising the step of combining a CDK2 inhibitor, or a pharmaceutically acceptable salt thereof; and one or more of: (a) at least one agent known to treat hearing impairment, or a pharmaceutically acceptable salt thereof; (b) at least one agent known to prevent hearing impairment, or a pharmaceutically acceptable salt thereof, wherein at least one is present in an effective amount; and a pharmaceutically acceptable carrier.

Also disclosed are kits comprising a CDK2 inhibitor, or a pharmaceutically acceptable salt thereof; and one or more of: (a) at least one agent known to treat a hearing impairment; (b) at least one agent known to prevent a hearing impairment; (c) at least one antibiotic agent; (d) at least one chemotherapeutic agent; (e) instructions for treating a hearing impairment; and (f) instructions for preventing a hearing impairment.

Also disclosed are kits comprising a compound selected from:

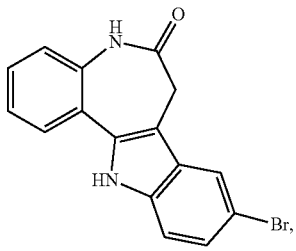

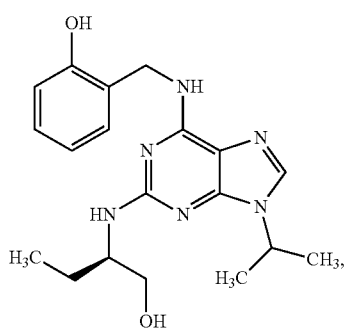

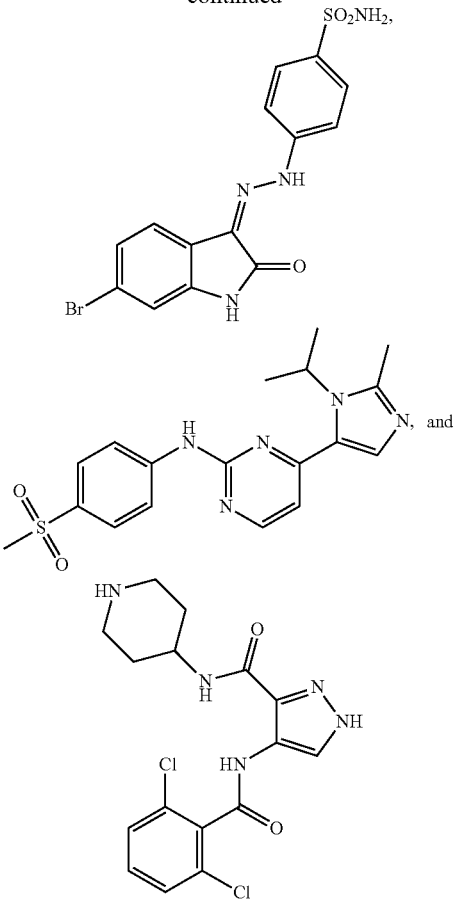

or a pharmaceutically acceptable salt thereof; and one or more of: (a) at least one agent known to treat a hearing impairment; (b) at least one agent known to prevent a hearing impairment; (c) at least one antibiotic agent; (d) at least one chemotherapeutic agent; (e) instructions for treating a hearing impairment; and (f) instructions for preventing a hearing impairment.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE DRAWINGS

The accompanying figures, which are incorporated in and constitute a part of this specification, illustrate several aspects and together with the description serve to explain the principles of the invention.

FIG. 3A-G show representative data illustrating that compounds 4 (FIG. 3A-E), 9 (olomoucine II or compound 9, FIG. 3F), and 12 (CDK2 inhibitor II or compound 12, FIG. 3G) protect against cisplatin-induced hair cell loss in cochlear explants.

Figure 1:
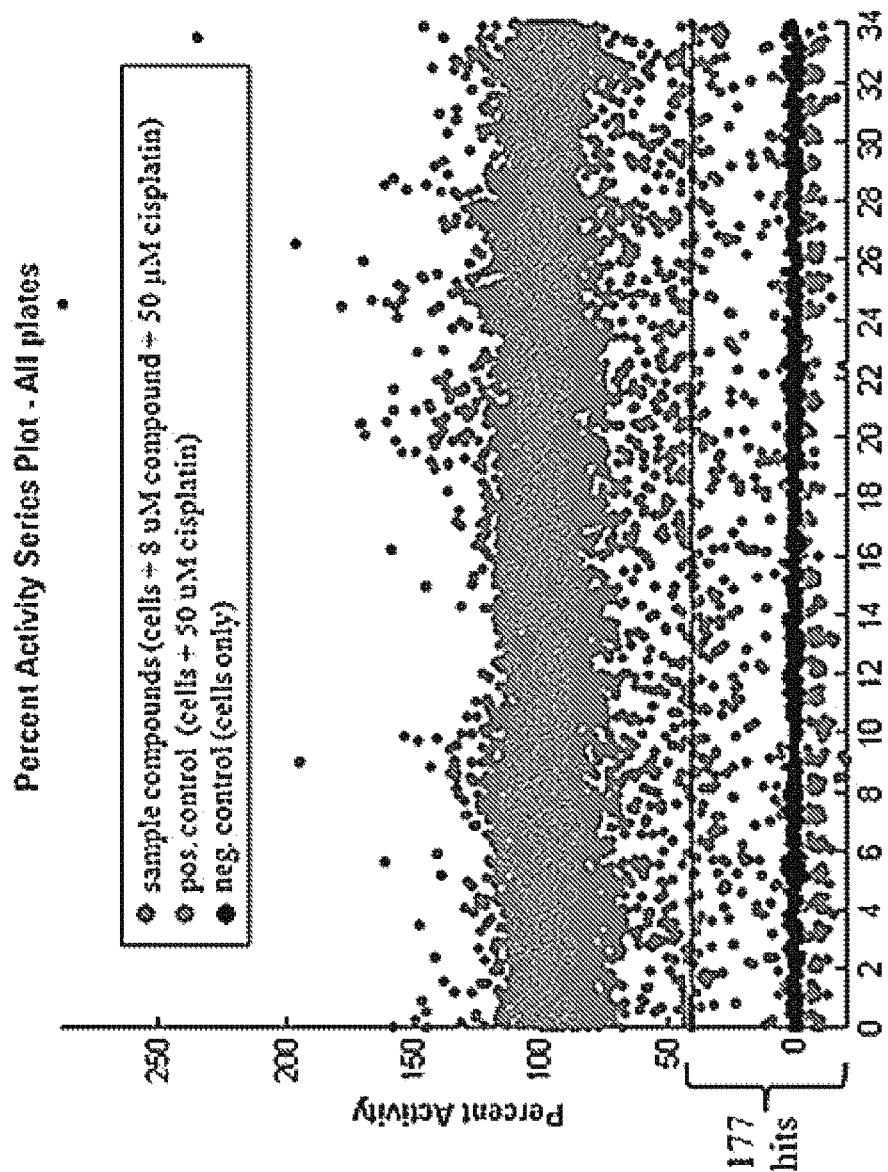
FIG. 1 shows a representative plot illustrating the percent activity of the bioactive compounds in a cell-based high-throughput screen.
Figures 2A, 2B, 2C:
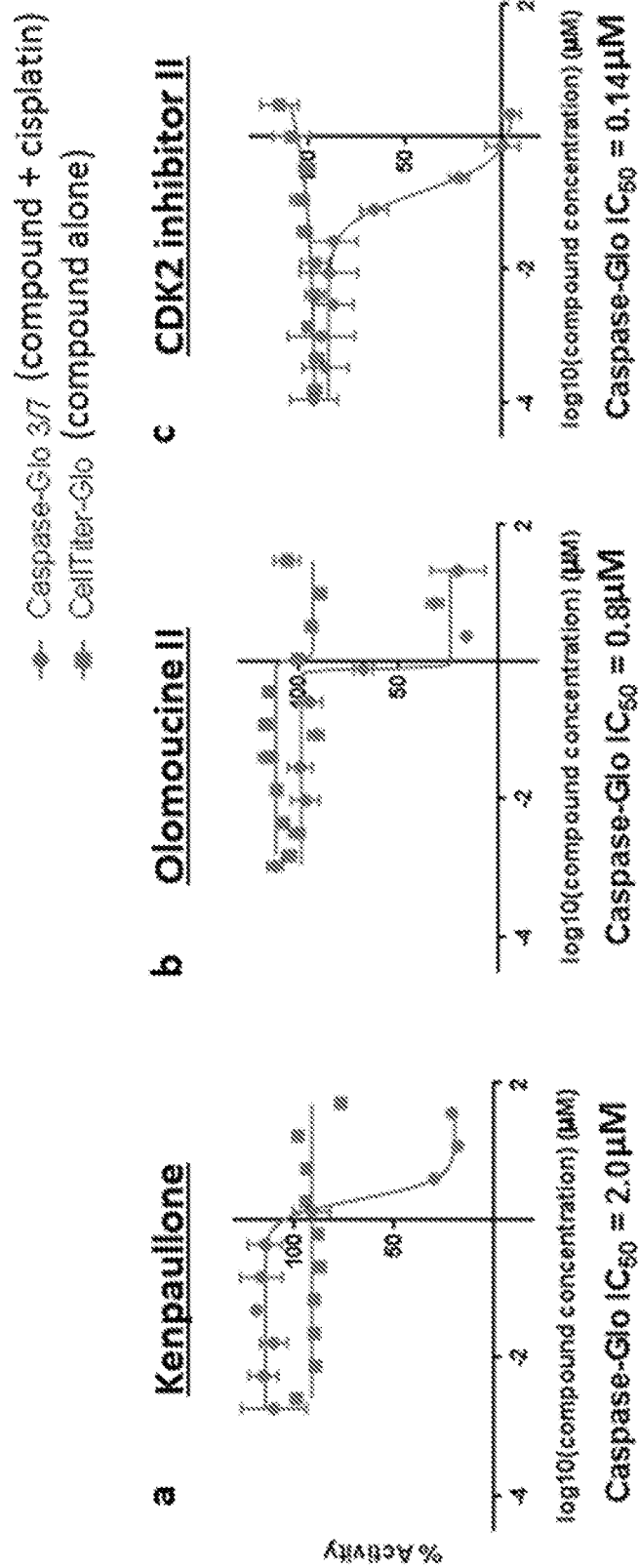
FIG. 2a-e show representative dose response curves of kenpaullone (compound 4) (FIG. 2a), Olomoucine II (compound 9) (FIG. 2b), CDK2 inhibitor II (compound 12) (FIG. 2c), compound 3 (FIG. 2d), and compound 1 (FIG. 2e), determined using the Caspase-/37 Glo assay and the Promega Cell Titer Glo assay (CTG).
Figures 2D, 2E:
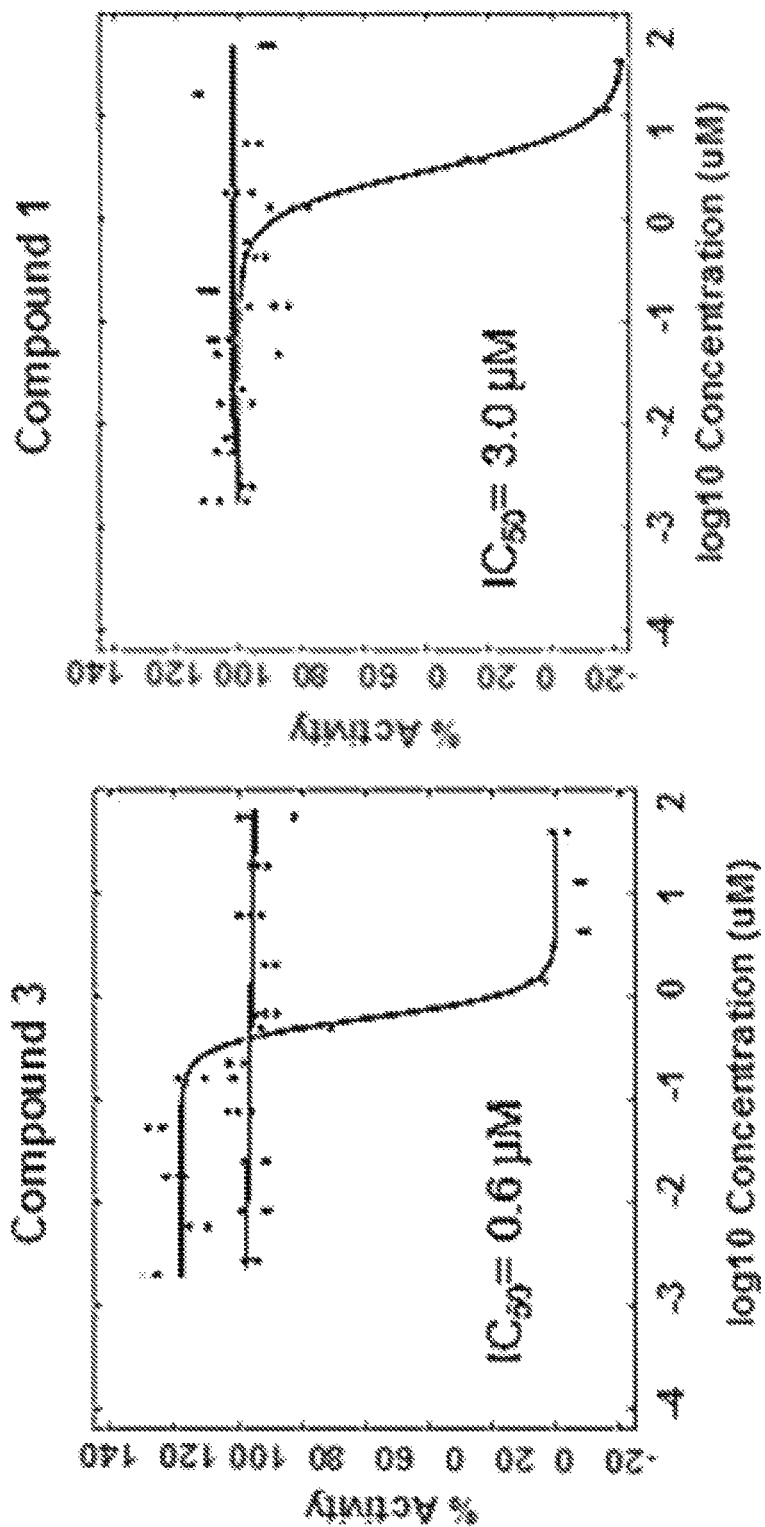

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. DEFINITIONS

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

As used in the specification and in the claims, the term "comprising" can include the aspects "consisting of" and "consisting essentially of."

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "dosage form" means a pharmacologically active material in a medium, carrier, vehicle, or device suitable for administration to a subject. A dosage forms can comprise inventive a disclosed compound, a product of a disclosed method of making, or a salt, solvate, or polymorph thereof, in combination with a pharmaceutically acceptable excipient, such as a preservative, buffer, saline, or phosphate buffered saline. Dosage forms can be made using conventional pharmaceutical manufacturing and compounding techniques. Dosage forms can comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene 9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), anti-foaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol). A dosage form formulated for injectable use can have a disclosed compound, a product of a disclosed method of making, or a salt, solvate, or polymorph thereof, suspended in sterile saline solution for injection together with a preservative.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

Figure 7:
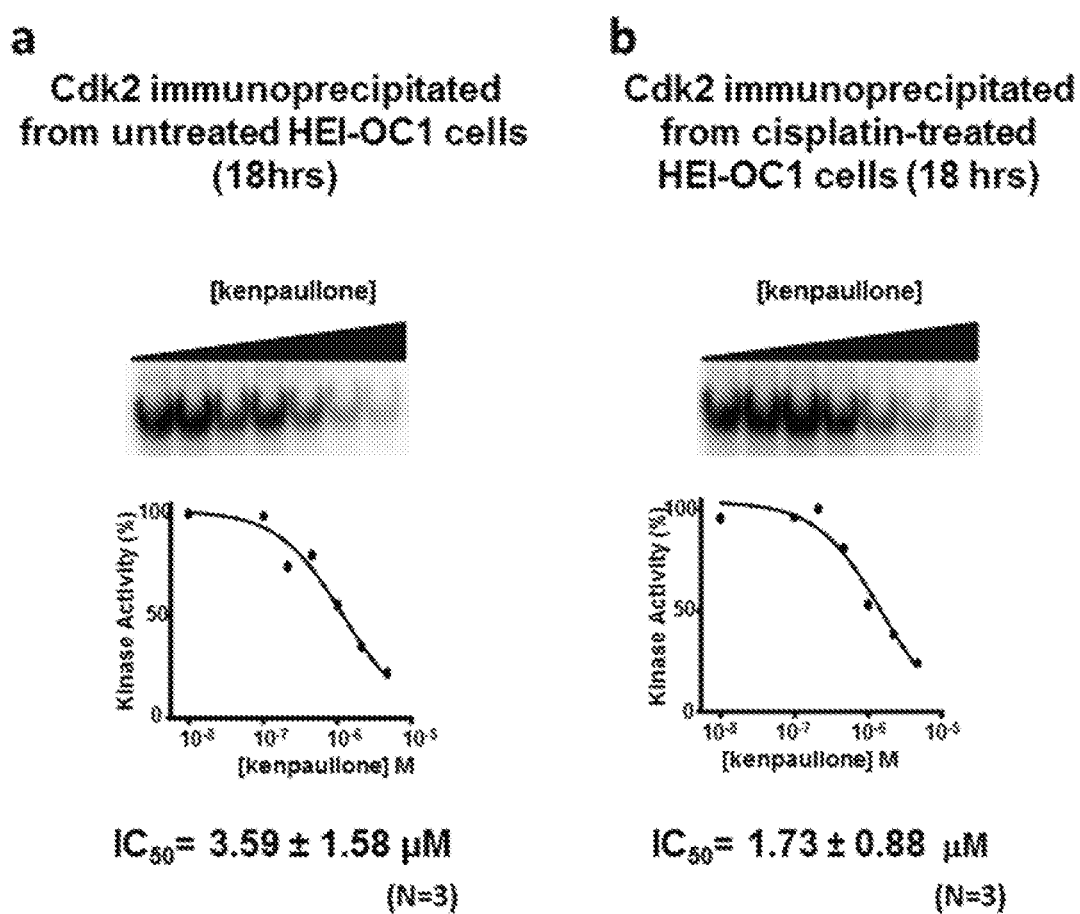
FIG. 7 shows kenpaullone inhibits CDK2 kinase activity in vitro. Increasing doses of kenpaullone were tested with Cdk2 immunoprecipitated from HEI-OC cells without (panel 7a) or with (panel 7b) cisplatin treatment and the kinase activity was quantified as the level of phosphorylation of the substrate histone H1. Three (N=3) independent experiments were used for calculation of $IC_{50}$.
Figure 8:
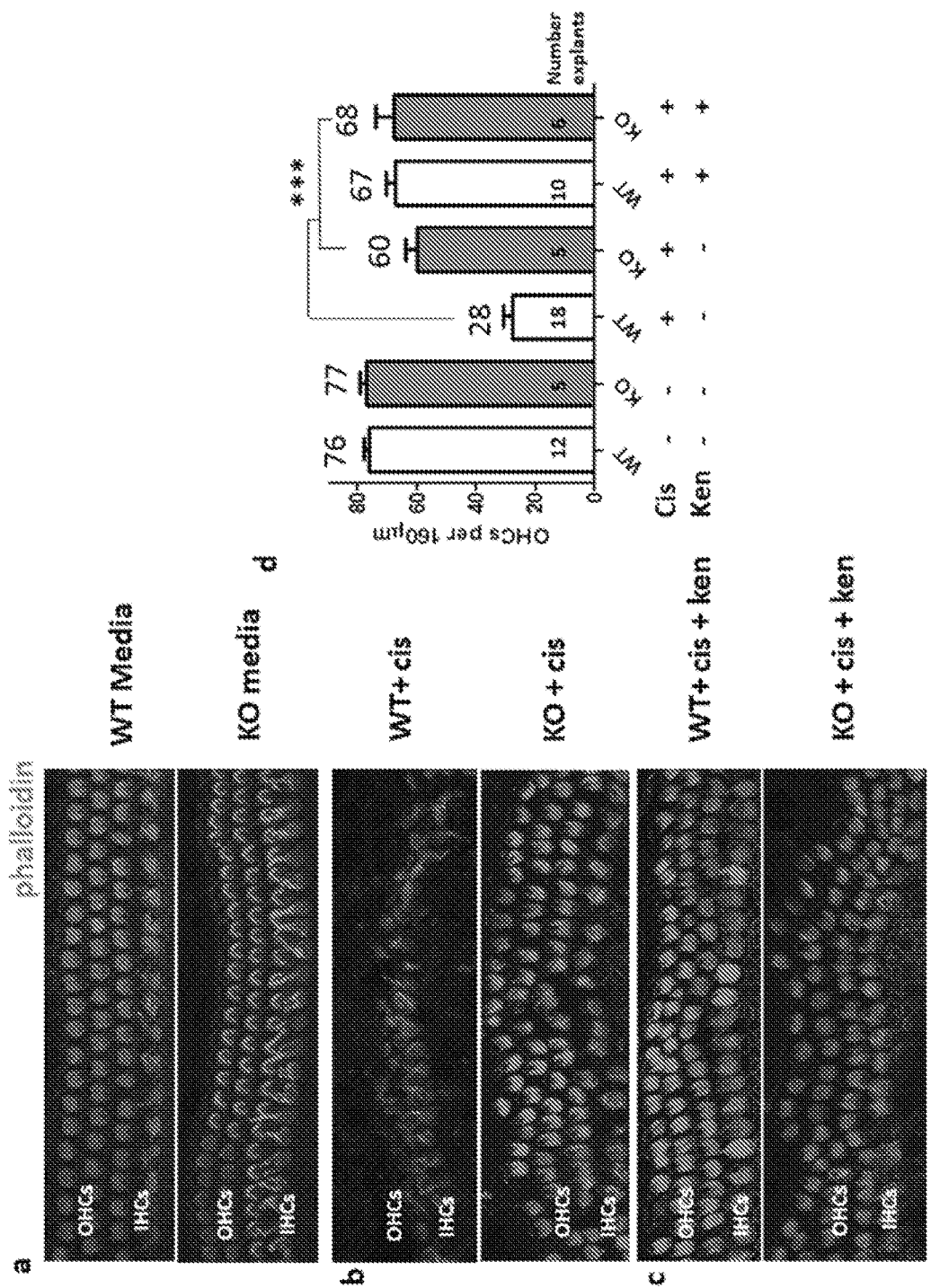
FIG. 8 shows germline CDK2 knockout (KO) cochlear explants confer resistance to cisplatin treatment and kenpaullone administration phenocopies CDK2 knockout resistance to cisplatin ototoxicity. Panels 8a-c show middle turn organs of Corti with actin staining (phalloidin-Alexa Flour 568) in WT and CDK2 KO cochleae without any treatment (Media, panel 8a), with 50 µM cisplatin treatment (panel 8b) and with 50 µM cisplatin and 5 µM kenpaullone (Panel 8c). Outer hair cell (OHCs) numbers of actin-positive cells per 160 µm of the middle turn cochleae were counted (panel 8d) and data are mean±s.e.m. Numbers of explants tested in each condition are indicated in the bars. *** $P<0.001$ by one-way ANOVA with Bonferroni's multiple comparison test.
Figure 9:
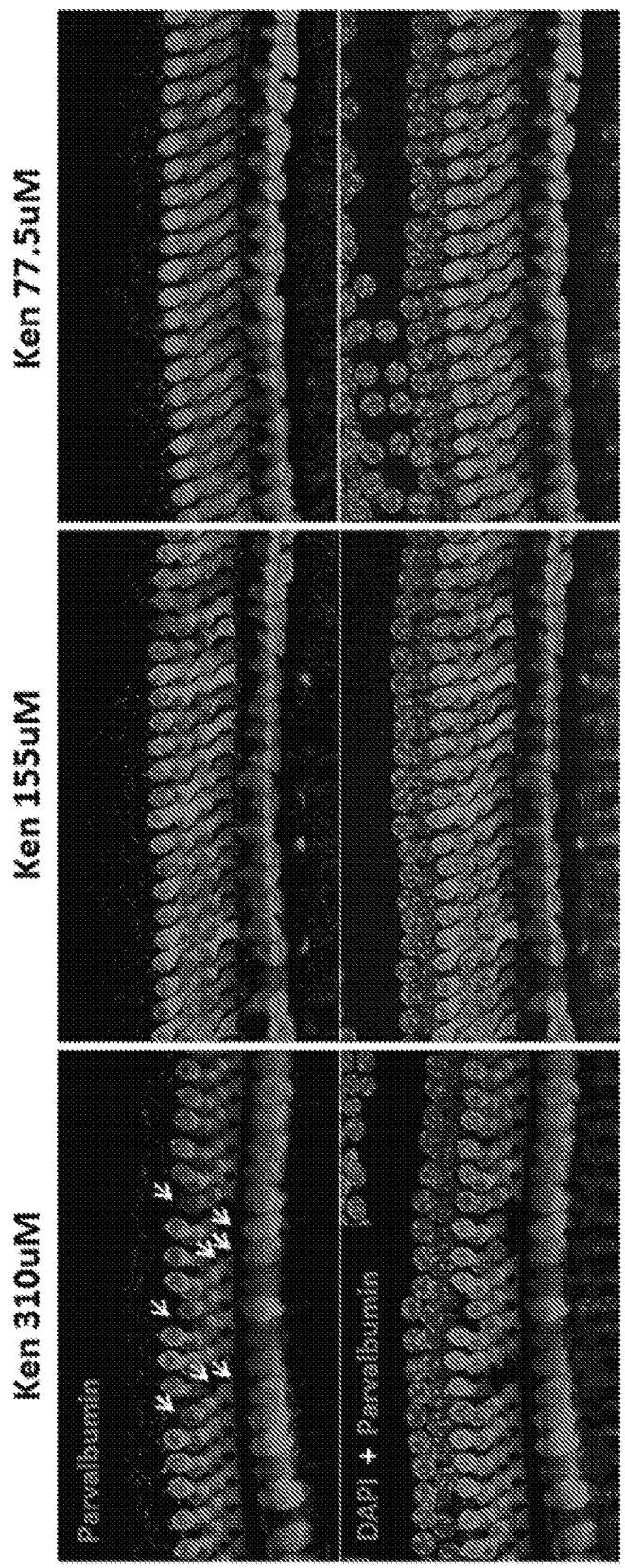
FIG. 9 shows testing of kenpaullone toxicity in vivo in adult FVB mice (~P28). FVB mice at P28 were administrated kenpaullone at various concentrations (310 µM, 155 µM and 77.5 µM) by transtympanic injection. Basel turn organs of Corti 24 hours post kenpaullone treatments as visualized by DAPI and Parvalbumin show that kenpaullone is toxic at 310 µM but not at lower doses. Arrows label lost outer hair cells. Two independent mice were tested for each dose.
Figure 10:
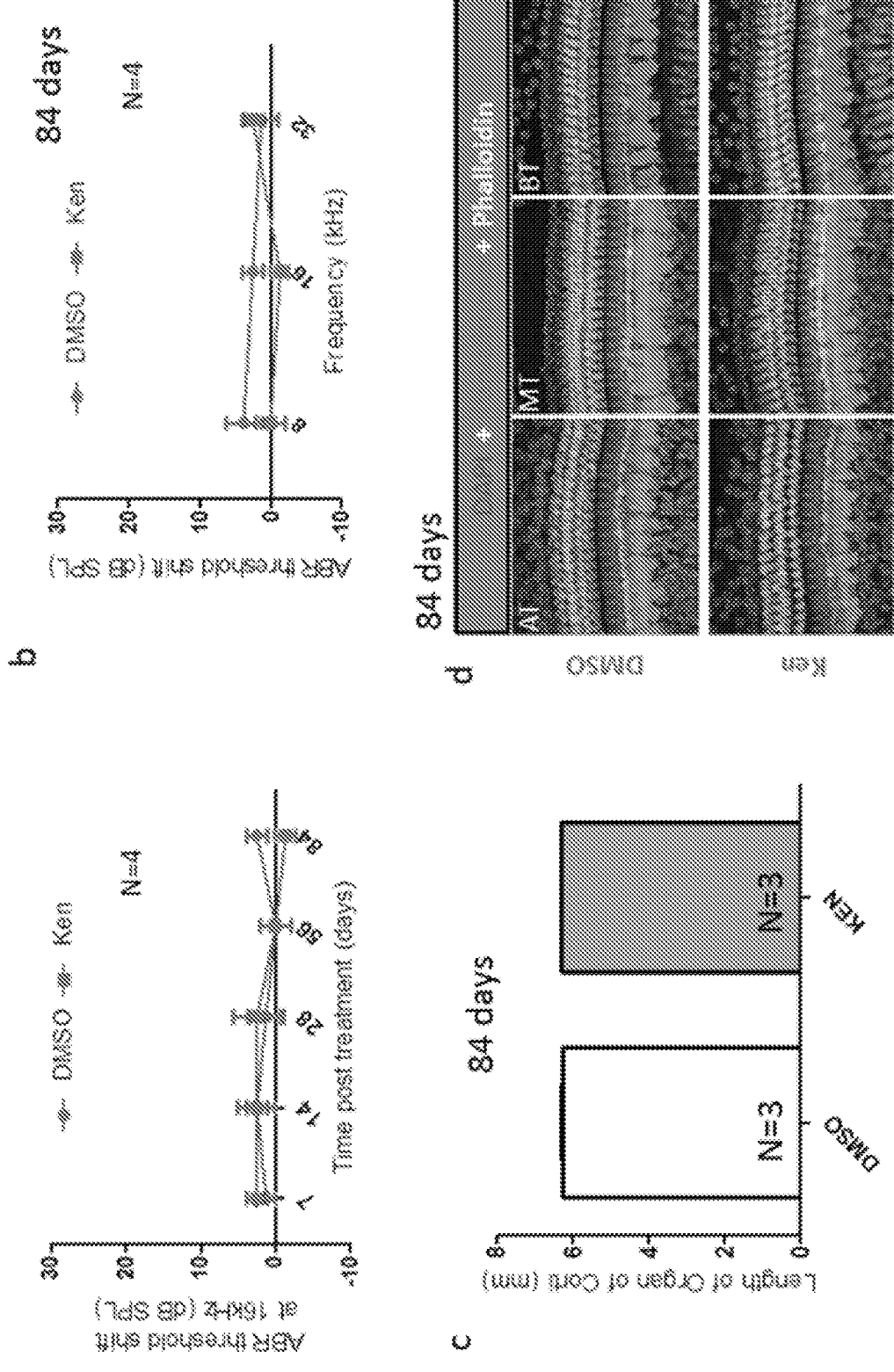
FIG. 10 shows the lack of toxicity of kenpaullone (at 250 µM by transtymapnic injection) in vivo. Panel 10a shows no significant ABR threshold shifts 7 days, 14 days, 28 days, 56 days and 84 days post kenpaullone or DMSO transtympanic injection at 16 kHz. Panel 10b demonstrates there are no detectable ABR threshold shifts 84 days post kenpaullone or DMSO transtympanic injection at 8 kHz, 16 kHz and 32 kHz. Panel 10c indicates kenpaullone treatment does not affect the length of the cochlea. Panel 10d visualizes organs of Corti 84 days post kenpaullone (Ken) treatment in vivo and demonstrates that kenpaullone lacks ototoxicity at 250 µM after 84 days in vivo.

As used herein, the term "CDK2 Inhibitor" refers to a small molecule chemical compound that binds to CDK2 protein isolated from cochlear cells and cochlear explants, inhibits CDK2 kinase or other activities with $IC_{50}$ of <10 μM, and thus prevents cisplatin-induced hair cell loss with $IC_{50}$ of <10 μM. See FIGS. 3, 7, and 8.

As used herein, the term "therapeutic agent" includes any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index ($14^{th}$ edition), the Physicians' Desk Reference ($64^{th}$ edition), and The Pharmacological Basis of Therapeutics ($12^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term "therapeutic agent" also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

The term "hearing impairment" as used herein refers to a neurologic disorder, oto-neurological in nature, typically sensorineural, but including composite loss (both sensorineural and conductive loss), preferably either a sensory or a neural ($8^{th}$ nerve related) hearing lost, and most preferably a sensory loss (cochlear related), in which the patient will display, complain of, or is diagnosed to have a hearing loss. Conductive hearing loss is typically related to the external or middle ear. These impairments of interest to the present invention are those associated with hair cell damage. Less preferably such impairments can occur along with conductive hearing loss damage or damage, loss, or degeneration of a neuron of the auditory system. Hair cells are epithelial cells possessing fine projections and located in the maculae and the organ of Corti.

Examples of hearing impairments and situations in which such hearing impairments can occur encompassed by the term "hearing impairment," as used herein, include sensory hearing loss due to end-organ lesions, e.g., acoustic trauma, viral endolymphatic labyrinthitis, and Meniere's disease.

The impairment can also be a neural hearing loss due to events including cerebellopontine angle tumors of the 8$^{th}$ nerve. Hearing impairments include tinnitus, this is a perception of sound in the absence of an acoustic stimulus, and may be intermittent or continuous, wherein there is a diagnosed sensorineural loss. Hearing loss may be due to bacterial or viral infection of the 8$^{th}$ nerve ganglia, such as in herpes zoster oticus, purulent labyrinthitis arising from acute otitis media, purulent meningitis, chronic otitis media, sudden deafness including that of viral origin, e.g., viral endolymphatic labyrinthitis caused by viruses including mumps, measles, influenza, chickenpox, mononucleosis, and adenoviruses. The hearing loss can be congenital, such as that caused by rubella, anoxia during birth, bleeding into the inner ear due to trauma during delivery, ototoxic drugs administered to the mother, erythroblastosis fetalis, and hereditary conditions including Waardenburg's syndrome and Hurler's syndrome. The hearing loss can be noise-induced, generally due to a noise greater than 85 decibels (db) SPL (sound pressure level) that damages the inner ear. Hearing loss includes presbycusis, which is a sensorineural hearing loss occurring as a normal part of aging, fractures of the temporal bone extending into the middle ear and rupturing the tympanic membrane and possibly the ossicular chain, fractures affecting the cochlea, and acoustic neurinoma, which are tumors generally of Shwann cell origin that arise from either the auditory or vestibular divisions of the 8$^{th}$ nerve. In various aspects, the hearing loss is caused by an ototoxic drug that affects the auditory portion of the inner ear, particularly the organ of Corti. The hearing loss may be due to chemotherapy or to cisplatin. The hearing loss can be related to a vestibular disorder including vertigo, dysequilibrium, increased susceptibility to motion sickness, nausea, vomiting, ataxia, labyrinthitis, oscillopsia, nystagmus, syncope, lightheadedness, dizziness, increased falling, difficulty walking at night, Meniere's disease, and difficulty in visual tracking and processing. Incorporated herein by reference are Chapters 196, 197, 198, and 199 of The Merck Index, 14$^{th}$ Edition (1982), Merck Sharp & Dome Research Laboratories, N.J. and related chapters in the most recent edition, relating to description and diagnosis of hearing impairments.

Tests are known and available for diagnosing hearing impairments. Neuro-otological, neuro-ophthalmological, neurological examinations, and electra-oculography can be used (Wennmo et al., *Acta Otolaryngol* 1982, 94, 507). Sensitive and specific measures are available to identify patients with auditory impairments. For example, tuning fork tests can be used to differentiate a conductive from a sensorineural hearing loss and determine whether the loss is unilateral. An audiometer is used to quantitate hearing loss, measured in decibels. With this device the hearing for each ear is measured, typically from 125 to 8000 Hz, and plotted as an audiogram. Speech audiometry can also be performed. The speech recognition threshold, the intensity at which speed is recognized as a meaningful symbol, can be determined at various speech frequencies. Speech or phoneme discrimination can also be determined and used as an indicator of sensorineural hearing loss since analysis of speech sounds relies upon the inner ear and 8$^{th}$ nerve. Tympanometry can be used to diagnose conductive hearing loss and aid in the diagnosis of those patients with sensorineural hearing loss. Electrocochleography, measuring the cochlear microphonic response and action potential of the 8$^{th}$ nerve, and evoked response audiometry, measuring evoked response from the brainstem and auditory cortex, to acoustic stimuli can be used in patients, particularly infants and children or patients with sensorineural hearing loss of obscure etiology. Auditory brainstem responses (ABRs) or distortion products otoacoustic emissions (DPOAEs) are most commonly used audiometry methods. These tests serve a diagnostic function as well as a clinical function in assessing response to therapy.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "A$^1$," "A$^2$," "A$^3$," and "A$^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more CH$_2$ groups linked to one another. The polyalkylene group can be represented by the formula —(CH$_2$)$_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —OA$^1$ where A$^1$ is alkyl or cycloalkyl as defined above. "Alkoxy" also includes polymers of alkoxy groups as just described; that is, an alkoxy can be a polyether such as —OA$^1$-OA$^2$ or —OA$^1$-(OA$^2$)$_a$-OA$^3$, where "a" is an integer of from 1 to 200 and A$^1$, A$^2$, and A$^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as (A$^1$A$^2$)C=C(A$^3$A$^4$) are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbomenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5$^{th}$ Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —NH$_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl can be two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —NA$^1$A$^2$, where A$^1$ and A$^2$ can be, independently, hydrogen or alkyl, cycloalkyl, alkenyl, cycloalkenyl, alkynyl, cycloalkynyl, aryl, or heteroaryl group as described herein. A specific example of amino is —NH$_2$.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$— or -(A$^1$O(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen," or "halide," as used herein can be used interchangeably and refer to F, Cl, Br, or I.

The terms "pseudohalide," "pseudohalogen," or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl," as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl," as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The terms "heterocycle" or "heterocyclyl," as used herein can be used interchangeably and refer to single and multi-cyclic aromatic or non-aromatic ring systems in which at least one of the ring members is other than carbon. Thus, the term is inclusive of, but not limited to, "heterocycloalkyl", "heteroaryl", "bicyclic heterocycle" and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl," as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxyl" or "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula —$N_3$.

The term "nitro" as used herein is represented by the formula —$NO_2$.

The term "nitrile" or "cyano" as used herein is represented by the formula —CN.

The term "silyl" as used herein is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogen of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —$(CH_2)_{0-4}R^\circ$; —$(CH_2)_{0-4}OR^\circ$; —O$(CH_2)_{0-4}R^\circ$, —O—$(CH_2)_{0-4}C(O)OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched)alkylene)O—N(R°)$_2$; or —(C$_{1-4}$ straight or branched)alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$ SR$^\bullet$, —(CH$_2$)$_{0-2}$ SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of IV, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R' is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

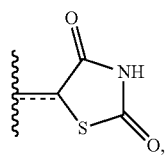

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and L or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Ingold-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

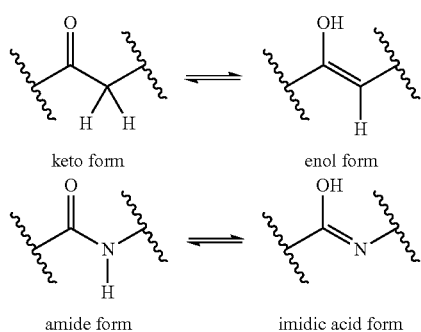

Likewise, amides with an N-hydrogen can exist in an equilibrium of the amide form and the imidic acid form. As another example, pyrazoles can exist in two tautomeric forms, AP-unsubstituted, 3-$A^3$ and $N^1$-unsubstituted, 5-$A^3$ as shown below.

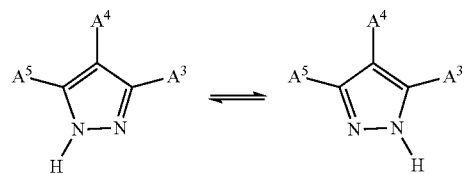

Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

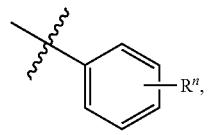

which is understood to be equivalent to a formula:

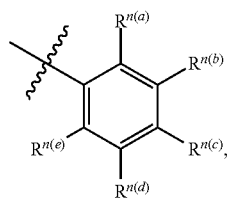

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and supplemental volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. COMPOUNDS

In one aspect, disclosed are compounds useful in treating or preventing hearing disorders. In a further aspect, the disclosed compounds exhibit inhibition of CDK2. In a still further aspect, the disclosed compounds exhibit antagonism of CDK2.

In one aspect, the compounds of the invention are useful in the treatment or prevention of hearing disorders associated with CDK2 dysfunction and other diseases in which CDK2s are involved, as further described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Paullone Derivatives

In various aspects, the compound is a paullone derivative, or a pharmaceutically acceptable solvate, salt, or polymorph thereof. Paullones are a family of benzazepinones characterized by a core framework represented by a structure:

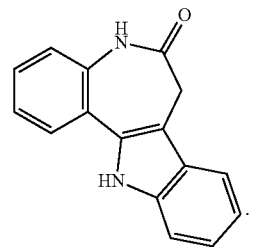 [SMILES: O=C1Cc2c([nH]c3ccccc23)-c2ccccc2N1]

Paullones constitute a well-established class of cyclin-dependent kinase (CDK) inhibitors. CDK's are a family of serine/threonine protein kinases known to play a central role in the normal growth and life cycle of eukaryotic cells. Inhibitors of CDK could potentially serve as pharmacological agents to treat diseases of proliferation such as cancer, psoriasis, and restenosis (Sharma, V. M., et al. (2008) *Indian J. of Biochem. & Biophysics* 45, 416; Leost, M., et al. (2000) *Eur. J. Biochem.* 267, 5983-5994).

Paullone derivatives have been previously described in, for example, US 2003/0181439 A1; U.S. Pat. No. 7,232,814 B2; Kunick, C., et al. (2005) *ChemBioChem* 6, 541-549; Zaharevitz, D., et al. (1999) *Cancer Res.* 59, 2566-2569; Leost, M., et al. (2000) *Eur. J. Biochem.* 267, 5983-5994; WO 2006/117212 A2; WO 2009/010298 A2; Sharma, V. M., et al. (2008) *Indian J. of Biochem. & Biophysics* 45, 416; Pies, T. (2003) Dissertation, Hamburg University, Hamburg, GER, which are herein incorporated by reference.

In one aspect, disclosed are paullone derivatives having a structure represented by a formula:

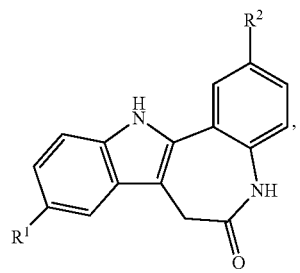

wherein $R^1$ is selected from hydrogen, halogen, —OH, —CN, —NO$_2$, —NH$_2$, —(S=O)R$^3$, —SO$_2$R$^3$, C1-C6 alkyl, C1-C6 monohaloalkyl, C1-C6 polyhaloalkyl, C1-C6 alkoxy, C1-C6 cyanoalkyl, C1-C6 aminoalkyl, C1-C6 hydroxyalkyl, C1-C6 monoalkylamino, and C1-C6 dialkylamino; wherein $R^3$, when present, is selected from hydrogen, —CH$_3$, —CFH$_2$, —CF$_2$H, —CF$_3$, —NH$_2$, —NH(CH$_3$), and —N(CH$_3$)$_2$; wherein $R^2$ is selected from hydrogen, halogen, —OH, —CN, —NO$_2$, —NH$_2$, —(S=O)R$^4$, —SO$_2$R$^4$, C1-C6 alkyl, C1-C6 monohaloalkyl, C1-C6 polyhaloalkyl, C1-C6 alkoxy, C1-C6 cyanoalkyl, C1-C6 aminoalkyl, C1-C6 hydroxyalkyl, C1-C6 monoalkylamino, and C1-C6 dialkylamino; and wherein $R^4$, when present, is selected from hydrogen, —$CH_3$, —$CFH_2$, —$CF_2H$, —$CF_3$, —$NH_2$, —$NH(CH_3)$, and —$N(CH_3)_2$, or a pharmaceutically acceptable salt thereof.

In a further aspect, the paullone derivative has a structure represented by a formula selected from:

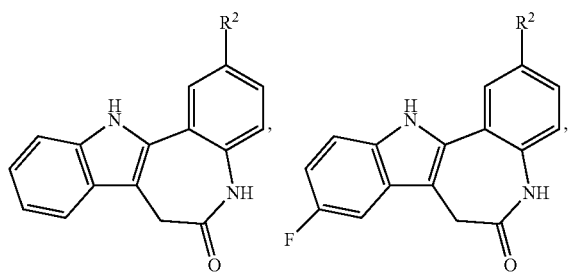

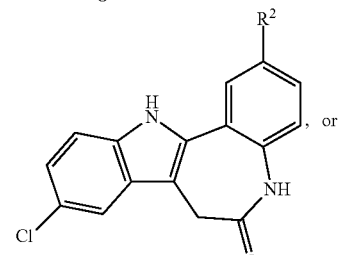

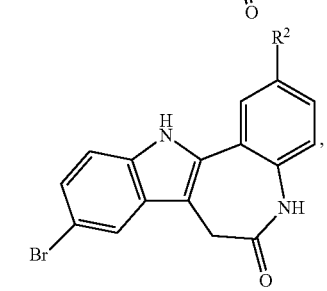

or a pharmaceutically acceptable salt thereof.

In a further aspect, the paullone derivative has a structure represented by a formula selected from:

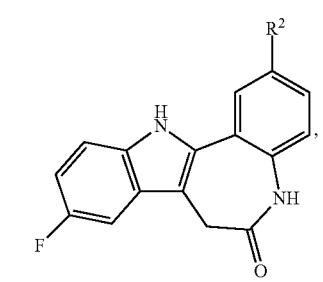

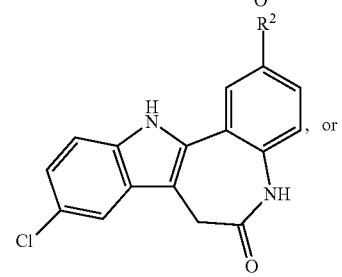

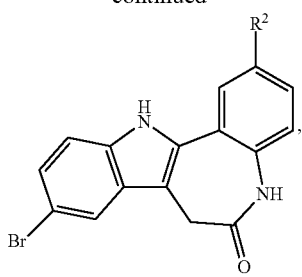

or a pharmaceutically acceptable salt thereof.

In a further aspect, the paullone derivative has a structure represented by a formula:

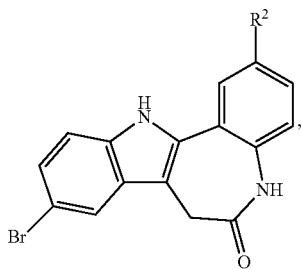

or a pharmaceutically acceptable salt thereof.

In a further aspect, the paullone derivative has a structure represented by a formula selected from:

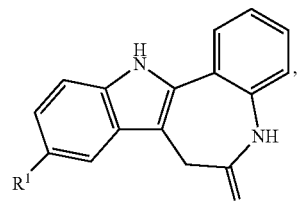

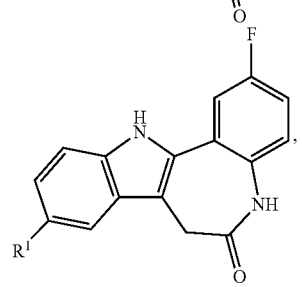

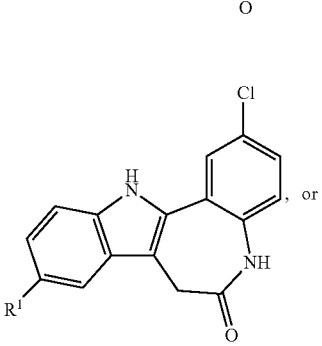

-continued

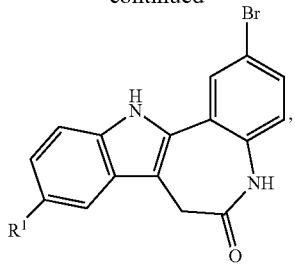

or a pharmaceutically acceptable salt thereof.

In a further aspect, the paullone derivative has a structure represented by a formula:

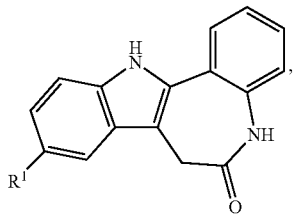

or a pharmaceutically acceptable salt thereof.

In a further aspect, the paullone derivative has a structure represented by a formula:

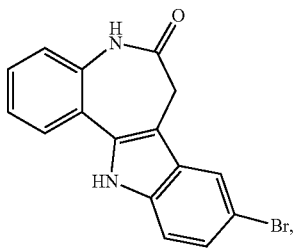 [SMILES: O=C1Cc2c([nH]c3ccc(Br)cc23)-c2ccccc2N1]

or a pharmaceutically acceptable salt thereof.

a. $R^1$ Groups

In one aspect, $R^1$ is selected from hydrogen, halogen, —OH, —CN, —NO$_2$, —NH$_2$, —(S═O)R$^3$, —SO$_2$R$^3$, C1-C6 alkyl, C1-C6 monohaloalkyl, C1-C6 polyhaloalkyl, C1-C6 alkoxy, C1-C6 cyanoalkyl, C1-C6 aminoalkyl, C1-C6 hydroxyalkyl, C1-C6 monoalkylamino, and C1-C6 dialkylamino. In a further aspect, $R^1$ is selected from hydrogen, halogen, —OH, —CN, —NO$_2$, —NH$_2$, —(S═O)R$^3$, —SO$_2$R$^3$, C1-C3 alkyl, C1-C3 monohaloalkyl, C1-C3 polyhaloalkyl, C1-C3 alkoxy, C1-C3 cyanoalkyl, C1-C3 aminoalkyl, C1-C3 hydroxyalkyl, C1-C3 monoalkylamino, and C1-C3 dialkylamino.

In a further aspect, $R^1$ is selected from hydrogen, halogen, —OH, —CN, —NO$_2$, —NH$_2$, C1-C6 alkyl, C1-C6 monohaloalkyl, C1-C6 polyhaloalkyl, C1-C6 alkoxy, C1-C6 cyanoalkyl, C1-C6 aminoalkyl, C1-C6 hydroxyalkyl, C1-C6 monoalkylamino, and C1-C6 dialkylamino. In a still further aspect, $R^1$ is selected from hydrogen, halogen, —OH, —CN, —NO$_2$, —NH$_2$, C1-C3 alkyl, C1-C3 monohaloalkyl, C1-C3 polyhaloalkyl, C1-C3 alkoxy, C1-C3 cyanoalkyl, C1-C3 aminoalkyl, C1-C3 hydroxyalkyl, C1-C3 monoalkylamino, and C1-C3 dialkylamino. In yet a further aspect, $R^1$ is selected from hydrogen, —F, —Cl, —Br, —OH, —CN, —NO$_2$, —NH$_2$, —CH$_3$, —CFH$_2$, —CF$_2$H, —CF$_3$, —OCH$_3$, —NH(CH$_3$), and —N(CH$_3$)$_2$.

In a further aspect, $R^1$ is selected from hydrogen, halogen, C1-C6 alkyl, C1-C6 monohaloalkyl, C1-C6 polyhaloalkyl, C1-C6 alkoxy, C1-C6 cyanoalkyl, C1-C6 aminoalkyl, C1-C6 hydroxyalkyl, C1-C6 monoalkylamino, and C1-C6 dialkylamino. In a still further aspect, $R^1$ is selected from hydrogen, halogen, C1-C3 alkyl, C1-C3 monohaloalkyl, C1-C3 polyhaloalkyl, C1-C3 alkoxy, C1-C3 cyanoalkyl, C1-C3 aminoalkyl, C1-C3 hydroxyalkyl, C1-C3 monoalkylamino, and C1-C3 dialkylamino. In yet a further aspect, $R^1$ is selected from hydrogen, —F, —Cl, —Br, —CH$_3$, —CFH$_2$, —CF$_2$H, —CF$_3$, —OCH$_3$, —NH(CH$_3$), and —N(CH$_3$)$_2$.

In a further aspect, $R^1$ is selected from hydrogen, C1-C6 monohaloalkyl, and C1-C6 polyhaloalkyl. In a still further aspect, $R^1$ is selected from hydrogen, C1-C3 monohaloalkyl, and C1-C3 polyhaloalkyl. In yet a further aspect, $R^1$ is selected from hydrogen, —CClH$_2$, —CCl$_2$H, —CCl$_3$, —CFH$_2$, —CF$_2$H, and —CF$_3$. In an even further aspect, $R^1$ is selected from hydrogen, —CFH$_2$, —CF$_2$H, and —CF$_3$.

In a further aspect, $R^1$ is selected from hydrogen and C1-C6 alkyl. In a still further aspect, $R^1$ is selected from hydrogen, methyl, ethyl, iso-propyl, n-propyl, tert-butyl, sec-butyl, iso-butyl, and n-butyl. In yet a further aspect, $R^1$ is selected from hydrogen, methyl, ethyl, iso-propyl, and n-propyl. In an even further aspect, $R^1$ is selected from hydrogen, methyl, and ethyl. In a still further aspect, $R^1$ is selected from hydrogen and methyl. In yet a further aspect, $R^1$ is selected from hydrogen and ethyl. In an even further aspect, $R^1$ is hydrogen. In a still further aspect, $R^1$ is methyl. In yet a further aspect, $R^1$ is ethyl.

In a further aspect, $R^1$ is selected from hydrogen and halogen. In a still further aspect, $R^1$ is selected from hydrogen, —F, —Cl, and —Br. In yet a further aspect, $R^1$ is selected from hydrogen, —F, and —Cl. In an even further aspect, $R^1$ is selected from hydrogen and —F. In a still further aspect, $R^1$ is selected from hydrogen and —Cl.

In a further aspect, $R^1$ is halogen. In a still further aspect, $R^1$ is selected from —F, —Cl, and —Br. In yet a further aspect, $R^1$ is selected from —F and —Cl. In an even further aspect, $R^1$ is —Br. In a still further aspect, $R^1$ is —Cl. In yet a further aspect, $R^1$ is —F.

b. $R^2$ Groups

In one aspect, $R^2$ is selected from hydrogen, halogen, —OH, —CN, —NO$_2$, —NH$_2$, —(S═O)R$^4$, —SO$_2$R$^4$, C1-C6 monohaloalkyl, C1-C6 polyhaloalkyl, C1-C6 alkoxy, C1-C6 cyanoalkyl, C1-C6 aminoalkyl, C1-C6 hydroxyalkyl, C1-C6 monoalkylamino, and C1-C6 dialkylamino. In a further aspect, $R^2$ is selected from hydrogen, halogen, —OH, —CN, —NO$_2$, —NH$_2$, —(S═O)R$^4$, —SO$_2$R$^4$, C1-C3 monohaloalkyl, C1-C3 polyhaloalkyl, C1-C3 alkoxy, C1-C3 cyanoalkyl, C1-C3 aminoalkyl, C1-C3 hydroxyalkyl, C1-C3 monoalkylamino, and C1-C3 dialkylamino.

In a further aspect, $R^2$ is selected from hydrogen, halogen, —OH, —CN, —NO$_2$, —NH$_2$, C1-C6 alkyl, C1-C6 monohaloalkyl, C1-C6 polyhaloalkyl, C1-C6 alkoxy, C1-C6 cyanoalkyl, C1-C6 aminoalkyl, C1-C6 hydroxyalkyl, C1-C6 monoalkylamino, and C1-C6 dialkylamino. In a still further aspect, $R^2$ is selected from hydrogen, halogen, —OH, —CN, —NO$_2$, —NH$_2$, C1-C3 alkyl, C1-C3 monohaloalkyl, C1-C3 polyhaloalkyl, C1-C3 alkoxy, C1-C3 cyanoalkyl, C1-C3 aminoalkyl, C1-C3 hydroxyalkyl, C1-C3 monoalkylamino, and C1-C3 dialkylamino. In yet a further aspect, $R^2$ is selected from hydrogen, —F, —Cl, —Br, —OH, —CN, —NO$_2$, —NH$_2$, —CH$_3$, —CFH$_2$, —CF$_2$H, —CF$_3$, —OCH$_3$, —NH(CH$_3$), and —N(CH$_3$)$_2$.

In a further aspect, $R^2$ is selected from hydrogen, halogen, C1-C6 alkyl, C1-C6 monohaloalkyl, C1-C6 polyhaloalkyl, C1-C6 alkoxy, C1-C6 cyanoalkyl, C1-C6 aminoalkyl, C1-C6 hydroxyalkyl, C1-C6 monoalkylamino, and C1-C6 dialkylamino. In a still further aspect, $R^2$ is selected from hydrogen, halogen, C1-C3 alkyl, C1-C3 monohaloalkyl, C1-C3 polyhaloalkyl, C1-C3 alkoxy, C1-C3 cyanoalkyl, C1-C3 aminoalkyl, C1-C3 hydroxyalkyl, C1-C3 monoalkylamino, and C1-C3 dialkylamino. In yet a further aspect, $R^2$ is selected from hydrogen, —F, —Cl, —Br, —CH$_3$, —CFH$_2$, —CF$_2$H, —CF$_3$, —OCH$_3$, —NH(CH$_3$), and —N(CH$_3$)$_2$.

In a further aspect, $R^2$ is selected from hydrogen, C1-C6 monohaloalkyl, and C1-C6 polyhaloalkyl. In a still further aspect, $R^2$ is selected from hydrogen, C1-C3 monohaloalkyl, and C1-C3 polyhaloalkyl. In yet a further aspect, $R^2$ is selected from hydrogen, —CClH$_2$, —CCl$_2$H, —CCl$_3$, —CFH$_2$, —CF$_2$H, and —CF$_3$. In an even further aspect, $R^2$ is selected from hydrogen, —CFH$_2$, —CF$_2$H, and —CF$_3$.

In a further aspect, $R^2$ is selected from hydrogen and C1-C6 alkyl. In a still further aspect, $R^2$ is selected from hydrogen, methyl, ethyl, iso-propyl, n-propyl, tert-butyl, sec-butyl, iso-butyl, and n-butyl. In yet a further aspect, $R^2$ is selected from hydrogen, methyl, ethyl, iso-propyl, and n-propyl. In an even further aspect, $R^2$ is selected from hydrogen, methyl, and ethyl. In a still further aspect, $R^2$ is selected from hydrogen and methyl. In yet a further aspect, $R^2$ is selected from hydrogen and ethyl. In an even further aspect, $R^2$ is hydrogen. In a still further aspect, $R^2$ is methyl. In yet a further aspect, $R^2$ is ethyl.

In a further aspect, $R^2$ is selected from hydrogen and halogen. In a still further aspect, $R^2$ is selected from hydrogen, —F, —Cl, and —Br. In yet a further aspect, $R^2$ is selected from hydrogen, —F, and —Cl. In an even further aspect, $R^2$ is selected from hydrogen and —F. In a still further aspect, $R^2$ is selected from hydrogen and —Cl.

In a further aspect, $R^2$ is halogen. In a still further aspect, $R^2$ is selected from —F, —Cl, and —Br. In yet a further aspect, $R^2$ is selected from —F and —Cl. In an even further aspect, $R^2$ is —Br. In a still further aspect, $R^2$ is —Cl. In yet a further aspect, $R^2$ is —F.

c. $R^3$ Groups

In one aspect, $R^3$, when present, is selected from hydrogen, —CH$_3$, —CFH$_2$, —CF$_2$H, —CF$_3$, —NH$_2$, —NH(CH$_3$), and —N(CH$_3$)$_2$. In a further aspect, $R^3$, when present, is selected from hydrogen, —CH$_3$, —CFH$_2$, —CF$_2$H, —NH$_2$, —NH(CH$_3$), and —N(CH$_3$)$_2$. In a still further aspect, $R^3$, when present, is selected from hydrogen, —CH$_3$, —CFH$_2$, —NH$_2$, and —NH(CH$_3$). In yet a further aspect, $R^3$, when present, is selected from hydrogen, —CH$_3$, and —NH$_2$. In an even further aspect, $R^3$, when present, is selected from hydrogen and —CH$_3$. In a still further aspect, $R^3$, when present, is selected from hydrogen and —NH$_2$. In yet a further aspect, $R^3$, when present, is hydrogen.

d. $R^4$ Groups

In one aspect, $R^4$, when present, is selected from hydrogen, —CH$_3$, —CFH$_2$, —CF$_2$H, —CF$_3$, —NH$_2$, —NH(CH$_3$), and —N(CH$_3$)$_2$. In a further aspect, $R^4$, when present, is selected from hydrogen, —CH$_3$, —CFH$_2$, —CF$_2$H, —NH$_2$, —NH(CH$_3$), and —N(CH$_3$)$_2$. In a still further aspect, $R^4$, when present, is selected from hydrogen, —CH$_3$, —CFH$_2$, —NH$_2$, and —NH(CH$_3$). In yet a further aspect, $R^4$, when present, is selected from hydrogen, —CH$_3$, and —NH$_2$. In an even further aspect, $R^4$, when present, is selected from hydrogen and —CH$_3$. In a still further aspect, $R^4$, when present, is selected from hydrogen and —NH$_2$. In yet a further aspect, $R^4$, when present, is hydrogen.

2. Purine Derivatives

In one aspect, disclosed are purine derivatives having a structure represented by a formula:

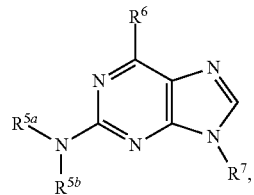

wherein each of $R^{5a}$ and $R^{5b}$ is independently selected from hydrogen, C1-C8 alkyl, $(CH_2)_qR^8$, and $C=O(CH_2)_qA^8$ and wherein each of $R^{5a}$ and $R^{5b}$ is independently substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl; wherein q, when present, is an integer selected from 1, 2, 3, and 4; wherein $R^8$, when present, is selected from hydrogen, —OH, —SH, —NH$_2$, C1-C4 alkoxy, C1-C4 thioalkoxy, C1-C4 alkylamino, and C1-C4 dialkylamino; wherein $R^6$ is selected from halogen, $OR^9$, and $NR^{10a}R^{10b}$; wherein $R^9$, when present, is selected from C1-C8 alkyl, $(CH_2)_pCy^1$, and $(CH_2)_pAr^1$ and wherein $R^9$, when present, is substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl; wherein p, when present, is an integer selected from 0, 1, 2, and 3; wherein $Cy^1$, when present, is selected from C3-C6 cycloalkyl and C3-C6 heterocycloalkyl and substituted with 0, 1, 2, or 3 groups independently selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl; wherein $Ar^1$, when present, is selected from aryl and heteroaryl and substituted with 0, 1, 2, or 3 groups independently selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl; wherein each of $R^{10a}$ and $R^{10b}$, when present, is independently selected from C1-C8 alkyl, $Cy^2$, $Ar^2$, $(CH_2)_rCy^2$, and $(CH_2)_rAr^2$ and substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl; wherein r, when present, is an integer selected from 0, 1, 2, and 3; wherein $Cy^2$, when present, is selected from C3-C6 cycloalkyl and C3-C6 heterocycloalkyl and substituted with 0, 1, 2, or 3 groups independently selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl; wherein $Ar^2$, when present, is selected from aryl and heteroaryl and substituted with 0, 1, 2, or 3 groups independently selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl; and wherein $R^7$, when present, is selected from hydrogen and C1-C8 alkyl, or a pharmaceutically acceptable salt thereof.

In one aspect, q, when present, is an integer selected from 1, 2, 3, and 4. In a further aspect, q, when present, is an integer selected from 1, 2, and 3. In a still further aspect, q, when present, is an integer selected from 2, 3, and 4. In yet a further aspect, q, when present, is an integer selected from 1, 2, and 4. In an even further aspect, q, when present, is an integer selected from 1, 3, and 4. In a still further aspect, q, when present, is an integer selected from 1 and 2. In yet a further aspect, q, when present, is an integer selected from 1 and 3. In an even further aspect, q, when present, is an integer selected from 1 and 4. In a still further aspect, q, when present, is an integer selected from 2 and 3. In yet a further aspect, q, when present, is an integer selected from 2 and 4. In an even further aspect, q, when present, is an integer selected from 3 and 4. In a still further aspect, q, when present, is 1. In yet a further aspect, q, when present, is 2. In an even further aspect, q, when present, is 3. In a still further aspect, q, when present, is 4.

In one aspect, p, when present, is an integer selected from 0, 1, 2, and 3. In a further aspect, p, when present, is an integer selected from 0, 1, and 2. In a still further aspect, p, when present, is an integer selected from 0, 1, and 3. In yet a further aspect, p, when present, is an integer selected from 0, 2, and 3. In an even further aspect, p, when present, is an integer selected from 1, 2, and 3. In a still further aspect, p, when present, is an integer selected from 0 and 1. In yet a further aspect, p, when present, is an integer selected from 0 and 2. In an even further aspect, p, when present, is an integer selected from 0 and 3. In a still further aspect, p, when present, is an integer selected from 1 and 2. In yet a further aspect, p, when present, is an integer selected from 1 and 3. In an even further aspect, p, when present, is an integer selected from 2 and 3. In a still further aspect, p, when present, is 0. In yet a further aspect, p, when present, is 1. In an even further aspect, p, when present, is 2. In a still further aspect, p, when present, is 3.

In one aspect, r, when present, is an integer selected from 0, 1, 2, and 3. In a further aspect, r, when present, is an integer selected from 0, 1, and 2. In a still further aspect, r, when present, is an integer selected from 0, 1, and 3. In yet a further aspect, r, when present, is an integer selected from 0, 2, and 3. In an even further aspect, r, when present, is an integer selected from 1, 2, and 3. In a still further aspect, r, when present, is an integer selected from 0 and 1. In yet a further aspect, r, when present, is an integer selected from 0 and 2. In an even further aspect, r, when present, is an integer selected from 0 and 3. In a still further aspect, r, when present, is an integer selected from 1 and 2. In yet a further aspect, r, when present, is an integer selected from 1 and 3. In an even further aspect, r, when present, is an integer selected from 2 and 3. In a still further aspect, r, when present, is 0. In yet a further aspect, r, when present, is 1. In an even further aspect, r, when present, is 2. In a still further aspect, r, when present, is 3.

In a further aspect, the purine derivative has a structure represented by a formula selected from:

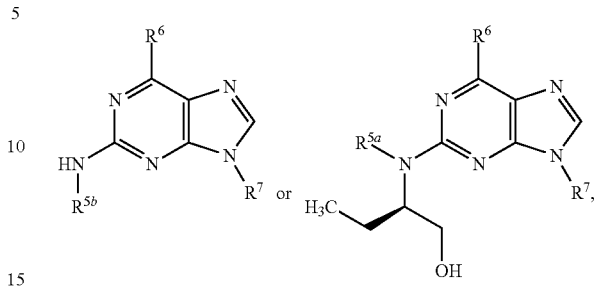

or a pharmaceutically acceptable salt thereof.

In a further aspect, the purine derivative has a structure represented by a formula:

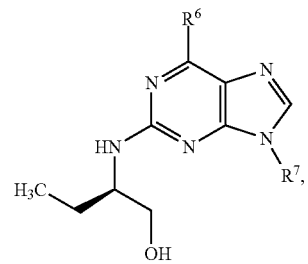

or a pharmaceutically acceptable salt thereof.

In a further aspect, the purine derivative has a structure represented by a formula selected from:

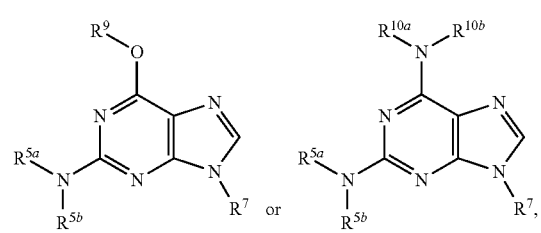

or a pharmaceutically acceptable salt thereof.

In a further aspect, the purine derivative has a structure represented by a formula selected from:

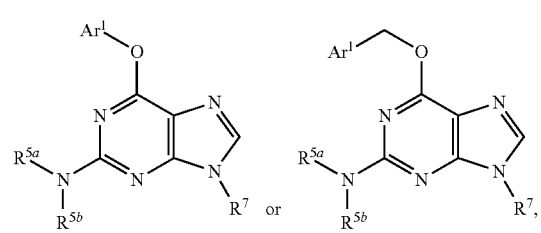

or a pharmaceutically acceptable salt thereof.

In a further aspect, the purine derivative has a structure represented by a formula:

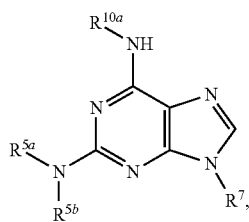

or a pharmaceutically acceptable salt thereof.

In a further aspect, the purine derivative has a structure represented by a formula selected from:

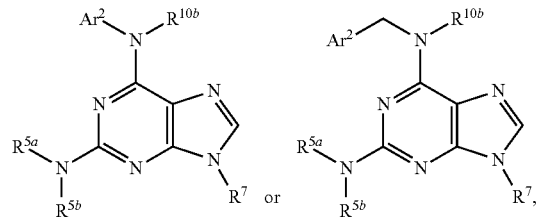

or a pharmaceutically acceptable salt thereof.

In a further aspect, the purine derivative has a structure represented by a formula selected from:

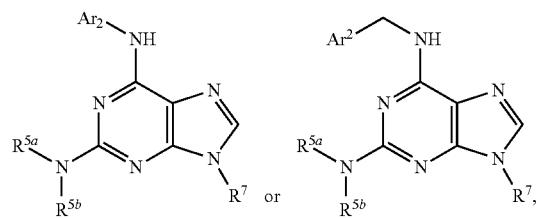

or a pharmaceutically acceptable salt thereof.

In a further aspect, the purine derivative has a structure represented by a formula selected from:

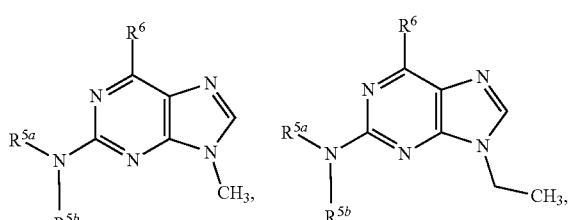

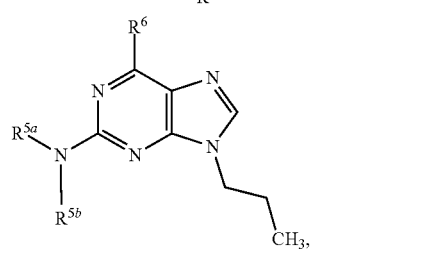

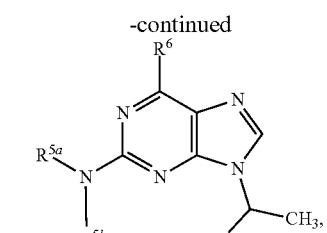

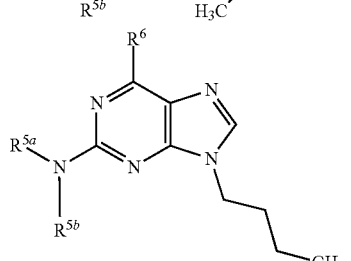

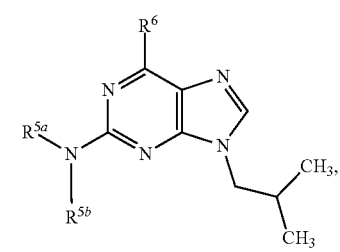

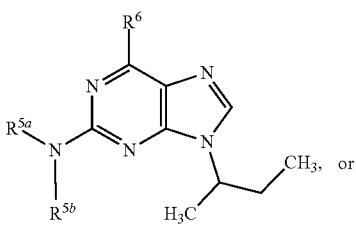

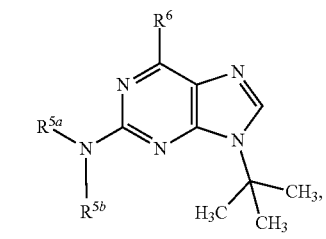

or a pharmaceutically acceptable salt thereof.

In a further aspect, the purine derivative has a structure represented by a formula selected from:

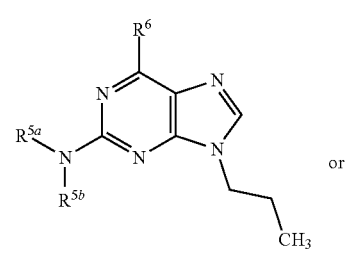

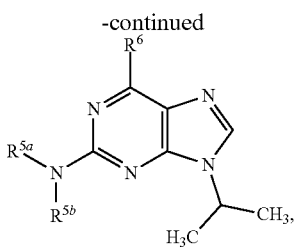

or a pharmaceutically acceptable salt thereof.

In a further aspect, the purine derivative has a structure represented by a formula selected from:

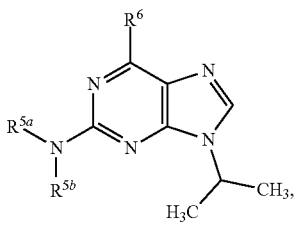

or a pharmaceutically acceptable salt thereof.

In a further aspect, the purine derivative has a structure represented by a formula:

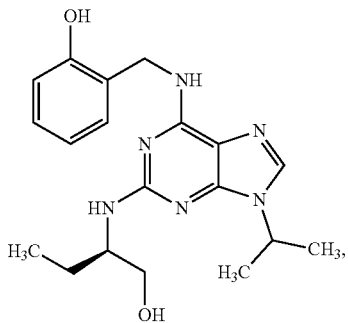

or a pharmaceutically acceptable salt thereof.

a. $R^{5a}$ and $R^{5b}$ Groups

In one aspect, each of $R^{5a}$ and $R^{5b}$ is independently selected from hydrogen, C1-C8 alkyl, $(CH_2)_q R^8$, and C=O $(CH_2)_q R^8$ and wherein each of $R^{5a}$ and $R^{5b}$ is independently substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a further aspect, each of $R^{5a}$ and $R^{5b}$ is independently selected from hydrogen, C1-C4 alkyl, $(CH_2)_q R^8$, and C=O$(CH_2)_q R^8$ and wherein each of $R^{5a}$ and $R^{5b}$ is independently substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl.

In a further aspect, each of $R^{5a}$ and $R^{5b}$ is independently selected from hydrogen, C1-C8 alkyl, $(CH_2)_q R^8$, and C=O $(CH_2)_q R^8$ and wherein each of $R^{5a}$ and $R^{5b}$ is independently substituted with 1 or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, each of $R^{5a}$ and $R^{5b}$ is independently selected from hydrogen, C1-C8 alkyl, $(CH_2)_q R^8$, and C=O$(CH_2)_q R^8$ and wherein each of $R^{5a}$ and $R^{5b}$ is independently substituted with 0 or 1 group selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In yet a further aspect, each of $R^{5a}$ and $R^{5b}$ is independently selected from hydrogen, C1-C8 alkyl, $(CH_2)_q R^8$, and C=O$(CH_2)_q R^8$ and wherein each of $R^{5a}$ and $R^{5b}$ is independently monosubstituted with a group selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In an even further aspect, each of $R^{5a}$ and $R^{5b}$ is independently selected from hydrogen, C1-C8 alkyl, $(CH_2)_q R^8$, and C=O $(CH_2)_q R^8$ and wherein each of $R^{5a}$ and $R^{5b}$ is unsubstituted.

In a further aspect, $R^{5a}$, when present, is hydrogen and $R^{5b}$ is selected from C1-C8 alkyl, $(CH_2)_q R^8$, and C=O $(CH_2)_q R^8$ and wherein $R^{5b}$ is substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $R^{5a}$, when present, is hydrogen and $R^{5b}$ is selected from C1-C4 alkyl, $(CH_2)_q R^8$, and C=O$(CH_2)_q R^8$ and wherein $R^{5b}$ is substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl.

In a further aspect, $R^{5a}$, when present, is hydrogen and $R^{5b}$ is selected from C1-C8 alkyl, $(CH_2)_q R^8$, and C=O $(CH_2)_q R^8$ and wherein $R^{5b}$ is substituted with 1 or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $R^{5a}$, when present, is hydrogen and $R^{5b}$ is selected from C1-C8 alkyl, $(CH_2)_q R^8$, and C=O$(CH_2)_q R^8$ and wherein $R^{5b}$ is substituted with 0 or 1 group selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In yet a further aspect, $R^{5a}$, when present, is hydrogen and $R^{5b}$ is selected from C1-C8 alkyl, $(CH_2)_q R^8$, and C=O$(CH_2)_q R^8$ and wherein $R^{5b}$ is monosubstituted with a group selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In an even further aspect, $R^{5a}$, when present, is hydrogen and $R^{5b}$ is selected from C1-C8 alkyl, $(CH_2)_q R^8$, and C=O$(CH_2)_q R^8$ and wherein $R^{5b}$ is unsubstituted.

In a further aspect, $R^{5a}$, when present, is hydrogen and $R^{5b}$ is selected from $(CH_2)_q R^8$ and C=O$(CH_2)_q R^8$ and wherein $R^{5b}$ is substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $R^{5a}$, when present, is hydrogen and $R^{5b}$ is selected from $(CH_2)_q R^8$ and $C=O(CH_2)_q R^8$ and wherein $R^{5b}$ is substituted with 1 or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In yet a further aspect, $R^{5a}$, when present, is hydrogen and $R^{5b}$ is selected from $(CH_2)_q R^8$ and $C=O(CH_2)_q R^8$ and wherein $R^{5b}$ is substituted with 0 or 1 group selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In an even further aspect, $R^{5a}$, when present, is hydrogen and $R^{5b}$ is selected from $(CH_2)_q R^8$ and $C=O(CH_2)_q R^8$ and wherein $R^{5b}$ is monosubstituted with a group selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $R^{5a}$, when present, is hydrogen and $R^{5b}$ is selected from $(CH_2)_q R^8$ and $C=O(CH_2)_q R^8$ and wherein $R^{5b}$ is unsubstituted.

In a further aspect, $R^{5a}$, when present, is hydrogen and $R^{5b}$ is C1-C8 alkyl substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $R^{5a}$, when present, is hydrogen and $R^{5b}$ is C1-C4 alkyl substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In yet a further aspect, $R^{5a}$, when present, is hydrogen and $R^{5b}$ is selected from methyl, ethyl, n-propyl, and iso-propyl and wherein $R^{5b}$ is substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In an even further aspect, $R^{5a}$, when present, is hydrogen and $R^{5b}$ is selected from methyl and ethyl and wherein $R^{5b}$ is substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $R^{5a}$, when present, is hydrogen and $R^{5b}$ is ethyl substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In yet a further aspect, $R^{5a}$, when present, is hydrogen and $R^{5b}$ is methyl substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl.

In a further aspect, $R^{5a}$, when present, is hydrogen and $R^{5b}$ is C1-C8 alkyl substituted with 1 or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $R^{5a}$, when present, is hydrogen and $R^{5b}$ is C1-C8 alkyl substituted with 0 or 1 group selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In yet a further aspect, $R^{5a}$, when present, is hydrogen and $R^{5b}$ is C1-C8 alkyl monosubstituted with a group selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In an even further aspect, $R^{5a}$, when present, is hydrogen and $R^{5b}$ is unsubstituted C1-C8 alkyl.

In a further aspect, $R^{5a}$, when present, is hydrogen and $R^{5b}$ is C1-C8 alkyl substituted with 1 or 2 groups independently selected from halogen, —OH, —CN, —NO$_2$, —NH$_2$, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylaminomethyl. In a still further aspect, $R^{5a}$, when present, is hydrogen and $R^{5b}$ is C1-C8 alkyl substituted with 0 or 1 group selected from halogen, —OH, —CN, —NO$_2$, —NH$_2$, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylaminomethyl. In yet a further aspect, $R^{5a}$, when present, is hydrogen and $R^{5b}$ is C1-C8 alkyl monosubstituted with a group selected from halogen, —OH, —CN, —NO$_2$, —NH$_2$, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylaminomethyl.

In a further aspect, $R^{5a}$, when present, is hydrogen and $R^{5b}$ is n-propyl monosubstituted with a C1-C4 hydroxyalkyl group. In a still further aspect, $R^{5a}$, when present, is hydrogen and $R^{5b}$ is n-propyl monosubstituted with a C1-C2 hydroxyalkyl group. In yet a further aspect, $R^{5a}$, when present, is hydrogen and $R^{5b}$ is n-propyl monosubstituted with a —CH$_2$OH group.

b. $R^6$ Groups

In one aspect, $R^6$ is selected from halogen, $OR^9$, and $NR^{10a}R^{10b}$. In a further aspect, $R^2$ is selected from $OR^9$ and $NR^{10a}R^{10b}$. In a still further aspect, $R^2$ is selected from halogen and $OR^9$. In a yet further aspect, $R^2$ is selected from halogen and $NR^{10a}R^{10b}$. In an even further aspect, $R^2$ is halogen. In a still further aspect, $R^2$ is $OR^9$. In a yet further aspect, $R^2$ is $NR^{10a}R^{10b}$.

c. $R^7$ Groups

In one aspect, $R^7$, when present, is selected from hydrogen and C1-C8 alkyl. In a further aspect, $R^7$, when present, is selected from hydrogen and C1-C4 alkyl. In a still further aspect, $R^7$, when present, is hydrogen.

In a further aspect, $R^7$, when present, is selected from hydrogen, methyl, ethyl, n-propyl, iso-propyl, n-butyl, iso-butyl, sec-butyl, and tert-butyl. In a still further aspect, $R^7$, when present, is selected from hydrogen, methyl, ethyl, n-propyl, and iso-propyl. In yet a further aspect, $R^7$, when present, is selected from hydrogen, methyl, and ethyl. In an even further aspect, $R^7$, when present, is selected from hydrogen and methyl. In a still further aspect, $R^7$, when present, is selected from hydrogen and ethyl.

In a further aspect, $R^7$, when present, is selected from methyl, ethyl, n-propyl, iso-propyl, n-butyl, iso-butyl, sec-butyl, and tert-butyl. In a still further aspect, $R^7$, when present, is selected from methyl, ethyl, n-propyl, and isopropyl. In yet a further aspect, $R^7$, when present, is selected from methyl, and ethyl. In an even further aspect, $R^7$, when present, is methyl. In a still further aspect, $R^7$, when present, is ethyl. In yet a further aspect, $R^7$, when present, is n-propyl. In an even further aspect, $R^7$, when present, is iso-propyl.

d. $R^8$ Groups

In one aspect, $R^8$, when present, is selected from hydrogen, —OH, —SH, —NH$_2$, C1-C4 alkoxy, C1-C4 thioalkoxy, C1-C4 alkylamino, and C1-C4 dialkylamino. In a further aspect, $R^8$, when present, is selected from hydrogen, —OH, —SH, —NH$_2$, C1-C4 alkoxy, C1-C2 thioalkoxy, C1-C2 alkylamino, and C1-C2 dialkylamino. In a still further aspect, $R^8$, when present, is hydrogen.

In a further aspect, $R^8$, when present, is selected from hydrogen, C1-C4 alkoxy, C1-C4 thioalkoxy, C1-C4 alkylamino, and C1-C4 dialkylamino. In a still further aspect, $R^8$, when present, is selected from hydrogen, C1-C2 alkoxy, C1-C2 thioalkoxy, C1-C2 alkylamino, and C1-C2 dialkylamino.

In a further aspect, $R^8$, when present, is selected from hydrogen, —OH, —SH, and —NH$_2$. In a still further aspect, $R^8$, when present, is selected from hydrogen, —OH, and —SH. In yet a further aspect, $R^8$, when present, is selected from hydrogen, —OH and —NH$_2$. In an even further aspect, $R^8$, when present, is selected from hydrogen and —OH. In a still further aspect, $R^8$, when present, is selected from hydrogen and —SH. In yet a further aspect, $R^8$, when present, is selected from hydrogen and —NH$_2$.

e. $R^9$ Groups

In one aspect, $R^9$, when present, is selected from C1-C8 alkyl, $(CH_2)_p Cy^1$, and $(CH_2)_p Ar^1$ and wherein $R^9$, when present, is substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a further aspect, $R^9$, when present, is selected from C1-C4 alkyl, $(CH_2)_p Cy^1$, and $(CH_2)_p Ar^1$ and wherein $R^9$, when present, is substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl.

In a further aspect, $R^9$, when present, is selected from C1-C8 alkyl, $(CH_2)_p Cy^1$, and $(CH_2)_p Ar^1$ and wherein $R^9$, when present, is substituted with 1 or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $R^9$, when present, is selected from C1-C8 alkyl, $(CH_2)_p Cy^1$, and $(CH_2)_p Ar^1$ and wherein $R^9$, when present, is substituted with 0 or 1 group selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In yet a further aspect, $R^9$, when present, is selected from C1-C8 alkyl, $(CH_2)_p Cy^1$, and $(CH_2)_p Ar^1$ and wherein $R^9$, when present, is monosubstituted with a group selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In an even further aspect, $R^9$, when present, is selected from C1-C8 alkyl, $(CH_2)_p Cy^1$, and $(CH_2)_p Ar^1$ and wherein $R^9$, when present, is unsubstituted.

In a further aspect, $R^9$, when present, is selected from $(CH_2)_p Cy^1$ and $(CH_2)_p Ar^1$ and wherein $R^9$, when present, is substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $R^9$, when present, is selected from $(CH_2)_p Cy^1$ and $(CH_2)_p Ar^1$ and wherein $R^9$, when present, is substituted with 1 or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In yet a further aspect, $R^9$, when present, is selected from $(CH_2)_p Cy^1$ and $(CH_2)_p Ar^1$ and wherein $R^9$, when present, is substituted with 0 or 1 group selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In an even further aspect, $R^9$, when present, is selected from $(CH_2)_p Cy^1$ and $(CH_2)_p Ar^1$ and wherein $R^9$, when present, is monosubstituted with a group selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $R^9$, when present, is selected from $(CH_2)_p Cy^1$ and $(CH_2)_p Ar^1$ and wherein $R^9$, when present, is unsubstituted.

In a further aspect, $R^9$, when present, is $(CH_2)_p Cy^1$ and wherein $R^9$, when present, is substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $R^9$, when present, is $(CH_2)_p Cy^1$ and wherein $R^9$, when present, is substituted with 1 or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In yet a further aspect, $R^9$, when present, is $(CH_2)_p Cy^1$ and wherein $R^9$, when present, is substituted with 0 or 1 group selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In an even further aspect, $R^9$, when present, is $(CH_2)_p Cy^1$ and wherein $R^9$, when present, is substituted with a group selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $R^9$, when present, is $(CH_2)_p Cy^1$ and wherein $R^9$, when present, is unsubstituted.

In a further aspect, $R^9$, when present, is $(CH_2)_p Ar^1$ and wherein $R^9$, when present, is substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $R^9$, when present, is $(CH_2)_p Ar^1$ and wherein $R^9$, when present, is substituted with 1 or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In yet a further aspect, $R^9$, when present, is $(CH_2)_pAr^1$ and wherein $R^9$, when present, is substituted with 0 or 1 group selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In an even further aspect, $R^9$, when present, is $(CH_2)_pAr^1$ and wherein $R^9$, when present, is substituted with a group selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $R^9$, when present, is $(CH_2)_pAr^1$ and wherein $R^9$, when present, is unsubstituted.

In a further aspect, $R^9$, when present, is C1-C8 alkyl and wherein $R^9$, when present, is substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $R^9$, when present, is C1-C8 alkyl and wherein $R^9$, when present, is substituted with 1 or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In yet a further aspect, $R^9$, when present, is C1-C8 alkyl and wherein $R^9$, when present, is substituted with 0 or 1 group selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In an even further aspect, $R^9$, when present, is C1-C8 alkyl and wherein $R^9$, when present, is substituted with a group selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $R^9$, when present, is C1-C8 alkyl and wherein $R^9$, when present, is unsubstituted.

In a further aspect, $R^9$, when present, is C1-C8 alkyl. In a still further aspect, $R^9$, when present, is selected from methyl, ethyl, n-propyl, iso-propyl, n-butyl, iso-butyl, sec-butyl, and tert-butyl. In yet a further aspect, $R^9$, when present, is selected from methyl, ethyl, n-propyl, and iso-propyl. In an even further aspect, $R^9$, when present, is selected from methyl and ethyl. In a still further aspect, $R^9$, when present, is ethyl. In yet a further aspect, $R^9$, when present, is methyl.

f. $R^{10a}$ and $R^{10b}$ Groups

In one aspect, each of $R^{10a}$ and $R^{10b}$, when present, is independently selected from C1-C8 alkyl, $Cy^2$, $Ar^2$, $(CH_2)_rCy^2$, and $(CH_2)_rAr^2$ and wherein each of $R^{10a}$ and $R^{10b}$ is independently substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a further aspect, each of $R^{10a}$ and $R^{10b}$, when present, is independently selected from C1-C4 alkyl, $Cy^2$, $Ar^2$, $(CH_2)_rCy^2$, and $(CH_2)_rAr^2$ and wherein each of $R^{10a}$ and $R^{10b}$ is independently substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl.

In a further aspect, each of $R^{10a}$ and $R^{10b}$, when present, is independently selected from C1-C8 alkyl, $Cy^2$, $Ar^2$, $(CH_2)_rCy^2$, and $(CH_2)_rAr^2$ and wherein each of $R^{10a}$ and $R^{10b}$ is independently substituted with 1 or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, each of $R^{10a}$ and $R^{10b}$, when present, is independently selected from C1-C8 alkyl, $Cy^2$, $Ar^2$, $(CH_2)_rCy^2$, and $(CH_2)_rAr^2$ and wherein each of $R^{10a}$ and $R^{10b}$ is independently substituted with 0 or 1 group selected from halogen, —OH, —CN, —NO$_2$, —NH$_2$, C1-C4 monohaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In yet a further aspect, each of $R^{10a}$ and $R^{10b}$, when present, is independently selected from C1-C8 alkyl, $Cy^2$, $Ar^2$, $(CH_2)_rCy^2$, and $(CH_2)_rAr^2$ and wherein each of $R^{10a}$ and $R^{10b}$ is independently monosubstituted with a group selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In an even further aspect, each of $R^{10a}$ and $R^{10b}$, when present, is independently selected from C1-C8 alkyl, $Cy^2$, $Ar^2$, $(CH_2)_rCy^2$, and $(CH_2)_rAr^2$ and wherein each of $R^{10a}$ and $R^{10b}$ is unsubstituted.

In a further aspect, $R^{10a}$, when present, is hydrogen and $R^{10b}$, when present, is selected from C1-C8 alkyl, $Cy^2$, $Ar^2$, $(CH_2)$, $Cy^2$, and $(CH_2)_rAr^2$ and wherein $R^{10b}$ is substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $R^{10a}$, when present, is hydrogen and $R^{10b}$, when present, is selected from C1-C4 alkyl, $Cy^2$, $Ar^2$, $(CH_2)_rCy^2$, and $(CH_2)_rAr^2$ and wherein $R^{10b}$ is substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl.

In a further aspect, $R^{10a}$, when present, is hydrogen and $R^{10b}$, when present, is selected from C1-C8 alkyl, $Cy^2$, $Ar^2$, $(CH_2)_rCy^2$, and $(CH_2)_rAr^2$ and wherein $R^{10b}$ is substituted with 1 or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $R^{10a}$, when present, is hydrogen and $R^{10b}$, when present, is selected from C1-C8 alkyl, $Cy^2$, $Ar^2$, $(CH_2)_rCy^2$, and $(CH_2)_rAr^2$ and wherein $R^{10b}$ is substituted with 0 or 1 group selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In yet a further aspect, $R^{10a}$, when present, is hydrogen and $R^{10b}$, when present, is selected from C1-C8 alkyl, $Cy^2$, $Ar^2$, $(CH_2)_rCy^2$, and $(CH_2)_rAr^2$ and wherein $R^{10b}$ is monosubstituted with a group selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In an even further aspect, $R^{10a}$, when present, is hydrogen and $R^{10b}$, when present, is selected from C1-C8 alkyl, $Cy^2$, $Ar^2$, $(CH_2)_rCy^2$, and $(CH_2)_rAr^2$ and wherein $R^{10b}$ is unsubstituted.

In a further aspect, $R^{10a}$, when present, is hydrogen and $R^{10b}$, when present, is C1-C8 alkyl and substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $R^{10a}$, when present, is hydrogen and $R^{10b}$, when present, is C1-C4 alkyl and substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In yet a further aspect, $R^{10a}$, when present, is hydrogen and $R^{10b}$, when present, is selected from methyl, ethyl, n-propyl, and iso-propyl and substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In an even further aspect, $R^{10a}$, when present, is hydrogen and $R^{10b}$, when present, is selected from methyl and ethyl and substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $R^{10a}$, when present, is hydrogen and $R^{10b}$, when present, is ethyl substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In yet a further aspect, $R^{10a}$, when present, is hydrogen and $R^{10b}$, when present, is methyl substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl.

In a further aspect, $R^{10a}$, when present, is hydrogen and $R^{10b}$, when present, is C1-C8 alkyl and substituted with 1 or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $R^{10a}$, when present, is hydrogen and $R^{10b}$, when present, is C1-C8 alkyl and substituted with 0 or 1 group selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In yet a further aspect, $R^{10a}$, when present, is hydrogen and $R^{10b}$, when present, is C1-C8 alkyl and monosubstituted with a group selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In an even further aspect, $R^{10a}$, when present, is hydrogen and $R^{10b}$, when present, is unsubstituted C1-C8 alkyl.

In a further aspect, $R^{10a}$, when present, is hydrogen and $R^{10b}$, when present, is selected from $Cy^2$ and $(CH_2)_rCy^2$ and wherein $R^{10b}$ is substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $R^{10a}$, when present, is hydrogen and $R^{10b}$, when present, is selected from $Cy^2$ and $(CH_2)_rCy^2$ and wherein $R^{10b}$ is substituted with 1 or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In yet a further aspect, $R^{10a}$, when present, is hydrogen and $R^{10b}$, when present, is selected from $Cy^2$ and $(CH_2)_rCy^2$ and wherein $R^{10b}$ is substituted with 0 or 1 group selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In an even further aspect, $R^{10a}$, when present, is hydrogen and $R^{10b}$, when present, is selected from $Cy^2$ and $(CH_2)_rCy^2$ and wherein $R^{10'}$ is monosubstituted with a group selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $R^{10a}$, when present, is hydrogen and $R^{10b}$, when present, is selected from $Cy^2$ and $(CH_2)_rCy^2$ and wherein $R^{10b}$ is unsubstituted.

In a further aspect, $R^{10a}$, when present, is hydrogen and $R^{10b}$, when present, is $Cy^2$ and substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $R^{10a}$, when present, is hydrogen and $R^{10b}$, when present, is $Cy^2$ and substituted with 1 or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In yet a further aspect, $R^{10a}$, when present, is hydrogen and $R^{10b}$, when present, is $Cy^2$ and substituted with 0 or 1 group selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In an even further aspect, $R^{10a}$, when present, is hydrogen and $R^{10b}$, when present, is $Cy^2$ and monosubstituted with a group selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $R^{10a}$, when present, is hydrogen and $R^{10b}$, when present, is unsubstituted $Cy^2$.

In a further aspect, $R^{10a}$, when present, is hydrogen and $R^{10b}$, when present, is $(CH_2)_rCy^2$ and substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $R^{10a}$, when present, is hydrogen and $R^{10b}$, when present, is $(CH_2)_rCy^2$ and substituted with 1 or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In yet a further aspect, $R^{10a}$, when present, is hydrogen and $R^{10b}$, when present, is $(CH_2)_rCy^2$ and substituted with 0 or 1 group selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In an even further aspect, $R^{10a}$, when present, is hydrogen and $R^{10b}$, when present, is $(CH_2)_rCy^2$ and monosubstituted with a group selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $R^{10a}$, when present, is hydrogen and $R^{10b}$, when present, is unsubstituted $(CH_2)_rCy^2$.

In a further aspect, $R^{10a}$, when present, is hydrogen and $R^{10b}$, when present, is $CH_2Cy^2$ and substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $R^{10a}$, when present, is hydrogen and $R^{10b}$, when present, is $CH_2Cy^2$ and substituted with 1 or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In yet a further aspect, $R^{10a}$, when present, is hydrogen and $R^{10b}$, when present, is $CH_2Cy^2$ and substituted with 0 or 1 group selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In an even further aspect, $R^{10a}$, when present, is hydrogen and $R^{10b}$, when present, is $CH_2Cy^2$ and monosubstituted with a group selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $R^{10a}$, when present, is hydrogen and $R^{10b}$, when present, is unsubstituted $CH_2Cy^2$.

In a further aspect, $R^{10a}$, when present, is hydrogen and $R^{10b}$, when present, is selected from $Ar^2$ and $(CH_2)_rAr^2$ and wherein $R^{10'}$ is substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $R^{10a}$, when present, is hydrogen and $R^{10b}$, when present, is selected from $Ar^2$ and $(CH_2)_rAr^2$ and wherein $R^{10'}$ is substituted with 1 or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In yet a further aspect, $R^{10a}$, when present, is hydrogen and $R^{10b}$, when present, is selected from $Ar^2$ and $(CH_2)_rAr^2$ and wherein $R^{10b}$ is substituted with 0 or 1 group selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In an even further aspect, $R^{10a}$, when present, is hydrogen and $R^{10b}$, when present, is selected from $Ar^2$ and $(CH_2)_rAr^2$ and wherein $R^{10b}$ is monosubstituted with a group selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $R^{10a}$, when present, is hydrogen and $R^{10b}$, when present, is selected from $Ar^2$ and $(CH_2)_rAr^2$ and wherein $R^{10'}$ is unsubstituted.

In a further aspect, $R^{10a}$, when present, is hydrogen and $R^{10b}$, when present, is $Ar^2$ and substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $R^{10a}$, when present, is hydrogen and $R^{10b}$, when present, is $Ar^2$ and substituted with 1 or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In yet a further aspect, $R^{10a}$, when present, is hydrogen and $R^{10b}$, when present, is $Ar^2$ and substituted with 0 or 1 group selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In an even further aspect, $R^{10a}$, when present, is hydrogen and $R^{10b}$, when present, is $Ar^2$ and monosubstituted with a group selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $R^{10a}$, when present, is hydrogen and $R^{10b}$, when present, is unsubstituted $Ar^2$.

In a further aspect, $R^{10a}$, when present, is hydrogen and $R^{10b}$, when present, is $(CH_2)_rAr^2$ and substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $R^{10a}$, when present, is hydrogen and $R^{10b}$, when present, is $(CH_2)_rAr^2$ and substituted with 1 or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In yet a further aspect, $R^{10a}$, when present, is hydrogen and $R^{10b}$, when present, is $(CH_2)_rAr^2$ and substituted with 0 or 1 group selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In an even further aspect, $R^{10a}$, when present, is hydrogen and $R^{10b}$, when present, is $(CH_2)_rAr^2$ and monosubstituted with a group selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $R^{10a}$, when present, is hydrogen and $R^{10b}$, when present, is unsubstituted $(CH_2)_rAr^2$.

In a further aspect, $R^{10a}$, when present, is hydrogen and $R^{10b}$, when present, is $(CH_2)Ar^2$ and substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $R^{10a}$, when present, is hydrogen and $R^{10b}$, when present, is $(CH_2)Ar^2$ and substituted with 1 or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In yet a further aspect, $R^{10a}$, when present, is hydrogen and $R^{10b}$, when present, is $(CH_2)Ar^2$ and substituted with 0 or 1 group selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In an even further aspect, $R^{10a}$, when present, is hydrogen and $R^{10b}$, when present, is $(CH_2)Ar^2$ and monosubstituted with a group selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $R^{10a}$, when present, is hydrogen and $R^{10b}$, when present, is unsubstituted $(CH_2)Ar^2$.

In a further aspect, $R^{10a}$, when present, is hydrogen and $R^{10b}$, when present, is $(CH_2)Ar^2$ and substituted with 0, 1, or 2 groups independently selected from halogen, —OH, —CN, —NO$_2$, and —NH$_2$. In a still further aspect, $R^{10a}$, when present, is hydrogen and $R^{10b}$, when present, is $(CH_2)Ar^2$ and substituted with 0, 1, or 2 groups independently selected from halogen, —OH, and —NH$_2$. In yet a further aspect, $R^{10a}$, when present, is hydrogen and $R^{10b}$, when present, is $(CH_2)Ar^2$ and substituted with 0, 1, or 2 groups independently selected from —OH and —NH$_2$. In an even further aspect, $R^{10a}$, when present, is hydrogen and $R^{10b}$, when present, is $(CH_2)Ar^2$ and substituted with 0, 1, or 2 —OH groups. In a still further aspect, $R^{10a}$, when present, is hydrogen and $R^{10b}$, when present, is $(CH_2)Ar^2$ and substituted with 0, 1, or 2 —NH$_2$ groups.

In a further aspect, $R^{10a}$, when present, is hydrogen and $R^{10b}$, when present, is $(CH_2)Ar^2$ monosubstituted with an —OH group.

g. $Cy^1$ Groups

In one aspect, $Cy^1$, when present, is selected from C3-C6 cycloalkyl and C3-C6 heterocycloalkyl and substituted with 0, 1, 2, or 3 groups independently selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a further aspect, $Cy^1$, when present, is selected from C3-C6 cycloalkyl and C3-C6 heterocycloalkyl and substituted with 0, 1, 2, or 3 groups independently selected from halogen, —OH, —CN, —NO$_2$, —NH$_2$, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylaminomethyl.

In a further aspect, $Cy^1$, when present, is selected from C3-C6 cycloalkyl and C3-C6 heterocycloalkyl and substituted with 0, 1, or 2 groups independently selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $Cy^1$, when present, is selected from C3-C6 cycloalkyl and C3-C6 heterocycloalkyl and substituted with 0 or 1 group selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In yet a further aspect, $Cy^1$, when present, is selected from C3-C6 cycloalkyl and C3-C6 heterocycloalkyl and monosubstituted with a group selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In an even further aspect, $Cy^1$, when present, is selected from C3-C6 cycloalkyl and C3-C6 heterocycloalkyl and unsubstituted.

In a further aspect, $Cy^1$, when present, is C3-C6 cycloalkyl and substituted with 0, 1, 2, or 3 groups independently selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $Cy^1$, when present, is C3-C6 cycloalkyl and substituted with 0, 1, 2, or 3 groups independently selected from halogen, —OH, —CN, —NO$_2$, —NH$_2$, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylaminomethyl.

In a further aspect, $Cy^1$, when present, is C3-C6 cycloalkyl and substituted with 0, 1, or 2 groups independently selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $Cy^1$, when present, is C3-C6 cycloalkyl and substituted with 0 or 1 group selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In yet a further aspect, $Cy^1$, when present, is C3-C6 cycloalkyl and monosubstituted with a group selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In an even further aspect, $Cy'$, when present, is unsubstituted C3-C6 cycloalkyl.

In a further aspect, $Cy^1$, when present, is C3-C6 heterocycloalkyl and substituted with 0, 1, 2, or 3 groups independently selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $Cy^1$, when present, is C3-C6 heterocycloalkyl and substituted with 0, 1, 2, or 3 groups independently selected from halogen, —OH, —CN, —NO$_2$, —NH$_2$, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylaminomethyl.

In a further aspect, $Cy^1$, when present, is C3-C6 heterocycloalkyl and substituted with 0, 1, or 2 groups independently selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $Cy^1$, when present, is C3-C6 heterocycloalkyl and substituted with 0 or 1 group selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In yet a further aspect, $Cy^1$, when present, is C3-C6 heterocycloalkyl and monosubstituted with a group selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In an even further aspect, $Cy^1$, when present, is unsubstituted C3-C6 heterocycloalkyl.

h. $Cy^2$ Groups

In one aspect, $Cy^2$, when present, is selected from C3-C6 cycloalkyl and C3-C6 heterocycloalkyl and substituted with 0, 1, 2, or 3 groups independently selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a further aspect, $Cy^2$, when present, is selected from C3-C6 cycloalkyl and C3-C6 heterocycloalkyl and substituted with 0, 1, 2, or 3 groups independently selected from halogen, —OH, —CN, —NO$_2$, —NH$_2$, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylaminomethyl.

In a further aspect, $Cy^2$, when present, is selected from C3-C6 cycloalkyl and C3-C6 heterocycloalkyl and substituted with 0, 1, or 2 groups independently selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $Cy^2$, when present, is selected from C3-C6 cycloalkyl and C3-C6 heterocycloalkyl and substituted with 0 or 1 group selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In yet a further aspect, $Cy^2$, when present, is selected from C3-C6 cycloalkyl and C3-C6 heterocycloalkyl and monosubstituted with a group selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In an even further aspect, $Cy^2$, when present, is selected from C3-C6 cycloalkyl and C3-C6 heterocycloalkyl and unsubstituted.

In a further aspect, $Cy^2$, when present, is C3-C6 cycloalkyl and substituted with 0, 1, 2, or 3 groups independently selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $Cy^2$, when present, is C3-C6 cycloalkyl and substituted with 0, 1, 2, or 3 groups independently selected from halogen, —OH, —CN, —NO$_2$, —NH$_2$, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylaminomethyl.

In a further aspect, $Cy^2$, when present, is C3-C6 cycloalkyl and substituted with 0, 1, or 2 groups independently selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $Cy^2$, when present, is C3-C6 cycloalkyl and substituted with 0 or 1 group selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In yet a further aspect, $Cy^2$, when present, is C3-C6 cycloalkyl and monosubstituted with a group selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In an even further aspect, $Cy^2$, when present, is unsubstituted C3-C6 cycloalkyl.

In a further aspect, $Cy^2$, when present, is C3-C6 heterocycloalkyl and substituted with 0, 1, 2, or 3 groups independently selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $Cy^2$, when present, is C3-C6 heterocycloalkyl and substituted with 0, 1, 2, or 3 groups independently selected from halogen, —OH, —CN, —NO$_2$, —NH$_2$, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylaminomethyl.

In a further aspect, $Cy^2$, when present, is C3-C6 heterocycloalkyl and substituted with 0, 1, or 2 groups independently selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, $Cy^2$, when present, is C3-C6 heterocycloalkyl and substituted with 0 or 1 group selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In yet a further aspect, $Cy^2$, when present, is C3-C6 heterocycloalkyl and monosubstituted with a group selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In an even further aspect, $Cy^2$, when present, is unsubstituted C3-C6 heterocycloalkyl.

l. $Ar^1$ Groups

In one aspect, $Ar^1$, when present, is selected from aryl and heteroaryl and substituted with 0, 1, 2, or 3 groups independently selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a further aspect, $Ar^1$, when present, is selected from aryl and heteroaryl and substituted with 0, 1, 2, or 3 groups independently selected from halogen, —OH, —CN, —NO$_2$, —NH$_2$, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylaminomethyl.

In a further aspect, Ar¹, when present, is selected from aryl and heteroaryl and substituted with 0, 1, or 2 groups independently selected from halogen, —OH, —CN, —NO₂, —NH₂, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, Ar¹, when present, is selected from aryl and heteroaryl and substituted with 0 or 1 group selected from halogen, —OH, —CN, —NO₂, —NH₂, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In yet a further aspect, Ar¹, when present, is selected from aryl and heteroaryl and monosubstituted with a group selected from halogen, —OH, —CN, —NO₂, —NH₂, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In an even further aspect, Ar¹, when present, is selected from aryl and heteroaryl and unsubstituted.

In a further aspect, Ar¹, when present, is aryl and substituted with 0, 1, 2, or 3 groups independently selected from halogen, —OH, —CN, —NO₂, —NH₂, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, Ar¹, when present, is aryl and substituted with 0, 1, 2, or 3 groups independently selected from halogen, —OH, —CN, —NO₂, —NH₂, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylaminomethyl.

In a further aspect, Ar¹, when present, is aryl and substituted with 0, 1, or 2 groups independently selected from halogen, —OH, —CN, —NO₂, —NH₂, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, Ar¹, when present, is aryl and substituted with 0 or 1 group selected from halogen, —OH, —CN, —NO₂, —NH₂, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In yet a further aspect, Ar¹, when present, is aryl and monosubstituted with a group selected from halogen, —OH, —CN, —NO₂, —NH₂, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In an even further aspect, Ar¹, when present, is unsubstituted aryl.

In a further aspect, Ar¹, when present, is phenyl and substituted with 0, 1, 2, or 3 groups independently selected from halogen, —OH, —CN, —NO₂, —NH₂, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, Ar¹, when present, is phenyl and substituted with 0, 1, 2, or 3 groups independently selected from halogen, —OH, —CN, —NO₂, —NH₂, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylaminomethyl.

In a further aspect, Ar¹, when present, is phenyl and substituted with 0, 1, or 2 groups independently selected from halogen, —OH, —CN, —NO₂, —NH₂, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, Ar¹, when present, is phenyl and substituted with 0 or 1 group selected from halogen, —OH, —CN, —NO₂, —NH₂, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In yet a further aspect, Ar¹, when present, is phenyl and monosubstituted with a group selected from halogen, —OH, —CN, —NO₂, —NH₂, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In an even further aspect, Ar¹, when present, is unsubstituted phenyl.

In a further aspect, Ar¹, when present, is heteroaryl and substituted with 0, 1, 2, or 3 groups independently selected from halogen, —OH, —CN, —NO₂, —NH₂, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, Ar¹, when present, is heteroaryl and substituted with 0, 1, 2, or 3 groups independently selected from halogen, —OH, —CN, —NO₂, —NH₂, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylaminomethyl.

In a further aspect, Ar¹, when present, is heteroaryl and substituted with 0, 1, or 2 groups independently selected from halogen, —OH, —CN, —NO₂, —NH₂, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, Ar¹, when present, is heteroaryl and substituted with 0 or 1 group selected from halogen, —OH, —CN, —NO₂, —NH₂, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In yet a further aspect, Ar¹, when present, is heteroaryl and monosubstituted with a group selected from halogen, —OH, —CN, —NO₂, —NH₂, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In an even further aspect, Ar¹, when present, is unsubstituted heteroaryl.

In a further aspect, Ar¹, when present, is pyridinyl and substituted with 0, 1, 2, or 3 groups independently selected from halogen, —OH, —CN, —NO₂, —NH₂, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, Ar¹, when present, is pyridinyl and substituted with 0, 1, 2, or 3 groups independently selected from halogen, —OH, —CN, —NO₂, —NH₂, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylaminomethyl.

In a further aspect, Ar¹, when present, is pyridinyl and substituted with 0, 1, or 2 groups independently selected from halogen, —OH, —CN, —NO₂, —NH₂, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, Ar¹, when present, is pyridinyl and substituted with 0 or 1 group selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In yet a further aspect, Ar$^1$, when present, is pyridinyl and monosubstituted with a group selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In an even further aspect, Ar$^1$, when present, is unsubstituted pyridinyl.

j. Ar$^2$ Groups

In one aspect, Ar$^2$, when present, is selected from aryl and heteroaryl and substituted with 0, 1, 2, or 3 groups independently selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a further aspect, Ar$^2$, when present, is selected from aryl and heteroaryl and substituted with 0, 1, 2, or 3 groups independently selected from halogen, —OH, —CN, —NO$_2$, —NH$_2$, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylaminomethyl.

In a further aspect, Ar$^2$, when present, is selected from aryl and heteroaryl and substituted with 0, 1, or 2 groups independently selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, Ar$^2$, when present, is selected from aryl and heteroaryl and substituted with 0 or 1 group selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In yet a further aspect, Ar$^2$, when present, is selected from aryl and heteroaryl and monosubstituted with a group selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In an even further aspect, Ar$^2$, when present, is selected from aryl and heteroaryl and unsubstituted.

In a further aspect, Ar$^2$, when present, is aryl and substituted with 0, 1, 2, or 3 groups independently selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, Ar$^2$, when present, is aryl and substituted with 0, 1, 2, or 3 groups independently selected from halogen, —OH, —CN, —NO$_2$, —NH$_2$, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylaminomethyl.

In a further aspect, Ar$^2$, when present, is aryl and substituted with 0, 1, or 2 groups independently selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, Ar$^2$, when present, is aryl and substituted with 0 or 1 group selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In yet a further aspect, Ar$^2$, when present, is aryl and monosubstituted with a group selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In an even further aspect, Ar$^2$, when present, is unsubstituted aryl.

In a further aspect, Ar$^2$, when present, is phenyl and substituted with 0, 1, 2, or 3 groups independently selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, Ar$^2$, when present, is phenyl and substituted with 0, 1, 2, or 3 groups independently selected from halogen, —OH, —CN, —NO$_2$, —NH$_2$, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylaminomethyl.

In a further aspect, Ar$^2$, when present, is phenyl and substituted with 0, 1, or 2 groups independently selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, Ar$^2$, when present, is phenyl and substituted with 0 or 1 group selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In yet a further aspect, Ar$^2$, when present, is phenyl and monosubstituted with a group selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In an even further aspect, Ar$^2$, when present, is unsubstituted phenyl.

In a further aspect, Ar$^2$, when present, is heteroaryl and substituted with 0, 1, 2, or 3 groups independently selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, Ar$^2$, when present, is heteroaryl and substituted with 0, 1, 2, or 3 groups independently selected from halogen, —OH, —CN, —NO$_2$, —NH$_2$, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylaminomethyl.

In a further aspect, Ar$^2$, when present, is heteroaryl and substituted with 0, 1, or 2 groups independently selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, Ar$^2$, when present, is heteroaryl and substituted with 0 or 1 group selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In yet a further aspect, Ar$^2$, when present, is heteroaryl and monosubstituted with a group selected from halogen, —OH, —CN, —NO$_2$, —NH₂, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In an even further aspect, Ar², when present, is unsubstituted heteroaryl.

In a further aspect, Ar², when present, is pyridinyl and substituted with 0, 1, 2, or 3 groups independently selected from halogen, —OH, —CN, —NO₂, —NH₂, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, Ar², when present, is pyridinyl and substituted with 0, 1, 2, or 3 groups independently selected from halogen, —OH, —CN, —NO₂, —NH₂, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylaminomethyl.

In a further aspect, Ar², when present, is pyridinyl and substituted with 0, 1, or 2 groups independently selected from halogen, —OH, —CN, —NO₂, —NH₂, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In a still further aspect, Ar², when present, is pyridinyl and substituted with 0 or 1 group selected from halogen, —OH, —CN, —NO₂, —NH₂, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In yet a further aspect, Ar², when present, is pyridinyl and monosubstituted with a group selected from halogen, —OH, —CN, —NO₂, —NH₂, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl. In an even further aspect, Ar², when present, is unsubstituted pyridinyl.

3. 3-(2-Phenylhydrazono)Indolin-2-One Derivatives

In one aspect, disclosed are 3-(2-phenylhydrazono)indolin-2-one derivatives having a structure represented by a formula:

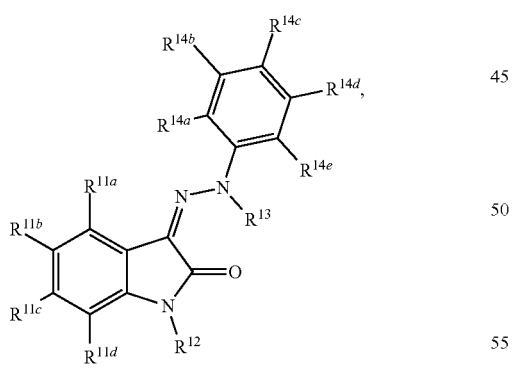

wherein each of $R^{11a}$, $R^{11b}$, $R^{11c}$, and $R^{11d}$ is independently selected from hydrogen, halogen, —OH, —SH, —CN, —NO₂, —NH₂, C1-C4 alkyl, C1-C4 alkoxy, C1-C4 monohaloalkyl, C1-C4 polyhaloalkyl, C1-C4 alkoxy, C1-C4 aminoalkyl, C1-C4 hydroxyalkyl, C1-C4 monoalkylamino, C1-C4 dialkylamino, —SO₂R¹⁵, and —CO₂R¹⁵; wherein each occurrence of R¹⁵, when present, is independently selected from hydrogen, —CH₃, —CFH₂, —CF₂H, —CF₃, —NH₂, —NH(CH₃), and —N(CH₃)₂; wherein each of R¹² and R¹³ is independently selected from hydrogen and C1-C4 alkyl; wherein each of $R^{14a}$, $R^{14b}$, $R^{14c}$, $R^{14d}$, and $R^{14e}$ is independently selected from hydrogen, halogen, —OH, —SH, —CN, —NO₂, —NH₂, C1-C4 alkyl, C1-C4 alkoxy, C1-C4 monohaloalkyl, C1-C4 polyhaloalkyl, C1-C4 alkoxy, C1-C4 aminoalkyl, C1-C4 hydroxyalkyl, C1-C4 monoalkylamino, C1-C4 dialkylamino, —SO₂R¹⁶, and —CO₂R¹⁶; and wherein each occurrence of R¹⁶, when present, is independently selected from hydrogen, —CH₃, —CFH₂, —CF₂H, —CF₃, —NH₂, —NH(CH₃), and —N(CH₃)₂, or a pharmaceutically acceptable salt thereof.

In a further aspect, the 3-(2-phenylhydrazono)indolin-2-one derivative has a structure represented by a formula selected from:

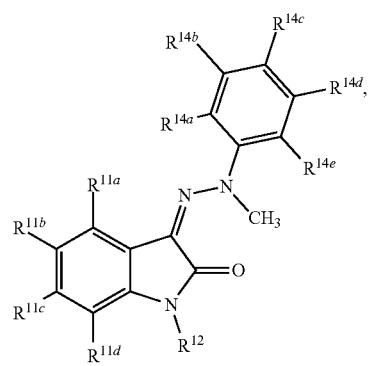

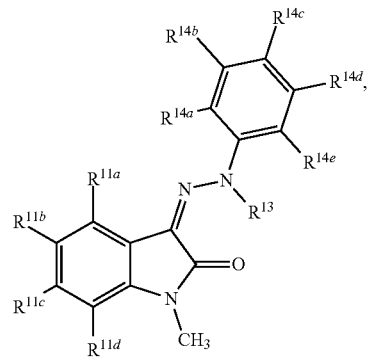

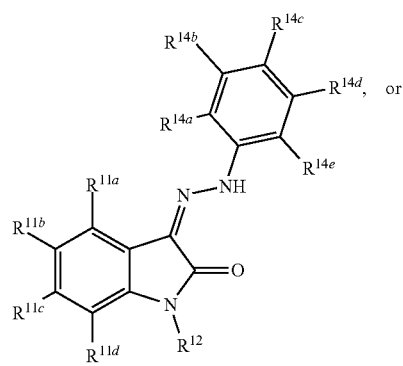

-continued

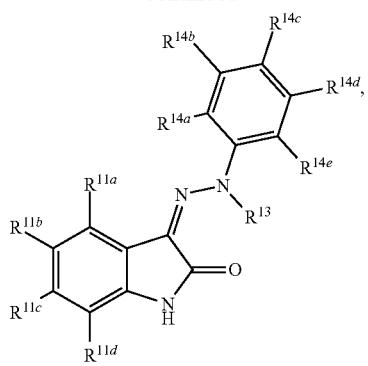

or a pharmaceutically acceptable salt thereof.

In a further aspect, the 3-(2-phenylhydrazono)indolin-2-one derivative has a structure represented by a formula selected from:

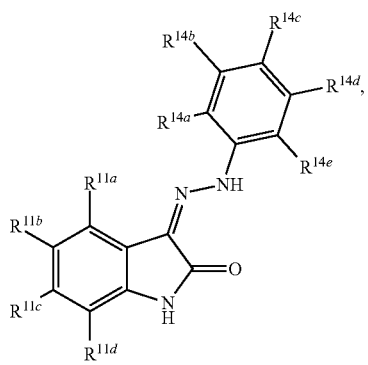

or a pharmaceutically acceptable salt thereof.

In a further aspect, the 3-(2-phenylhydrazono)indolin-2-one derivative has a structure represented by a formula selected from:

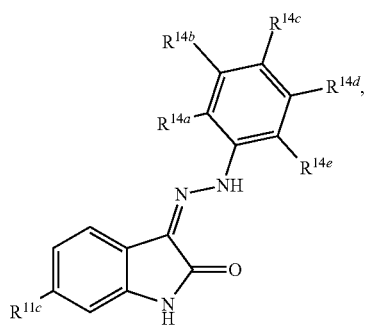

or a pharmaceutically acceptable salt thereof.

In a further aspect, the 3-(2-phenylhydrazono)indolin-2-one derivative has a structure represented by a formula selected from:

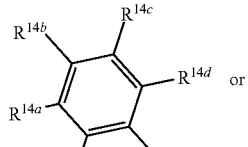

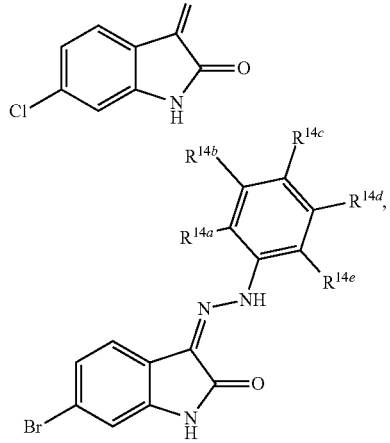

or a pharmaceutically acceptable salt thereof.

In a further aspect, the 3-(2-phenylhydrazono)indolin-2-one derivative has a structure represented by a formula selected from:

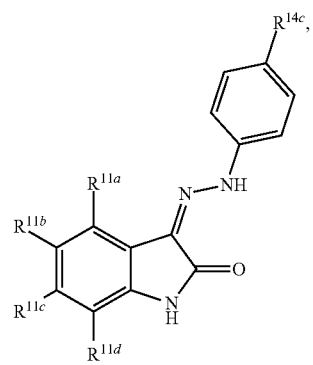

or a pharmaceutically acceptable salt thereof.

In a further aspect, the 3-(2-phenylhydrazono)indolin-2-one derivative has a structure represented by a formula selected from:

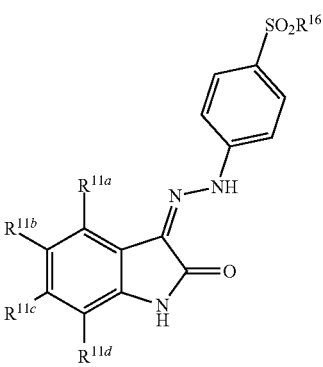

or

-continued

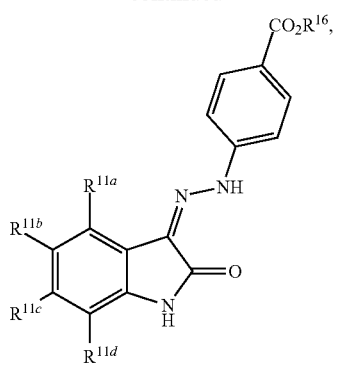

or a pharmaceutically acceptable salt thereof.

In a further aspect, the 3-(2-phenylhydrazono)indolin-2-one derivative has a structure represented by a formula selected from:

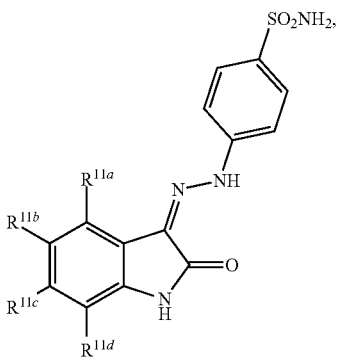

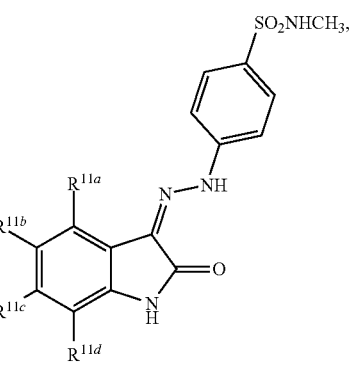

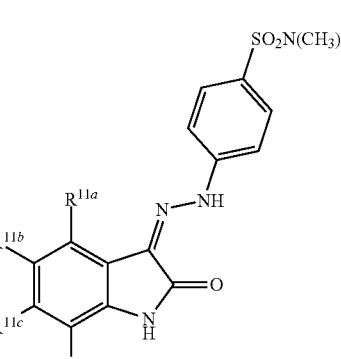

-continued

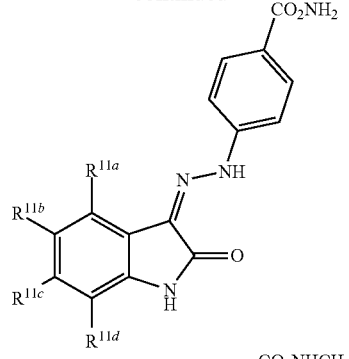

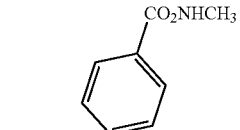

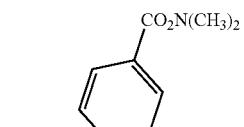

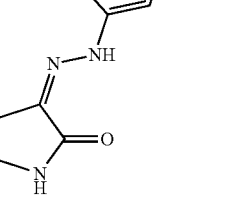

or a pharmaceutically acceptable salt thereof.

In a further aspect, the 3-(2-phenylhydrazono)indolin-2-one derivative has a structure represented by a formula selected from:

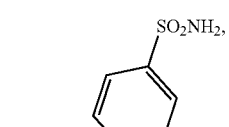

or a pharmaceutically acceptable salt thereof.

In a further aspect, the 3-(2-phenylhydrazono)indolin-2-one derivative has a structure represented by a formula:

[Structure: 6-bromo-3-(2-(4-sulfamoylphenyl)hydrazinylidene)indolin-2-one]

or a pharmaceutically acceptable salt thereof.

a. $R^{11a}$, $R^{11b}$, $R^{11c}$, and $R^{11d}$ Groups

In one aspect, each of $R^{11a}$, $R^{11b}$, $R^{11c}$, and $R^{11d}$ is independently selected from hydrogen, halogen, —OH, —SH, —CN, —NO$_2$, —NH$_2$, C1-C4 alkyl, C1-C4 alkoxy, C1-C4 monohaloalkyl, C1-C4 polyhaloalkyl, C1-C4 alkoxy, C1-C4 aminoalkyl, C1-C4 hydroxyalkyl, C1-C4 monoalkylamino, C1-C4 dialkylamino, —SO$_2$R$^{15}$, and —CO$_2$R$^{15}$. In a further aspect, each of $R^{11a}$, $R^{11b}$, $R^{11c}$, and $R^{11d}$ is independently selected from hydrogen, halogen, —OH, —SH, —CN, —NO$_2$, —NH$_2$, C1-C2 alkyl, C1-C2 alkoxy, C1-C2 monohaloalkyl, C1-C2 polyhaloalkyl, C1-C2 alkoxy, C1-C2 aminoalkyl, C1-C2 hydroxyalkyl, C1-C2 monoalkylamino, C1-C2 dialkylamino, —SO$_2$R$^{15}$, and —CO$_2$R$^{15}$. In yet a further aspect, each of $R^{11a}$, $R^{11b}$, $R^{11c}$, and $R^{11d}$ is hydrogen.

In a further aspect, each of $R^{11a}$, $R^{11b}$, $R^{11c}$, and $R^{11d}$ is independently selected from hydrogen, halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylamino. In a still further aspect, each of $R^{11a}$, $R^{11b}$, $R^{11c}$, and $R^{11d}$ is independently selected from hydrogen, halogen, —OH, —CN, —NO$_2$, —NH$_2$, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylamino. In yet a further aspect, each of $R^{11a}$, $R^{11b}$, $R^{11c}$, and $R^{11d}$ is independently selected from hydrogen, —F, —Cl, —Br, —OH, —CN, —NO$_2$, —NH$_2$, —CH$_3$, —CFH$_2$, —CF$_2$H, —CF$_3$, —OCH$_3$, —NH(CH$_3$), and —N(CH$_3$)$_2$.

In a further aspect, each of $R^{11a}$, $R^{11b}$, $R^{11c}$, and $R^{11d}$ is independently selected from hydrogen, halogen, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylamino. In a still further aspect, each of $R^{11a}$, $R^{11b}$, $R^{11c}$, and $R^{11d}$ is independently selected from hydrogen, halogen, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylamino. In yet a further aspect, each of $R^{11a}$, $R^{11b}$, $R^{11c}$, and $R^{11d}$ is independently selected from hydrogen, —F, —Cl, —Br, —CH$_3$, —CFH$_2$, —CF$_2$H, —CF$_3$, —OCH$_3$, —NH(CH$_3$), and —N(CH$_3$)$_2$.

In a further aspect, each of $R^{11a}$, $R^{11b}$, $R^{11c}$, and $R^{11d}$ is independently selected from hydrogen, C1-C4 monohaloalkyl, and C1-C4 polyhaloalkyl. In a still further aspect, each of $R^{11a}$, $R^{11b}$, $R^{11c}$, and $R^{11d}$ is independently selected from hydrogen, C1-C2 monohaloalkyl, and C1-C2 polyhaloalkyl.

In yet a further aspect, each of $R^{11a}$, $R^{11b}$, $R^{11c}$, and $R^{11d}$ is independently is selected from hydrogen, —CFH$_2$, —CF$_2$H, and —CF$_3$.

In a further aspect, each of $R^{11a}$, $R^{11b}$, $R^{11c}$, and $R^{11d}$ is independently selected from hydrogen and C1-C4 alkyl. In a still further aspect, each of $R^{11a}$, $R^{11b}$, $R^{11c}$, and $R^{11d}$ is independently selected from hydrogen, methyl, ethyl, isopropyl, and n-propyl. In yet a further aspect, each of $R^{11a}$, $R^{11b}$, $R^{11c}$, and $R^{11d}$ is independently selected from hydrogen, methyl, and ethyl. In an even further aspect, each of $R^{11a}$, $R^{11b}$, $R^{11c}$, and $R^{11d}$ is independently selected from hydrogen and methyl. In a still further aspect, each of $R^{11a}$, $R^{11b}$, $R^{11c}$, and $R^{11d}$ is independently selected from hydrogen and ethyl.

In a further aspect, each of $R^{11a}$, $R^{11b}$, $R^{11c}$, and $R^{11d}$ is independently selected from hydrogen and halogen. In a still further aspect, each of $R^{11a}$, $R^{11b}$, $R^{11c}$, and $R^{11d}$ is independently selected from hydrogen, —F, —Cl, and —Br. In yet a further aspect, each of $R^{11a}$, $R^{11b}$, $R^{11c}$, and $R^{11d}$ is independently selected from hydrogen, —F, and —Cl. In an even further aspect, each of $R^{11a}$, $R^{11b}$, $R^{11c}$, and $R^{11d}$ is independently selected from hydrogen and —F. In a still further aspect, each of $R^{11a}$, $R^{11b}$, $R^{11c}$, and $R^{11d}$ is independently selected from hydrogen and —Cl.

In a further aspect, $R^{11a}$ is hydrogen and each of $R^{11b}$, $R^{11c}$, and $R^{11d}$ is independently selected from hydrogen, halogen, —OH, —SH, —CN, —NO$_2$, —NH$_2$, C1-C4 alkyl, C1-C4 alkoxy, C1-C4 monohaloalkyl, C1-C4 polyhaloalkyl, C1-C4 alkoxy, C1-C4 aminoalkyl, C1-C4 hydroxyalkyl, C1-C4 monoalkylamino, C1-C4 dialkylamino, —SO$_2$R$^{15}$, and —CO$_2$R$^{15}$. In a still further aspect, $R^{11a}$ is hydrogen and each of $R^{11b}$, $R^{11c}$, and $R^{11d}$ is independently selected from hydrogen, halogen, —OH, —SH, —CN, —NO$_2$, —NH$_2$, C1-C2 alkyl, C1-C2 alkoxy, C1-C2 monohaloalkyl, C1-C2 polyhaloalkyl, C1-C2 alkoxy, C1-C2 aminoalkyl, C1-C2 hydroxyalkyl, C1-C2 monoalkylamino, C1-C2 dialkylamino, —SO$_2$R$^{15}$, and —CO$_2$R$^{15}$.

In a further aspect, $R^{11a}$ is hydrogen and each of $R^{11b}$, $R^{11c}$, and $R^{11d}$ is independently selected from hydrogen, halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylamino. In a still further aspect, $R^{11a}$ is hydrogen and each of $R^{11b}$, $R^{11c}$, and $R^{11d}$ is independently selected from hydrogen, halogen, —OH, —CN, —NO$_2$, —NH$_2$, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylamino. In yet a further aspect, $R^{11a}$ is hydrogen and each of $R^{11b}$, $R^{11c}$, and $R^{11d}$ is independently selected from hydrogen, —F, —Cl, —Br, —OH, —CN, —NO$_2$, —NH$_2$, —CH$_3$, —CFH$_2$, —CF$_2$H, —CF$_3$, —OCH$_3$, —NH(CH$_3$), and —N(CH$_3$)$_2$.

In a further aspect, $R^{11a}$ is hydrogen and each of $R^{11b}$, $R^{11c}$, and $R^{11d}$ is independently selected from hydrogen, halogen, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylamino. In a still further aspect, $R^{11a}$ is hydrogen and each of $R^{11b}$, $R^{11c}$, and $R^{11d}$ is independently selected from hydrogen, halogen, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylamino. In yet a further aspect, $R^{11a}$ is hydrogen and each of $R^{11b}$, $R^{11c}$, and $R^{11d}$ is independently selected from hydrogen, —F, —Cl, —Br, —CH$_3$, —CFH$_2$, —CF$_2$H, —CF$_3$, —OCH$_3$, —NH(CH$_3$), and —N(CH$_3$)$_2$.

In a further aspect, R$^{11a}$ is hydrogen and each of R$^{11b}$, R$^{11c}$, and R$^{11d}$ is independently selected from hydrogen, C1-C4 monohaloalkyl, and C1-C4 polyhaloalkyl. In a still further aspect, R$^{11a}$ is hydrogen and each of R$^{11b}$, R$^{11c}$, and R$^{11d}$ is independently selected from hydrogen, C1-C2 monohaloalkyl, and C1-C2 polyhaloalkyl. In yet a further aspect, R$^{11a}$ is hydrogen and each of R$^{11b}$, R$^{11c}$, and R$^{11d}$ is independently is selected from hydrogen, —CFH$_2$, —CF$_2$H, and —CF$_3$.

In a further aspect, R$^{11a}$ is hydrogen and each of R$^{11b}$, R$^{11c}$, and R$^{11d}$ is independently selected from hydrogen and C1-C4 alkyl. In a still further aspect, R$^{11a}$ is hydrogen and each of R$^{11b}$, R$^{11c}$, and R$^{11d}$ is independently selected from hydrogen, methyl, ethyl, iso-propyl, and n-propyl. In yet a further aspect, R$^{11a}$ is hydrogen and each of R$^{11b}$, R$^{11c}$, and R$^{11d}$ is independently selected from hydrogen, methyl, and ethyl. In an even further aspect, R$^{11a}$ is hydrogen and each of R$^{11b}$, R$^{11c}$, and R$^{11d}$ is independently selected from hydrogen and methyl. In a still further aspect, R$^{11a}$ is hydrogen and each of R$^{11b}$, R$^{11c}$, and R$^{11d}$ is independently selected from hydrogen and ethyl.

In a further aspect, R$^{11a}$ is hydrogen and each of R$^{11b}$, R$^{11c}$, and R$^{11d}$ is independently selected from hydrogen and halogen. In a still further aspect, R$^{11a}$ is hydrogen and each of R$^{11b}$, R$^{11c}$, and R$^{11d}$ is independently selected from hydrogen, —F, —Cl, and —Br. In yet a further aspect, R$^{11a}$ is hydrogen and each of R$^{11b}$, R$^{11c}$, and R$^{11d}$ is independently selected from hydrogen, —F, and —Cl. In an even further aspect, R$^{11a}$ is hydrogen and each of R$^{11b}$, R$^{11c}$, and R$^{11d}$ is independently selected from hydrogen and —F. In a still further aspect, R$^{11a}$ is hydrogen and each of R$^{11b}$, R$^{11c}$, and R$^{11d}$ is independently selected from hydrogen and —Cl.

In a further aspect, R$^{11b}$ is hydrogen and each of R$^{11a}$, R$^{11c}$, and R$^{11d}$ is independently selected from hydrogen, halogen, —OH, —SH, —CN, —NO$_2$, —NH$_2$, C1-C4 alkyl, C1-C4 alkoxy, C1-C4 monohaloalkyl, C1-C4 polyhaloalkyl, C1-C4 alkoxy, C1-C4 aminoalkyl, C1-C4 hydroxyalkyl, C1-C4 monoalkylamino, C1-C4 dialkylamino, —SO$_2$R$^{15}$, and —CO$_2$R$^{15}$. In a still further aspect, R$^{11b}$ is hydrogen and each of R$^{11a}$, R$^{11c}$, and R$^{11d}$ is independently selected from hydrogen, halogen, —OH, —SH, —CN, —NO$_2$, —NH$_2$, C1-C2 alkyl, C1-C2 alkoxy, C1-C2 monohaloalkyl, C1-C2 polyhaloalkyl, C1-C2 alkoxy, C1-C2 aminoalkyl, C1-C2 hydroxyalkyl, C1-C2 monoalkylamino, C1-C2 dialkylamino, —SO$_2$R$^{15}$, and —CO$_2$R$^{15}$.

In a further aspect, R$^{11b}$ is hydrogen and each of R$^{11a}$, R$^{11c}$, and R$^{11d}$ is independently selected from hydrogen, halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylamino. In a still further aspect, R$^{11b}$ is hydrogen and each of R$^{11a}$, R$^{11c}$, and R$^{11d}$ is independently selected from hydrogen, halogen, —OH, —CN, —NO$_2$, —NH$_2$, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylamino. In yet a further aspect, R$^{11b}$ is hydrogen and each of R$^{11a}$, R$^{11c}$, and R$^{11d}$ is independently selected from hydrogen, —F, —Cl, —Br, —OH, —CN, —NO$_2$, —NH$_2$, —CH$_3$, —CFH$_2$, —CF$_2$H, —CF$_3$, —OCH$_3$, —NH(CH$_3$), and —N(CH$_3$)$_2$.

In a further aspect, R$^{11b}$ is hydrogen and each of R$^{11a}$, R$^{11c}$, and R$^{11d}$ is independently selected from hydrogen, halogen, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylamino. In a still further aspect, R$^{11b}$ is hydrogen and each of R$^{11a}$, R$^{11c}$, and R$^{11d}$ is independently selected from hydrogen, halogen, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylamino. In yet a further aspect, R$^{11b}$ is hydrogen and each of R$^{11a}$, R$^{11c}$, and R$^{11d}$ is independently selected from hydrogen, —F, —Cl, —Br, —CH$_3$, —CFH$_2$, —CF$_2$H, —CF$_3$, —OCH$_3$, —NH(CH$_3$), and —N(CH$_3$)$_2$.

In a further aspect, R$^{11b}$ is hydrogen and each of R$^{11a}$, R$^{11c}$, and R$^{11d}$ is independently selected from hydrogen, C1-C4 monohaloalkyl, and C1-C4 polyhaloalkyl. In a still further aspect, R$^{11b}$ is hydrogen and each of R$^{11a}$, R$^{11c}$, and R$^{11d}$ is independently selected from hydrogen, C1-C2 monohaloalkyl, and C1-C2 polyhaloalkyl. In yet a further aspect, R$^{11b}$ is hydrogen and each of R$^{11a}$, R$^{11c}$, and R$^{11d}$ is independently is selected from hydrogen, —CFH$_2$, —CF$_2$H, and —CF$_3$.

In a further aspect, R$^{11b}$ is hydrogen and each of R$^{11a}$, R$^{11c}$, and R$^{11d}$ is independently selected from hydrogen and C1-C4 alkyl. In a still further aspect, R$^{11b}$ is hydrogen and each of R$^{11a}$, R$^{11c}$, and R$^{11d}$ is independently selected from hydrogen, methyl, ethyl, iso-propyl, and n-propyl. In yet a further aspect, R$^{11b}$ is hydrogen and each of R$^{11a}$, R$^{11c}$, and R$^{11d}$ is independently selected from hydrogen, methyl, and ethyl. In an even further aspect, R$^{11b}$ is hydrogen and each of R$^{11a}$, R$^{11c}$, and R$^{11d}$ is independently selected from hydrogen and methyl. In a still further aspect, R$^{11b}$ is hydrogen and each of R$^{11a}$, R$^{11c}$, and R$^{11d}$ is independently selected from hydrogen and ethyl.

In a further aspect, R$^{11b}$ is hydrogen and each of R$^{11a}$, R$^{11c}$, and R$^{11d}$ is independently selected from hydrogen and halogen. In a still further aspect, R$^{11b}$ is hydrogen and each of R$^{11a}$, R$^{11c}$, and R$^{11d}$ is independently selected from hydrogen, —F, —Cl, and —Br. In yet a further aspect, R$^{11b}$ is hydrogen and each of R$^{11a}$, R$^{11c}$, and R$^{11d}$ is independently selected from hydrogen, —F, and —Cl. In an even further aspect, R$^{11b}$ is hydrogen and each of R$^{11a}$, R$^{11c}$, and R$^{11d}$ is independently selected from hydrogen and —F. In a still further aspect, R$^{11b}$ is hydrogen and each of R$^{11a}$, R$^{11c}$, and R$^{11d}$ is independently selected from hydrogen and —Cl.

In a further aspect, R$^{11c}$ is hydrogen and each of R$^{11a}$, R$^{11b}$, and R$^{11d}$ is independently selected from hydrogen, halogen, —OH, —SH, —CN, —NO$_2$, —NH$_2$, C1-C4 alkyl, C1-C4 alkoxy, C1-C4 monohaloalkyl, C1-C4 polyhaloalkyl, C1-C4 alkoxy, C1-C4 aminoalkyl, C1-C4 hydroxyalkyl, C1-C4 monoalkylamino, C1-C4 dialkylamino, —SO$_2$R$^{15}$, and —CO$_2$R$^{15}$. In a still further aspect, R$^{11c}$ is hydrogen and each of R$^{11a}$, R$^{11b}$, and R$^{11d}$ is independently selected from hydrogen, halogen, —OH, —SH, —CN, —NO$_2$, —NH$_2$, C1-C2 alkyl, C1-C2 alkoxy, C1-C2 monohaloalkyl, C1-C2 polyhaloalkyl, C1-C2 alkoxy, C1-C2 aminoalkyl, C1-C2 hydroxyalkyl, C1-C2 monoalkylamino, C1-C2 dialkylamino, —SO$_2$R$^{15}$, and —CO$_2$R$^{15}$.

In a further aspect, R$^{11c}$ is hydrogen and each of R$^{11a}$, R$^{11b}$, and R$^{11d}$ is independently selected from hydrogen, halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylamino. In a still further aspect, R$^{11c}$ is hydrogen and each of R$^{11a}$, R$^{11b}$, and R$^{11d}$ is independently selected from hydrogen, halogen, —OH, —CN, —NO$_2$, —NH$_2$, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylamino. In yet a further aspect, $R^{11c}$ is hydrogen and each of $R^{11a}$, $R^{11b}$, and $R^{11d}$ is independently selected from hydrogen, —F, —Cl, —Br, —OH, —CN, —NO$_2$, —NH$_2$, —CH$_3$, —CFH$_2$, —CF$_2$H, —CF$_3$, —OCH$_3$, —NH(CH$_3$), and —N(CH$_3$)$_2$.

In a further aspect, $R^{11c}$ is hydrogen and each of $R^{11a}$, $R^{11b}$, and $R^{11d}$ is independently selected from hydrogen, halogen, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylamino. In a still further aspect, $R^{11c}$ is hydrogen and each of $R^{11a}$, $R^{11b}$, and $R^{11d}$ is independently selected from hydrogen, halogen, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylamino. In yet a further aspect, $R^{11c}$ is hydrogen and each of $R^{11a}$, $R^{11b}$, and $R^{11d}$ is independently selected from hydrogen, —F, —Cl, —Br, —CH$_3$, —CFH$_2$, —CF$_2$H, —CF$_3$, —OCH$_3$, —NH(CH$_3$), and —N(CH$_3$)$_2$.

In a further aspect, $R^{11c}$ is hydrogen and each of $R^{11a}$, $R^{11b}$, and $R^{11d}$ is independently selected from hydrogen, C1-C4 monohaloalkyl, and C1-C4 polyhaloalkyl. In a still further aspect, $R^{11c}$ is hydrogen and each of $R^{11a}$, $R^{11b}$, and $R^{11d}$ is independently selected from hydrogen, C1-C2 monohaloalkyl, and C1-C2 polyhaloalkyl. In yet a further aspect, $R^{11c}$ is hydrogen and each of $R^{11a}$, $R^{11b}$, and $R^{11d}$ is independently is selected from hydrogen, —CFH$_2$, —CF$_2$H, and —CF$_3$.

In a further aspect, $R^{11c}$ is hydrogen and each of $R^{11a}$, $R^{11b}$, and $R^{11d}$ is independently selected from hydrogen and C1-C4 alkyl. In a still further aspect, $R^{11c}$ is hydrogen and each of $R^{11a}$, $R^{11b}$, and $R^{11d}$ is independently selected from hydrogen, methyl, ethyl, iso-propyl, and n-propyl. In yet a further aspect, $R^{11c}$ is hydrogen and each of $R^{11a}$, $R^{11b}$, and $R^{11d}$ is independently selected from hydrogen, methyl, and ethyl. In an even further aspect, $R^{11c}$ is hydrogen and each of $R^{11a}$, $R^{11b}$, and $R^{11d}$ is independently selected from hydrogen and methyl. In a still further aspect, $R^{11c}$ is hydrogen and each of $R^{11a}$, $R^{11b}$, and $R^{11d}$ is independently selected from hydrogen and ethyl.

In a further aspect, $R^{11c}$ is hydrogen and each of $R^{11a}$, $R^{11b}$, and $R^{11d}$ is independently selected from hydrogen and halogen. In a still further aspect, $R^{11c}$ is hydrogen and each of $R^{11a}$, $R^{11b}$, and $R^{11d}$ is independently selected from hydrogen, —F, —Cl, and —Br. In yet a further aspect, $R^{11c}$ is hydrogen and each of $R^{11a}$, $R^{11b}$, and $R^{11d}$ is independently selected from hydrogen, —F, and —Cl. In an even further aspect, $R^{11c}$ is hydrogen and each of $R^{11a}$, $R^{11b}$, and $R^{11d}$ is independently selected from hydrogen and —F. In a still further aspect, $R^{11c}$ is hydrogen and each of $R^{11a}$, $R^{11b}$, and $R^{11d}$ is independently selected from hydrogen and —Cl.

In a further aspect, $R^{11d}$ is hydrogen and each of $R^{11a}$, $R^{11b}$, and $R^{11c}$ is independently selected from hydrogen, halogen, —OH, —SH, —CN, —NO$_2$, —NH$_2$, C1-C4 alkyl, C1-C4 alkoxy, C1-C4 monohaloalkyl, C1-C4 polyhaloalkyl, C1-C4 alkoxy, C1-C4 aminoalkyl, C1-C4 hydroxyalkyl, C1-C4 monoalkylamino, C1-C4 dialkylamino, —SO$_2$R$^{15}$, and —CO$_2$R$^{15}$. In a still further aspect, $R^{11d}$ is hydrogen and each of $R^{11a}$, $R^{11b}$, and $R^{11c}$ is independently selected from hydrogen, halogen, —OH, —SH, —CN, —NO$_2$, —NH$_2$, C1-C2 alkyl, C1-C2 alkoxy, C1-C2 monohaloalkyl, C1-C2 polyhaloalkyl, C1-C2 alkoxy, C1-C2 aminoalkyl, C1-C2 hydroxyalkyl, C1-C2 monoalkylamino, C1-C2 dialkylamino, —SO$_2$R$^{15}$, and —CO$_2$R$^{15}$.

In a further aspect, $R^{11d}$ is hydrogen and each of $R^{11a}$, $R^{11b}$, and $R^{11c}$ is independently selected from hydrogen, halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylamino. In a still further aspect, $R^{11d}$ is hydrogen and each of $R^{11a}$, $R^{11b}$, and $R^{11c}$ is independently selected from hydrogen, halogen, —OH, —CN, —NO$_2$, —NH$_2$, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylamino. In yet a further aspect, $R^{11d}$ is hydrogen and each of $R^{11a}$, $R^{11b}$, and $R^{11c}$ is independently selected from hydrogen, —F, —Cl, —Br, —OH, —CN, —NO$_2$, —NH$_2$, —CH$_3$, —CFH$_2$, —CF$_2$H, —CF$_3$, —OCH$_3$, —NH(CH$_3$), and —N(CH$_3$)$_2$.

In a further aspect, $R^{11d}$ is hydrogen and each of $R^{11a}$, $R^{11b}$, and $R^{11c}$ is independently selected from hydrogen, halogen, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylamino. In a still further aspect, $R^{11d}$ is hydrogen and each of $R^{11a}$, $R^{11b}$, and $R^{11c}$ is independently selected from hydrogen, halogen, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylamino. In yet a further aspect, $R^{11d}$ is hydrogen and each of $R^{11a}$, $R^{11b}$, and $R^{11c}$ is independently selected from hydrogen, —F, —Cl, —Br, —CH$_3$, —CFH$_2$, —CF$_2$H, —CF$_3$, —OCH$_3$, —NH(CH$_3$), and —N(CH$_3$)$_2$.

In a further aspect, $R^{11d}$ is hydrogen and each of $R^{11a}$, $R^{11b}$, and $R^{11c}$ is independently selected from hydrogen, C1-C4 monohaloalkyl, and C1-C4 polyhaloalkyl. In a still further aspect, $R^{11d}$ is hydrogen and each of $R^{11a}$, $R^{11b}$, and $R^{11c}$ is independently selected from hydrogen, C1-C2 monohaloalkyl, and C1-C2 polyhaloalkyl. In yet a further aspect, $R^{11d}$ is hydrogen and each of $R^{11a}$, $R^{11b}$, and $R^{11c}$ is independently is selected from hydrogen, —CFH$_2$, —CF$_2$H, and —CF$_3$.

In a further aspect, $R^{11d}$ is hydrogen and each of $R^{11a}$, $R^{11b}$, and $R^{11c}$ is independently selected from hydrogen and C1-C4 alkyl. In a still further aspect, $R^{11d}$ is hydrogen and each of $R^{11a}$, $R^{11b}$, and $R^{11c}$ is independently selected from hydrogen, methyl, ethyl, iso-propyl, and n-propyl. In yet a further aspect, $R^{11d}$ is hydrogen and each of $R^{11a}$, $R^{11b}$, and $R^{11c}$ is independently selected from hydrogen, methyl, and ethyl. In an even further aspect, $R^{11d}$ is hydrogen and each of $R^{11a}$, $R^{11b}$, and $R^{11c}$ is independently selected from hydrogen and methyl. In a still further aspect, $R^{11d}$ is hydrogen and each of $R^{11a}$, $R^{11b}$, and $R^{11c}$ is independently selected from hydrogen and ethyl.

In a further aspect, $R^{11d}$ is hydrogen and each of $R^{11a}$, $R^{11b}$, and $R^{11c}$ is independently selected from hydrogen and halogen. In a still further aspect, $R^{11d}$ is hydrogen and each of $R^{11a}$, $R^{11b}$, and $R^{11c}$ is independently selected from hydrogen, —F, —Cl, and —Br.

In yet a further aspect, $R^{11d}$ is hydrogen and each of $R^{11a}$, $R^{11b}$, and $R^{11c}$ is independently selected from hydrogen, —F, and —Cl. In an even further aspect, $R^{11d}$ is hydrogen and each of $R^{11a}$, $R^{11b}$, and $R^{11c}$ is independently selected from hydrogen and —F. In a still further aspect, $R^{11d}$ is hydrogen and each of $R^{11a}$, $R^{11b}$, and $R^{11c}$ is independently selected from hydrogen and —Cl.

In a further aspect, two of $R^{11a}$, $R^{11b}$, $R^{11c}$, and $R^{11d}$ are hydrogen and two of $R^{11a}$, $R^{11b}$, $R^{11c}$, and $R^{11d}$ are independently selected from halogen, —OH, —SH, —CN, —NO$_2$, —NH$_2$, C1-C4 alkyl, C1-C4 alkoxy, C1-C4 monohaloalkyl, C1-C4 polyhaloalkyl, C1-C4 alkoxy, C1-C4 aminoalkyl, C1-C4 hydroxyalkyl, C1-C4 monoalkylamino, C1-C4 dialkylamino, —SO$_2$R$^{15}$, and —CO$_2$R$^{15}$. In a still further aspect, two of R$^{11a}$, R$^{11b}$, R$^{11c}$, and R$^{11d}$ are hydrogen and two of R$^{11a}$, R$^{11b}$, R$^{11c}$, and R$^{11d}$ are independently selected from halogen, —OH, —SH, —CN, —NO$_2$, —NH$_2$, C1-C2 alkyl, C1-C2 alkoxy, C1-C2 monohaloalkyl, C1-C2 polyhaloalkyl, C1-C2 alkoxy, C1-C2 aminoalkyl, C1-C2 hydroxyalkyl, C1-C2 monoalkylamino, C1-C2 dialkylamino, —SO$_2$R$^{15}$, and —CO$_2$R$^{15}$.

In a further aspect, two of R$^{11a}$, R$^{11b}$, R$^{11c}$, and R$^{11d}$ are hydrogen and two of R$^{11a}$, R$^{11b}$, R$^{11c}$, and R$^{11d}$ are independently selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylamino. In a still further aspect, two of R$^{11a}$, R$^{11b}$, R$^{11c}$, and R$^{11d}$ are hydrogen and two of R$^{11a}$, R$^{11b}$, R$^{11c}$, and R$^{11d}$ are independently selected from halogen, —OH, —CN, —NO$_2$, —NH$_2$, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylamino. In yet a further aspect, two of R$^{11a}$, R$^{11b}$, R$^{11c}$, and R$^{11d}$ are hydrogen and two of R$^{11a}$, R$^{11b}$, R$^{11c}$, and R$^{11d}$ is independently selected from —F, —Cl, —Br, —OH, —CN, —NO$_2$, —NH$_2$, —CH$_3$, —CFH$_2$, —CF$_2$H, —CF$_3$, —OCH$_3$, —NH(CH$_3$), and —N(CH$_3$)$_2$.

In a further aspect, two of R$^{11a}$, R$^{11b}$, R$^{11c}$, and R$^{11d}$ are hydrogen and two of R$^{11a}$, R$^{11b}$, R$^{11c}$, and R$^{11d}$ are independently selected from halogen, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylamino. In a still further aspect, two of R$^{11a}$, R$^{11b}$, R$^{11c}$, and R$^{11d}$ are hydrogen and two of R$^{11a}$, R$^{11b}$, R$^{11c}$, and R$^{11d}$ are independently selected from halogen, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylamino. In yet a further aspect, two of R$^{11a}$, R$^{11b}$, R$^{11c}$, and R$^{11d}$ are hydrogen and two of R$^{11a}$, R$^{11b}$, R$^{11c}$, and R$^{11d}$ is independently selected from —F, —Cl, —Br, —CH$_3$, —CFH$_2$, —CF$_2$H, —CF$_3$, —OCH$_3$, —NH(CH$_3$), and —N(CH$_3$)$_2$.

In a further aspect, two of R$^{11a}$, R$^{11b}$, R$^{11c}$, and R$^{11d}$ are hydrogen and two of R$^{11a}$, R$^{11b}$, R$^{11c}$ and R$^{11d}$ are independently selected from C1-C4 monohaloalkyl and C1-C4 polyhaloalkyl. In a still further aspect, two of R$^{11a}$, R$^{11b}$, R$^{11c}$, and R$^{11d}$ are hydrogen and two of R$^{11a}$, R$^{11b}$, R$^{11c}$, and R$^{11d}$ are independently selected from C1-C2 monohaloalkyl and C1-C2 polyhaloalkyl. In yet a further aspect, two of R$^{11a}$, R$^{11b}$, R$^{11c}$, and R$^{11d}$ are hydrogen and two of R$^{11a}$, R$^{11b}$, R$^{11c}$, and R$^{11d}$ are independently selected from —CFH$_2$, —CF$_2$H, and —CF$_3$.

In a further aspect, two of R$^{11a}$, R$^{11b}$, R$^{11c}$, and R$^{11d}$ are hydrogen and two of R$^{11a}$, R$^{11b}$, R$^{11c}$, and R$^{11d}$ are independently selected from C1-C4 alkyl. In a still further aspect, two of R$^{11a}$, R$^{11b}$, R$^{11c}$, and R$^{11d}$ are hydrogen and two of R$^{11a}$, R$^{11b}$, R$^{11c}$, and R$^{11d}$ are independently selected from methyl, ethyl, iso-propyl, and n-propyl. In yet a further aspect, two of R$^{11a}$, R$^{11b}$, R$^{11c}$, and R$^{11d}$ are hydrogen and two of R$^{11a}$, R$^{11b}$, R$^{11c}$, and R$^{11d}$ are independently selected from methyl and ethyl. In an even further aspect, two of R$^{11a}$, R$^{11b}$, R$^{11c}$, and R$^{11d}$ are hydrogen and two of R$^{11a}$, R$^{11b}$, R$^{11c}$, and R$^{11d}$ are methyl. In a still further aspect, two of R$^{11a}$, R$^{11b}$, R$^{11c}$, and R$^{11d}$ are hydrogen and two of R$^{11a}$, R$^{11b}$, R$^{11c}$, and R$^{11d}$ are ethyl.

In a further aspect, two of R$^{11a}$, R$^{11b}$, R$^{11c}$, and R$^{11d}$ are hydrogen and two of R$^{11a}$, R$^{11b}$, R$^{11c}$, and R$^{11d}$ are independently selected from halogen. In a still further aspect, two of R$^{11a}$, R$^{11b}$, R$^{11c}$, and R$^{11d}$ are hydrogen and two of R$^{11a}$, R$^{11b}$, R$^{11c}$, and R$^{11d}$ are independently selected from —Cl, and —Br. In yet a further aspect, two of R$^{11a}$, R$^{11b}$, R$^{11c}$, and R$^{11d}$ are hydrogen and two of R$^{11a}$, R$^{11b}$, R$^{11c}$, and R$^{11d}$ are independently selected from —F and —Cl. In an even further aspect, two of R$^{11a}$, R$^{11b}$, R$^{11c}$, and R$^{11d}$ are hydrogen and two of R$^{11a}$, R$^{11b}$, R$^{11c}$, and R$^{11d}$ are —F. In a still further aspect, two of R$^{11a}$, R$^{11b}$, R$^{11c}$, and R$^{11d}$ are hydrogen and two of R$^{11a}$, R$^{11b}$, R$^{11c}$, and R$^{11d}$ are —Cl. In yet a further aspect, two of R$^{11a}$, R$^{11b}$, R$^{11c}$, and R$^{11d}$ are hydrogen and two of R$^{11a}$, R$^{11b}$, R$^{11c}$, and R$^{11d}$ are —Br.

In a further aspect, three of R$^{11a}$, R$^{11b}$, R$^{11c}$, and R$^{11d}$ are hydrogen and one of R$^{11a}$, R$^{11b}$, R$^{11c}$, and R$^{11d}$ is selected from halogen, —OH, —SH, —CN, —NO$_2$, —NH$_2$, C1-C4 alkyl, C1-C4 alkoxy, C1-C4 monohaloalkyl, C1-C4 polyhaloalkyl, C1-C4 alkoxy, C1-C4 aminoalkyl, C1-C4 hydroxyalkyl, C1-C4 monoalkylamino, C1-C4 dialkylamino, —SO$_2$R$^{15}$, and —CO$_2$R$^{15}$. In a still further aspect, three of R$^{11a}$, R$^{11b}$, R$^{11c}$, and R$^{11d}$ are hydrogen and one of R$^{11a}$, R$^{11b}$, R$^{11c}$, and R$^{11d}$ is selected from halogen, —OH, —SH, —CN, —NO$_2$, —NH$_2$, C1-C2 alkyl, C1-C2 alkoxy, C1-C2 monohaloalkyl, C1-C2 polyhaloalkyl, C1-C2 alkoxy, C1-C2 aminoalkyl, C1-C2 hydroxyalkyl, C1-C2 monoalkylamino, C1-C2 dialkylamino, —SO$_2$R$^{15}$, and —CO$_2$R$^{15}$.

In a further aspect, three of R$^{11a}$, R$^{11b}$, R$^{11c}$, and R$^{11d}$ are hydrogen and one of R$^{11a}$, R$^{11b}$, R$^{11c}$, and R$^{11d}$ is selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylamino. In a still further aspect, three of R$^{11a}$, R$^{11b}$, R$^{11c}$, and R$^{11d}$ are hydrogen and one of R$^{11a}$, R$^{11b}$, R$^{11c}$, and R$^{11d}$ is selected from halogen, —OH, —CN, —NO$_2$, —NH$_2$, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylamino. In yet a further aspect, three of R$^{11a}$, R$^{11b}$, R$^{11c}$, and R$^{11d}$ are hydrogen and one of R$^{11a}$, R$^{11b}$, R$^{11c}$, and R$^{11d}$ is selected from —F, —Cl, —Br, —OH, —CN, —NO$_2$, —NH$_2$, —CH$_3$, —CFH$_2$, —CF$_3$, —OCH$_3$, —NH(CH$_3$), and N(CH$_3$)$_2$.

In a further aspect, three of R$^{11a}$, R$^{11b}$, R$^{11c}$, and R$^{11d}$ are hydrogen and one of R$^{11a}$, R$^{11b}$, R$^{11c}$, and R$^{11d}$ is selected from halogen, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylamino. In a still further aspect, three of R$^{11a}$, R$^{11b}$, R$^{11c}$, and R$^{11d}$ are hydrogen and one of Rim, R$^{11a}$, R$^{11b}$, R$^{11c}$, and R$^{11d}$ is selected from halogen, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylamino. In yet a further aspect, three of R$^{11a}$, R$^{11b}$, R$^{11c}$, and R$^{11d}$ are hydrogen and one of R$^{11a}$, R$^{11b}$, R$^{11c}$, and R$^{11d}$ is selected from —F, —Cl, —Br, —CH$_3$, —CFH$_2$, —CF$_2$H, —CF$_3$, —OCH$_3$, —NH(CH$_3$), and —N(CH$_3$)$_2$.

In a further aspect, three of R$^{11a}$, R$^{11b}$, R$^{11c}$, and R$^{11d}$ are hydrogen and one of R$^{11a}$, R$^{11b}$, R$^{11c}$, and R$^{11d}$ is selected from C1-C4 monohaloalkyl and C1-C4 polyhaloalkyl. In a still further aspect, three of R$^{11a}$, R$^{11b}$, R$^{11c}$, and R$^{11d}$ are hydrogen and R$^{11a}$, R$^{11b}$, R$^{11c}$, and R$^{11d}$ is selected from C1-C2 monohaloalkyl and C1-C2 polyhaloalkyl. In yet a further aspect, three of $R^{11a}$, $R^{11b}$, $R^{11c}$, and $R^{11d}$ are hydrogen and one of $R^{11a}$, $R^{11b}$, $R^{11c}$, and $R^{11d}$ is selected from —$CFH_2$, —$CF_2H$, and —$CF_3$.

In a further aspect, three of $R^{11a}$, $R^{11b}$, $R^{11c}$, and $R^{11d}$ are hydrogen and one of $R^{11a}$, $R^{11b}$, $R^{11c}$, and $R^{11d}$ is selected from C1-C4 alkyl. In a still further aspect, three of $R^{11a}$, $R^{11b}$, $R^{11c}$, and $R^{11d}$ are hydrogen and one of $R^{11a}$, $R^{11b}$, $R^{11c}$, and $R^{11d}$ is selected from methyl, ethyl, iso-propyl, and n-propyl. In yet a further aspect, three of $R^{11a}$, $R^{11b}$, $R^{11c}$, and $R^{11d}$ are hydrogen and one of $R^{11a}$, $R^{11b}$, $R^{11c}$, and $R^{11d}$ is selected from methyl and ethyl. In an even further aspect, three of $R^{11a}$, $R^{11b}$, $R^{11c}$, and $R^{11d}$ are hydrogen and one of $R^{11a}$, $R^{11b}$, $R^{11c}$, and $R^{11d}$ is methyl. In a still further aspect, three of $R^{11a}$, $R^{11b}$, $R^{11c}$, and $R^{11d}$ are hydrogen and one of $R^{11a}$, $R^{11b}$, $R^{11c}$, and $R^{11d}$ is ethyl.

In a further aspect, three of $R^{11a}$, $R^{11b}$, $R^{11c}$, and $R^{11d}$ are hydrogen and one of $R^{11a}$, $R^{11b}$, $R^{11c}$, and $R^{11d}$ is selected from halogen. In a still further aspect, three of $R^{11a}$, $R^{11b}$, $R^{11c}$, and $R^{11d}$ are hydrogen and one of $R^{11a}$, $R^{11b}$, $R^{11c}$, and $R^{11d}$ is selected from —F, —Cl, and —Br. In yet a further aspect, three of $R^{11a}$, $R^{11b}$, $R^{11c}$, and $R^{11d}$ are hydrogen and one of $R^{11a}$, $R^{11b}$, $R^{11c}$, and $R^{11d}$ is selected from —F and —Cl. In an even further aspect, three of $R^{11a}$, $R^{11b}$, $R^{11c}$, and $R^{11d}$ are hydrogen and one of $R^{11a}$, $R^{11b}$, $R^{11c}$, and $R^{11d}$ is —F. In a still further aspect, three of $R^{11a}$, $R^{11b}$, $R^{11c}$, and $R^{11d}$ are hydrogen and one of $R^{11a}$, $R^{11b}$, $R^{11c}$, and $R^{11d}$ is —Cl. In yet a further aspect, three of $R^{11a}$, $R^{11b}$, $R^{11c}$, and $R^{11d}$ are hydrogen and one of $R^{11a}$, $R^{11b}$, $R^{11c}$, and $R^{11d}$ is —Br.

b. $R^{12}$ and $R^{13}$ Groups

In one aspect, each of $R^{12}$ and $R^{13}$ is independently selected from hydrogen and C1-C4 alkyl. In a further aspect, each of $R^{12}$ and $R^{13}$ is hydrogen.

In a further aspect, each of $R^{12}$ and $R^{13}$ is independently selected from hydrogen, methyl, ethyl, n-propyl, and iso-propyl. In a still further aspect, each of $R^{12}$ and $R^{13}$ is independently selected from hydrogen, methyl, and ethyl. In yet a further aspect, each of $R^{12}$ and $R^{13}$ is independently selected from hydrogen and ethyl. In an even further aspect, each of Ru and $R^{13}$ is independently selected from hydrogen and methyl.

In a further aspect, $R^{12}$ is hydrogen and $R^{13}$ is C1-C4 alkyl. In a still further aspect, $R^{12}$ is hydrogen and $R^{13}$ is selected from methyl, ethyl, n-propyl, and iso-propyl. In yet a further aspect, $R^{12}$ is hydrogen and $R^{13}$ is selected from methyl and ethyl. In an even further aspect, $R^{12}$ is hydrogen and $R^{13}$ is ethyl. In a still further aspect, $R^{12}$ is hydrogen and $R^{13}$ is methyl.

In a further aspect, $R^{13}$ is hydrogen and $R^{12}$ is C1-C4 alkyl. In a still further aspect, $R^{13}$ is hydrogen and $R^{12}$ is selected from methyl, ethyl, n-propyl, and iso-propyl. In yet a further aspect, $R^{13}$ is hydrogen and $R^{12}$ is selected from methyl and ethyl. In an even further aspect, $R^{13}$ is hydrogen and $R^{12}$ is ethyl. In a still further aspect, $R^{13}$ is hydrogen and $R^{12}$ is methyl.

c. $R^{14a}$, $R^{14b}$, $R^{14c}$, $R^{14d}$, and $R^{14e}$ Groups

In one aspect, each of $R^{14a}$, $R^{14b}$, $R^{14c}$, $R^{14d}$, and $R^{14e}$ is independently selected from hydrogen, halogen, —OH, —SH, —CN, —$NO_2$, —$NH_2$, C1-C4 alkyl, C1-C4 alkoxy, C1-C4 monohaloalkyl, C1-C4 polyhaloalkyl, C1-C4 alkoxy, C1-C4 aminoalkyl, C1-C4 hydroxyalkyl, C1-C4 monoalkylamino, C1-C4 dialkylamino, —$SO_2R^{16}$, and —$CO_2R^{16}$. In a still further aspect, each of $R^{14a}$, $R^{14b}$, $R^{14c}$, $R^{14d}$, and $R^{14e}$ is independently selected from hydrogen, halogen, —OH, —SH, —CN, —$NO_2$, —$NH_2$, C1-C2 alkyl, C1-C2 alkoxy, C1-C2 monohaloalkyl, C1-C2 polyhaloalkyl, C1-C2 alkoxy, C1-C2 aminoalkyl, C1-C2 hydroxyalkyl, C1-C2 monoalkylamino, C1-C2 dialkylamino, —$SO_2R^{16}$, and —$CO_2R^{16}$.

In a further aspect, each of $R^{14a}$, $R^{14b}$, $R^{14c}$, $R^{14d}$, and $R^{14e}$ is independently selected from hydrogen, halogen, —OH, —SH, —CN, —$NO_2$, —$NH_2$, C1-C4 alkyl, C1-C4 alkoxy, C1-C4 monohaloalkyl, C1-C4 polyhaloalkyl, C1-C4 alkoxy, C1-C4 aminoalkyl, C1-C4 hydroxyalkyl, C1-C4 monoalkylamino, and C1-C4 dialkylamino. In a still further aspect, each of $R^{14a}$, $R^{14b}$, $R^{14c}$, $R^{14d}$, and $R^{14e}$ is independently selected from hydrogen, halogen, —OH, —SH, —CN, —$NO_2$, —$NH_2$, C1-C2 alkyl, C1-C2 alkoxy, C1-C2 monohaloalkyl, C1-C2 polyhaloalkyl, C1-C2 alkoxy, C1-C2 aminoalkyl, C1-C2 hydroxyalkyl, C1-C2 monoalkylamino, and C1-C2 dialkylamino.

In a further aspect, each of $R^{14a}$, $R^{14b}$, $R^{14c}$, $R^{14d}$, and $R^{14e}$ is independently selected from hydrogen, halogen, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylamino. In a still further aspect, each of $R^{14a}$, $R^{14b}$, $R^{14c}$, $R^{14d}$, and $R^{14e}$ is independently selected from hydrogen, halogen, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylamino. In yet a further aspect, each of $R^{14a}$, $R^{14b}$, $R^{14c}$, $R^{14d}$, and $R^{14e}$ is independently selected from hydrogen, —F, —Cl, —Br, —$CH_3$, —$CFH_2$, —$CF_2H$, —$CF_3$, —$OCH_3$, —$NH(CH_3)$, and —$N(CH_3)_2$.

In a further aspect, each of $R^{14a}$, $R^{14b}$, $R^{14c}$, $R^{14d}$, and $R^{14e}$ is independently selected from hydrogen, C1-C4 monohaloalkyl, and C1-C4 polyhaloalkyl. In a still further aspect, each of $R^{14a}$, $R^{14b}$, $R^{14c}$, $R^{14d}$, and $R^{14e}$ is independently selected from hydrogen, C1-C2 monohaloalkyl, and C1-C2 polyhaloalkyl. In yet a further aspect, each of $R^{14a}$, $R^{14b}$, $R^{14c}$, $R^{14d}$, and $R^{14e}$ is independently is selected from hydrogen, —$CFH_2$, —$CF_2H$, and —$CF_3$.

In a further aspect, each of $R^{14a}$, $R^{14b}$, $R^{14c}$, $R^{14d}$, and $R^{14e}$ is independently selected from hydrogen and C1-C4 alkyl. In a still further aspect, each of $R^{14a}$, $R^{14b}$, $R^{14c}$, $R^{14d}$, and $R^{14e}$ is independently selected from hydrogen, methyl, ethyl, iso-propyl, and n-propyl. In yet a further aspect, each of $R^{14a}$, $R^{14b}$, $R^{14c}$, $R^{14d}$, and $R^{14e}$ is independently selected from hydrogen, methyl, and ethyl. In an even further aspect, each of $R^{14a}$, $R^{14b}$, $R^{14c}$, $R^{14d}$, and $R^{14e}$ is independently selected from hydrogen and methyl. In a still further aspect, each of $R^{14a}$, $R^{14b}$, $R^{14c}$, $R^{14d}$, and $R^{14e}$ is independently selected from hydrogen and ethyl.

In a further aspect, each of $R^{14a}$, $R^{14b}$, $R^{14c}$, $R^{14d}$, and $R^{14e}$ is independently selected from hydrogen and halogen. In a still further aspect, each of $R^{14a}$, $R^{14b}$, $R^{14c}$, $R^{14d}$, and $R^{14e}$ is independently selected from hydrogen, —F, —Cl, and —Br. In yet a further aspect, each of $R^{14a}$, $R^{14b}$, $R^{14c}$, $R^{14d}$, and $R^{14e}$ is independently selected from hydrogen, —F, and —Cl. In an even further aspect, each of $R^{14a}$, $R^{14b}$, $R^{14c}$, $R^{14d}$, and $R^{14e}$ is independently selected from hydrogen and —F. In a still further aspect, each of $R^{14a}$, $R^{14b}$, $R^{14c}$, $R^{14d}$, and $R^{14e}$ is independently selected from hydrogen and —Cl.

In a further aspect, each of $R^{14a}$, $R^{14b}$, $R^{14c}$, $R^{14d}$, and $R^{14e}$ is independently selected from hydrogen, —OH, —SH, —CN, —$NO_2$, —$NH_2$, —$SO_2R^{16}$, and —$CO_2R^{16}$. In a still further aspect, each of $R^{14a}$, $R^{14b}$, $R^{14c}$, $R^{14d}$, and $R^{14e}$ is independently selected from hydrogen, —OH, —SH, —$NH_2$, —$SO_2R^{16}$, and —$CO_2R^{16}$. In yet a further aspect, each of $R^{14a}$, $R^{14b}$, $R^{14c}$, $R^{14d}$, and $R^{14e}$ is independently selected from hydrogen, —$SO_2R^{16}$, and —$CO_2R^{16}$. In an even further aspect, each of $R^{14a}$, $R^{14b}$, $R^{14c}$, $R^{14d}$, and $R^{14e}$ is independently selected from hydrogen and —$SO_2R^{16}$. In a still further aspect, each of $R^{14a}$, $R^{14b}$, $R^{14c}$, $R^{14d}$, and $R^{14e}$ is independently selected from hydrogen and —$CO_2R^{16}$.

In a further aspect, $R^{14a}$ is hydrogen and each of $R^{14b}$, $R^{14c}$, $R^{14d}$, and $R^{14e}$ is independently selected from hydrogen, halogen, —OH, —SH, —CN, —$NO_2$, —$NH_2$, C1-C4 alkyl, C1-C4 alkoxy, C1-C4 monohaloalkyl, C1-C4 polyhaloalkyl, C1-C4 alkoxy, C1-C4 aminoalkyl, C1-C4 hydroxyalkyl, C1-C4 monoalkylamino, C1-C4 dialkylamino, —$SO_2R^{16}$, and —$CO_2R^{16}$. In a still further aspect, $R^{14a}$ is hydrogen and each of $R^{14b}$, $R^{14c}$, $R^{14d}$, and $R^{14e}$ is independently selected from hydrogen, halogen, —OH, —SH, —CN, —$NO_2$, —$NH_2$, C1-C2 alkyl, C1-C2 alkoxy, C1-C2 monohaloalkyl, C1-C2 polyhaloalkyl, C1-C2 alkoxy, C1-C2 aminoalkyl, C1-C2 hydroxyalkyl, C1-C2 monoalkylamino, C1-C2 dialkylamino, —$SO_2R^{16}$, and —$CO_2R^{16}$.

In a further aspect, $R^{14a}$ is hydrogen and each of $R^{14b}$, $R^{14c}$, $R^{14d}$, and $R^{14e}$ is independently selected from hydrogen, halogen, —OH, —CN, —$NO_2$, —$NH_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylamino. In a still further aspect, $R^{14a}$ is hydrogen and each of $R^{14b}$, $R^{14c}$, $R^{14d}$, and $R^{14e}$ is independently selected from hydrogen, halogen, —OH, —CN, —$NO_2$, —$NH_2$, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylamino. In yet a further aspect, $R^{14a}$ is hydrogen and each of $R^{14b}$, $R^{14c}$, $R^{14d}$, and $R^{14e}$ is independently selected from hydrogen, —F, —Cl, —Br, —OH, —CN, —$NO_2$, —$NH_2$, —$CH_3$, —$CFH_2$, —$CF_2H$, —$CF_3$, —$OCH_3$, —$NH(CH_3)$, and —$N(CH_3)_2$.

In a further aspect, $R^{14a}$ is hydrogen and each of $R^{14b}$, $R^{14c}$, $R^{14d}$, and $R^{14e}$ is independently selected from hydrogen, halogen, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylamino. In a still further aspect, $R^{14a}$ is hydrogen and each of $R^{14b}$, $R^{14c}$, $R^{14d}$, and $R^{14e}$ is independently selected from hydrogen, halogen, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylamino. In yet a further aspect, $R^{14a}$ is hydrogen and each of $R^{14b}$, $R^{14c}$, $R^{14d}$, and $R^{14e}$ is independently selected from hydrogen, —F, —Cl, —Br, —$CH_3$, —$CFH_2$, —$CF_2H$, —$CF_3$, —$OCH_3$, —$NH(CH_3)$, and —$N(CH_3)_2$.

In a further aspect, $R^{14a}$ is hydrogen and each of $R^{14b}$, $R^{14c}$, $R^{14d}$, and $R^{14e}$ is independently selected from hydrogen, C1-C4 monohaloalkyl, and C1-C4 polyhaloalkyl. In a still further aspect, $R^{14a}$ is hydrogen and each of $R^{14b}$, $R^{14c}$, $R^{14d}$, and $R^{14e}$ is independently selected from hydrogen, C1-C2 monohaloalkyl, and C1-C2 polyhaloalkyl. In yet a further aspect, $R^{14a}$ is hydrogen and each of $R^{14b}$, $R^{14c}$, $R^{14d}$, and $R^{14e}$ is independently is selected from hydrogen, —$CFH_2$, —$CF_2H$, and —$CF_3$.

In a further aspect, $R^{14a}$ is hydrogen and each of $R^{14b}$, $R^{14c}$, $R^{14d}$, and $R^{14e}$ is independently selected from hydrogen and C1-C4 alkyl. In a still further aspect, $R^{14a}$ is hydrogen and each of $R^{14b}$, $R^{14c}$, $R^{14d}$, and $R^{14e}$ is independently selected from hydrogen, methyl, ethyl, iso-propyl, and n-propyl. In yet a further aspect, $R^{14a}$ is hydrogen and each of $R^{14b}$, $R^{14c}$, $R^{14d}$, and $R^{14e}$ is independently selected from hydrogen, methyl, and ethyl. In an even further aspect, $R^{14a}$ is hydrogen and each of $R^{14b}$, $R^{14c}$, $R^{14d}$, and $R^{14e}$ is independently selected from hydrogen and methyl. In a still further aspect, $R^{14a}$ is hydrogen and each of $R^{14b}$, $R^{14c}$, $R^{14d}$, and $R^{14e}$ is independently selected from hydrogen and ethyl.

In a further aspect, $R^{14a}$ is hydrogen and each of $R^{14b}$, $R^{14c}$, $R^{14d}$, and $R^{14e}$ is independently selected from hydrogen and halogen. In a still further aspect, $R^{14a}$ is hydrogen and each of $R^{14b}$, $R^{14c}$, $R^{14d}$, and $R^{14e}$ is independently selected from hydrogen, —F, —Cl, and —Br. In yet a further aspect, $R^{14a}$ is hydrogen and each of $R^{14b}$, $R^{14c}$, $R^{14d}$, and $R^{14e}$ is independently selected from hydrogen, —F, and —Cl. In an even further aspect, $R^{14a}$ is hydrogen and each of $R^{14b}$, $R^{14c}$, $R^{14d}$, and $R^{14e}$ is independently selected from hydrogen and —F. In a still further aspect, $R^{14a}$ is hydrogen and each of $R^{14b}$, $R^{14c}$, $R^{14d}$, and $R^{14e}$ is independently selected from hydrogen and —Cl.

In a further aspect, $R^{14a}$ is hydrogen and each of $R^{14b}$, $R^{14c}$, $R^{14d}$, and $R^{14e}$ is independently selected from hydrogen, —OH, —SH, —CN, —$NO_2$, —$NH_2$, —$SO_2R^{16}$, and —$CO_2R^{16}$. In a still further aspect, $R^{14a}$ is hydrogen and each of $R^{14b}$, $R^{14c}$, $R^{14d}$, and $R^{14e}$ is independently selected from hydrogen, —OH, —SH, —$NH_2$, —$SO_2R^{16}$, and —$CO_2R^{16}$. In yet a further aspect, $R^{14a}$ is hydrogen and each of $R^{14b}$, $R^{14c}$, $R^{14d}$, and $R^{14e}$ is independently selected from hydrogen, —$SO_2R^{16}$, and —$CO_2R^{16}$. In an even further aspect, $R^{14a}$ is hydrogen and each of $R^{14b}$, $R^{14c}$, $R^{14d}$, and $R^{14e}$ is independently selected from hydrogen and —$SO_2R^{16}$. In a still further aspect, $R^{14a}$ is hydrogen and each of $R^{14b}$, $R^{14c}$, $R^{14d}$, and $R^{14e}$ is independently selected from hydrogen and —$CO_2R^{16}$.

In a further aspect, $R^{14b}$ is hydrogen and each of $R^{14a}$, $R^{14c}$, $R^{14d}$, and $R^{14e}$ is independently selected from hydrogen, halogen, —OH, —SH, —CN, —$NO_2$, —$NH_2$, C1-C4 alkyl, C1-C4 alkoxy, C1-C4 monohaloalkyl, C1-C4 polyhaloalkyl, C1-C4 alkoxy, C1-C4 aminoalkyl, C1-C4 hydroxyalkyl, C1-C4 monoalkylamino, C1-C4 dialkylamino, —$SO_2R^{16}$, and —$CO_2R^{16}$. In a still further aspect, $R^{14b}$ is hydrogen and each of $R^{14a}$, $R^{14c}$, $R^{14d}$, and $R^{14e}$ is independently selected from hydrogen, halogen, —OH, —SH, —CN, —$NO_2$, —$NH_2$, C1-C2 alkyl, C1-C2 alkoxy, C1-C2 monohaloalkyl, C1-C2 polyhaloalkyl, C1-C2 alkoxy, C1-C2 aminoalkyl, C1-C2 hydroxyalkyl, C1-C2 monoalkylamino, C1-C2 dialkylamino, —$SO_2R^{16}$, and —$CO_2R^{16}$.

In a further aspect, $R^{14b}$ is hydrogen and each of $R^{14a}$, $R^{14c}$, $R^{14d}$, and $R^{14e}$ is independently selected from hydrogen, halogen, —OH, —CN, —$NO_2$, —$NH_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylamino. In a still further aspect, $R^{14b}$ is hydrogen and each of $R^{14a}$, $R^{14c}$, $R^{14d}$, and $R^{14e}$ is independently selected from hydrogen, halogen, —OH, —CN, —$NO_2$, —$NH_2$, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylamino. In yet a further aspect, $R^{14b}$ is hydrogen and each of $R^{14a}$, $R^{14c}$, $R^{14d}$, and $R^{14e}$ is independently selected from hydrogen, —F, —Cl, —Br, —OH, —CN, —$NO_2$, —$NH_2$, —$CH_3$, —$CFH_2$, —$CF_2H$, —$CF_3$, —$OCH_3$, —$NH(CH_3)$, and —$N(CH_3)_2$.

In a further aspect, $R^{14b}$ is hydrogen and each of $R^{14a}$, $R^{14c}$, $R^{14d}$, and $R^{14e}$ is independently selected from hydrogen, halogen, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylamino. In a still further aspect, $R^{14b}$ is hydrogen and each of $R^{14a}$, $R^{14c}$, $R^{14d}$, and $R^{14e}$ is independently selected from hydrogen, halogen, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylamino. In yet a further aspect, $R^{14b}$ is hydrogen and each of $R^{14a}$, $R^{14c}$, $R^{14d}$, and $R^{14e}$ is independently selected from hydrogen, —F, —Cl, —Br, —CH$_3$, —CFH$_2$, —CF$_2$H, —CF$_3$, —OCH$_3$, —NH(CH$_3$), and —N(CH$_3$)$_2$.

In a further aspect, $R^{14b}$ is hydrogen and each of $R^{14a}$, $R^{14c}$, $R^{14d}$, and $R^{14e}$ is independently selected from hydrogen, C1-C4 monohaloalkyl, and C1-C4 polyhaloalkyl. In a still further aspect, $R^{14b}$ is hydrogen and each of $R^{14a}$, $R^{14c}$, $R^{14d}$, and $R^{14e}$ is independently selected from hydrogen, C1-C2 monohaloalkyl, and C1-C2 polyhaloalkyl. In yet a further aspect, $R^{14b}$ is hydrogen and each of $R^{14a}$, $R^{14c}$, $R^{14d}$, and $R^{14e}$ is independently is selected from hydrogen, —CFH$_2$, —CF$_2$H, and —CF$_3$.

In a further aspect, $R^{14b}$ is hydrogen and each of $R^{14a}$, $R^{14c}$, $R^{14d}$, and $R^{14e}$ is independently selected from hydrogen and C1-C4 alkyl. In a still further aspect, $R^{14b}$ is hydrogen and each of $R^{14a}$, $R^{14c}$, $R^{14d}$, and $R^{14e}$ is independently selected from hydrogen, methyl, ethyl, iso-propyl, and n-propyl. In yet a further aspect, $R^{14b}$ is hydrogen and each of $R^{14a}$, $R^{14c}$, $R^{14d}$, and $R^{14e}$ is independently selected from hydrogen, methyl, and ethyl. In an even further aspect, $R^{14b}$ is hydrogen and each of $R^{14a}$, $R^{14c}$, $R^{14d}$, and $R^{14e}$ is independently selected from hydrogen and methyl. In a still further aspect, $R^{14b}$ is hydrogen and each of $R^{14a}$, $R^{14c}$, $R^{14d}$, and $R^{14e}$ is independently selected from hydrogen and ethyl.

In a further aspect, $R^{14b}$ is hydrogen and each of $R^{14a}$, $R^{14c}$, $R^{14d}$, and $R^{14e}$ is independently selected from hydrogen and halogen. In a still further aspect, $R^{14b}$ is hydrogen and each of $R^{14a}$, $R^{14c}$, $R^{14d}$, and $R^{14e}$ is independently selected from hydrogen, —F, —Cl, and —Br. In yet a further aspect, $R^{14b}$ is hydrogen and each of $R^{14a}$, $R^{14c}$, $R^{14d}$, and $R^{14e}$ is independently selected from hydrogen, —F, and —Cl. In an even further aspect, $R^{14b}$ is hydrogen and each of $R^{14a}$, $R^{14c}$, $R^{14d}$, and $R^{14e}$ is independently selected from hydrogen and —F. In a still further aspect, $R^{14b}$ is hydrogen and each of $R^{14a}$, $R^{14c}$, $R^{14d}$, and $R^{14e}$ is independently selected from hydrogen and —Cl.

In a further aspect, $R^{14b}$ is hydrogen and each of $R^{14a}$, $R^{14c}$, $R^{14d}$, and $R^{14e}$ is independently selected from hydrogen, —OH, —SH, —CN, —NO$_2$, —NH$_2$, —SO$_2$R$^{16}$, and —CO$_2$R$^{16}$. In a still further aspect, $R^{14b}$ is hydrogen and each of $R^{14a}$, $R^{14c}$, $R^{14d}$, and $R^{14e}$ is independently selected from hydrogen, —OH, —SH, —NH$_2$, —SO$_2$R$^{16}$, and —CO$_2$R$^{16}$. In yet a further aspect, $R^{14b}$ is hydrogen and each of $R^{14a}$, $R^{14c}$, $R^{14d}$, and $R^{14e}$ is independently selected from hydrogen, —SO$_2$R$^{16}$, and —CO$_2$R$^{16}$. In an even further aspect, $R^{14b}$ is hydrogen and each of $R^{14a}$, $R^{14c}$, $R^{14d}$, and $R^{14e}$ is independently selected from hydrogen and —SO$_2$R$^{16}$. In a still further aspect, $R^{14b}$ is hydrogen and each of $R^{14a}$, $R^{14c}$, $R^{14d}$, and $R^{14e}$ is independently selected from hydrogen and —CO$_2$R$^{16}$.

In a further aspect, $R^{14c}$ is hydrogen and each of $R^{14a}$, $R^{14b}$, $R^{14d}$, and $R^{14e}$ is independently selected from hydrogen, halogen, —OH, —SH, —CN, —NO$_2$, —NH$_2$, C1-C4 alkyl, C1-C4 alkoxy, C1-C4 monohaloalkyl, C1-C4 polyhaloalkyl, C1-C4 alkoxy, C1-C4 aminoalkyl, C1-C4 hydroxyalkyl, C1-C4 monoalkylamino, C1-C4 dialkylamino, —SO$_2$R$^{16}$, and —CO$_2$R$^{16}$. In a still further aspect, $R^{14c}$ is hydrogen and each of $R^{14a}$, $R^{14b}$, $R^{14d}$, and $R^{14e}$ is independently selected from hydrogen, halogen, —OH, —SH, —CN, —NO$_2$, —NH$_2$, C1-C2 alkyl, C1-C2 alkoxy, C1-C2 monohaloalkyl, C1-C2 polyhaloalkyl, C1-C2 alkoxy, C1-C2 aminoalkyl, C1-C2 hydroxyalkyl, C1-C2 monoalkylamino, C1-C2 dialkylamino, —SO$_2$R$^{16}$, and —CO$_2$R$^{16}$.

In a further aspect, $R^{14c}$ is hydrogen and each of $R^{14a}$, $R^{14b}$, $R^{14d}$, and $R^{14e}$ is independently selected from hydrogen, halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylamino. In a still further aspect, $R^{14c}$ is hydrogen and each of $R^{14a}$, $R^{14b}$, $R^{14d}$, and $R^{14e}$ is independently selected from hydrogen, halogen, —OH, —CN, —NO$_2$, —NH$_2$, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylamino. In yet a further aspect, $R^{14c}$ is hydrogen and each of $R^{14a}$, $R^{14b}$, $R^{14d}$, and $R^{14e}$ is independently selected from hydrogen, —F, —Cl, —Br, —OH, —CN, —NO$_2$, —NH$_2$, —CH$_3$, —CFH$_2$, —CF$_2$H, —CF$_3$, —OCH$_3$, —NH(CH$_3$), and —N(CH$_3$)$_2$.

In a further aspect, $R^{14c}$ is hydrogen and each of $R^{14a}$, $R^{14b}$, $R^{14d}$, and $R^{14e}$ is independently selected from hydrogen, halogen, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylamino. In a still further aspect, $R^{14c}$ is hydrogen and each of $R^{14a}$, $R^{14b}$, $R^{14d}$, and $R^{14e}$ is independently selected from hydrogen, halogen, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylamino. In yet a further aspect, $R^{14c}$ is hydrogen and each of $R^{14a}$, $R^{14b}$, $R^{14d}$, and $R^{14e}$ is independently selected from hydrogen, —F, —Cl, —Br, —CH$_3$, —CFH$_2$, —CF$_2$H, —CF$_3$, —OCH$_3$, —NH(CH$_3$), and —N(CH$_3$)$_2$.

In a further aspect, $R^{14c}$ is hydrogen and each of $R^{14a}$, $R^{14b}$, $R^{14d}$, and $R^{14e}$ is independently selected from hydrogen, C1-C4 monohaloalkyl, and C1-C4 polyhaloalkyl. In a still further aspect, $R^{14c}$ is hydrogen and each of $R^{14a}$, $R^{14b}$, $R^{14d}$, and $R^{14e}$ is independently selected from hydrogen, C1-C2 monohaloalkyl, and C1-C2 polyhaloalkyl. In yet a further aspect, $R^{14c}$ is hydrogen and each of $R^{14a}$, $R^{14b}$, $R^{14d}$, and $R^{14e}$ is independently is selected from hydrogen, —CFH$_2$, —CF$_2$H, and —CF$_3$.

In a further aspect, $R^{14c}$ is hydrogen and each of $R^{14a}$, $R^{14b}$, $R^{14d}$, and $R^{14e}$ is independently selected from hydrogen and C1-C4 alkyl. In a still further aspect, $R^{14c}$ is hydrogen and each of $R^{14a}$, $R^{14b}$, $R^{14d}$, and $R^{14e}$ is independently selected from hydrogen, methyl, ethyl, iso-propyl, and n-propyl. In yet a further aspect, $R^{14c}$ is hydrogen and each of $R^{14a}$, $R^{14b}$, $R^{14d}$, and $R^{14e}$ is independently selected from hydrogen, methyl, and ethyl. In an even further aspect, $R^{14c}$ is hydrogen and each of $R^{14a}$, $R^{14b}$, $R^{14d}$, and $R^{14e}$ is independently selected from hydrogen and methyl. In a still further aspect, $R^{14c}$ is hydrogen and each of $R^{14a}$, $R^{14b}$, $R^{14d}$, and $R^{14e}$ is independently selected from hydrogen and ethyl.

In a further aspect, $R^{14c}$ is hydrogen and each of $R^{14a}$, $R^{14b}$, $R^{14d}$, and $R^{14e}$ is independently selected from hydrogen and halogen. In a still further aspect, $R^{14c}$ is hydrogen and each of $R^{14a}$, $R^{14b}$, $R^{14d}$, and $R^{14e}$ is independently selected from hydrogen, —F, —Cl, and —Br. In yet a further aspect, $R^{14c}$ is hydrogen and each of $R^{14a}$, $R^{14b}$, $R^{14d}$, and $R^{14e}$ is independently selected from hydrogen, —F, and —Cl. In an even further aspect, $R^{14c}$ is hydrogen and each of $R^{14a}$, $R^{14b}$, $R^{14d}$, and $R^{14e}$ is independently selected from hydrogen and —F. In a still further aspect, $R^{14c}$ is hydrogen and each of $R^{14a}$, $R^{14b}$, $R^{14d}$, and $R^{14e}$ is independently selected from hydrogen and —Cl.

In a further aspect, $R^{14c}$ is hydrogen and each of $R^{14a}$, $R^{14b}$, $R^{14d}$, and $R^{14e}$ is independently selected from hydrogen, —OH, —SH, —CN, —NO$_2$, —NH$_2$, —SO$_2$R$^{16}$, and —CO$_2$R$^{16}$. In a still further aspect, R$^{14c}$ is hydrogen and each of R$^{14a}$, R$^{14b}$, R$^{14d}$, and R$^{14e}$ is independently selected from hydrogen, —OH, —SH, —NH$_2$, —SO$_2$R$^{16}$, and —CO$_2$R$^{16}$. In yet a further aspect, R$^{14c}$ is hydrogen and each of R$^{14a}$, R$^{14b}$, R$^{14d}$, and R$^{14e}$ is independently selected from hydrogen, —SO$_2$R$^{16}$, and —CO$_2$R$^{16}$. In an even further aspect, R$^{14c}$ is hydrogen and each of R$^{14a}$, R$^{14b}$, R$^{14d}$, and R$^{14e}$ is independently selected from hydrogen and —SO$_2$R$^{16}$. In a still further aspect, R$^{14c}$ is hydrogen and each of R$^{14a}$, R$^{14b}$, R$^{14d}$, and R$^{14e}$ is independently selected from hydrogen and —CO$_2$R$^{16}$.

In a further aspect, R$^{14d}$ is hydrogen and each of R$^{14a}$, R$^{14b}$, R$^{14c}$, and R$^{14e}$ is independently selected from hydrogen, halogen, —OH, —SH, —CN, —NO$_2$, —NH$_2$, C1-C4 alkyl, C1-C4 alkoxy, C1-C4 monohaloalkyl, C1-C4 polyhaloalkyl, C1-C4 alkoxy, C1-C4 aminoalkyl, C1-C4 hydroxyalkyl, C1-C4 monoalkylamino, C1-C4 dialkylamino, —SO$_2$R$^{16}$, and —CO$_2$R$^{16}$. In a still further aspect, R$^{14d}$ is hydrogen and each of R$^{14a}$, R$^{14b}$, R$^{14c}$, and R$^{14e}$ is independently selected from hydrogen, halogen, —OH, —SH, —CN, —NO$_2$, —NH$_2$, C1-C2 alkyl, C1-C2 alkoxy, C1-C2 monohaloalkyl, C1-C2 polyhaloalkyl, C1-C2 alkoxy, C1-C2 aminoalkyl, C1-C2 hydroxyalkyl, C1-C2 monoalkylamino, C1-C2 dialkylamino, —SO$_2$R$^{16}$, and —CO$_2$R$^{16}$.

In a further aspect, R$^{14d}$ is hydrogen and each of R$^{14a}$, R$^{14b}$, R$^{14c}$, and R$^{14e}$ is independently selected from hydrogen, halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylamino. In a still further aspect, R$^{14d}$ is hydrogen and each of R$^{14a}$, R$^{14b}$, R$^{14c}$, and R$^{14e}$ is independently selected from hydrogen, halogen, —OH, —CN, —NO$_2$, —NH$_2$, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylamino. In yet a further aspect, R$^{14d}$ is hydrogen and each of R$^{14a}$, R$^{14b}$, R$^{14c}$, and R$^{14e}$ is independently selected from hydrogen, —F, —Cl, —Br, —OH, —CN, —NO$_2$, —NH$_2$, —CH$_3$, —CFH$_2$, —CF$_2$H, —CF$_3$, —OCH$_3$, —NH(CH$_3$), and —N(CH$_3$)$_2$.

In a further aspect, R$^{14d}$ is hydrogen and each of R$^{14a}$, R$^{14b}$, R$^{14c}$, and R$^{14e}$ is independently selected from hydrogen, halogen, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylamino. In a still further aspect, R$^{14d}$ is hydrogen and each of R$^{14a}$, R$^{14b}$, R$^{14c}$, and R$^{14e}$ is independently selected from hydrogen, halogen, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylamino. In yet a further aspect, R$^{14d}$ is hydrogen and each of R$^{14a}$, R$^{14b}$, R$^{14c}$, and R$^{14e}$ is independently selected from hydrogen, —F, —Cl, —Br, —CH$_3$, —CFH$_2$, —CF$_2$H, —CF$_3$, —OCH$_3$, —NH(CH$_3$), and —N(CH$_3$)$_2$.

In a further aspect, R$^{14d}$ is hydrogen and each of R$^{14a}$, R$^{14b}$, R$^{14c}$, and R$^{14e}$ is independently selected from hydrogen, C1-C4 monohaloalkyl, and C1-C4 polyhaloalkyl. In a still further aspect, R$^{14d}$ is hydrogen and each of R$^{14a}$, R$^{14b}$, R$^{14c}$, and R$^{14e}$ is independently selected from hydrogen, C1-C2 monohaloalkyl, and C1-C2 polyhaloalkyl. In yet a further aspect, R$^{14d}$ is hydrogen and each of R$^{14a}$, R$^{14b}$, R$^{14c}$, and R$^{14e}$ is independently is selected from hydrogen, —CFH$_2$, —CF$_2$H, and —CF$_3$.

In a further aspect, R$^{14d}$ is hydrogen and each of R$^{14a}$, R$^{14b}$, R$^{14c}$, and R$^{14e}$ is independently selected from hydrogen and C1-C4 alkyl. In a still further aspect, R$^{14d}$ is hydrogen and each of R$^{14a}$, R$^{14b}$, R$^{14c}$, and R$^{14e}$ is independently selected from hydrogen, methyl, ethyl, iso-propyl, and n-propyl. In yet a further aspect, R$^{14d}$ is hydrogen and each of R$^{14a}$, R$^{14b}$, R$^{14c}$, and R$^{14e}$ is independently selected from hydrogen, methyl, and ethyl. In an even further aspect, R$^{14d}$ is hydrogen and each of R$^{14a}$, R$^{14b}$, R$^{14c}$, and R$^{14e}$ is independently selected from hydrogen and methyl. In a still further aspect, R$^{14d}$ is hydrogen and each of R$^{14a}$, R$^{14b}$, R$^{14c}$, and R$^{14e}$ is independently selected from hydrogen and ethyl.

In a further aspect, R$^{14d}$ is hydrogen and each of R$^{14a}$, R$^{14b}$, R$^{14c}$, and R$^{14e}$ is independently selected from hydrogen and halogen. In a still further aspect, R$^{14d}$ is hydrogen and each of R$^{14a}$, R$^{14b}$, R$^{14c}$, and R$^{14e}$ is independently selected from hydrogen, —F, —Cl, and —Br. In yet a further aspect, R$^{14d}$ is hydrogen and each of R$^{14a}$, R$^{14b}$, R$^{14c}$, and R$^{14e}$ is independently selected from hydrogen, —F, and —Cl. In an even further aspect, R$^{14d}$ is hydrogen and each of R$^{14a}$, R$^{14b}$, R$^{14c}$, and R$^{14e}$ is independently selected from hydrogen and —F. In a still further aspect, R$^{14d}$ is hydrogen and each of R$^{14a}$, R$^{14b}$, R$^{14c}$, and R$^{14e}$ is independently selected from hydrogen and —Cl.

In a further aspect, R$^{14d}$ is hydrogen and each of R$^{14a}$, R$^{14b}$, R$^{14c}$, and R$^{14e}$ is independently selected from hydrogen, —OH, —SH, —CN, —NO$_2$, —NH$_2$, —SO$_2$R$^{16}$, and —CO$_2$R$^{16}$. In a still further aspect, R$^{14d}$ is hydrogen and each of R$^{14a}$, R$^{14b}$, R$^{14c}$, and R$^{14e}$ is independently selected from hydrogen, —OH, —SH, —NH$_2$, —SO$_2$R$^{16}$, and —CO$_2$R$^{16}$. In yet a further aspect, R$^{14d}$ is hydrogen and each of R$^{14a}$, R$^{14b}$, R$^{14c}$, and R$^{14e}$ is independently selected from hydrogen, —SO$_2$R$^{16}$, and —CO$_2$R$^{16}$. In an even further aspect, R$^{14d}$ is hydrogen and each of R$^{14a}$, R$^{14b}$, R$^{14c}$, and R$^{14e}$ is independently selected from hydrogen and —SO$_2$R$^{16}$. In a still further aspect, R$^{14d}$ is hydrogen and each of R$^{14a}$, R$^{14b}$, R$^{14c}$, and R$^{14e}$ is independently selected from hydrogen and —CO$_2$R$^{16}$.

In a further aspect, R$^{14e}$ is hydrogen and each of R$^{14a}$, R$^{14b}$, R$^{14c}$, and R$^{14d}$ is independently selected from hydrogen, halogen, —OH, —SH, —CN, —NO$_2$, —NH$_2$, C1-C4 alkyl, C1-C4 alkoxy, C1-C4 monohaloalkyl, C1-C4 polyhaloalkyl, C1-C4 alkoxy, C1-C4 aminoalkyl, C1-C4 hydroxyalkyl, C1-C4 monoalkylamino, C1-C4 dialkylamino, —SO$_2$R$^{16}$, and —CO$_2$R$^{16}$. In a still further aspect, R$^{14e}$ is hydrogen and each of R$^{14a}$, R$^{14b}$, R$^{14c}$, and R$^{14d}$ is independently selected from hydrogen, halogen, —OH, —SH, —CN, —NO$_2$, —NH$_2$, C1-C2 alkyl, C1-C2 alkoxy, C1-C2 monohaloalkyl, C1-C2 polyhaloalkyl, C1-C2 alkoxy, C1-C2 aminoalkyl, C1-C2 hydroxyalkyl, C1-C2 monoalkylamino, C1-C2 dialkylamino, —SO$_2$R$^{16}$, and —CO$_2$R$^{16}$.

In a further aspect, R$^{14e}$ is hydrogen and each of R$^{14a}$, R$^{14b}$, R$^{14c}$, and R$^{14d}$ is independently selected from hydrogen, halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylamino. In a still further aspect, R$^{14e}$ is hydrogen and each of R$^{14a}$, R$^{14b}$, R$^{14c}$, and R$^{14d}$ is independently selected from hydrogen, halogen, —OH, —CN, —NO$_2$, —NH$_2$, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylamino. In yet a further aspect, R$^{14e}$ is hydrogen and each of R$^{14a}$, R$^{14b}$, R$^{14c}$, and R$^{14d}$ is independently selected from hydrogen, —F, —Cl, —Br, —OH, —CN, —NO$_2$, —NH$_2$, —CH$_3$, —CFH$_2$, —CF$_2$H, —CF$_3$, —OCH$_3$, —NH(CH$_3$), and —N(CH$_3$)$_2$.

In a further aspect, $R^{14e}$ is hydrogen and each of $R^{14a}$, $R^{14b}$, $R^{14c}$, and $R^{14d}$ is independently selected from hydrogen, halogen, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylamino. In a still further aspect, $R^{14e}$ is hydrogen and each of $R^{14a}$, $R^{14b}$, $R^{14c}$, and $R^{14d}$ is independently selected from hydrogen, halogen, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylamino. In yet a further aspect, $R^{14e}$ is hydrogen and each of $R^{14a}$, $R^{14b}$, $R^{14c}$, and $R^{14d}$ is independently selected from hydrogen, —F, —Cl, —Br, —CH$_3$, —CFH$_2$, —CF$_2$H, —CF$_3$, —OCH$_3$, —NH(CH$_3$), and —N(CH$_3$)$_2$.

In a further aspect, $R^{14e}$ is hydrogen and each of $R^{14a}$, $R^{14b}$, $R^{14c}$, and $R^{14d}$ is independently selected from hydrogen, C1-C4 monohaloalkyl, and C1-C4 polyhaloalkyl. In a still further aspect, $R^{14e}$ is hydrogen and each of $R^{14a}$, $R^{14b}$, $R^{14c}$, and $R^{14d}$ is independently selected from hydrogen, C1-C2 monohaloalkyl, and C1-C2 polyhaloalkyl. In yet a further aspect, $R^{14e}$ is hydrogen and each of $R^{14a}$, $R^{14b}$, $R^{14c}$, and $R^{14d}$ is independently is selected from hydrogen, —CFH$_2$, —CF$_2$H, and —CF$_3$.

In a further aspect, $R^{14e}$ is hydrogen and each of $R^{14a}$, $R^{14b}$, $R^{14c}$, and $R^{14d}$ is independently selected from hydrogen and C1-C4 alkyl. In a still further aspect, $R^{14e}$ is hydrogen and each of $R^{14a}$, $R^{14b}$, $R^{14c}$, and $R^{14d}$ is independently selected from hydrogen, methyl, ethyl, iso-propyl, and n-propyl. In yet a further aspect, $R^{14e}$ is hydrogen and each of $R^{14a}$, $R^{14b}$, $R^{14c}$, and $R^{14d}$ is independently selected from hydrogen, methyl, and ethyl. In an even further aspect, $R^{14e}$ is hydrogen and each of $R^{14a}$, $R^{14b}$, $R^{14c}$, and $R^{14d}$ is independently selected from hydrogen and methyl. In a still further aspect, $R^{14e}$ is hydrogen and each of $R^{14a}$, $R^{14b}$, $R^{14c}$, and $R^{14d}$ is independently selected from hydrogen and ethyl.

In a further aspect, $R^{14e}$ is hydrogen and each of $R^{14a}$, $R^{14b}$, $R^{14c}$, and $R^{14d}$ is independently selected from hydrogen and halogen. In a still further aspect, $R^{14e}$ is hydrogen and each of $R^{14a}$, $R^{14b}$, $R^{14c}$, and $R^{14d}$ is independently selected from hydrogen, —F, —Cl, and —Br. In yet a further aspect, $R^{14e}$ is hydrogen and each of $R^{14a}$, $R^{14b}$, $R^{14c}$, and $R^{14d}$ is independently selected from hydrogen, —F, and —Cl. In an even further aspect, $R^{14e}$ is hydrogen and each of $R^{14a}$, $R^{14b}$, $R^{14c}$, and $R^{14d}$ is independently selected from hydrogen and —F. In a still further aspect, $R^{14e}$ is hydrogen and each of $R^{14a}$, $R^{14b}$, $R^{14c}$, and $R^{14d}$ is independently selected from hydrogen and —Cl.

In a further aspect, $R^{14e}$ is hydrogen and each of $R^{14a}$, $R^{14b}$, $R^{14c}$, and $R^{14d}$ is independently selected from hydrogen, —OH, —SH, —CN, —NO$_2$, —NH$_2$, —SO$_2$R$^{16}$, and —CO$_2$R$^{16}$. In a still further aspect, $R^{14e}$ is hydrogen and each of $R^{14a}$, $R^{14b}$, $R^{14c}$, and $R^{14d}$ is independently selected from hydrogen, —OH, —SH, —NH$_2$, —SO$_2$R$^{16}$, and —CO$_2$R$^{16}$. In yet a further aspect, $R^{14e}$ is hydrogen and each of $R^{14a}$, $R^{14b}$, $R^{14c}$, and $R^{14d}$ is independently selected from hydrogen, —SO$_2$R$^{16}$, and —CO$_2$R$^{16}$. In an even further aspect, $R^{14e}$ is hydrogen and each of $R^{14a}$, $R^{14b}$, $R^{14c}$, and $R^{14d}$ is independently selected from hydrogen and —SO$_2$R$^{16}$. In a still further aspect, $R^{14e}$ is hydrogen and each of $R^{14a}$, $R^{14b}$, $R^{14c}$, and $R^{14d}$ is independently selected from hydrogen and —CO$_2$R$^{16}$.

In a further aspect, two of $R^{14a}$, $R^{14b}$, $R^{14c}$, $R^{14d}$, and $R^{14e}$ are hydrogen and three of $R^{14a}$, $R^{14b}$, $R^{14c}$, $R^{14d}$, and $R^{14e}$ are independently selected from halogen, —OH, —SH, —CN, —NO$_2$, —NH$_2$, C1-C4 alkyl, C1-C4 alkoxy, C1-C4 monohaloalkyl, C1-C4 polyhaloalkyl, C1-C4 alkoxy, C1-C4 aminoalkyl, C1-C4 hydroxyalkyl, C1-C4 monoalkylamino, C1-C4 dialkylamino, —SO$_2$R$^{15}$, and —CO$_2$R$^{15}$. In a still further aspect, two of $R^{14a}$, $R^{14b}$, $R^{14c}$, $R^{14d}$, and $R^{14e}$ are hydrogen and three of $R^{14a}$, $R^{14b}$, $R^{14c}$, $R^{14d}$, and $R^{14e}$ are independently selected from halogen, —OH, —SH, —CN, —NO$_2$, —NH$_2$, C1-C2 alkyl, C1-C2 alkoxy, C1-C2 monohaloalkyl, C1-C2 polyhaloalkyl, C1-C2 alkoxy, C1-C2 aminoalkyl, C1-C2 hydroxyalkyl, C1-C2 monoalkylamino, C1-C2 dialkylamino, —SO$_2$R$^{15}$, and —CO$_2$R$^{15}$.

In a further aspect, two of $R^{14a}$, $R^{14b}$, $R^{14c}$, $R^{14d}$, and $R^{14e}$ are hydrogen and three of $R^{14a}$, $R^{14b}$, $R^{14c}$, $R^{14d}$, and $R^{14e}$ are independently selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylamino. In a still further aspect, two of $R^{14a}$, $R^{14b}$, $R^{14c}$, $R^{14d}$, and $R^{14e}$ are hydrogen and three of $R^{14a}$, $R^{14b}$, $R^{14c}$, $R^{14d}$, and $R^{14e}$ are independently selected from halogen, —OH, —CN, —NO$_2$, —NH$_2$, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylamino. In yet a further aspect, two of $R^{14a}$, $R^{14b}$, $R^{14c}$, $R^{14d}$, and $R^{14e}$ are hydrogen and three of $R^{14a}$, $R^{14b}$, $R^{14c}$, $R^{14d}$, and $R^{14e}$ is independently selected from —F, —Cl, —Br, —OH, —CN, —NO$_2$, —NH$_2$, —CH$_3$, —CFH$_2$, —CF$_2$H, —CF$_3$, —OCH$_3$, —NH(CH$_3$), and —N(CH$_3$)$_2$.

In a further aspect, two of $R^{14a}$, $R^{14b}$, $R^{14c}$, $R^{14d}$, and $R^{14e}$ are hydrogen and three of $R^{14a}$, $R^{14b}$, $R^{14c}$, $R^{14d}$, and $R^{14e}$ are independently selected from halogen, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylamino. In a still further aspect, two of $R^{14a}$, $R^{14b}$, $R^{14c}$, $R^{14d}$, and $R^{14e}$ are hydrogen and three of $R^{14a}$, $R^{14b}$, $R^{14c}$, $R^{14d}$, and $R^{14e}$ are independently selected from halogen, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylamino. In yet a further aspect, two of $R^{14a}$, $R^{14b}$, $R^{14c}$, $R^{14d}$, and $R^{14e}$ are hydrogen and three of $R^{14a}$, $R^{14b}$, $R^{14c}$, $R^{14d}$, and $R^{14e}$ is independently selected from —F, —Cl, —Br, —CH$_3$, —CFH$_2$, —CF$_2$H, —CF$_3$, —OCH$_3$, —NH(CH$_3$), and —N(CH$_3$)$_2$.

In a further aspect, two of $R^{14a}$, $R^{14b}$, $R^{14c}$, $R^{14d}$, and $R^{14e}$ are hydrogen and three of $R^{14a}$, $R^{14b}$, $R^{14c}$, $R^{14d}$, and $R^{14e}$ are independently selected from C1-C4 monohaloalkyl and C1-C4 polyhaloalkyl. In a still further aspect, two of $R^{14a}$, $R^{14b}$, $R^{14c}$, $R^{14d}$, and $R^{14e}$ are hydrogen and three of $R^{14a}$, $R^{14b}$, $R^{14c}$, $R^{14d}$, and $R^{14e}$ are independently selected from C1-C2 monohaloalkyl and C1-C2 polyhaloalkyl. In yet a further aspect, two of $R^{14a}$, $R^{14b}$, $R^{14c}$, $R^{14d}$, and $R^{14e}$ are hydrogen and three of $R^{14a}$, $R^{14b}$, $R^{14c}$, $R^{14d}$, and $R^{14e}$ are independently selected from —CFH$_2$, —CF$_2$H, and —CF$_3$.

In a further aspect, two of $R^{14a}$, $R^{14b}$, $R^{14c}$, $R^{14d}$, and $R^{14e}$ are hydrogen and three of $R^{14a}$, $R^{14b}$, $R^{14c}$, $R^{14d}$, and $R^{14e}$ are independently selected from C1-C4 alkyl. In a still further aspect, two of $R^{14a}$, $R^{14b}$, $R^{14c}$, $R^{14d}$, and $R^{14e}$ are hydrogen and three of $R^{14a}$, $R^{14b}$, $R^{14c}$, $R^{14d}$, and $R^{14e}$ are independently selected from methyl, ethyl, iso-propyl, and n-propyl. In yet a further aspect, two of $R^{14a}$, $R^{14b}$, $R^{14c}$, $R^{14d}$, and $R^{14e}$ are hydrogen and three of $R^{14a}$, $R^{14b}$, $R^{14c}$, $R^{14d}$, and $R^{14e}$ are independently selected from methyl and ethyl. In an even further aspect, two of $R^{14a}$, $R^{14b}$, $R^{14c}$, $R^{14d}$, and $R^{14e}$ are hydrogen and three of $R^{14a}$, $R^{14b}$, $R^{14c}$, $R^{14d}$, and $R^{14e}$ are methyl. In a still further aspect, two of $R^{14a}$, $R^{14b}$, $R^{14c}$, $R^{14d}$, and $R^{14e}$ are hydrogen and three of $R^{14a}$, $R^{14b}$, $R^{14c}$, $R^{14d}$, and $R^{14e}$ are ethyl.

In a further aspect, two of $R^{14a}$, $R^{14b}$, $R^{14c}$, $R^{14d}$, and $R^{14e}$ are hydrogen and three of $R^{14a}$, $R^{14b}$, $R^{14c}$, $R^{14d}$, and $R^{14e}$ are independently selected from halogen. In a still further aspect, two of $R^{14a}$, $R^{14b}$, $R^{14c}$, $R^{14d}$, and $R^{14e}$ are hydrogen and three of $R^{14a}$, $R^{14b}$, $R^{14c}$, $R^{14d}$, and $R^{14e}$ are independently selected from —F, —Cl, and —Br. In yet a further aspect, two of $R^{14a}$, $R^{14b}$, $R^{14c}$, $R^{14d}$, and $R^{14e}$ are hydrogen and three of $R^{14a}$, $R^{14b}$, $R^{14c}$, $R^{14d}$, and $R^{14e}$ are independently selected from —F and —Cl. In an even further aspect, two of $R^{14a}$, $R^{14b}$, $R^{14c}$, $R^{14d}$, and $R^{14e}$ are hydrogen and three of $R^{14a}$, $R^{14b}$, $R^{14c}$, $R^{14d}$, and $R^{14e}$ are —F. In a still further aspect, two of $R^{14a}$, $R^{14b}$, $R^{14c}$, $R^{14d}$, and $R^{14e}$ are hydrogen and three of $R^{14a}$, $R^{14b}$, $R^{14c}$, $R^{14d}$, and $R^{14e}$ are —Cl. In yet a further aspect, two of $R^{14a}$, $R^{14b}$, $R^{14c}$, $R^{14d}$, and $R^{14e}$ are hydrogen and three of $R^{14a}$, $R^{14b}$, $R^{14c}$, $R^{14d}$, and $R^{14e}$ are —Br.

In a further aspect, two of $R^{14a}$, $R^{14b}$, $R^{14c}$, $R^{14d}$, and $R^{14e}$ are hydrogen and three of $R^{14a}$, $R^{14b}$, $R^{14c}$, $R^{14d}$, and $R^{14e}$ are independently selected from hydrogen, —OH, —SH, —CN, —NO$_2$, —NH$_2$, —SO$_2$R$^{16}$, and —CO$_2$R$^{16}$. In a still further aspect, two of $R^{14a}$, $R^{14b}$, $R^{14c}$, $R^{14d}$, and $R^{14e}$ are hydrogen and three of $R^{14a}$, $R^{14b}$, $R^{14c}$, $R^{14d}$, and $R^{14e}$ are independently selected from hydrogen, —OH, —SH, —NH$_2$, —SO$_2$R$^{16}$, and —CO$_2$R$^{16}$. In yet a further aspect, two of $R^{14a}$, $R^{14b}$, $R^{14c}$, $R^{14d}$, and $R^{14e}$ are hydrogen and three of $R^{14a}$, $R^{14b}$, $R^{14c}$, $R^{14d}$, and $R^{14e}$ are independently selected from hydrogen, —SO$_2$R$^{16}$, and —CO$_2$R$^{16}$. In an even further aspect, two of $R^{14a}$, $R^{14b}$, $R^{14c}$, $R^{14d}$, and $R^{14e}$ are hydrogen and three of $R^{14a}$, $R^{14b}$, $R^{14c}$, $R^{14d}$, and $R^{14e}$ are independently selected from hydrogen and —SO$_2$R$^{16}$. In a still further aspect, two of $R^{14a}$, $R^{14b}$, $R^{14c}$, $R^{14d}$, and $R^{14e}$ are hydrogen and three of $R^{14a}$, $R^{14b}$, $R^{14c}$, $R^{14d}$, and $R^{14e}$ are independently selected from hydrogen and —CO$_2$R$^{16}$.

In a further aspect, three of $R^{14a}$, $R^{14b}$, $R^{14c}$, $R^{14d}$, and $R^{14e}$ are hydrogen and two of $R^{14a}$, $R^{14b}$, $R^{14c}$, $R^{14d}$, and $R^{14e}$ are independently selected from halogen, —OH, —SH, —CN, —NO$_2$, —NH$_2$, C1-C4 alkyl, C1-C4 alkoxy, C1-C4 monohaloalkyl, C1-C4 polyhaloalkyl, C1-C4 alkoxy, C1-C4 aminoalkyl, C1-C4 hydroxyalkyl, C1-C4 monoalkylamino, C1-C4 dialkylamino, —SO$_2$R$^{15}$, and —CO$_2$R$^{15}$. In a still further aspect, three of $R^{14a}$, $R^{14b}$, $R^{14c}$, $R^{14d}$, and $R^{14e}$ are hydrogen and two of $R^{14a}$, $R^{14b}$, $R^{14c}$, $R^{14d}$, and $R^{14e}$ is independently selected from halogen, —OH, —SH, —CN, —NO$_2$, —NH$_2$, C1-C2 alkyl, C1-C2 alkoxy, C1-C2 monohaloalkyl, C1-C2 polyhaloalkyl, C1-C2 alkoxy, C1-C2 aminoalkyl, C1-C2 hydroxyalkyl, C1-C2 monoalkylamino, C1-C2 dialkylamino, —SO$_2$R$^{15}$, and —CO$_2$R$^{15}$.

In a further aspect, three of $R^{14a}$, $R^{14b}$, $R^{14c}$, $R^{14d}$, and $R^{14e}$ are hydrogen and two of $R^{14a}$, $R^{14b}$, $R^{14c}$, $R^{14d}$, and $R^{14e}$ are independently selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylamino. In a still further aspect, three of $R^{14a}$, $R^{14b}$, $R^{14c}$, $R^{14d}$, and $R^{14e}$ are hydrogen and two of $R^{14a}$, $R^{14b}$, $R^{14c}$, $R^{14d}$, and $R^{14e}$ are independently selected from halogen, —OH, —CN, —NO$_2$, —NH$_2$, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylamino. In yet a further aspect, three of $R^{14a}$, $R^{14b}$, $R^{14c}$, $R^{14d}$, and $R^{14e}$ are hydrogen and two of $R^{14a}$, $R^{14b}$, $R^{14c}$, $R^{14d}$, and $R^{14e}$ is independently selected from —F, —Cl, —Br, —OH, —CN, —NO$_2$, —NH$_2$, —CH$_3$, —CFH$_2$, —CF$_2$H, —CF$_3$, —OCH$_3$, —NH(CH$_3$), and —N(CH$_3$)$_2$.

In a further aspect, three of $R^{14a}$, $R^{14b}$, $R^{14c}$, $R^{14d}$, and $R^{14e}$ are hydrogen and two of $R^{14a}$, $R^{14b}$, $R^{14c}$, $R^{14d}$, and $R^{14e}$ are independently selected from halogen, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylamino. In a still further aspect, three of $R^{14a}$, $R^{14b}$, $R^{14c}$, $R^{14d}$, and $R^{14e}$ are hydrogen and two of $R^{14a}$, $R^{14b}$, $R^{14c}$, $R^{14d}$, and $R^{14e}$ are independently selected from halogen, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylamino. In yet a further aspect, three of $R^{14a}$, $R^{14b}$, $R^{14c}$, $R^{14d}$, and $R^{14e}$ are hydrogen and two of $R^{14a}$, $R^{14b}$, $R^{14c}$, $R^{14d}$, and $R^{14e}$ is independently selected from —F, —Cl, —Br, —CH$_3$, —CFH$_2$, —CF$_2$H, —CF$_3$, —OCH$_3$, —NH(CH$_3$), and —N(CH$_3$)$_2$.

In a further aspect, three of $R^{14a}$, $R^{14b}$, $R^{14c}$, $R^{14d}$, and $R^{14e}$ are hydrogen and two of $R^{14a}$, $R^{14b}$, $R^{14c}$, $R^{14d}$, and $R^{14e}$ are independently selected from C1-C4 monohaloalkyl and C1-C4 polyhaloalkyl. In a still further aspect, three of $R^{14a}$, $R^{14b}$, $R^{14c}$, $R^{14d}$, and $R^{14e}$ are hydrogen and two of $R^{14a}$, $R^{14b}$, $R^{14c}$, $R^{14d}$, and $R^{14e}$ are independently selected from C1-C2 monohaloalkyl and C1-C2 polyhaloalkyl. In yet a further aspect, three of $R^{14a}$, $R^{14b}$, $R^{14c}$, $R^{14d}$, and $R^{14e}$ are hydrogen and two of $R^{14a}$, $R^{14b}$, $R^{14c}$, $R^{14d}$, and $R^{14e}$ are independently selected from —CFH$_2$, —CF$_2$H, and —CF$_3$.

In a further aspect, three of $R^{14a}$, $R^{14b}$, $R^{14c}$, $R^{14d}$, and $R^{14e}$ are hydrogen and two of $R^{14a}$, $R^{14b}$, $R^{14c}$, $R^{14d}$, and $R^{14e}$ are independently selected from C1-C4 alkyl. In a still further aspect, three of $R^{14a}$, $R^{14b}$, $R^{14c}$, $R^{14d}$, and $R^{14e}$ are hydrogen and two of $R^{14a}$, $R^{14b}$, $R^{14c}$, $R^{14d}$, and $R^{14e}$ are selected from methyl, ethyl, iso-propyl, and n-propyl. In yet a further aspect, three of $R^{14a}$, $R^{14b}$, $R^{14c}$, $R^{14d}$, and $R^{14e}$ are hydrogen and two of $R^{14a}$, $R^{14b}$, $R^{14c}$, $R^{14d}$, and $R^{14e}$ are independently selected from methyl and ethyl. In an even further aspect, three of $R^{14a}$, $R^{14b}$, $R^{14c}$, $R^{14d}$, and $R^{14e}$ are hydrogen and two of $R^{14a}$, $R^{14b}$, $R^{14c}$, $R^{14d}$, and $R^{14e}$ are methyl. In a still further aspect, three of $R^{14a}$, $R^{14b}$, $R^{14c}$, $R^{14d}$, and $R^{14e}$ are hydrogen and two of $R^{14a}$, $R^{14b}$, $R^{14c}$, $R^{14d}$, and $R^{14e}$ are ethyl.

In a further aspect, three of $R^{14a}$, $R^{14b}$, $R^{14c}$, $R^{14d}$, and $R^{14e}$ are hydrogen and two of $R^{14a}$, $R^{14b}$, $R^{14c}$, $R^{14d}$, and $R^{14e}$ are independently selected from halogen. In a still further aspect, three of $R^{14a}$, $R^{14b}$, $R^{14c}$, $R^{14d}$, and $R^{14e}$ are hydrogen and two of $R^{14a}$, $R^{14b}$, $R^{14c}$, $R^{14d}$, and $R^{14e}$ are independently selected from —F, —Cl, and —Br. In yet a further aspect, three of $R^{14a}$, $R^{14b}$, $R^{14c}$, $R^{14d}$, and $R^{14e}$ are hydrogen and two of $R^{14a}$, $R^{14b}$, $R^{14c}$, $R^{14d}$, and $R^{14e}$ are independently selected from —F and —Cl. In an even further aspect, three of $R^{14a}$, $R^{14b}$, $R^{14c}$, $R^{14d}$, and $R^{14e}$ are hydrogen and two of $R^{14a}$, $R^{14b}$, $R^{14c}$, $R^{14d}$, and $R^{14e}$ are —F. In a still further aspect, three of $R^{14a}$, $R^{14b}$, $R^{14c}$, $R^{14d}$, and $R^{14e}$ are hydrogen and two of $R^{14a}$, $R^{14b}$, $R^{14c}$, $R^{14d}$, and $R^{14e}$ are —Cl. In yet a further aspect, three of $R^{14a}$, $R^{14b}$, $R^{14c}$, $R^{14d}$, and $R^{14e}$ are hydrogen and two of $R^{14a}$, $R^{14b}$, $R^{14c}$, $R^{14d}$, and $R^{14e}$ are —Br.

In a further aspect, three of $R^{14a}$, $R^{14b}$, $R^{14c}$, $R^{14d}$, and $R^{14e}$ are hydrogen and two of $R^{14a}$, $R^{14b}$, $R^{14c}$, $R^{14d}$, and $R^{14e}$ are independently selected from hydrogen, —OH, —SH, —CN, —NO$_2$, —NH$_2$, —SO$_2$R$^{16}$, and —CO$_2$R$^{16}$. In a still further aspect, three of $R^{14a}$, $R^{14b}$, $R^{14c}$, $R^{14d}$, and $R^{14e}$ are hydrogen and two of $R^{14a}$, $R^{14b}$, $R^{14c}$, $R^{14d}$, and $R^{14e}$ are independently selected from hydrogen, —OH, —SH, —NH$_2$, —SO$_2$R$^{16}$, and —CO$_2$R$^{16}$. In yet a further aspect, three of $R^{14a}$, $R^{14b}$, $R^{14c}$, $R^{14d}$, and $R^{14e}$ are hydrogen and two of $R^{14a}$, $R^{14b}$, $R^{14c}$, $R^{14d}$, and $R^{14e}$ are independently selected from hydrogen, —SO$_2$R$^{16}$, and —CO$_2$R$^{16}$. In an even further aspect, three of $R^{14a}$, $R^{14b}$, $R^{14c}$, $R^{14d}$, and $R^{14e}$ are hydrogen and two of $R^{14a}$, $R^{14b}$, $R^{14c}$, $R^{14d}$, and $R^{14e}$ are independently selected from hydrogen and —SO$_2$R$^{16}$. In a still further aspect, three of R$^{14a}$, R$^{14b}$, R$^{14c}$, R$^{14d}$, and R$^{14e}$ are hydrogen and two of R$^{14a}$, R$^{14b}$, R$^{14c}$, R$^{14d}$, and R$^{14e}$ are independently selected from hydrogen and —CO$_2$R$^{16}$.

In a further aspect, four of R$^{14a}$, R$^{14b}$, R$^{14c}$, R$^{14d}$, and R$^{14e}$ are hydrogen and one of R$^{14a}$, R$^{14b}$, R$^{14c}$, R$^{14d}$, and R$^{14e}$ is selected from halogen, —OH, —SH, —CN, —NO$_2$, —NH$_2$, C1-C4 alkyl, C1-C4 alkoxy, C1-C4 monohaloalkyl, C1-C4 polyhaloalkyl, C1-C4 alkoxy, C1-C4 aminoalkyl, C1-C4 hydroxyalkyl, C1-C4 monoalkylamino, C1-C4 dialkylamino, —SO$_2$R$^{15}$, and —CO$_2$R$^{15}$. In a still further aspect, four of R$^{14a}$, R$^{14b}$, R$^{14c}$, R$^{14d}$, and R$^{14e}$ are hydrogen and one of R$^{14a}$, R$^{14b}$, R$^{14c}$, R$^{14d}$, and R$^{14e}$ is selected from halogen, —OH, —SH, —CN, —NO$_2$, —NH$_2$, C1-C2 alkyl, C1-C2 alkoxy, C1-C2 monohaloalkyl, C1-C2 polyhaloalkyl, C1-C2 alkoxy, C1-C2 aminoalkyl, C1-C2 hydroxyalkyl, C1-C2 monoalkylamino, C1-C2 dialkylamino, —SO$_2$R$^{15}$, and —CO$_2$R$^{15}$.

In a further aspect, four of R$^{14a}$, R$^{14b}$, R$^{14c}$, R$^{14d}$, and R$^{14e}$ are hydrogen and one of R$^{14a}$, R$^{14b}$, R$^{14c}$, R$^{14d}$, and R$^{14e}$ is selected from halogen, —OH, —CN, —NO$_2$, —NH$_2$, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylamino. In a still further aspect, four of R$^{14a}$, R$^{14b}$, R$^{14c}$, R$^{14d}$, and R$^{14e}$ are hydrogen and one of R$^{14a}$, R$^{14b}$, R$^{14c}$, R$^{14d}$, and R$^{14e}$ is selected from halogen, —OH, —CN, —NO$_2$, —NH$_2$, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylamino. In yet a further aspect, four of R$^{14a}$, R$^{14b}$, R$^{14c}$, R$^{14d}$, and R$^{14e}$ are hydrogen and one of R$^{14a}$, R$^{14b}$, R$^{14c}$, R$^{14d}$, and R$^{14e}$ is selected from —F, —Cl, —Br, —OH, —CN, —NO$_2$, —NH$_2$, —CH$_3$, —CFH$_2$, —CF$_2$H, —CF$_3$, —OCH$_3$, —NH(CH$_3$), and N(CH$_3$)$_2$.

In a further aspect, four of R$^{14a}$, R$^{14b}$, R$^{14c}$, R$^{14d}$, and R$^{14e}$ are hydrogen and one of R$^{14a}$, R$^{14b}$, R$^{14c}$, R$^{14d}$, and R$^{14e}$ is selected from halogen, C1-C4 alkyl, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylamino. In a still further aspect, four of R$^{14a}$, R$^{14b}$, R$^{14c}$, R$^{14d}$, and R$^{14e}$ are hydrogen and one of R$^{14a}$, R$^{14b}$, R$^{14c}$, R$^{14d}$, and R$^{14e}$ is selected from halogen, C1-C2 alkyl, C1-C2 monohaloalkyl, C1-C2 polyhaloalkyl, C1-C2 alkoxy, C1-C2 cyanoalkyl, C1-C2 aminoalkyl, C1-C2 hydroxyalkyl, C1-C2 monoalkylamino, and C1-C2 dialkylamino. In yet a further aspect, four of R$^{14a}$, R$^{14b}$, R$^{14c}$, R$^{14d}$, and R$^{14e}$ are hydrogen and one of R$^{14a}$, R$^{14b}$, R$^{14c}$, R$^{14d}$, and R$^{14e}$ is selected from —F, —Cl, —Br, —CH$_3$, —CFH$_2$, —CF$_2$H, —CF$_3$, —OCH$_3$, —NH(CH$_3$), and —N(CH$_3$)$_2$.

In a further aspect, four of R$^{14a}$, R$^{14b}$, R$^{14c}$, R$^{14d}$, and R$^{14e}$ are hydrogen and one of R$^{14a}$, R$^{14b}$, R$^{14c}$, R$^{14d}$, and R$^{14e}$ is selected from C1-C4 monohaloalkyl and C1-C4 polyhaloalkyl. In a still further aspect, four of R$^{14a}$, R$^{14b}$, R$^{14c}$, R$^{14d}$, and R$^{14e}$ are hydrogen and one of R$^{14a}$, R$^{14b}$, R$^{14c}$, R$^{14d}$, and R$^{14e}$ is selected from C1-C2 monohaloalkyl and C1-C2 polyhaloalkyl. In yet a further aspect, four of R$^{14a}$, R$^{14b}$, R$^{14c}$, R$^{14d}$, and R$^{14e}$ are hydrogen and one of R$^{14a}$, R$^{14b}$, R$^{14c}$, R$^{14d}$, and R$^{14e}$ is selected from —CFH$_2$, —CF$_2$H, and —CF$_3$.

In a further aspect, four of R$^{14a}$, R$^{14b}$, R$^{14c}$, R$^{14d}$, and R$^{14e}$ are hydrogen and one of R$^{14a}$, R$^{14b}$, R$^{14c}$, R$^{14d}$, and R$^{14e}$ is selected from C1-C4 alkyl. In a still further aspect, four of R$^{14a}$, R$^{14b}$, R$^{14c}$, R$^{14d}$, and R$^{14e}$ are hydrogen and one of R$^{14a}$, R$^{14b}$, R$^{14c}$, R$^{14d}$, and R$^{14e}$ is selected from methyl, ethyl, iso-propyl, and n-propyl. In yet a further aspect, four of R$^{14a}$, R$^{14b}$, R$^{14c}$, R$^{14d}$, and R$^{14e}$ are hydrogen and one of R$^{14a}$, R$^{14b}$, R$^{14c}$, R$^{14d}$, and R$^{14e}$ is selected from methyl and ethyl. In an even further aspect, four of R$^{14a}$, R$^{14b}$, R$^{14c}$, R$^{14d}$, and R$^{14e}$ are hydrogen and one of R$^{14a}$, R$^{14b}$, R$^{14c}$, R$^{14d}$, and R$^{14e}$ is methyl. In a still further aspect, four of R$^{14a}$, R$^{14b}$, R$^{14c}$, R$^{14d}$, and R$^{14e}$ are hydrogen and one of R$^{14a}$, R$^{14b}$, R$^{14c}$, R$^{14d}$, and R$^{14e}$ is ethyl.

In a further aspect, four of R$^{14a}$, R$^{14b}$, R$^{14c}$, R$^{14d}$, and R$^{14e}$ are hydrogen and one of R$^{14a}$, R$^{14b}$, R$^{14c}$, R$^{14d}$, and R$^{14e}$ is selected from halogen. In a still further aspect, four of R$^{14a}$, R$^{14b}$, R$^{14c}$, R$^{14d}$, and R$^{14e}$ are hydrogen and one of R$^{14a}$, R$^{14b}$, R$^{14c}$, R$^{14d}$, and R$^{14e}$ is selected from —F, —Cl, and —Br. In yet a further aspect, four of R$^{14a}$, R$^{14b}$, R$^{14c}$, R$^{14d}$, and R$^{14e}$ are hydrogen and one of R$^{14a}$, R$^{14b}$, R$^{14c}$, R$^{14d}$, and R$^{14e}$ is selected from —F and —Cl. In an even further aspect, four of R$^{14a}$, R$^{14b}$, R$^{14c}$, R$^{14d}$, and R$^{14e}$ are hydrogen and one of R$^{14a}$, R$^{14b}$, R$^{14c}$, R$^{14d}$, and R$^{14e}$ is-F. In a still further aspect, four of R$^{14a}$, R$^{14b}$, R$^{14c}$, R$^{14d}$, and R$^{14e}$ are hydrogen and one of R$^{14a}$, R$^{14b}$, R$^{14c}$, R$^{14d}$, and R$^{14e}$ is —Cl. In yet a further aspect, four of R$^{14a}$, R$^{14b}$, R$^{14c}$, R$^{14d}$, and R$^{14e}$ are hydrogen and one of R$^{14a}$, R$^{14b}$, R$^{14c}$, R$^{14d}$, and R$^{14e}$ is —Br.

In a further aspect, four of R$^{14a}$, R$^{14b}$, R$^{14c}$, R$^{14d}$, and R$^{14e}$ are hydrogen and one of R$^{14a}$, R$^{14b}$, R$^{14c}$, R$^{14d}$, and R$^{14e}$ is selected from —OH, —SH, —CN, —NO$_2$, —NH$_2$, —SO$_2$R$^{16}$, and —CO$_2$R$^{16}$. In a still further aspect, four of R$^{14a}$, R$^{14b}$, R$^{14c}$, R$^{14d}$, and R$^{14e}$ are hydrogen and one of R$^{14a}$, R$^{14b}$, R$^{14c}$, R$^{14d}$, and R$^{14e}$ is selected from —OH, —SH, —NH$_2$, —SO$_2$R$^{16}$, and —CO$_2$R$^{16}$. In yet a further aspect, four of R$^{14a}$, R$^{14b}$, R$^{14c}$, R$^{14d}$, and R$^{14e}$ are hydrogen and one of R$^{14a}$, R$^{14b}$, R$^{14c}$, R$^{14d}$, and R$^{14e}$ is selected from —SO$_2$R$^{16}$ and —CO$_2$R$^{16}$. In an even further aspect, four of R$^{14a}$, R$^{14b}$, R$^{14c}$, R$^{14d}$, and R$^{14e}$ are hydrogen and one of R$^{14a}$, R$^{14b}$, R$^{14c}$, R$^{14d}$, and R$^{14e}$ is —SO$_2$R$^{16}$. In a still further aspect, four of R$^{14a}$, R$^{14b}$, R$^{14c}$, R$^{14d}$, and R$^{14e}$ are hydrogen and one of R$^{14a}$, R$^{14b}$, R$^{14c}$, R$^{14d}$, and R$^{14e}$ is —CO$_2$R$^{16}$.

d. R$^{15}$ Groups

In one aspect, each occurrence of R$^{15}$, when present, is independently selected from hydrogen, —CH$_3$, —CFH$_2$, —CF$_2$H, —CF$_3$, —NH$_2$, —NH(CH$_3$), and —N(CH$_3$)$_2$. In a further aspect, each occurrence of R$^{15}$, when present, is hydrogen.

In a further aspect, each occurrence of R$^{15}$, when present, is independently selected from hydrogen and —CH$_3$. In a still further aspect, each occurrence of R$^{15}$, when present, is —CH$_3$.

In a further aspect, each occurrence of R$^{15}$, when present, is independently selected from hydrogen, —CFH$_2$, —CF$_2$H, and —CF$_3$. In a still further aspect, each occurrence of R$^{15}$, when present, is independently selected from hydrogen, —CFH$_2$, and —CF$_2$H. In yet a further aspect, each occurrence of R$^{15}$, when present, is independently selected from hydrogen and —CFH$_2$. In an even further aspect, each occurrence of R$^{15}$, when present, is —CF$_3$. In a still further aspect, each occurrence of R$^{15}$, when present, is —CF$_2$H. In yet a further aspect, each occurrence of R$^{15}$, when present, is —CFH$_2$.

In a further aspect, each occurrence of R$^{15}$, when present, is independently selected from hydrogen, —NH$_2$, —NH(CH$_3$), and —N(CH$_3$)$_2$. In a still further aspect, each occurrence of R$^{15}$, when present, is independently selected from hydrogen, —NH$_2$, and —NH(CH$_3$). In yet a further aspect, each occurrence of R$^{15}$, when present, is independently selected from hydrogen and —NH$_2$. In an even further aspect, each occurrence of R$^{15}$, when present, is —N(CH$_3$)$_2$. In a still further aspect, each occurrence of R$^{15}$, when present, is —NH(CH₃). In yet a further aspect, each occurrence of $R^{15}$, when present, is —NH₂.

e. $R^{16}$ Groups

In one aspect, each occurrence of $R^{16}$, when present, is independently selected from hydrogen, —CH₃, —CFH₂, —CF₂H, —CF₃, —NH₂, —NH(CH₃), and —N(CH₃)₂. In a further aspect, each occurrence of $R^{16}$, when present, is hydrogen.

In a further aspect, each occurrence of $R^{16}$, when present, is independently selected from hydrogen and —CH₃. In a still further aspect, each occurrence of $R^{16}$, when present, is —CH₃.

In a further aspect, each occurrence of $R^{16}$, when present, is independently selected from hydrogen, —CFH₂, —CF₂H, and —CF₃. In a still further aspect, each occurrence of $R^{16}$, when present, is independently selected from hydrogen, —CFH₂, and —CF₂H. In yet a further aspect, each occurrence of $R^{16}$, when present, is independently selected from hydrogen and —CFH₂. In an even further aspect, each occurrence of $R^{16}$, when present, is —CF₃. In a still further aspect, each occurrence of $R^{16}$, when present, is —CF₂H. In yet a further aspect, each occurrence of $R^{16}$, when present, is —CFH₂.

In a further aspect, each occurrence of $R^{16}$, when present, is independently selected from hydrogen, —NH₂, —NH(CH₃), and —N(CH₃)₂. In a still further aspect, each occurrence of $R^{16}$, when present, is independently selected from hydrogen, —NH₂, and —NH(CH₃). In yet a further aspect, each occurrence of $R^{16}$, when present, is independently selected from hydrogen and —NH₂. In an even further aspect, each occurrence of $R^{16}$, when present, is —N(CH₃)₂. In a still further aspect, each occurrence of $R^{16}$, when present, is —NH(CH₃). In yet a further aspect, each occurrence of $R^{16}$, when present, is —NH₂.

4. Other Cdk2 Inhibitors

In one aspect, disclosed are CDK2 inhibitors having a structure represented by a formula:

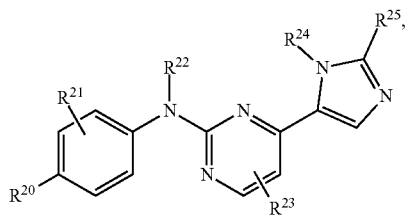

wherein $R^{20}$ is selected from —SO₂$R^{20a}$, —OH, NH₂, substituted amide, C1-C4 alkyl carbonyl, C1-C4 monoalkylamino, C1-C4 dialkylaminomethyl, and C1-C8 alkyl and is substituted with 0, 1, or 2 groups independently selected from halogen, —OH, —CN, —NO₂, —NH₂, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl; wherein each of $R^{21}$, $R^{23}$, and $R^{25}$ is independently selected from hydrogen, halogen, —OH, NH₂, C1-C4 monoalkylamino, C1-C4 dialkylaminomethyl, and C1-C8 alkyl and is independently substituted with 0, 1, or 2 groups independently selected from halogen, —OH, —CN, —NO₂, —NH₂, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl; and wherein each of $R^{22}$ and $R^{24}$ is independently selected from hydrogen and C1-C8 alkyl and is independently substituted with 0, 1, or 2 groups independently selected from halogen, —OH, —CN, —NO₂, —NH₂, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl, or a pharmaceutically acceptable salt thereof.

For example, a CDK2 inhibitor can have a structure represented by a formula:

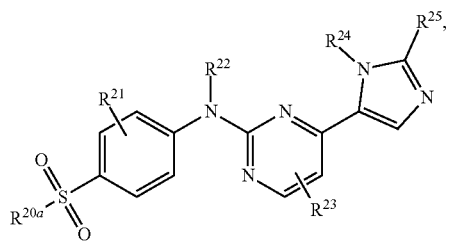

wherein $R^{20a}$ is selected from —OH, NH₂, C1-C4 monoalkylamino, C1-C4 dialkylaminomethyl, and C1-C8 alkyl and is substituted with 0, 1, or 2 groups independently selected from halogen, —OH, —CN, —NO₂, —NH₂, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl; wherein each of $R^{21}$, $R^{23}$, and $R^{25}$ is independently selected from hydrogen, halogen, —OH, NH₂, C1-C4 monoalkylamino, C1-C4 dialkylaminomethyl, and C1-C8 alkyl and is independently substituted with 0, 1, or 2 groups independently selected from halogen, —OH, —CN, —NO₂, —NH₂, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl; and wherein each of $R^{22}$ and $R^{24}$ is independently selected from hydrogen and C1-C8 alkyl and is independently substituted with 0, 1, or 2 groups independently selected from halogen, —OH, —CN, —NO₂, —NH₂, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl, or a pharmaceutically acceptable salt thereof.

In one aspect, a CDK2 inhibitor is provided as a compound having the formula:

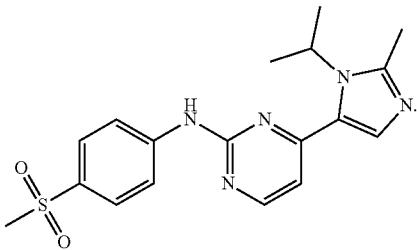 [SMILES: Cc1ncc(-c2ccnc(Nc3ccc(S(C)(=O)=O)cc3)n2)n1C(C)C]

This compound is a potent inhibitor of CDK1/2/9 with $IC_{50}$ of 16 nM/6 nM/20 nM. This compound has high oral bioavailability, F=91%.

a. $R^{20}$ Groups

In one aspect, each occurrence of $R^{20}$, when present, is selected from —OH, NH₂, C1-C4 monoalkylamino (e.g., methylamino, ethylamino, propylamino, or butylamino), C1-C4 dialkylaminomethyl (e.g., dimethylamino, methylethylamino, methylpropylamino, methylbutylamino, diethylamino, ethylpropylamino, ethylbutylamino, dipropylamino, propylbutylamino, or dibutylamino), and C1-C8 alkyl (e.g., methyl, ethyl, propyl, butyl, pentyl, hexyl, heptyl, or octyl). As an example, C1-C8 alkyl can be selected to be C1-C6 alkyl, C1-C4 alkyl, or C1-C2 alkyl.

In a further aspect, each occurrence of $R^{20a}$ can be selected from —OH, $NH_2$, C1-C4 monoalkylamino, C1-C4 dialkylaminomethyl, and C1-C8 alkyl.

In a further aspect, each occurrence of $R^{20}$ and $R^{20a}$ can be substituted with 0, 1, or 2 groups independently selected from halogen, —OH, —CN, —$NO_2$, —$NH_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl.

b. $R^{21}$ Groups

In one aspect, each occurrence of $R^{21}$, when present, is selected from hydrogen, halogen (e.g., fluoride, chloride, bromide, or iodide), —OH, $NH_2$, C1-C4 monoalkylamino (e.g., methylamino, ethylamino, propylamino, or butylamino), C1-C4 dialkylaminomethyl (e.g., dimethylamino, methylethylamino, methylpropylamino, methylbutylamino, diethylamino, ethylpropylamino, ethylbutylamino, dipropylamino, propylbutylamino, or dibutylamino), and C1-C8 alkyl (e.g., methyl, ethyl, propyl, butyl, pentyl, hexyl, heptyl, or octyl). As an example, C1-C8 alkyl can be selected to be C1-C6 alkyl, C1-C4 alkyl, or C1-C2 alkyl.

In a further aspect, each occurrence of $R^{21}$ can be substituted with 0, 1, or 2 groups independently selected from halogen, —OH, —CN, —$NO_2$, —$NH_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl.

c. $R^{22}$ Groups

In one aspect, each occurrence of $R^{22}$, when present, is selected from hydrogen and C1-C8 alkyl (e.g., methyl, ethyl, propyl, butyl, pentyl, hexyl, heptyl, or octyl). As an example, C1-C8 alkyl can be selected to be C1-C6 alkyl, C1-C4 alkyl, or C1-C2 alkyl.

In a further aspect, each occurrence of $R^{22}$ can be substituted with 0, 1, or 2 groups independently selected from halogen, —OH, —CN, —$NO_2$, —$NH_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl.

d. $R^{23}$ Groups

In one aspect, each occurrence of $R^{23}$, when present, is selected from hydrogen, halogen (e.g., fluoride, chloride, bromide, or iodide), —OH, $NH_2$, C1-C4 monoalkylamino (e.g., methylamino, ethylamino, propylamino, or butylamino), C1-C4 dialkylaminomethyl (e.g., dimethylamino, methylethylamino, methylpropylamino, methylbutylamino, diethylamino, ethylpropylamino, ethylbutylamino, dipropylamino, propylbutylamino, or dibutylamino), and C1-C8 alkyl (e.g., methyl, ethyl, propyl, butyl, pentyl, hexyl, heptyl, or octyl). As an example, C1-C8 alkyl can be selected to be C1-C6 alkyl, C1-C4 alkyl, or C1-C2 alkyl.

In a further aspect, each occurrence of $R^{23}$ can be substituted with 0, 1, or 2 groups independently selected from halogen, —OH, —CN, —$NO_2$, —$NH_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl.

e. $R^{24}$ Groups

In one aspect, each occurrence of $R^{24}$, when present, is selected from hydrogen and C1-C8 alkyl (e.g., methyl, ethyl, propyl, butyl, pentyl, hexyl, heptyl, or octyl). As an example, C1-C8 alkyl can be selected to be C1-C6 alkyl, C1-C4 alkyl, or C1-C2 alkyl.

In a further aspect, each occurrence of $R^{24}$ can be substituted with 0, 1, or 2 groups independently selected from halogen, —OH, —CN, —$NO_2$, —$NH_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl.

f. $R^{25}$ Groups

In one aspect, each occurrence of $R^{25}$, when present, is selected from hydrogen, halogen (e.g., fluoride, chloride, bromide, or iodide), —OH, $NH_2$, C1-C4 monoalkylamino (e.g., methylamino, ethylamino, propylamino, or butylamino), C1-C4 dialkylaminomethyl (e.g., dimethylamino, methylethylamino, methylpropylamino, methylbutylamino, diethylamino, ethylpropylamino, ethylbutylamino, dipropylamino, propylbutylamino, or dibutylamino), and C1-C8 alkyl (e.g., methyl, ethyl, propyl, butyl, pentyl, hexyl, heptyl, or octyl). As an example, C1-C8 alkyl can be selected to be C1-C6 alkyl, C1-C4 alkyl, or C1-C2 alkyl.

In a further aspect, each occurrence of $R^{25}$ can be substituted with 0, 1, or 2 groups independently selected from halogen, —OH, —CN, —$NO_2$, —$NH_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl.

In one aspect, disclosed are CDK2 inhibitors having a structure represented by a formula:

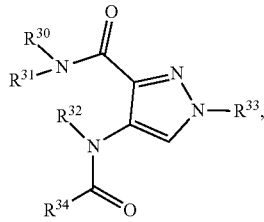

wherein each occurrence of $R^{30}$ is independently selected from substituted phenyl, C1-C8 alkyl, carbocyclic, substituted cyclohexyl, piperidine wherein each of $R^{31}$, $R^{32}$, and $R^{33}$ is independently selected from hydrogen and C1-C8 alkyl and is independently substituted with 0, 1, or 2 groups independently selected from halogen, —OH, —CN, —$NO_2$, —$NH_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl; and wherein $R^{34}$ is selected from hydroxy alkyl, substituted or unsubstituted phenyl, substituted or unsubstituted benzyl or a pharmaceutically acceptable salt thereof.

In a further aspect, disclosed are CDK2 inhibitors having a structure represented by a formula:

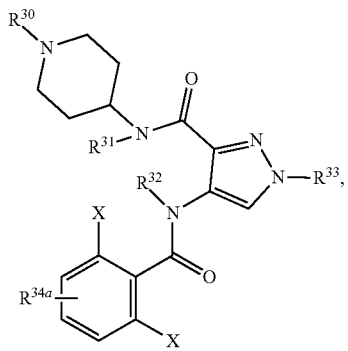

wherein each occurrence of X is independently a halogen (e.g., fluoride, chloride, bromide, or iodide), wherein each of $R^{30}$, $R^{31}$, $R^{32}$, and $R^{33}$ is independently selected from hydrogen and C1-C8 alkyl and is independently substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl; and wherein $R^{34}$ is selected from —OH, NH$_2$, C1-C4 monoalkylamino, C1-C4 dialkylaminomethyl, and C1-C8 alkyl and is substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl, or a pharmaceutically acceptable salt thereof.

In one aspect, a CDK2 inhibitor is provided as a compound having the formula:

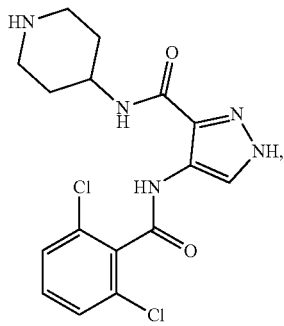

This compound is a multi-CDK inhibitor for CDK1, 2, 4, 6 and 9 with IC$_{50}$ of 10-210 nM. In certain aspects, this compound can have a low oral bioavailability (<1%). This compound is a potent cell cycle inhibitor and can be useful for the treatment of chronic lymphocytic leukemia and for the treatment of mantle cell lymphoma.

g. $R^{30}$ Groups

In one aspect, each occurrence of $R^{30}$, when present, is selected from hydrogen and C1-C8 alkyl (e.g., methyl, ethyl, propyl, butyl, pentyl, hexyl, heptyl, or octyl). As an example, C1-C8 alkyl can be selected to be C1-C6 alkyl, C1-C4 alkyl, or C1-C2 alkyl.

In a further aspect, each occurrence of $R^{30}$ can be substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl.

h. $R^{31}$ Groups

In one aspect, each occurrence of $R^{31}$, when present, is selected from hydrogen and C1-C8 alkyl (e.g., methyl, ethyl, propyl, butyl, pentyl, hexyl, heptyl, or octyl). As an example, C1-C8 alkyl can be selected to be C1-C6 alkyl, C1-C4 alkyl, or C1-C2 alkyl.

In a further aspect, each occurrence of $R^{31}$ can be substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl.

i. $R^{32}$ Groups

In one aspect, each occurrence of $R^{32}$, when present, is selected from hydrogen and C1-C8 alkyl (e.g., methyl, ethyl, propyl, butyl, pentyl, hexyl, heptyl, or octyl). As an example, C1-C8 alkyl can be selected to be C1-C6 alkyl, C1-C4 alkyl, or C1-C2 alkyl.

In a further aspect, each occurrence of $R^{32}$ can be substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl.

j. $R^{33}$ Groups

In one aspect, each occurrence of $R^{33}$, when present, is selected from hydrogen and C1-C8 alkyl (e.g., methyl, ethyl, propyl, butyl, pentyl, hexyl, heptyl, or octyl). As an example, C1-C8 alkyl can be selected to be C1-C6 alkyl, C1-C4 alkyl, or C1-C2 alkyl.

In a further aspect, each occurrence of $R^{33}$ can be substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl.

k. $R^{34}$ Groups

In one aspect, each occurrence of $R^{30}$ is independently selected from substituted phenyl, C1-C8 alkyl, carbocyclic, substituted cyclohexyl, piperidine wherein each of $R^{31}$, $R^{32}$, and $R^{33}$ is independently selected from hydrogen and C1-C8 alkyl and is independently substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl; and wherein $R^{34}$ is selected from hydroxy alkyl, substituted or unsubstituted phenyl, substituted or unsubstituted benzyl or a pharmaceutically acceptable salt thereof.

In a further aspect, each occurrence of $R^{34a}$, when present, is selected from —OH, NH$_2$, C1-C4 monoalkylamino (e.g., methylamino, ethylamino, propylamino, or butylamino), C1-C4 dialkylaminomethyl (e.g., dimethylamino, methylethylamino, methylpropylamino, methylbutylamino, diethylamino, ethylpropylamino, ethylbutylamino, dipropylamino, propylbutylamino, or dibutylamino), and C1-C8 alkyl (e.g., methyl, ethyl, propyl, butyl, pentyl, hexyl, heptyl, or octyl). As an example, C1-C8 alkyl can be selected to be C1-C6 alkyl, C1-C4 alkyl, or C1-C2 alkyl.

In a further aspect, each occurrence of $R^{34}$ and $R^{34a}$ can be substituted with 0, 1, or 2 groups independently selected from halogen, —OH, —CN, —NO$_2$, —NH$_2$, C1-C4 monohaloalkyl, C1-C4 polyhaloalkyl, C1-C4 alkoxy, C1-C4 cyanoalkyl, C1-C4 aminoalkyl, C1-C4 hydroxyalkyl, C1-C4 monoalkylamino, and C1-C4 dialkylaminomethyl.

| Compound (Scaffold) | Structure | HEI-OC1 IC50 (nM) | Explant Cisplatin IC50 (nM) | Explant Cisplatin LD50 (nM) | Therapeutic Index LD50/IC50 |
|---|---|---|---|---|---|
| SJZuo-4 Kenpaullone (Paullone) | | 2100 | 150 | >30,000 | >200 |
| SJZuo-19 AZD5438 (Pyrimidine) | | | ~25 | <1,000 | <40 |
| SJZuo-20 AT7519 (Pyrazole) | | 380 | ~25 | <1,000 | <40 |
| SJZuo-12 CDK2 inhibitor II (Indole) | | 500 | 1,000 | >12,000 | 12 |
| SJZuo-9 Olomoucine II (Purine) | | 800 | 3,000 | >33,000 | 11 |

5. Example Compounds
In one aspect, a compound can be present as one or more of the following structures:
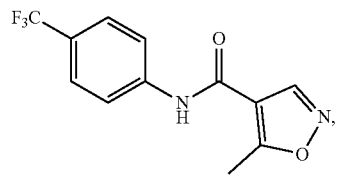 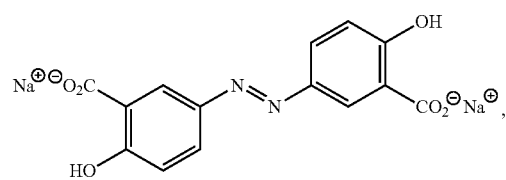
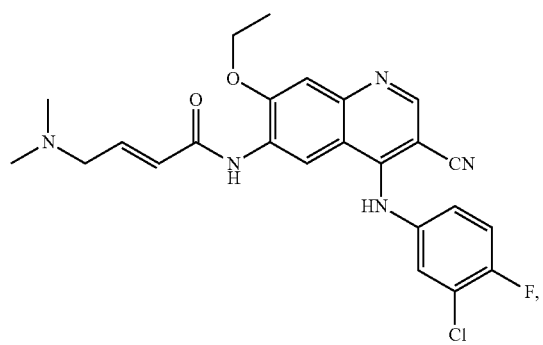 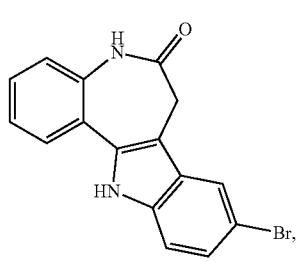
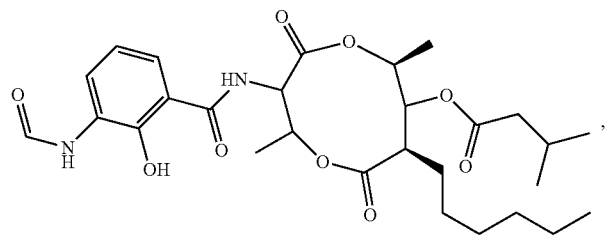 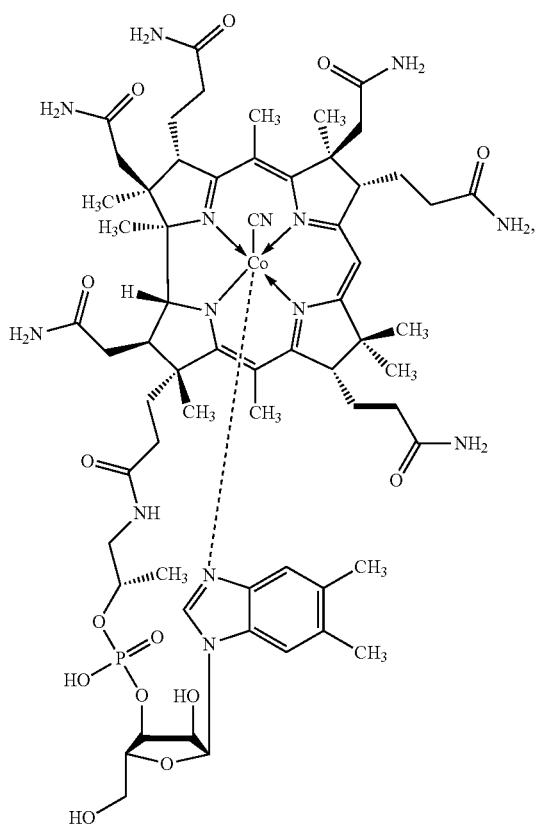

-continued
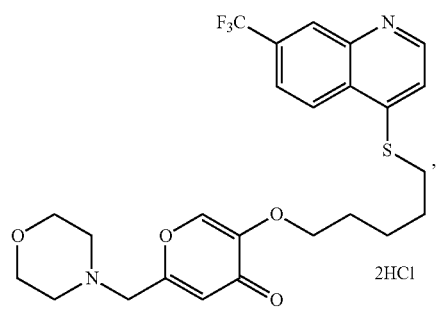
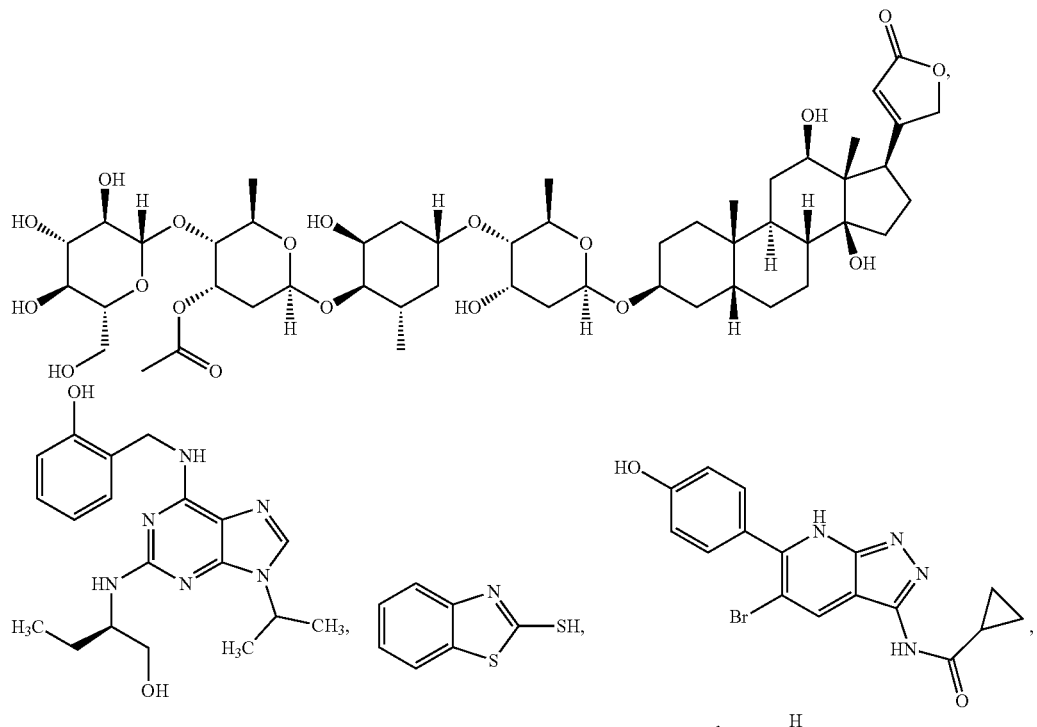
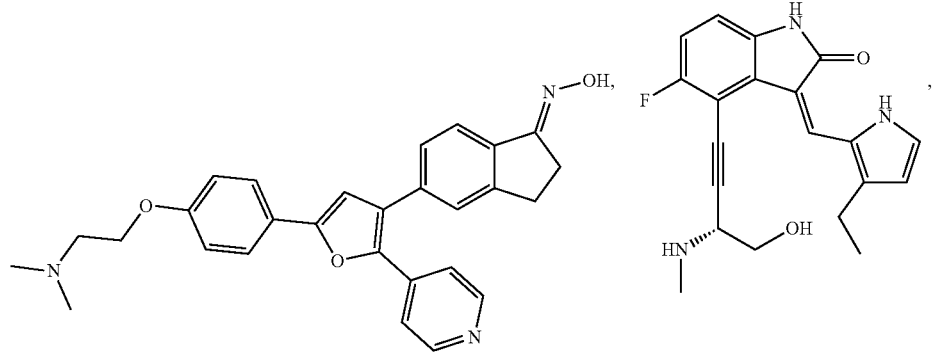
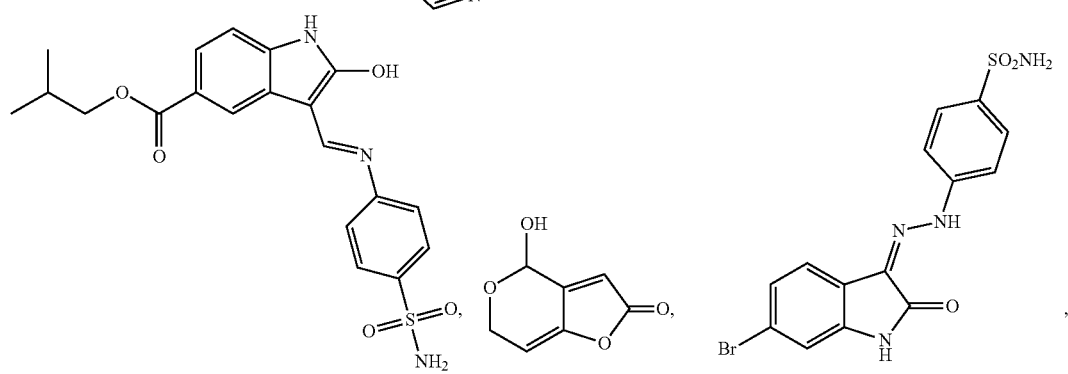

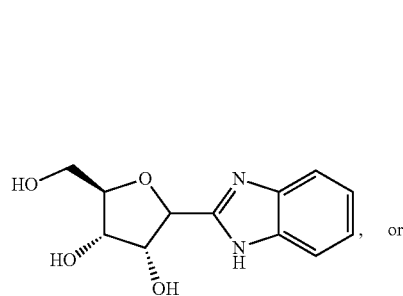, or 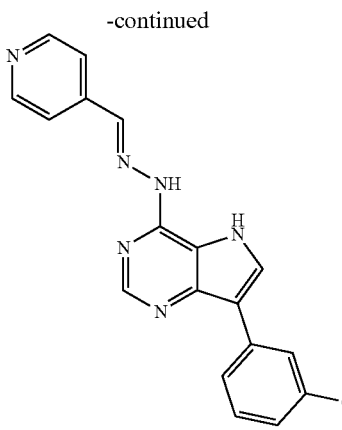
or a pharmaceutically acceptable salt thereof.
In one aspect, a compound can be present as one or more of the following structures:
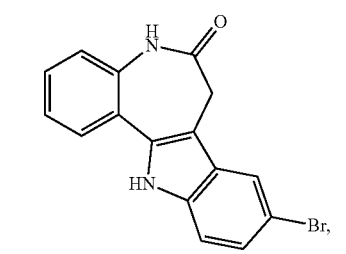
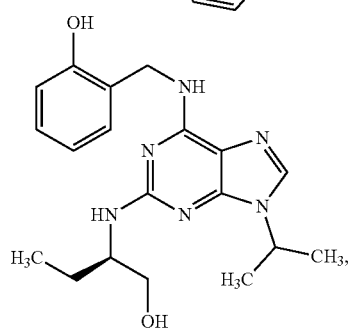
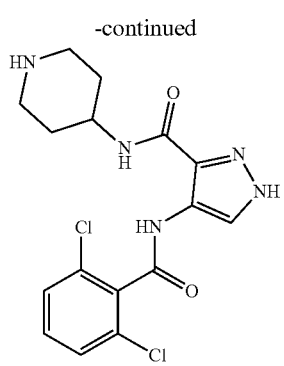
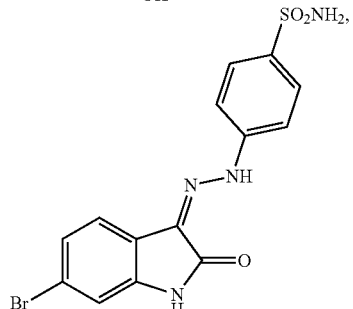
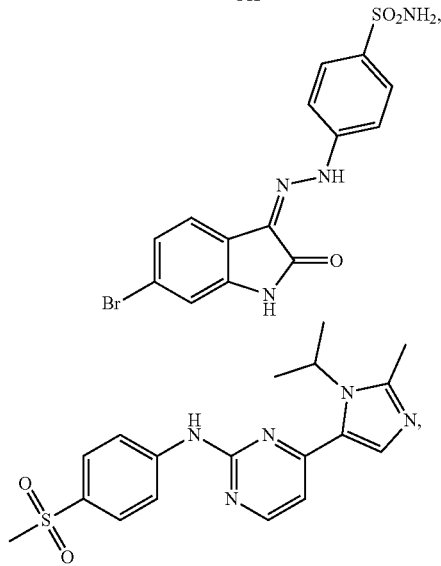 and
In one aspect, a compound can be present as one or more of the following structures:
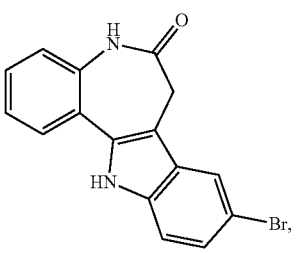
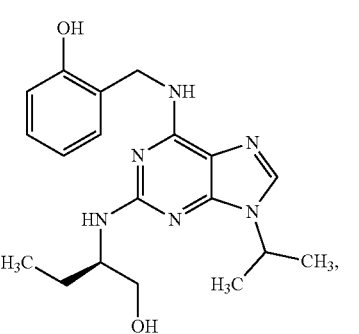 or -continued

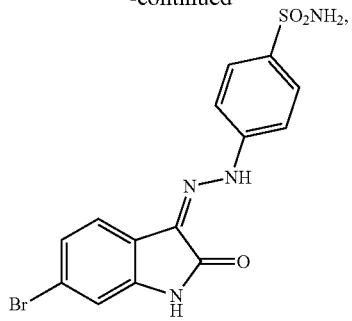

or a pharmaceutically acceptable salt thereof.

C. METHODS OF MAKING A COMPOUND

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the compounds of this invention are prepared by employing reactions as shown in the following Reaction Schemes, as described and exemplified below. In certain specific examples, the disclosed compounds can be prepared by Route I and Route II, as described and exemplified below. The following examples are provided so that the invention might be more fully understood, are illustrative only, and should not be construed as limiting.

1. Route I

In one aspect, paullone derivatives can be prepared as shown below.

SCHEME 1A.

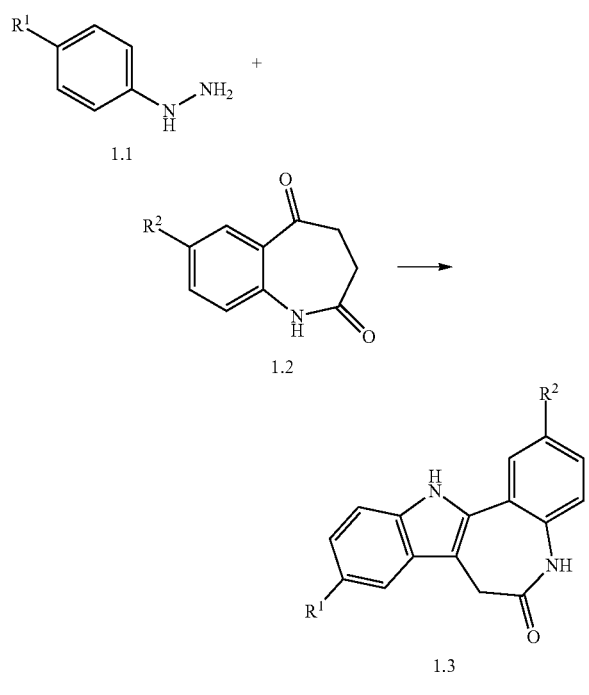

Compounds are represented in generic form, with substituents as noted in compound descriptions elsewhere herein. A more specific example is set forth below.

SCHEME 1B.

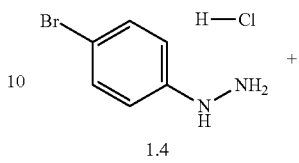
1.4

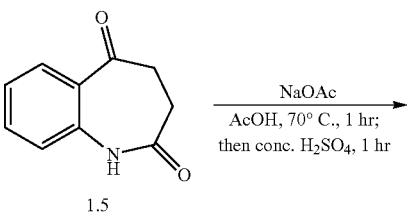

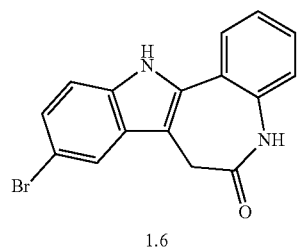
1.6

In one aspect, compounds of type 1.3, and similar compounds, can be prepared according to reaction Scheme 1B above. Thus, compounds of type 1.6 can be prepared by a cyclization reaction (e.g., Fischer indole reaction) of an appropriate hydrazine, e.g., 1.4 as shown above, with an appropriate benzazepine, e.g., 1.5 as shown above. Appropriate hydrazines and appropriate benzazepines are commercially available or prepared by methods known to one skilled in the art. The cyclization reaction is carried out in the presence of an appropriate base, e.g., sodium acetate, in an appropriate protic solvent, e.g., acetic acid, at an appropriate temperature, e.g., 70° C., for an appropriate period of time, e.g., 1 hour. As can be appreciated by one skilled in the art, the above reaction provides an example of a generalized approach wherein compounds similar in structure to the specific reactants above (compounds similar to compounds of type 1.1 and 1.2), can be substituted in the reaction to provide paullone derivatives similar to Formula 1.3.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

2. Route II

In one aspect, purine derivatives can be prepared as shown below.

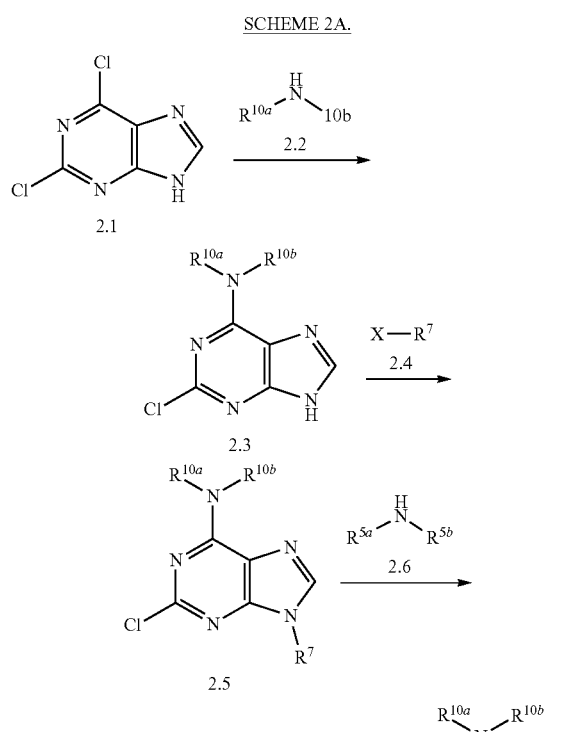

SCHEME 2A.

Compounds are represented in generic form, wherein X is a halogen, and other substituents are as noted in compound descriptions elsewhere herein. A more specific example is set forth below.

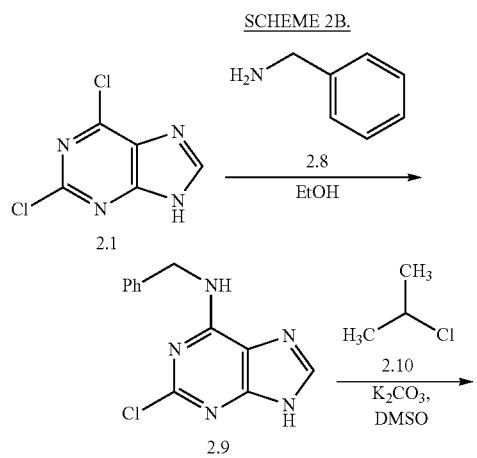

SCHEME 2B.

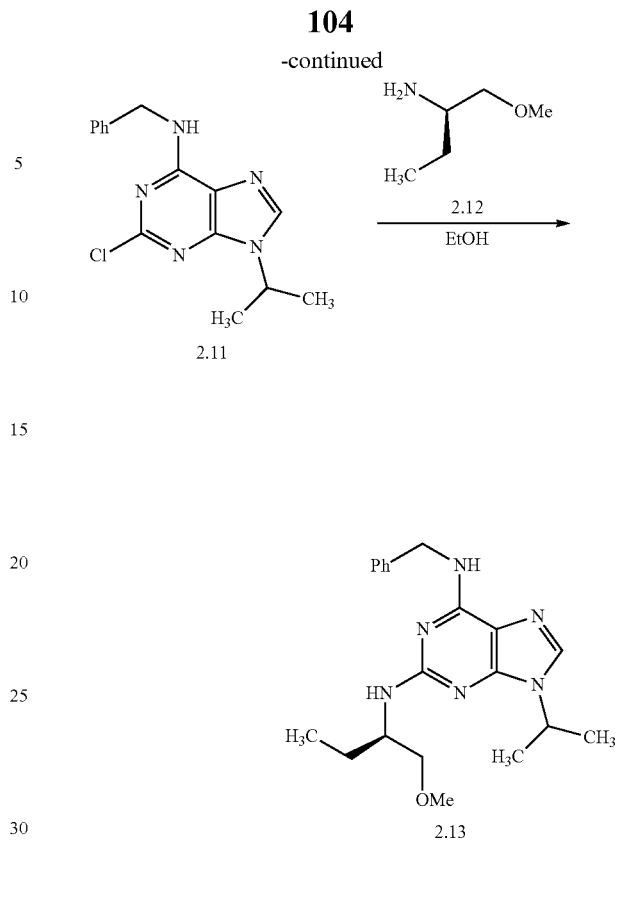

In one aspect, compounds of type 2.7, and similar compounds, can be prepared according to reaction Scheme 2B above. Thus, compounds of type 2.9 can be prepared by a substitution reaction of an appropriate aryl halide, e.g., 2.7 as shown above. Appropriate aryl halides are commercially available or prepared by methods known to one skilled in the art. The substitution reaction is carried out in the presence of an appropriate amine, e.g., 2.8 as shown above, in an appropriate solvent, e.g., ethanol. Compounds of type 2.11 can be prepared an alkylation reaction of an appropriate amine, e.g., 2.9 as shown above. The alkylation reaction is carried out in the presence of an appropriate alkyl halide, e.g., 2.10, and an appropriate base, e.g., potassium carbonate, in an appropriate solvent, e.g., dimethylsulfoxide. Compounds of type 2.13 can be prepared by a substitution reaction of an appropriate aryl halide, e.g., 2.11 as shown above. The substitution reaction is carried out in the presence of an appropriate amine, e.g., 2.12 as shown above, in an appropriate solvent, e.g., ethanol. As can be appreciated by one skilled in the art, the above reaction provides an example of a generalized approach wherein compounds similar in structure to the specific reactants above (compounds similar to compounds of type 2.1, 2.2, 2.3, 2.4, 2.5, and 2.6), can be substituted in the reaction to provide purine derivatives similar to Formula 2.7.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

3. Route III

In one aspect, purine derivatives can be prepared as shown below.

SCHEME 3A.

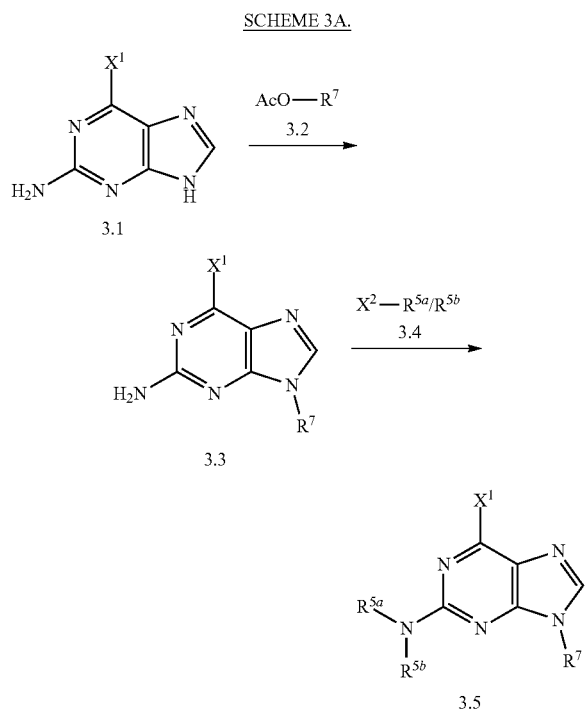

Compounds are represented in generic form, wherein each of $X^1$ and $X^2$ are independently halogen, and where substituents are as noted in compound descriptions elsewhere herein. A more specific example is set forth below.

SCHEME 3B.

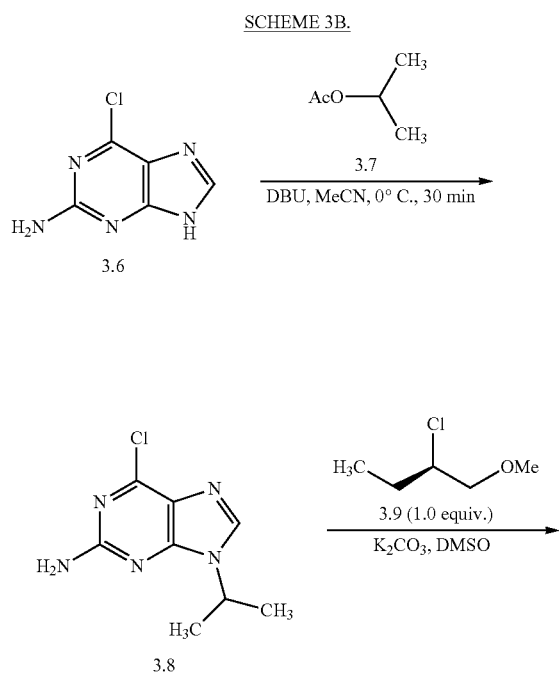

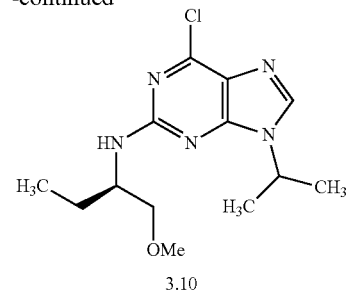

In one aspect, compounds of type 3.5, and similar compounds, can be prepared according to reaction Scheme 3B above. Thus, compounds of type 3.8 can be prepared by a displacement reaction of an appropriate guanine derivative, e.g., 3.6 as shown above. Appropriate guanine derivatives are commercially available or prepared by methods known to one skilled in the art. The displacement reaction is carried out in the presence of an appropriate acetate, e.g., 3.7 as shown above, and an appropriate base, e.g., 1,8-diazobicyclo[5.4.0] undec-7-ene (DBU), in an appropriate solvent, e.g., acetonitrile, at an appropriate temperature, e.g., 0° C., for an appropriate period of time, e.g., thirty minutes. Compounds of type 3.10 can be prepared by an alkylation reaction of an appropriate amine, e.g., 3.8 as shown above. The alkylation reaction is carried out in the presence of an appropriate alkyl halide, e.g., 3.9 as shown above, and an appropriate base, e.g., potassium carbonate, in an appropriate solvent, e.g., dimethylsulfoxide. As can be appreciated by one skilled in the art, the above reaction provides an example of a generalized approach wherein compounds similar in structure to the specific reactants above (compounds similar to compounds of type 3.1, 3.2, 3.3, and 3.4), can be substituted in the reaction to provide para-substituted arenes similar to Formula 3.5.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

4. Route IV

In one aspect, purine derivatives can be prepared as shown below.

SCHEME 4A.

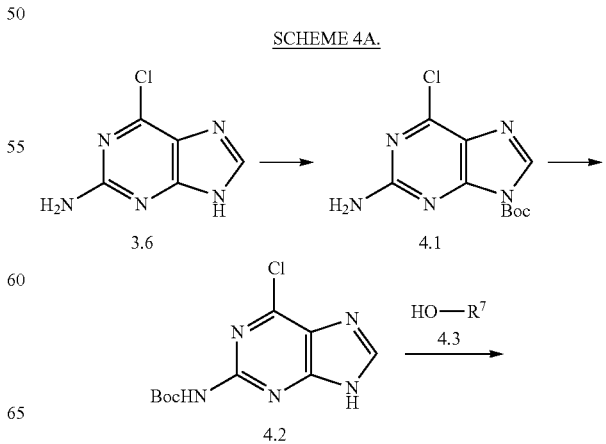

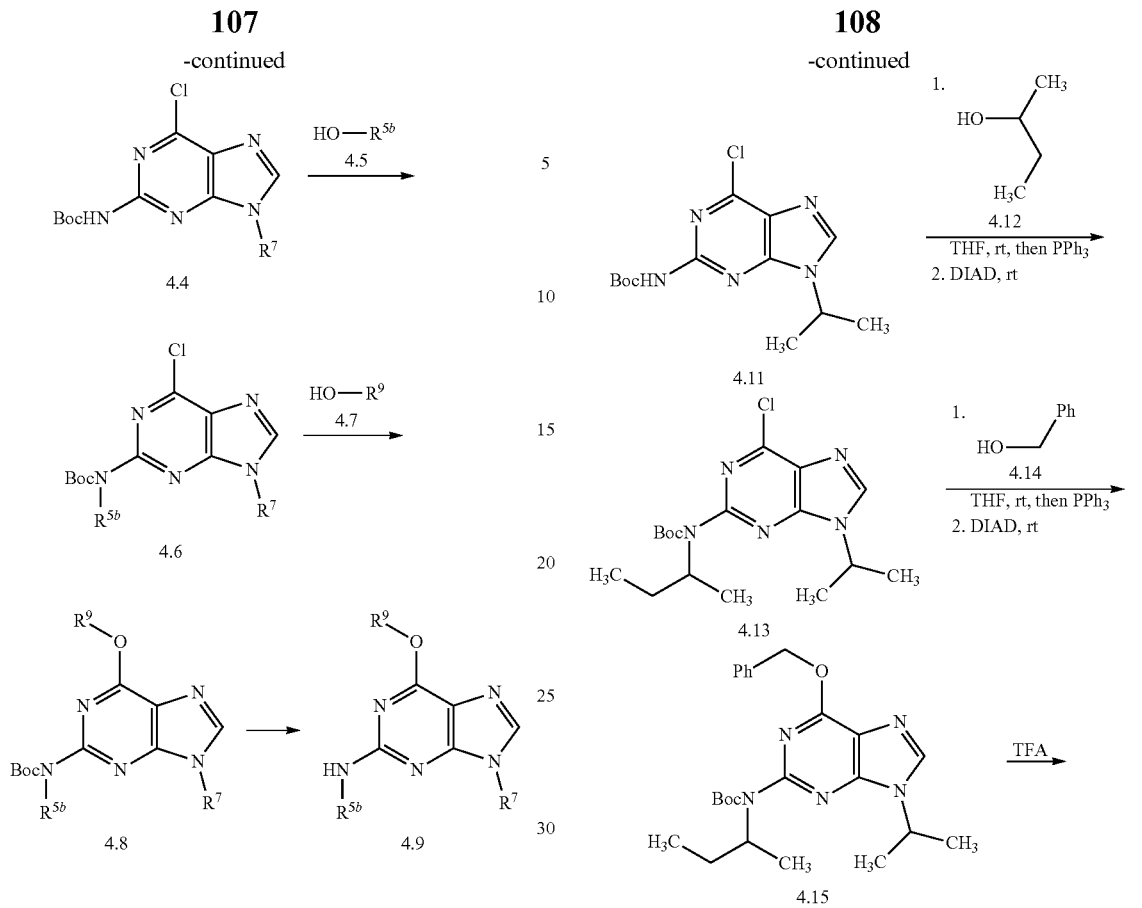

Compounds are represented in generic form, where substituents are as noted in compound descriptions elsewhere herein. A more specific example is set forth below.

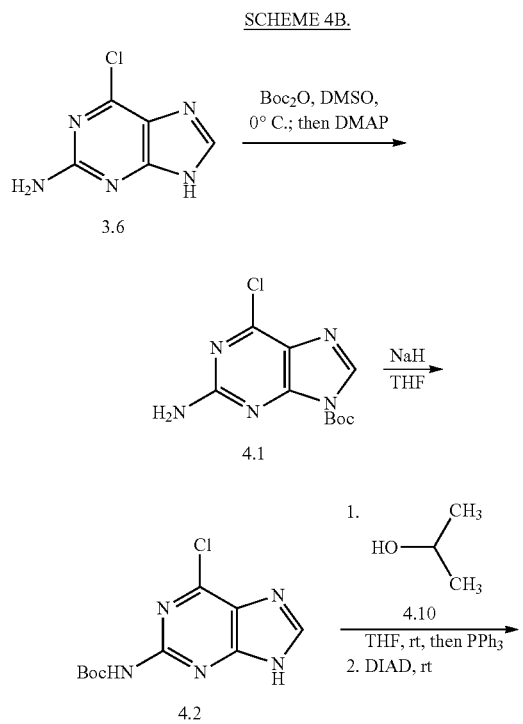

In one aspect, compounds of type 4.9, and similar compounds, can be prepared according to reaction Scheme 4B above. Thus, compounds of type 4.1 can be prepared by protection of an appropriate purine derivative, e.g., 3.6 as shown above. Appropriate purine derivatives are commercially available or prepared by methods known to one skilled in the art. The protection is carried out in the presence of an appropriate protecting group, e.g., di-tert-butyldicarbonate as shown above, and an appropriate catalytic base, e.g., DMAP as shown above, in an appropriate solvent, e.g., dimethylsulfoxide, at an appropriate temperature, e.g., 0° C. The reaction is then warmed to an appropriate temperature, e.g., room temperature, over a period of time sufficient to allow the reaction to proceed, e.g., 2 hours. Compounds of type 4.2 can be prepared by protection of an appropriate amine, e.g., 4.1 as shown above. The protection is carried out in the presence of an appropriate base, e.g., sodium hydride, in an appropriate solvent, e.g., tetrahydrofuran. Compounds of type 4.11 can be prepared by a displacement reaction of an appropriate amine, e.g., 4.2 as shown above. The displacement reaction is carried out in the presence of an appropriate alcohol, e.g., 4.10 as shown above, and an appropriate nucleophile, e.g., triphenylphosphine, followed by the addition of an appropriate azodicarboxylate, e.g., diisopropyl azodicarboxylate. Compounds of type 4.13 can be prepared by a displacement reaction of an appropriate amine, e.g., 4.11 as shown above. The displacement reaction is carried out in the presence of an appropriate alcohol, e.g., 4.12 as shown above, and an appropriate nucleophile, e.g., triphenylphosphine, followed by the addition of an appropriate azodicarboxylate, e.g., diisopropyl azodicarboxylate. Compounds of type 4.15 can be prepared by a displacement reaction of an appropriate halide, e.g., 4.13 as shown above. The displacement reaction is carried out in the presence of an appropriate alcohol, e.g., 4.14 as shown above, and an appropriate nucleophile, e.g., triphenylphosphine, followed by the addition of an appropriate azodicarboxylate, e.g., diisopropyl azodicarboxylate. Compounds of type 4.16 can be prepared by deprotection of an appropriate amine, e.g., 4.15 as shown above. The deprotection is carried out in the presence of an appropriate acid, e.g., trifluoroacetic acid. As can be appreciated by one skilled in the art, the above reaction provides an example of a generalized approach wherein compounds similar in structure to the specific reactants above (compounds similar to compounds of type 3.6, 4.1, 4.2, 4.3, 4.4, 4.5, 4.6, 4.7, and 4.8), can be substituted in the reaction to provide purine derivatives similar to Formula 4.9.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

5. Route V

In one aspect, 3-(2-phenylhydrazono)indolin-2-one derivatives can be prepared as shown below.

SCHEME 5A.

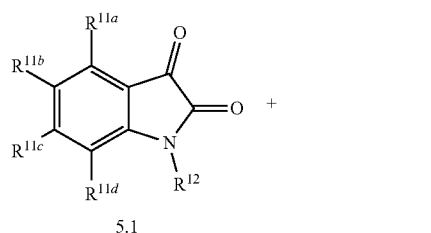

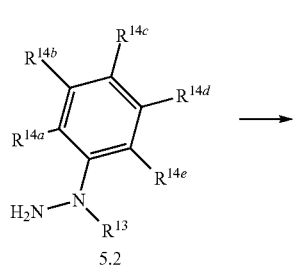

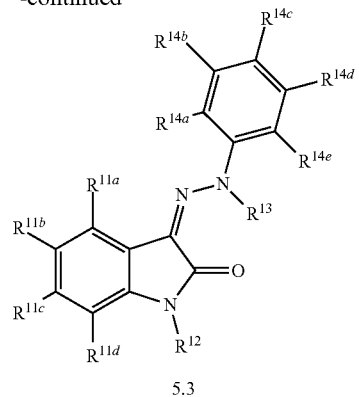

Compounds are represented in generic form, with substituents as noted in compound descriptions elsewhere herein. A more specific example is set forth below.

SCHEME 5B.

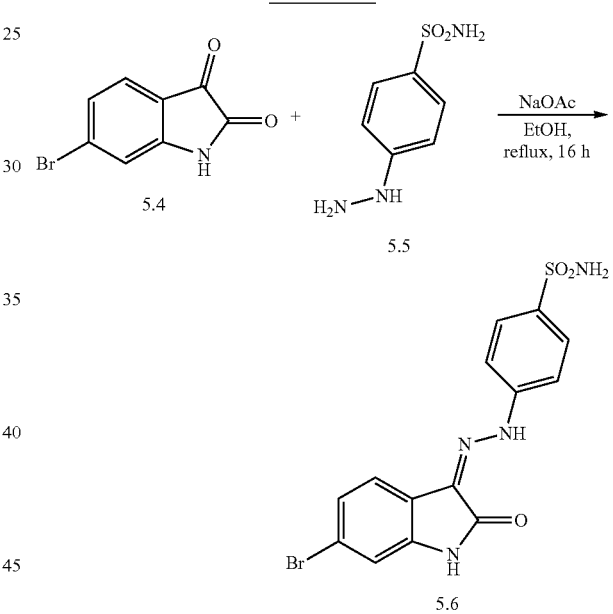

In one aspect, compounds of type 5.3, and similar compounds, can be prepared according to reaction Scheme 5B above. Thus, compounds of type 5.6 can be prepared by a hydrolysis reaction of an appropriate hydrazone, e.g., 5.4 as shown above. Appropriate hydrazones are commercially available or prepared by methods known to one skilled in the art. The hydrolysis reaction is carried out in the presence of an appropriate hydrazine, e.g., 5.5 as shown above, which are commercially available or prepared by methods known to one skilled in the art, in an appropriate solvent, e.g, ethanol, at an appropriate temperature, e.g., refluxing conditions, for an appropriate period of time, e.g, 16 hours. As can be appreciated by one skilled in the art, the above reaction provides an example of a generalized approach wherein compounds similar in structure to the specific reactants above (compounds similar to compounds of type 5.1 and 5.2), can be substituted in the reaction to provide 3-(2-phenylhydrazono)indolin-2-one derivatives similar to Formula 5.3.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

6. Route VI

In one aspect, 4-(1H-imidazol-5-yl)-N-(phenyl)pyrimidin-2-amine derivatives can be prepared as shown below.

SCHEME 6A.

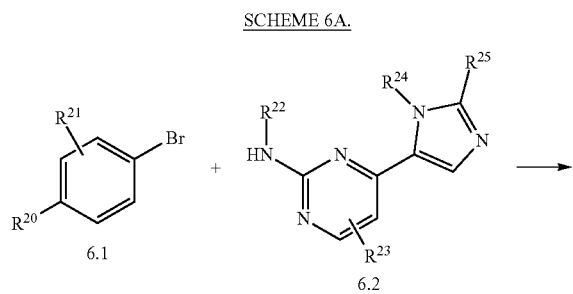

6.1

6.2

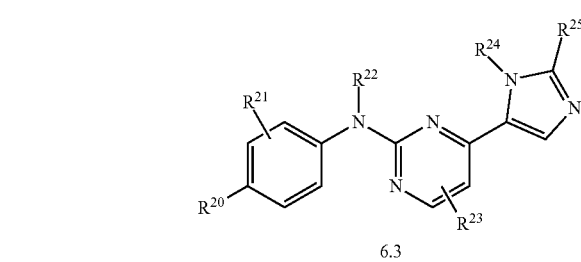

6.3

Compounds are represented in generic form, with substituents as noted in compound descriptions elsewhere herein. A more specific example is set forth below.

SCHEME 6B.

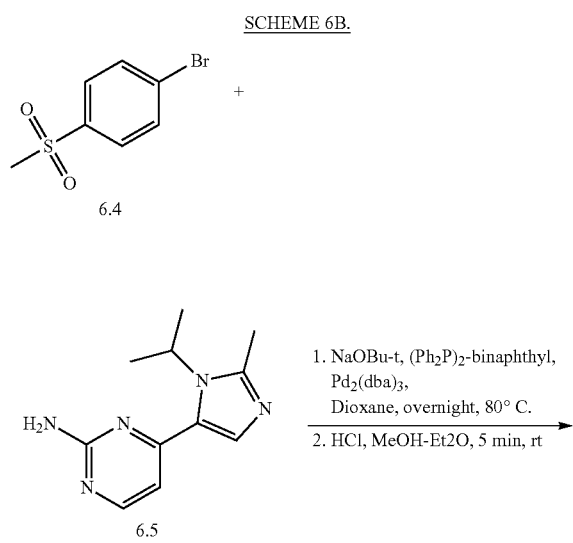

6.4

6.5

1. NaOBu-t, (Ph₂P)₂-binaphthyl, Pd₂(dba)₃, Dioxane, overnight, 80° C.
2. HCl, MeOH-Et2O, 5 min, rt

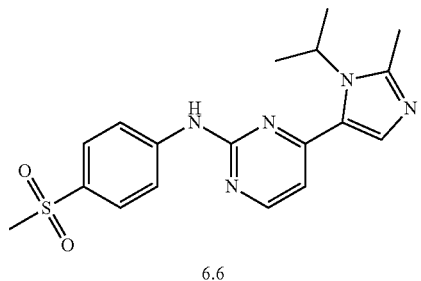

6.6

In one aspect, compounds of type 6.3, and similar compounds, can be prepared according to reaction Scheme 6B above. Thus, compounds of type 6.6 can be prepared by a coupling reaction between appropriate aryl halide and amino pyrimidines, e.g., 6.4 and 6.5 respectively as shown above. Appropriate aryl halides are commercially available or prepared by methods known to one skilled in the art. The coupling reaction is carried out in the presence of an appropriate imidazoyl pyrimidines, e.g., 6.5 as shown above, which are commercially available or prepared by methods known to one skilled in the art, in an appropriate solvent, e.g, dioxane, at an appropriate temperature, e.g., refluxing conditions, for an appropriate period of time, e.g, 16 hours. As can be appreciated by one skilled in the art, the above reaction provides an example of a generalized approach wherein compounds similar in structure to the specific reactants above (compounds similar to compounds of type 6.1 and 6.2), can be substituted in the reaction to provide 4-(1H-imidazol-5-yl)-N-(phenyl)pyrimidin-2-amine derivatives similar to Formula 6.3.

SCHEME 7A.

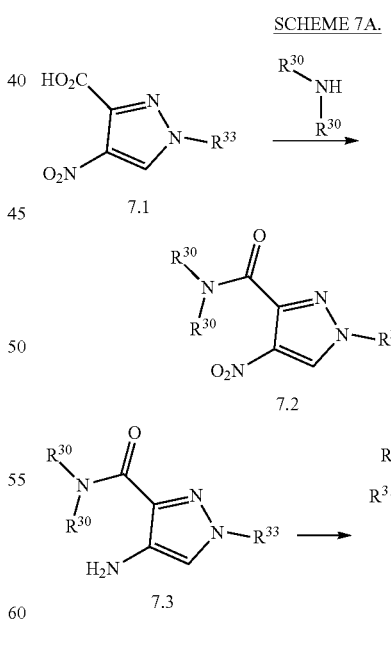

7.1

7.2

7.3

7.4

Compounds are represented in generic form, with substituents as noted in compound descriptions elsewhere herein. A more specific example is set forth below.

SCHEME 7B.

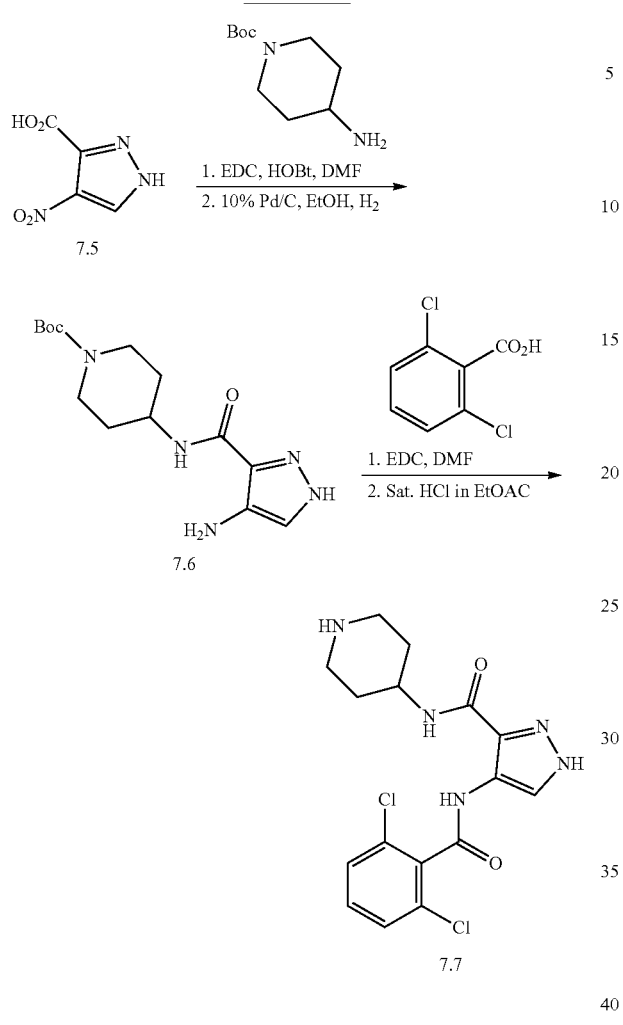

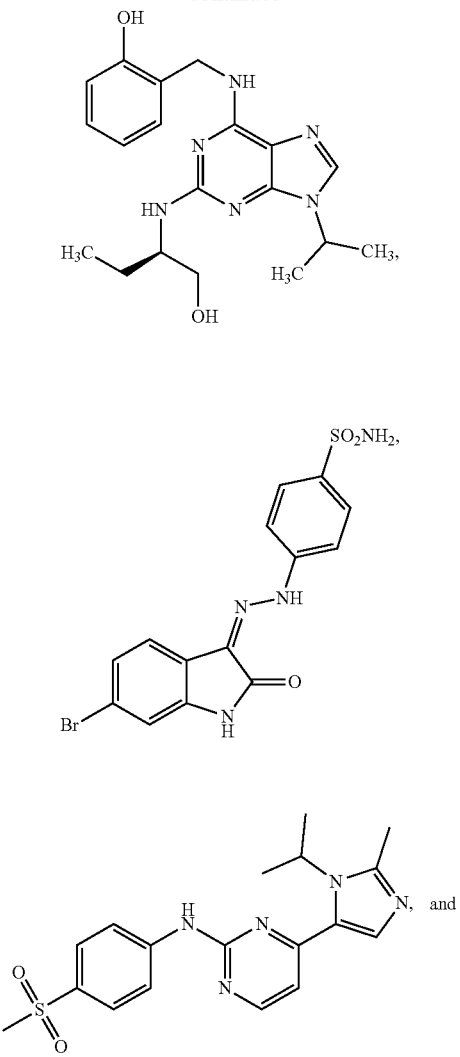

D. PHARMACEUTICAL COMPOSITIONS

In one aspect, disclosed are pharmaceutical compositions comprising a CDK2 inhibitor, or a pharmaceutically acceptable salt thereof; and one or more of: (a) at least one agent known to treat hearing impairment, or a pharmaceutically acceptable salt thereof; and (b) at least one agent known to prevent hearing impairment, or a pharmaceutically acceptable salt thereof; and a pharmaceutically acceptable carrier.

In one aspect, disclosed are pharmaceutical compositions comprising a compound selected from:

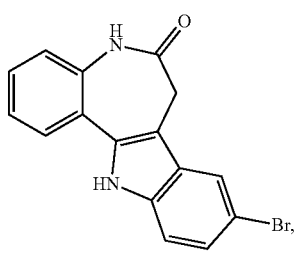

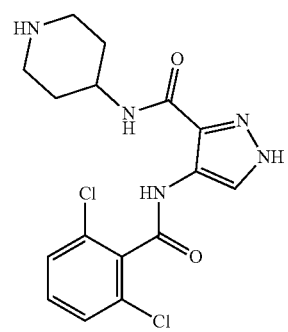 [SMILES: O=C(NC1CCNCC1)c1n[nH]cc1NC(=O)c1c(Cl)cccc1Cl]

or a pharmaceutically acceptable salt thereof; and one or more of: at least one agent known to treat hearing impairment, or a pharmaceutically acceptable salt thereof; at least one agent known to prevent hearing impairment, or a pharmaceutically acceptable salt thereof; wherein at least one is present in an effective amount; and a pharmaceutically acceptable carrier.

In one aspect, disclosed are pharmaceutical compositions comprising a compound selected from:

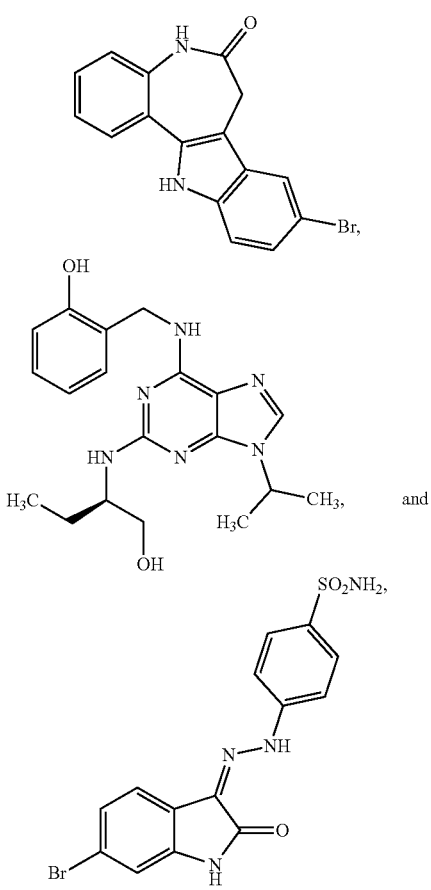

or a pharmaceutically acceptable salt thereof; and one or more of: (a) at least one agent known to treat hearing impairment, or a pharmaceutically acceptable salt thereof; and (b) at least one agent known to prevent hearing impairment, or a pharmaceutically acceptable salt thereof; and a pharmaceutically acceptable carrier.

In various aspects, the compounds and compositions of the invention can be administered in pharmaceutical compositions, which are formulated according to the intended method of administration. The compounds and compositions described herein can be formulated in a conventional manner using one or more physiologically acceptable carriers or excipients. For example, a pharmaceutical composition can be formulated for local or systemic administration, e.g., administration by drops or injection into the ear, insufflation (such as into the ear), intravenous, topical, or oral administration.

The nature of the pharmaceutical compositions for administration is dependent on the mode of administration and can readily be determined by one of ordinary skill in the art. In various aspects, the pharmaceutical composition is sterile or sterilizable. The therapeutic compositions featured in the invention can contain carriers or excipients, many of which are known to skilled artisans. Excipients that can be used include buffers (for example, citrate buffer, phosphate buffer, acetate buffer, and bicarbonate buffer), amino acids, urea, alcohols, ascorbic acid, phospholipids, polypeptides (for example, serum albumin), EDTA, sodium chloride, liposomes, mannitol, sorbitol, water, and glycerol. The nucleic acids, polypeptides, small molecules, and other modulatory compounds featured in the invention can be administered by any standard route of administration. For example, administration can be parenteral, intravenous, subcutaneous, or oral. A modulatory compound can be formulated in various ways, according to the corresponding route of administration. For example, liquid solutions can be made for administration by drops into the ear, for injection, or for ingestion; gels or powders can be made for ingestion or topical application. Methods for making such formulations are well known and can be found in, for example, Remington's Pharmaceutical Sciences, 18th Ed., Gennaro, ed., Mack Publishing Co., Easton, PA 1990.

In various aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

In various aspects, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In a further aspect, the CDK2 inhibitor is selected from a paullone derivative, a purine derivative, and a 3-(2-phenyl-hydrazono)indolin-2-one derivative, or a pharmaceutically acceptable salt thereof. In a still further aspect, the CDK2 inhibitor is selected from:

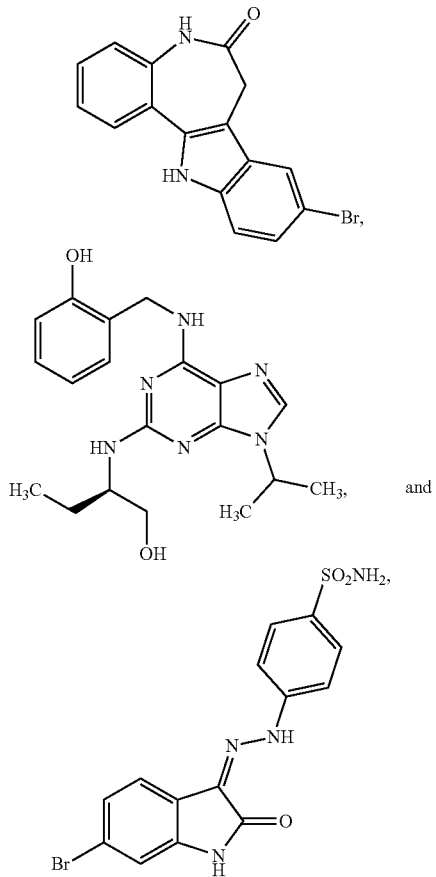

or a pharmaceutically acceptable salt thereof.

In a further aspect, an effective amount is a therapeutically effective amount. In a still further aspect, an effective amount is a prophylactically effective amount.

In a further aspect, the pharmaceutical composition is administered to a mammal. In a still further aspect, the mammal is a human. In an even further aspect, the human is a patient.

In a further aspect, the agent known to treat hearing impairment is selected from an antiepileptic drug blocking T-type calcium channels; an anticonvulsant; a synthetic glucocorticoid; a loop diuretic; an anti-oxidant; a proton pump inhibitor; a PDE5 inhibitor; and a mGluR7 inhibitor. In a still further aspect, the agent known to treat a hearing impairment is selected from trimethadione; mibefradil; ethosuximide; 3,5-dichloro-N-[1-(2,2-dimethyl-tetrahydro-pyran-4-ylmethyl)-4-fluoro-piperidin-4-ylmethyl]-benz-amide (TTA-P2); NNC 55-0396; ML 218; nilvadipine; valproic acid; oxcarbazepine; phenobarbital; phenytoin; zonisamide; nicardipine; chlordiazepoxide; sipatrigine; halothane; octanol; pimozide; penfluridol; fluspirilene; thioridazine; clozapine; haloperidol; tetramethrin; tetrandrine; amiodarone; bepridil; cinnarizine; flunarizine; amiloride; anandamide; dexamethasone; methylprednisolone; N2-[(2S)-2-(3,5-Difluorophenyl)-2-hydroxyethanoyl]-N1-[(7S)-5-methyl-6-oxo-6,7-dihydro-5H-dibenzo[b,d]azepin-7-yl]-L-alaninamide; 2-phenyl-1,2-benzisoselenazol-3-one (ebselen); sodium thiosulfate; D-methionine; furosemide; N-acetyl-L-cysteine; vitamin A; vitamin C; vitamin E; vigabatrin; omeprazole; lansoprazole; pantoprazole; rabeprazole; esomeprazole; pariprazole; leminoprazole; 3,3'-diindolylmethane; vardenafil; sildenafil; tadalafil; udenafil; dasantafil; avanafil; SLx2101; LAS34179; N,N'-dibenzhydrylethane-1,2-diamine dihydrochloride; R(+)-N-propargyl-1-aminoindan; and L-carnitine.

In a further aspect, the chemotherapeutic agent is selected from a platinum-based agent. In a still further aspect, the platinum-based agent is selected from carboplatin, cisplatin, transplatin, nedaplatin, oxaliplatin, picoplatin, satraplatin, transplatin, and triplatin. In yet a further aspect, the platinum-based agent is cisplatin.

In a further aspect, the ototoxic agent is selected from one or more of an antibiotic, a loop diuretic, an antimetabilite, and a salicyclate. In a still further aspect, the antibiotic agent is selected from one or more of daunorubicin, doxorubicin, epirubicin, idarubicin, actinomycin-D, bleomycin, and mitomycin-C, or a pharmaceutically acceptable salt thereof. In yet a further aspect, the antibiotic agent is an aminoglycoside. In an even further aspect, the aminoglycoside is selected from one or more of amikacin, apramycin, arbekacin, astromicin, bekanamycin, dibekacin, framycetin, gentamicin, hygromycin B, isepamicin, kanamycin, neomycin, netilmicin, paromomycin, rhodostreptomycin, ribostamycin, sisomicin, spectinomycin, streptomycin, tobramycin, and verdamicin, or a pharmaceutically acceptable salt thereof.

In a further aspect, the loop diuretic is selected from one or more of furosemide; ethacrynic acid; or bumetanide, or a pharmaceutically acceptable salt thereof.

In a further aspect, the antimetabilite is selected one or more of an anti-folate, a fluoropyridimidine, a deoxynucleoside analogue, and a thiopurine. In a still further aspect, the antimetabolite is selected from one or more of methotrexate, pemetrexed, fluorouracil, capecitabine, cytarabine, gemcitabine, decitabine, 5-azacytidine, fludarabine, nelarabine, cladribine, clofarabine, pentostatin, thioguanine, and mercaptopurine, or a pharmaceutically acceptable salt thereof.

In a further aspect, the salicylate is selected from one or more of salicylic acid, methyl salicylate, and trolamine salicylate, or pharmaceutically acceptable salts thereof.

In a further aspect, the agent known to prevent hearing impairment is selected from one or more of fish oil, an omega-3 fatty acid, magnesium, folic acid, vitamin A, vitamin C, vitamin E, rebamipide, alpha-lipoic acid, N-acetylcysteine (NAC), Elselen, D-methionine, magnesium, ABC magnesium (vitamins A, B, and C, plus magnesium). Molecular hydrogen (hydrogen-rich water), dexamethasone, Acuval, CoQ10, L-arginine, Ginko biloba, coenzyme Q10, Z-VAD-fmk, thymidylate kinase (TMK, AM111), retinoic acid, calcium, calcineurin inhibitors, or a pharmaceutically acceptable salt thereof.

In a further aspect, the pharmaceutical composition is used to treat hearing impairment.

In a further aspect, the pharmaceutical composition is used to prevent a hearing impairment.

It is understood that the disclosed compositions can be prepared from the disclosed compounds. It is also understood that the disclosed compositions can be employed in the disclosed methods of using.

E. METHODS OF PREPARING A COMPOSITION

In one aspect, disclosed are methods of preparing a pharmaceutical composition, the method comprising the step of combining a CDK2 inhibitor, or a pharmaceutically acceptable salt thereof and one or more of: (a) at least one agent known to treat hearing impairment, or a pharmaceutically acceptable salt thereof (b) at least one agent known to prevent hearing impairment, or a pharmaceutically acceptable salt thereof; wherein at least one is present in an effective amount; and a pharmaceutically acceptable carrier. In a further aspect, the effective amount is a prophylactically effective amount. In a still further aspect, the effective amount is a therapeutically effective amount.

In one aspect, disclosed are methods of preparing a pharmaceutical composition, the method comprising the step of combining a compound selected from:

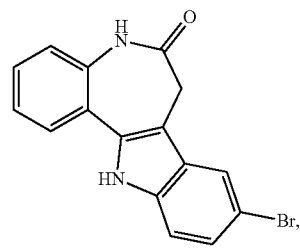

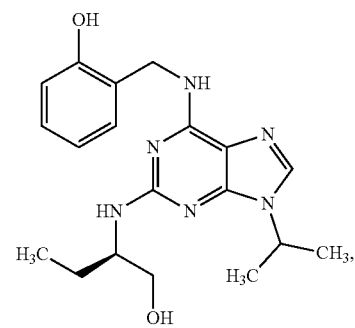

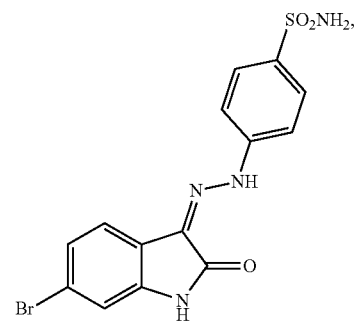

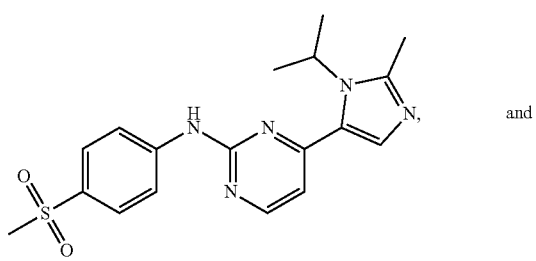

and

-continued

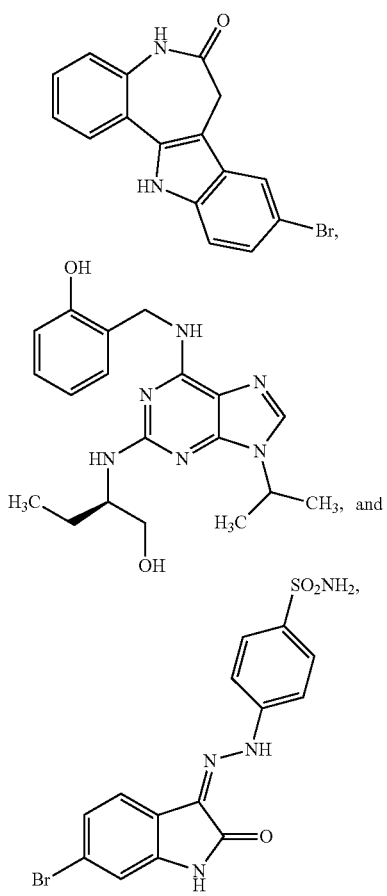

or a pharmaceutically acceptable salt thereof; and one or more of: at least one agent known to treat hearing impairment, or a pharmaceutically acceptable salt thereof; at least one agent known to prevent hearing impairment, or a pharmaceutically acceptable salt thereof; wherein at least one is present in an effective amount; and a pharmaceutically acceptable carrier.

In one aspect, disclosed are methods of preparing a pharmaceutical composition, the method comprising the step of combining a compound selected from:

or a pharmaceutically acceptable salt thereof and one or more of: (a) at least one agent known to treat hearing impairment, or a pharmaceutically acceptable salt thereof (b) at least one agent known to prevent hearing impairment, or a pharmaceutically acceptable salt thereof; wherein at least one is present in an effective amount; and a pharmaceutically acceptable carrier.

In a further aspect, the CDK2 inhibitor is selected from a paullone derivative, a purine derivative, and a 3-(2-phenylhydrazono)indolin-2-one derivative, or a pharmaceutically acceptable salt thereof. In a still further aspect, the CDK2 inhibitor is selected from:

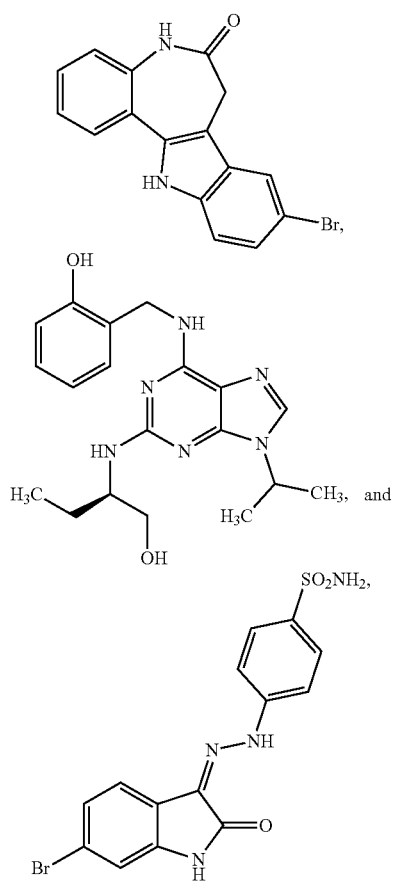

or a pharmaceutically acceptable salt thereof.

In a further aspect, an effective amount is a therapeutically effective amount. In a still further aspect, an effective amount is a prophylactically effective amount.

In a further aspect, combining is co-formulation of the CDK2 inhibitor, the agent known to treat hearing impairment and/or the agent known to prevent hearing impairment with the pharmaceutically acceptable carrier. In a still further aspect, co-formulation is an oral solid dosage form comprising the CDK2 inhibitor, the agent known to treat hearing impairment, and/or the agent known to prevent hearing impairment, and the pharmaceutically acceptable carrier. In yet a further aspect, the solid dosage form is a tablet. In an even further aspect, the solid dosage dorm is a capsule.

In a further aspect, co-formulation is an inhaled dosage form comprising the CDK2 inhibitor, the agent known to treat hearing impairment, and/or the agent known to prevent hearing impairment, and the pharmaceutically acceptable carrier.

In a further aspect, co-formulation is an injectable dosage form comprising the CDK2 inhibitor, the agent known to treat hearing impairment, and/or the agent known to prevent hearing impairment, and the pharmaceutically acceptable carrier.

In a further aspect, the pharmaceutical composition is used to treat hearing impairment. In a further aspect, the pharmaceutical composition is used to prevent hearing impairment.

F. METHODS OF TREATING HEARING IMPAIRMENT

In one aspect, disclosed are methods of treating hearing impairment comprising administering to a subject diagnosed with a need for treatment of hearing impairment a therapeutically effective amount of a cyclin-dependent kinase 2 (CDK2) inhibitor, or a pharmaceutically acceptable salt thereof.

In one aspect, disclosed are methods of treating hearing impairment, the method comprising administering to a subject diagnosed with a need for treatment of hearing impairment a therapeutically effective amount of a compound selected from:

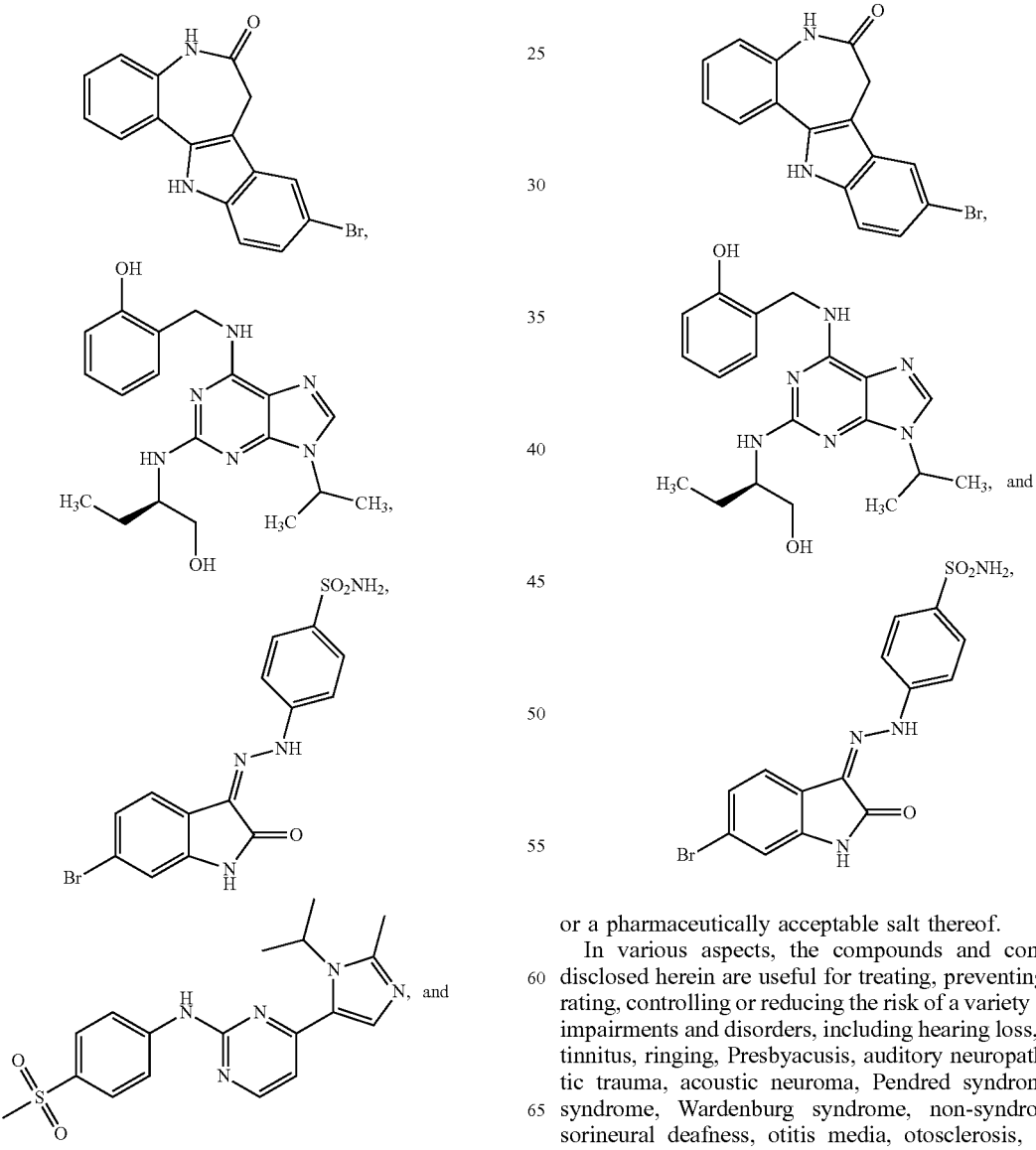

or a pharmaceutically acceptable salt thereof.

In one aspect, disclosed are methods of treating hearing impairment, the method comprising administering to a subject diagnosed with a need for treatment of hearing impairment a therapeutically effective amount of a compound selected from:

or a pharmaceutically acceptable salt thereof.

In various aspects, the compounds and compositions disclosed herein are useful for treating, preventing, ameliorating, controlling or reducing the risk of a variety of hearing impairments and disorders, including hearing loss, deafness, tinnitus, ringing, Presbyacusis, auditory neuropathy, acoustic trauma, acoustic neuroma, Pendred syndrome, Usher syndrome, Wardenburg syndrome, non-syndromic sensorineural deafness, otitis media, otosclerosis, Meniere's disease, ototoxicity, labyrinthitis, as well as hearing impairments caused by infection (i.e., measles, mumps, or meningitis), medicines such as antibiotics, and some cancer treatments (i.e., chemotherapy and radiation therapy).

Noise-induced hearing loss (NIHL) caused by intense or constant noise exposure is irreversible, resulting in a permanent disability to military personnel. NIHL is the No. 1 diagnosis among U.S. soldiers who served in Afghanistan (http://issuu.com/hearinghealthmagazine/docs/hearinghealthwinter2010issuurev3). Of 1,250 Marine Commandos who served in Afghanistan, 69% suffered hearing loss due to the intense noise of combat. Hearing impairment significantly affects performance (Consideration of Hazardous Noise in the Acquisition of Selected Major Department of the Navy Weapon Systems and Platforms N2010-0038, 22 Jun. 2010). Given the importance of auditory acuity in perceiving commands and sensing enemy activity, it is clear that even mild loss of hearing increases the risk to soldiers. While hearing aids and cochlear implants are helpful devices in the civilian and non-combatant community, they are not an appropriate remedy in a combat setting. When hearing loss restricts continued military service, forces suffer loss of personnel, often including the most effective and experienced officers and non-commissioned officers (NCOs). Finally, even the best available protection cannot prevent NIHL. As a result, 2.3 million veterans now receive disability compensation and treatment that exceeds $2 billion annually (Annual Benefits Report Fiscal Year 2012, U.S. Dept. Veterans Affairs). Among veterans who suffer from NIHL, difficulty in communicating with clinicians and family impedes reintegration into society and exacerbates depression and anxiety. A preventive solution would cost-effectively and significantly improve the effectiveness of military personnel and the quality of life of veterans.

Traumatic brain injury (TBI) and blast-associated injury occur most frequently in military situations where blast exposure cannot be predicted, trauma intensity exceeds the effectiveness of protective devices, or protective devices are not available. TBI is often accompanied by a diverse range of disruption or damage to the auditory sensory system, which is highly vulnerable to blast injury. Extreme physical blast force can cause damage of various types to the peripheral auditory system, including rupture of the tympanic membrane (TM, eardrum), fracture of the middle ear bones, dislocation of sensory hair cells from the basilar membrane, and loss of spiral ganglia that innervate hair cells. In human studies of blast injury, approximately 17-29% of cases involve severe TM rupture, while 33-78% involve moderate to severe sensorineural hearing loss (hair cell and ganglion loss). Therefore, TBI and blast injury are a common, although extreme, cause of hearing loss.

In various aspects, the disclosed compounds can be used in combination with one or more other drugs in the treatment, prevention, control, amelioration, or reduction of risk of hearing impairments and disorders for which disclosed compounds or the other drugs can have utility, where the combination of the drugs together are safer or more effective than either drug alone. Such other drug(s) can be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and a disclosed compound is preferred. However, the combination therapy can also include therapies in which a disclosed compound and one or more other drugs are administered on different overlapping schedules. It is also contemplated that when used in combination with one or more other active ingredients, the disclosed compounds and the other active ingredients can be used in lower doses than when each is used singly. Accordingly, the pharmaceutical compositions include those that contain one or more other active ingredients, in addition to a compound of the present invention.

Where appropriate, following treatment, the subject (e.g., human or other animal) can be tested for an improvement in hearing or in other symptoms related to hearing disorders. Methods for measuring hearing are well-known and include pure tone audiometry, air conduction, and bone conduction tests. These exams measure the limits of loudness (intensity) and pitch (frequency) that a human can hear. Hearing tests in humans include behavioral observation audiometry (for infants to seven months), visual reinforcement orientation audiometry (for children 7 months to 3 years) and play audiometry for children older than 3 years. Oto-acoustic emission testing can be used to test the functioning of the cochlear hair cells, and electro-cochleography provides information about the functioning of the cochlea and the first part of the nerve pathway to the brain. In various aspects, treatment can be continued with or without modification or can be stopped.

In a further aspect, the CDK2 inhibitor is selected from a paullone derivative, a purine derivative, and a 3-(2-phenyl-hydrazono)indolin-2-one derivative, or a pharmaceutically acceptable salt thereof. In a still further aspect, the CDK2 inhibitor is selected from:

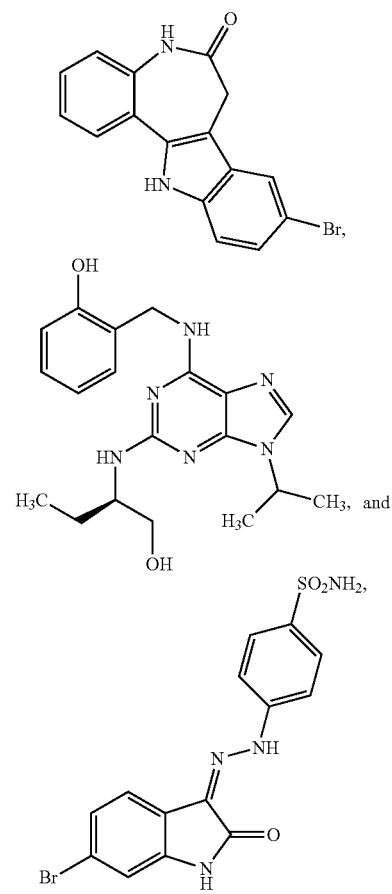

or a pharmaceutically acceptable salt thereof.

In a further aspect, the subject is a mammal. In a still further aspect, the mammal is human.

In a further aspect, the subject has been diagnosed with a need for treatment of a hearing impairment prior to the administering step. In a still further aspect, the subject is at risk for developing a hearing impairment prior to the administering step.

In a further aspect, the CDK2 inhibitor is administered locally. In a still further aspect, the CDK2 inhibitor is administered systemically. In yet a further aspect, the CDK2 inhibitor is administered locally to the inner ear of the subject. In an even further aspect, the CDK2 inhibitor is administered via injection into one or more of the scala tympani, cochlear duct, scala vestibule of the cochlea, into the auditory nerve trunk in the internal auditory meatus, or into the middle ear space across the transtympanic membrane/ear drum.

In a further aspect, the CDK2 inhibitor is administered in an amount of from about 0.001 µM to about $1.0 \times 10^4$ µM. In a still further aspect, the CDK2 inhibitor is administered in an amount of from about 0.001 µM to about $1.0 \times 10^2$ µM. In yet a further aspect, the CDK2 inhibitor is administered in an amount of from about 0.001 µM to about 10 µM. In an even further aspect, the CDK2 inhibitor is administered in an amount of from about 0.01 µM to about $1.0 \times 10^4$ µM. In a still further aspect, the CDK2 inhibitor is administered in an amount of from about 0.1 µM to about $1.0 \times 10^4$ µM. In yet a further aspect, the CDK2 inhibitor is administered in an amount of from about 1.0 µM to about $1.0 \times 10^4$ µM.

In a further aspect, the CDK2 inhibitor is administered locally. In a still further aspect, the CDK2 inhibitor is administered systemically.

In a further aspect, the CDK2 inhibitor is administered at least once every three weeks. In a still further aspect, the CDK2 inhibitor is administered at least once every week. In yet a further aspect, the CDK2 inhibitor is administered at least once every 24 h. In an even further aspect, the CDK2 inhibitor is administered at least once every four hours. In a still further aspect, the CDK2 inhibitor is administered at least once every one hour.

In a further aspect, the CDK2 inhibitor is administered in an amount of from about 0.001 µM to about $1.0 \times 10^4$ µM at least once every three weeks.

In a further aspect, the hearing impairment is noise-induced. In a still further aspect, the noise-induced hearing loss is temporary. In yet a further aspect, the noise-induced hearing loss is permanent.

In a further aspect, the hearing impairment is drug-induced. In a still further aspect, the drug is a chemotherapeutic agent. In yet a further aspect, the chemotherapeutic agent is platinum-based. In an even further aspect, the platinum-based chemotherapeutic agent is selected from carboplatin, cisplatin, transplatin, nedaplatin, oxaliplatin, picoplatin, satraplatin, transplatin, and triplatin, or a pharmaceutically acceptable salt thereof. In a still further aspect, the platinum-based chemotherapeutic agent is cisplatin, or a pharmaceutically acceptable salt thereof. In yet a further aspect, the drug is an antibiotic. In an even further aspect, the antibiotic is selected from daunorubicin, doxorubicin, epirubicin, idarubicin, actinomycin-D, bleomycin, mitomycin-C, amikacin, apramycin, arbekacin, astromicin, bekanamycin, dibekacin, framycetin, gentamicin, hygromycin B, isepamicin, kanamycin, neomycin, netilmicin, paromomycin, rhodostreptomycin, ribostamycin, sisomicin, spectinomycin, streptomycin, tobramycin, and verdamicin, or a pharmaceutically acceptable salt thereof.

In a further aspect, the hearing impairment is age-related.

In a further aspect, the hearing impairment is related to a balance or orientation-related disorder. Examples of balance disorders include, but are not limited to, induced or spontaneous vertigo, dysequilibrium, increased susceptibility to motion sickness, nausea, vomiting, ataxia, labyrinthitis, oscillopsia, nystagmus, syncope, lightheadedness, dizziness, increased falling, difficulty walking at night, Meniere's disease, and difficulty in visual tracking and processing.

In a further aspect, the subject has been diagnosed with a need for prevention of hearing impairment prior to the administering step.

In a further aspect, the method further comprises identifying a subject at risk for developing a hearing impairment prior to the administering step.

G. METHODS OF PREVENTING HEARING IMPAIRMENT

In one aspect, disclosed are methods of preventing hearing impairment, the method comprising administering to a subject a CDK2 inhibitor in an amount of from about 0.001 µM to about $1.0 \times 10^4$ µM at least once every three weeks, or a pharmaceutically acceptable salt thereof.

In one aspect, disclosed are methods of preventing hearing impairment, the method comprising administering to a subject a compound selected from:

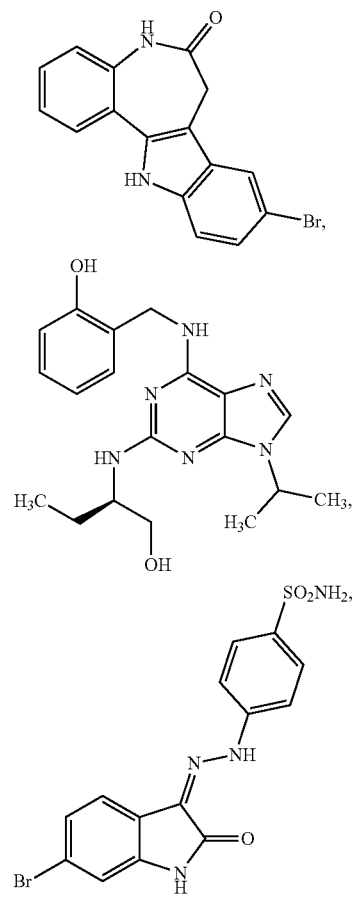

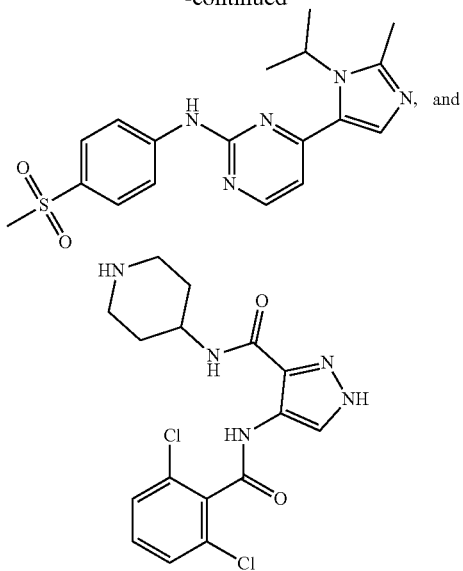

or a pharmaceutically acceptable salt thereof, in an amount of from about 0.001 μM to about 1.0×10⁴ μM at least once every three weeks.

In one aspect, disclosed are method of preventing hearing impairment, the method comprising administering to a subject a compound selected from:

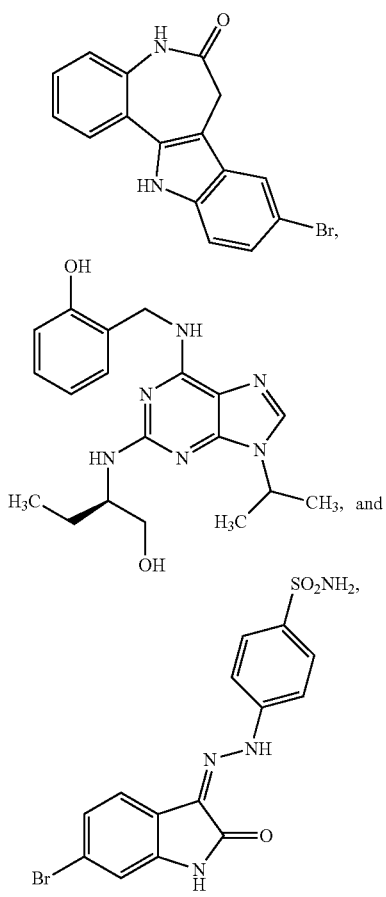

or a pharmaceutically acceptable salt thereof, in an amount of from about 0.001 μM to about 1.0×10⁴ at least once every three weeks.

Examples of hearing impairment include, but are not limited to, hearing loss, deafness, tinnitus, ringing, Presbyacusis, auditory neuropathy, acoustic trauma, acoustic neuroma, Pendred syndrome, Usher syndrome, Wardenburg syndrome, non-syndromic sensorineural deafness, otitis media, otosclerosis, Meniere's disease, ototoxicity, labyrinthitis, as well as hearing impairments caused by infection (i.e., measles, mumps, or meningitis), medicines such as antibiotics, and some cancer treatments (i.e., chemotherapy and radiation therapy).

More than one billion teens and young adults worldwide are at risk of hearing loss from exposure to loud music, as recently reported by the World Health Organization (http://www.cnn.com/2015/03/06/health/hearing-loss-loud-music/index). Many other noise exposures, including occupational settings and consumer-operated devices, also cause NIHL, which is among the most common physical complaints and which detracts significantly from the ability to converse, communicate, and participate in everyday life (thus reducing general quality of life of the individual and the family). Acute or chronic acoustic overexposure has put more than 40 million US workers at risk of permanent hearing loss (Kopke et al., 2007).

Biological protection of hearing is more promising than currently available mechanical protective devices. Hearing aids are frequently problematic because of their high cost and their many technical issues. Ideally, service men and women could take protective drugs before entering high-risk or high-noise settings and would then be protected from noise injury with no effect on performance. To date, there are no FDA-approved drugs for protection against noise- and TBI-associated hearing loss.

In a further aspect, the CDK2 inhibitor is selected from a paullone derivative, a purine derivative, and a 3-(2-phenylhydrazono)indolin-2-one derivative, or a pharmaceutically acceptable salt thereof. In a still further aspect, the CDK2 inhibitor is selected from:

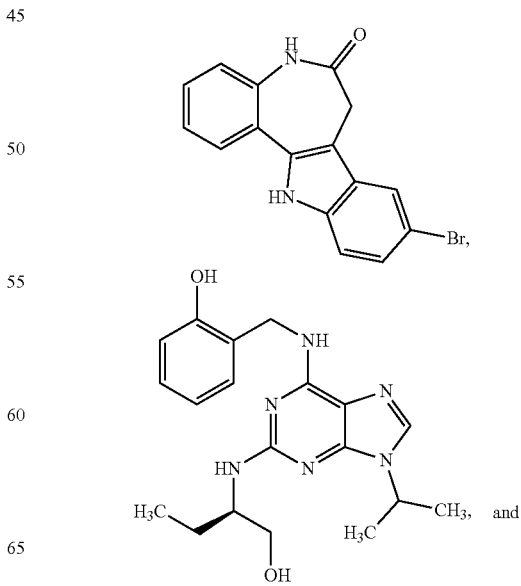

-continued

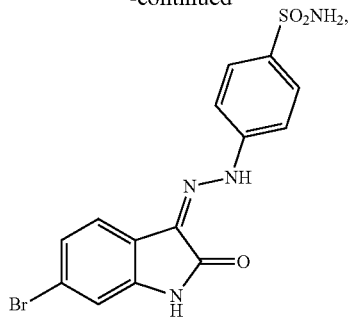

or a pharmaceutically acceptable salt thereof.

In a further aspect, the subject is a mammal. In a still further aspect, the mammal is human.

In a further aspect, the CDK2 inhibitor is administered locally. In a still further aspect, the CDK2 inhibitor is administered systemically. In yet a further aspect, the CDK2 inhibitor is administered locally to the inner ear of the subject. In an even further aspect, the CDK2 inhibitor is administered via injection into one or more of the scala tympani, cochlear duct, scala vestibule of the cochlea, into the auditory nerve trunk in the internal auditory meatus, or into the middle ear space across the transtympanic membrane/ear drum.

In a further aspect, the hearing impairment is noise-induced. In a still further aspect, the noise-induced hearing loss is temporary. In yet a further aspect, the noise-induced hearing loss is permanent.

In a further aspect, the hearing impairment is drug-induced. In a still further aspect, the drug is a chemotherapeutic agent. In yet a further aspect, the chemotherapeutic agent is platinum-based. In an even further aspect, the platinum-based chemotherapeutic agent is selected from carboplatin, cisplatin, transplatin, nedaplatin, oxaliplatin, picoplatin, satraplatin, transplatin, and triplatin, or a pharmaceutically acceptable salt thereof. In a still further aspect, the platinum-based chemotherapeutic agent is cisplatin, or a pharmaceutically acceptable salt thereof. In yet a further aspect, the drug is an antibiotic. In an even further aspect, the antibiotic is selected from daunorubicin, doxorubicin, epirubicin, idarubicin, actinomycin-D, bleomycin, mitomycin-C, amikacin, apramycin, arbekacin, astromicin, bekanamycin, dibekacin, framycetin, gentamicin, hygromycin B, isepamicin, kanamycin, neomycin, netilmicin, paromomycin, rhodostreptomycin, ribostamycin, sisomicin, spectinomycin, streptomycin, tobramycin, and verdamicin, or a pharmaceutically acceptable salt thereof.

In a further aspect, the hearing impairment is age-related.

In a further aspect, the hearing impairment is related to a balance or orientation-related disorder. Examples of balance disorders include, but are not limited to, induced or spontaneous vertigo, dysequilibrium, increased susceptibility to motion sickness, nausea, vomiting, ataxia, labyrinthitis, oscillopsia, nystagmus, syncope, lightheadedness, dizziness, increased falling, difficulty walking at night, Meniere's disease, and difficulty in visual tracking and processing.

H. METHODS OF USING THE COMPOSITIONS

The compounds and compositions are further useful in methods for the prevention, treatment, control, amelioration, or reduction of risk of the hearing impairments and disorders noted herein. The compounds and compositions are further useful in a method for the prevention, treatment, control, amelioration, or reduction of risk of the aforementioned hearing impairments and disorders in combination with other agents.

Also provided are methods of using of a disclosed composition or medicament. In one aspect, the method of use is directed to the treatment of a disorder. In a further aspect, the disclosed compounds can be used as single agents or in combination with one or more other drugs in the treatment, prevention, control, amelioration, or reduction of risk of the aforementioned diseases, disorders and conditions for which the compound or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound can be more efficacious than either as a single agent.

The pharmaceutical compositions and methods of the present invention can further comprise other therapeutically active compounds as noted herein which are usually applied in the treatment of the above mentioned pathological conditions.

1. Manufacture of a Medicament

In one aspect, the invention relates to a medicament comprising a CDK2 inhibitor, or a pharmaceutically acceptable salt thereof; and one or more of at least one agent known to treat a hearing impairment, or a pharmaceutically acceptable salt thereof, and at least one agent known to prevent a hearing impairment, or a pharmaceutically acceptable salt thereof.

In various aspects, the invention relates methods for the manufacture of a medicament for treating and/or preventing hearing impairment comprising combining one or more disclosed compounds, products, or compositions or a pharmaceutically acceptable salt thereof, with a pharmaceutically acceptable carrier. It is understood that the disclosed methods can be performed with the disclosed compounds, products, and pharmaceutical compositions. It is also understood that the disclosed methods can be employed in connection with the disclosed methods of using.

2. Use of Compounds and Compositions

Also provided are the uses of the disclosed compounds and compositions. Thus, in one aspect, the invention relates to the uses of a CDK2 inhibitor, or a pharmaceutically acceptable salt thereof; and one or more of at least one agent known to treat a hearing impairment, or a pharmaceutically acceptable salt thereof, and at least one agent known to prevent a hearing impairment, or a pharmaceutically acceptable salt thereof.

In a further aspect, the invention relates to the use of a CDK2 inhibitor, or a pharmaceutically acceptable salt thereof in the manufacture of a medicament for the treatment of a hearing impairment or disorder.

In a further aspect, the use relates to a process for preparing a pharmaceutical composition comprising a therapeutically effective amount of a CDK2 inhibitor, or a pharmaceutically acceptable salt thereof, and one or more of at least one agent known to treat a hearing impairment, or a pharmaceutically acceptable salt thereof, and at least one agent known to prevent a hearing impairment, or a pharmaceutically acceptable salt thereof, for use as a medicament.

In a further aspect, the use relates to a process for preparing a pharmaceutical composition comprising a therapeutically effective amount of a CDK2 inhibitor, or a pharmaceutically acceptable salt thereof, and one or more of at least one agent known to treat a hearing impairment, or a pharmaceutically acceptable salt thereof, and at least one agent known to prevent a hearing impairment, or a pharmaceutically acceptable salt thereof, wherein a pharmaceutically acceptable carrier is intimately mixed with a therapeutically effective amount of the CDK2 inhibitor, the at least one agent known to treat a hearing impairment, or the at least one agent known to prevent a hearing impairment.

In various aspects, the use relates to the treatment of a hearing impairment or disorder in a vertebrate animal. In a further aspect, the use relates to the treatment of a hearing impairment or disorder in a human subject.

In a further aspect, the use is the treatment of a hearing impairment or disorder. In a still further aspect, the use is the treatment of a hearing impairment. In yet a further aspect, the use is the treatment of a hearing disorder.

It is understood that the disclosed uses can be employed in connection with the disclosed compounds, methods, compositions, and kits. In a further aspect, the invention relates to the use of a disclosed compound or composition of a medicament for the treatment of a hearing impairment or disorder in a mammal.

In a further aspect, the invention relates to the use of a disclosed compound or composition in the manufacture of a medicament for the treatment of a hearing impairment or disorder selected from hearing loss, deafness, tinnitus, ringing, Presbyacusis, auditory neuropathy, acoustic trauma, acoustic neuroma, Pendred syndrome, Usher syndrome, Wardenburg syndrome, non-syndromic sensorineural deafness, otitis media, otosclerosis, Meniere's disease, ototoxicity, labyrinthitis, as well as hearing impairments caused by infection (i.e., measles, mumps, or meningitis), medicines such as antibiotics, and some cancer treatments (i.e., chemotherapy and radiation therapy).

In a further aspect, the invention relates to the use of a disclosed compound or composition in the manufacture of a medicament for the treatment of a hearing impairment or disorder.

In a further aspect, the invention relates to the use of a disclosed compound or composition in the treatment of hair cell loss and any disorder that arises as a consequence of cell loss in the ear, such as hearing impairments (e.g., because of trauma or prolonged exposure to loud noises), deafness (e.g., because of a genetic or congenital defect), and vestibular disorders (e.g., including bilateral and unilateral vestibular dysfunction), for example, by promoting differentiation (e.g., complete or partial differentiation) of one or more cells into one or more cells capable of functioning as sensory cells of the ear, e.g., hair cells. Subjects benefiting from such treatment include those at risk of hair cell loss and/or a patient with hair cell loss. For example, a subject having or at risk for developing a hearing loss can hear less well than the average subject (e.g., an average human being), or less well than a subject before experiencing the hearing loss. For example, hearing can be diminished by at least 5%, 10%, 30%, 50% or more.

In various aspects, the methods described herein can be used to generate hair cell growth in the ear and/or to increase the number of hair cells in the ear (e.g., in the inner, middle, and/or outer ear). In this respect, an effective amount of a stimulatory agent and an inhibitory agent described herein is an amount that increases the number of hair cells in the ear by about 2-, 3-, 4-, 6-, 8-, or 10-fold, or more, as compared to the number of hair cells before treatment. This new hair cell growth can effectively restore or establish at least a partial improvement in the subject's ability to hear. For example, administration of a stimulatory agent and an inhibitory agent of this invention can improve hearing loss by about 5, 10, 15, 20, 40, 60, 80, 100% or more.

In various aspects, the agents and methods described herein can be used prophylactically, such as to prevent, reduce, or delay progression of hearing loss, deafness, or other auditory disorders associated with loss of inner ear function.

3. Kits

In one aspect, disclosed are kits comprising a CDK2 inhibitor, or a pharmaceutically acceptable salt thereof; and one or more of: (a) at least one agent known to treat a hearing impairment; (b) at least one agent known to prevent a hearing impairment; (c) at least one antibiotic agent; (d) at least one chemotherapeutic agent; (e) instructions for treating a hearing impairment; and (0 instructions for preventing a hearing impairment.

In one aspect, disclosed are kits comprising a compound selected from:

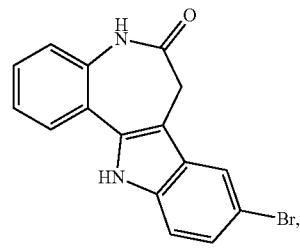

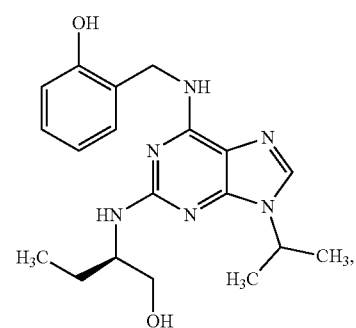

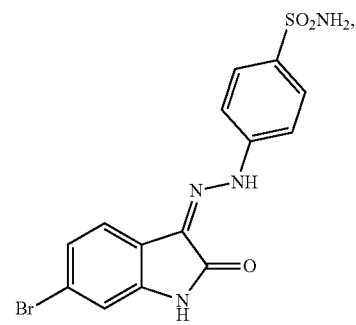

-continued

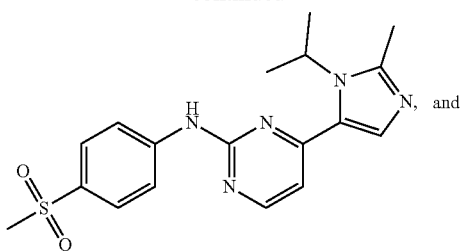

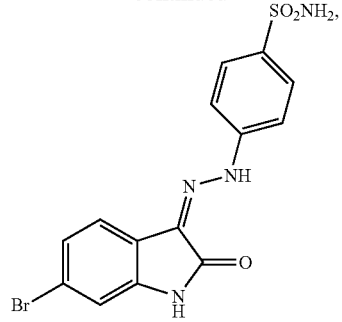

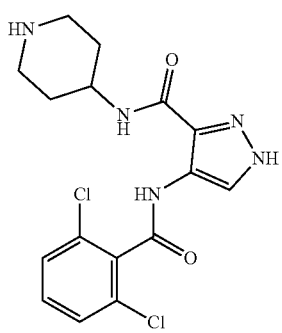 [SMILES: O=C(NC1CCNCC1)c1n[nH]cc1NC(=O)c1c(Cl)cccc1Cl]

or a pharmaceutically acceptable salt thereof; and one or more of: at least one agent known to treat a hearing impairment; at least one agent known to prevent a hearing impairment; at least one antibiotic agent; at least one chemotherapeutic agent; instructions for treating a hearing impairment; and instructions for preventing a hearing impairment.

In one aspect, disclosed are kits comprising a compound selected from:

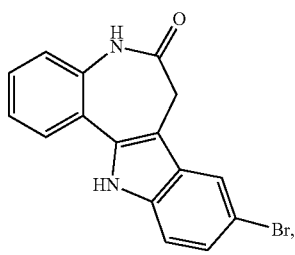

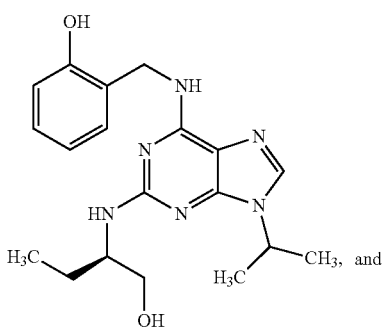

or a pharmaceutically acceptable salt thereof; and one or more of: (a) at least one agent known to treat a hearing impairment; (b) at least one agent known to prevent a hearing impairment; (c) at least one antibiotic agent; (d) at least one chemotherapeutic agent; (e) instructions for treating a hearing impairment; and (f) instructions for preventing a hearing impairment.

In various aspects, the agents and pharmaceutical compositions described herein can be provided in a kit. The kit can also include combinations of the agents and pharmaceutical compositions described herein.

In various aspects, the informational material can be descriptive, instructional, marketing or other material that relates to the methods described herein and/or to the use of the agents for the methods described herein. For example, the informational material may relate to the use of the agents herein to treat a subject who has, or who is at risk for developing, a hearing impairment. The kits can also include paraphernalia for administering the agents of this invention to a cell (in culture or in vivo) and/or for administering a cell to a patient.

In various aspects, the informational material can include instructions for administering the pharmaceutical composition and/or cell(s) in a suitable manner to treat a human, e.g., in a suitable dose, dosage form, or mode of administration (e.g., a dose, dosage form, or mode of administration described herein). In a further aspect, the informational material can include instructions to administer the pharmaceutical composition to a suitable subject, e.g., a human having, or at risk for developing, a hearing impairment.

In various aspects, the composition of the kit can include other ingredients, such as a solvent or buffer, a stabilizer, a preservative, a fragrance or other cosmetic ingredient. In such aspects, the kit can include instructions for admixing the agent and the other ingredients, or for using one or more compounds together with the other ingredients.

In a further aspect, the CDK2 inhibitor and the at least one agent known to treat a hearing impairment are co-formulated. In a still further aspect, the CDK2 inhibitor and the at least one agent known to treat a hearing impairment are co-packaged.

In a further aspect, the agent known to treat a hearing impairment is selected from an antiepileptic drug blocking T-type calcium channels; an anticonvulsant; a synthetic glucocorticoid; a loop diuretic; an anti-oxidant; a proton pump inhibitor; a PDE5 inhibitor; and a mGluR7 inhibitor. In a still further aspect, the agent known to treat a hearing impairment is selected from trimethadione; mibefradil; ethosuximide; 3,5-dichloro-N-[1-(2,2-dimethyl-tetrahydro-pyran-4-ylmethyl)-4-fluoro-piperidin-4-ylmethyl]-benzamide (TTA-P2); NNC 55-0396; ML 218; nilvadipine; valproic acid; oxcarbazepine; phenobarbital; phenytoin;

zonisamide; nicardipine; chlordiazepoxide; sipatrigine; halothane; octanol; pimozide; penfluridol; fluspirilene; thioridazine; clozapine; haloperidol; tetramethrin; tetrandrine; amiodarone; bepridil; cinnarizine; flunarizine; amiloride; anandamide; dexamethasone; methylprednisolone; N2-[(2S)-2-(3,5-Difluorophenyl)-2-hydroxyethanoyl]-N1-[(7S)-5-methyl-6-oxo-6,7-dihydro-5H-dibenzo[b,d]azepin-7-yl]-L-alaninamide; 2-phenyl-1,2-benzisoselenazol-3-one (ebselen); sodium thiosulfate; D-methionine; furosemide; N-acetyl-L-cysteine; vitamins A; vitamin C; vitamin E; vigabatrin; omeprazole; lansoprazole; pantoprazole; rabeprazole; esomerprazole; pariprazole; leminoprazole; 3,3'-diindolylmethane; vardenafil; sildenafil; tadalafil; udenafil; dasantafil; avanafil; SLx2101; LAS34179; N,N'-dibenzhydrylethane-1,2-diamine dihydrochloride; R(+)-N-propargyl-1-aminoindan; and L-carnitine.

In a further aspect, the CDK2 inhibitor and the at least one agent known to prevent a hearing impairment are co-formulated. In a still further aspect, the CDK2 inhibitor and the at least one agent known to prevent a hearing impairment are co-packaged.

In a further aspect, the CDK2 inhibitor and the at least one antibiotic agent are co-formulated. In a still further aspect, the CDK2 inhibitor and the at least one antibiotic agent are co-packaged.

In a further aspect, the CDK2 inhibitor and the at least one chemotherapeutic agent are co-formulated. In a still further aspect, the CDK2 inhibitor and the at least one chemotherapeutic agent are co-packaged.

In a further aspect, the chemotherapeutic agent is a platinum-based agent. In a still further aspect, the platinum-based agent is selected from carboplatin, cisplatin, transplatin, nedaplatin, oxaliplatin, picoplatin, satraplatin, transplatin, and triplatin. In yet a further aspect, the platinum-based agent is cisplatin.

In a further aspect, the kit further comprises a plurality of dosage forms, the plurality comprising one or more doses; wherein each dose comprises an effective amount of a CDK2 inhibitor and the at least one agent known to treat a hearing impairment. In a still further aspect, the effective amount is a therapeutically effective amount. In yet a further aspect, the effective amount is a prophylactically effective amount. In an even further aspect, each dose of the CDK2 inhibitor and the agent known to treat a hearing impairment are co-packaged. In a still further aspect, each dose of the CDK2 inhibitor and the agent known to treat a hearing impairment are co-formulated.

In a further aspect, the kit further comprises a plurality of dosage forms, the plurality comprising one or more doses; wherein each dose comprises an effective amount of a CDK2 inhibitor and the at least one agent known to prevent a hearing impairment. In a still further aspect, the effective amount is a therapeutically effective amount. In yet a further aspect, the effective amount is a prophylactically effective amount. In an even further aspect, each dose of the CDK2 inhibitor and the agent known to prevent a hearing impairment are co-packaged. In a still further aspect, each dose of the CDK2 inhibitor and the agent known to prevent a hearing impairment are co-formulated.

In a further aspect, the kit further comprises a plurality of dosage forms, the plurality comprising one or more doses; wherein each dose comprises an effective amount of a CDK2 inhibitor and the at least one antibiotic agent. In a still further aspect, the effective amount is a therapeutically effective amount. In yet a further aspect, the effective amount is a prophylactically effective amount. In an even further aspect, each dose of the CDK2 inhibitor and the antibiotic agent are co-packaged. In a still further aspect, each dose of the CDK2 inhibitor and the antibiotic agent are co-formulated.

In a further aspect, the kit further comprises a plurality of dosage forms, the plurality comprising one or more doses; wherein each dose comprises an effective amount of a CDK2 inhibitor and the at least one chemotherapeutic agent. In a still further aspect, the effective amount is a therapeutically effective amount. In yet a further aspect, the effective amount is a prophylactically effective amount. In an even further aspect, each dose of the CDK2 inhibitor and the chemotherapeutic agent are co-packaged. In a still further aspect, each dose of the CDK2 inhibitor and the chemotherapeutic agent are co-formulated.

In a further aspect, the dosage forms are formulated for topical administration. In a still further aspect, the dosage forms are formulated for injection into the luminae of the cochlea, the auditory nerve trunk in the internal auditory meatus, the scala tympani, or the middle ear space across the transtympanic membrane/ear drum; or, if present, into a cochlear implant.

In a further aspect, the CDK2 inhibitor is formulated for topical administration; and the agent known to treat a hearing impairment is formulated for injection into the luminae of the cochlea, the auditory nerve trunk in the internal auditory meatus, the scala tympani, or the middle ear space across the transtympanic membrane/ear drum; or, if present, into a cochlear implant. In a still further aspect, the CDK2 inhibitor is formulated for injection into the luminae of the cochlea, the auditory nerve trunk in the internal auditory meatus, the scala tympani, or the middle ear space across the transtympanic membrane/ear drum; or, if present, into a cochlear implant; and the agent known to treat a hearing impairment is formulated for topical administration.

In a further aspect, the CDK2 inhibitor is formulated for topical administration; and the agent known to prevent a hearing impairment is formulated for injection into the luminae of the cochlea, the auditory nerve trunk in the internal auditory meatus, the scala tympani, or the middle ear space across the transtympanic membrane/ear drum; or, if present, into a cochlear implant. In a still further aspect, the CDK2 inhibitor is formulated for injection into the luminae of the cochlea, the auditory nerve trunk in the internal auditory meatus, the scala tympani, or the middle ear space across the transtympanic membrane/ear drum; or, if present, into a cochlear implant; and the agent known to prevent a hearing impairment is formulated for topical administration.

In a further aspect, the CDK2 inhibitor is formulated for intravenous administration and the chemotherapeutic agent is formulated for oral administration. In a still further aspect, the CDK2 inhibitor is formulated for oral administration and the chemotherapeutic agent is formulated for intravenous administration. In yet a further aspect, the CDK2 inhibitor is formulated for intravenous administration and the antibiotic agent is formulated for oral administration. In an even further aspect, the CDK2 inhibitor is formulated for oral administration and the antibiotic agent is formulated for intravenous administration.

4. Subjects

In various aspects, the subject of the herein disclosed methods is a vertebrate, e.g., a mammal. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

In some aspects of the disclosed methods, the subject has been diagnosed with a need for treatment prior to the administering step. In some aspects of the disclosed method, the subject has been diagnosed with a hearing impairment or disorder prior to the administering step. In some aspects of the disclosed methods, the subject has been identified with a need for treatment prior to the administering step. In one aspect, a subject can be treated prophylactically with a compound or composition disclosed herein, as discussed herein elsewhere.

a. Dosage

Toxicity and therapeutic efficacy of the agents and pharmaceutical compositions described herein can be determined by standard pharmaceutical procedures, using either cells in culture or experimental animals to determine the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio $LD_{50}/ED_{50}$. Polypeptides or other compounds that exhibit large therapeutic indices are preferred.

Data obtained from cell culture assays and further animal studies can be used in formulating a range of dosage for use in humans. The dosage of such compounds lies preferably within a range of circulating concentrations that include the $ED_{50}$ with little or no toxicity, and with little or no adverse effect on a human's ability to hear. The dosage may vary within this range depending upon the dosage form employed and the route of administration utilized. For any agents used in the methods described herein, the therapeutically effective dose can be estimated initially from cell culture assays. A dose can be formulated in animal models to achieve a circulating plasma concentration range that includes the $IC_{50}$ (that is, the concentration of the test compound which achieves a half-maximal inhibition of symptoms) as determined in cell culture. Such information can be used to more accurately determine useful doses in humans. Exemplary dosage amounts of a differentiation agent are at least from about 0.01 to 3000 mg per day, e.g., at least about 0.00001, 0.0001, 0.001, 0.01, 0.1, 1, 2, 5, 10, 25, 50, 100, 200, 500, 1000, 2000, or 3000 mg per kg per day, or more.

The formulations and routes of administration can be tailored to the disease or disorder being treated, and for the specific human being treated. For example, a subject can receive a dose of the agent once or twice or more daily for one week, one month, six months, one year, or more. The treatment can continue indefinitely, such as throughout the lifetime of the human. Treatment can be administered at regular or irregular intervals (once every other day or twice per week), and the dosage and timing of the administration can be adjusted throughout the course of the treatment. The dosage can remain constant over the course of the treatment regimen, or it can be decreased or increased over the course of the treatment.

In various aspects, the dosage facilitates an intended purpose for both prophylaxis and treatment without undesirable side effects, such as toxicity, irritation or allergic response. Although individual needs may vary, the determination of optimal ranges for effective amounts of formulations is within the skill of the art. Human doses can readily be extrapolated from animal studies (Katocs et al., (1990) Chapter 27 in Remington's Pharmaceutical Sciences, 18$^{th}$ Ed., Gennaro, ed., Mack Publishing Co., Easton, PA). In general, the dosage required to provide an effective amount of a formulation, which can be adjusted by one skilled in the art, will vary depending on several factors, including the age, health, physical condition, weight, type and extent of the disease or disorder of the recipient, frequency of treatment, the nature of concurrent therapy, if required, and the nature and scope of the desired effect(s) (Nies et al., (1996) Chapter 3, In: Goodman & Gilman's The Pharmacological Basis of Therapeutics, 9th Ed., Hardman et al., eds., McGraw-Hill, New York, NY).

b. Routes of Administration

Also provided are routes of administering the disclosed compounds and compositions. The compounds and compositions of the present invention can be administered by direct therapy using systemic administration and/or local administration. In various aspects, the route of administration can be determined by a patient's health care provider or clinician, for example following an evaluation of the patient. In various aspects, an individual patient's therapy may be customized, e.g., the type of agent used, the routes of administration, and the frequency of administration can be personalized. Alternatively, therapy may be performed using a standard course of treatment, e.g., using pre-selected agents and pre-selected routes of administration and frequency of administration.

Systemic routes of administration can include, but are not limited to, parenteral routes of administration, e.g., intravenous injection, intramuscular injection, and intraperitoneal injection; enteral routes of administration e.g., administration by the oral route, lozenges, compressed tablets, pills, tablets, capsules, drops (e.g., ear drops), syrups, suspensions and emulsions; rectal administration, e.g., a rectal suppository or enema; a vaginal suppository; a urethral suppository; transdermal routes of administration; and inhalation (e.g., nasal sprays).

In various aspects, the compounds and compositions described herein can be administered to a patient, e.g., a patient identified as being in need of treatment for hair cell loss, using a local route of administration. Such local routes of administration include administering the agents described herein into the ear of a patient and/or the inner ear of a patient, for example, by injection and/or using a pump or placing a gelfoam for constant release of compounds into the inner ear.

In various aspects, a pharmaceutical composition can be injected into the ear (e.g., auricular administration), such as into the luminae of the cochlea (e.g., the Scala media, Sc vestibulae, and Sc tympani), e.g., using a syringe, e.g., a single-dose syringe. For example, the compounds and compositions described herein can be administered by intratympanic injection (e.g., into the middle ear), and/or injections into the outer, middle, and/or inner ear. Such methods are routinely used in the art, for example, for the administration of steroids and antibiotics into human ears. Injection can be, for example, through the round window of the ear or through the cochlear capsule. Other inner ear administration methods are known in the art (see, e.g., Salt and Plontke, *Drug Discovery Today* 2005, 10, 1299).

In various aspects, the pharmaceutical composition can be administered in situ, via a catheter or pump. A catheter or pump can, for example, direct a pharmaceutical composition into the cochlear luminae or the round window of the ear and/or the lumen of the colon. Exemplary drug delivery apparatus and methods suitable for administering one or more of the compounds described herein into an ear, e.g., a human ear, are described in US 2006/0030837 and U.S. Pat. No. 7,206,639. In a further aspect, a catheter or pump can be positioned, e.g., in the ear (e.g., the outer, middle, and/or inner ear) of a patient during a surgical procedure. In a still further aspect, a catheter or pump can be positioned, e.g., in the ear (e.g., the outer, middle, and/or inner ear) of a patient without the need for a surgical procedure.

In various aspects, one or more of the compounds and compositions described herein can be administered in combination with a mechanical device such as a cochlear implant or a hearing aid, which is worn in the outer ear. An exemplary cochlear implant that is suitable for use with the present invention is described in US 2007/0093878.

In various aspects, the modes of administration described above may be combined in any order.

In various aspects, the compounds and compositions described herein can be administered via cell therapy, wherein cells are contacted ex vivo with the combination of agents described herein to promote complete or partial differentiation of the cells to or toward a mature cell type of the inner ear (e.g., a hair cell) in vitro. Cells resulting from such methods can then be transplanted or implanted into a patient in need of such treatment.

In various aspects, suitable cells can be derived from a mammal, such as a human, mouse, rat, pig, sheep, goat, or non-human primate. For example, stem cells have been identified and isolated from the mouse utricular macula (Li, H., et al. (2003) *Nature Medicine* 9, 1293-1299). The cells can also be obtained from a patient to whom they will subsequently be re-administered.

In various aspects, suitable cells (e.g., a stem cell, progenitor cell, and/or support cell) may be isolated from the inner ear of an animal. Specifically, suitable cells can be obtained from the cochlear organ of Corti, the modiolus (center) of the cochlea, the spiral ganglion of the cochlea, the vestibular sensory epithelia of the saccular macula, the utricular macula, or the cristae of the semicircular canals. The stem cell, progenitor cell, and/or supporting cells can also be obtained, however, from other tissues such as bone marrow, blood, skin, or an eye. The cells employed can be obtained from a single source (e.g., the ear or a structure or tissue within the ear) or a combination of sources (e.g., the ear and one or more peripheral tissues (e.g., bone marrow, blood, skin, or an eye).

I. EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided herein to illustrate the invention, and should not be construed as limiting the invention in any way. Examples are provided herein to illustrate the invention and should not be construed as limiting the invention in any way.

1. Primary Screen of a Bioactive Library for Reduction of Cisplatin-Induced Apoptosis in the HEI-OC1 Cell Line Caspase-3 activation is an important downstream molecular event known to occur in the majority of cellular pathways leading to apoptosis, including apoptosis of inner ear cells. Previous work has shown that inhibition of caspases, for example, by zVAD-fmk, an irreversible general caspase inhibitor, confers robust protection against cisplatin-induced cell death (Liu et al. (1998) *Neuroreport* 9: 2609-2614). For this screen, caspase-3 cleavage was chosen as the endpoint indicating cisplatin-induced cell death, as it allowed the inhibition of cell death to be monitored at the level of any intracellular molecular target upstream of caspase-3 cleavage in the cell line. Pifithrin-α was also chosen as a reference compound for the screen, as it provided good protection against cisplatin ototoxicity by inhibiting caspase-3 cleavage with an $IC_{50}$ of 17 μM. Pifithrin-α, a small molecule that inhibits p53, was shown to suppress the expression of p53, caspase-3, and caspase-1 in mouse cochlear explants (Zhang et al. (2003) *Neuroscience* 120: 191-205). Pifithrin-α has previously been shown to confer reasonable protection from cisplatin-induced cell death in cell lines and, importantly, in mouse cochlear explants at concentrations of 20-100 μM (Zhang et al. (2003) *Neuroscience* 120: 191-205), although at these doses it was reported to damage the hair cell stereocillia.

To measure cell death induced by cisplatin in cochlear hair cells, the HEI-OC1 immortalized inner ear cell line isolated originally from P7 organs of Corti of the Immortomouse (Kalinec et al. (2003) *Adiol. Neurootol.* 8: 177-189) was used. This cell line has been shown to serve as a good model of inner ear cells (Kim et al. (2010) *J. Neurosci.* 30: 3933-3946), and it was independently confirmed by qRT-PCR that the cells used in this screen express the hair cell markers Myo6 and Myo7a.

This screen is also described in Teitz, T., Goktug, A. N., Chen, T., Zuo, J., 2016. Development of cell-based high throughput chemical screens for protection against cisplatin-induced ototoxicity In: Sokolowski, B., (Ed.), Auditory and Vestibular Research, Methods and Protocols, Second Edition. Humana Press. pp 419-430. doi: 10.1007/978-1-4939-3615-1_22.

Before starting the automated high-throughput screen (HTS) accomplished with the help of robots in 384-well plates, assay conditions were optimized on the bench, including the cell number plated (1600 cells per well), cisplatin concentration (50 μM, based on the dose-response curve), incubation time (22 hrs at 33° C., 10% $CO_2$), and concentration of the reference compound, pifithrin-α. The Promega Caspase-3/7 Glo assay, which allows measurement of light emitted as the result of caspase cleavage and is suitable for HTS, was used. The linearity of the Caspase-3/7 Glo assay was validated and it was verified that 0.5% DMSO had no effect on cell death kinetics. The Caspase-3/7 Glo assay was then tested for reproducibility on the St. Jude robot systems. By using a pintool, test compounds were added to the screen to a final concentration of 8 μM, and cisplatin solution was added immediately to each well to a final concentration of 50 μM. Cells were incubated with the test compounds and cisplatin for 22 hrs at 33° C., 10% $CO_2$ with the medium as previously described (Kalinec et al. (2003) *Adiol. Neurootol.* 8: 177-189); no γ-interferon was added. The 384-well plates were shaken and spun after compound addition to enhance assay reproducibility.

The assay positive control, pifithrin-α, induced 50% reduction of caspase-3/7 activity at 17 μM ($IC_{50}$) and full reduction at 34 μM. Pifithrin-α was added to each of the 34 plates as a screening quality control. FIG. 1 shows the percent activity of caspase-3/7 in screening of the 4,359 unique bioactive compounds, including >844 FDA approved drugs. Cisplatin-induced caspase-3/7 activity was reduced by 60% or more by 177 compounds, which were further analyzed for dose response and toxicity.

Referring to FIG. 1, a screen of a bioactive compound library, including 4,359 unique compounds and 844 FDA-approved drugs, was conducted. The cell-based screen average z' was 0.75, signal window was 12, and signal fold was 4.9. Cells treated with 50 cisplatin were assigned 100% caspase-3/7 activity. Cells not treated with cisplatin (grown in media only) were assigned 0% caspase-3/7 activity. 177 compounds were found to decrease cisplatin-induced caspase-3/7 activity by 60% or more (see black line and below).

2. Dose-Response and Toxicity of the Top Hits from the Primary Screen

The Caspase-3/7 Glo assay was used as described above to test the 177 top hit compounds for protection against cisplatin-induced cell death. Ten serial 1:3 dilutions (40 μM to 40 nM) of each compound were tested in triplicate in the presence of 50 μM cisplatin. To measure the viability of the HEI-OC1 cells treated with these compounds alone, the compounds were added to the cells without cisplatin at the same final concentrations of 40 μM to 40 nM. Cell viability was assayed in triplicate by using the Promega Cell Titer Glo assay (CTG), which quantifies the ATP released from live cells and is suitable for HTS. Cells grown in media only, without compounds, under identical conditions served as positive control for 100% viability. Cells treated with a 100% lethal concentration of staurosporine for 22 hours were controls for 0% viability. The results of the caspase-3/7 assay and the CTG viability assay are shown for three known compounds (pifithrin-α, zVAD-fmk, and Ebselen, shown in Teitz et al., 2016, Auditory and Vestibular Research, Methods and Protocols, Second Edition. Humana Press. pp 419-430) and five representative compounds (3, 4, 1, 12, and 9) in FIG. 2a-e. Each plate contained wells for the reference compound pifithrin-α. One of the top hits was zVAD-fmk, an irreversible, potent general caspase inhibitor predicted to appear in this screen. zVAD-fmk has been shown to inhibit cisplatin-induced cell death in the mouse cochlea with high potency ($IC_{50}$=0.2 μM) (Atar and Avraham (2010) *Neuroscience* 168: 851-857; Liu et al. (1998) *Neuroreport* 9: 2609-2614). However, this compound is unlikely to be the best choice for therapeutic use in vivo. Another interesting hit from the screen was Ebselen, which is currently being tested for protection against noise-induced hearing loss in a clinical Phase 2 trial (www.soundpharmaceuticals.com). Ebselen showed low potency in protection against cisplatin and was toxic at the concentration that inhibited caspase-3/7.

Referring to FIG. 2a-e, dose response curves were generated after 22 hr culture in HEI-OC1 cells. Shown are Caspase-3/7 Glo assay (cisplatin-induced cell death; compound+cisplatin) and Cell Titer Glo (CTG) assay (cell viability; compound only) data for compounds 4, 9, 12, 3, and 1 (FIG. 2a-e, respectively). The Caspase-3/7 $IC_{50}$ activity is indicated for each compound.

Table 1 lists the top 18 compound hits in the screen in terms of high potency and low toxicity. Their drug status for other diseases and corresponding mechanism of action are listed in Table 2. The top ten compounds were further evaluated by a viability assay (Cell Titer Glo, Promega) in medulloblastoma neurosphere cell lines and neuroblastoma cell lines to test whether they inhibit the ability of cisplatin to kill the tumor cells. The majority had no antagonistic effect on cisplatin's antitumor activity (data not shown) and are therefore safe to use systemically together with cisplatin during chemotherapy to protect against cisplatin-induced hearing loss.

TABLE 1

| Cmpd. No. | Cmpd. Name | Chemical Structure | HEI-OC1 $IC_{50}$ (μM) | HEI-OC1 $LD_{50}$ (μM) |
|---|---|---|---|---|
| 1 | Leflunomide | 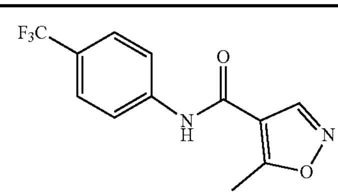 | 3.0 | >40 |
| 2 | Olsalazine sodium | 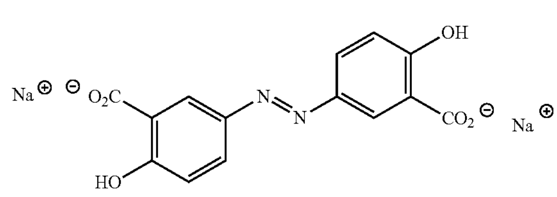 | 6.2 | >40 |

TABLE 1-continued
| Cmpd. No. | Cmpd. Name | Chemical Structure | HEI-OC1 IC$_{50}$ (μM) | HEI-OC1 LD$_{50}$ (μM) |
|---|---|---|---|---|
| 3 | Pelitinib | 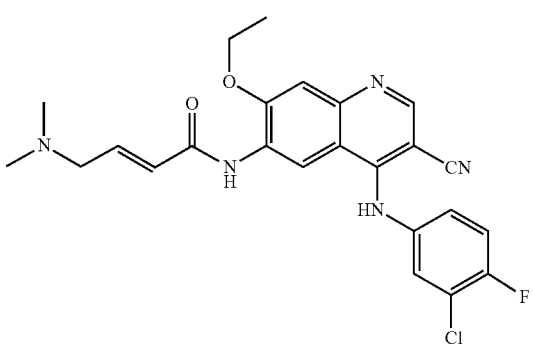 [SMILES: CCOc1cc2ncc(C#N)c(Nc3ccc(F)c(Cl)c3)c2cc1NC(=O)/C=C/CN(C)C] | 0.6 | >40 |
| 4 | Kenpaullone | 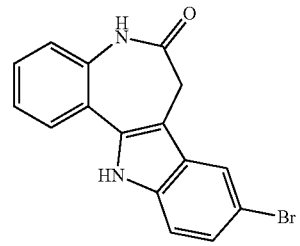 [SMILES: O=C1Cc2c([nH]c3ccc(Br)cc23)-c2ccccc2N1] | 2.1 | >40 |
| 5 | Antimycin A | 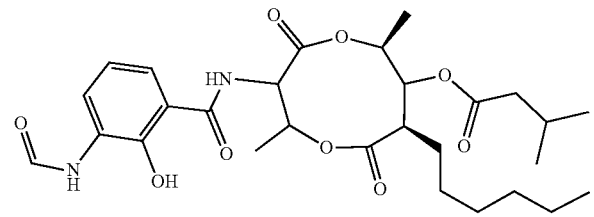 [SMILES: CCCCCC[C@H]1C(=O)OC(C)C(NC(=O)c2cccc(NC=O)c2O)C(=O)O[C@@H](C)C1OC(=O)CC(C)C] | 0.04 | >10 |
| 6 | Cyanocobalamin (vitamin B12) | 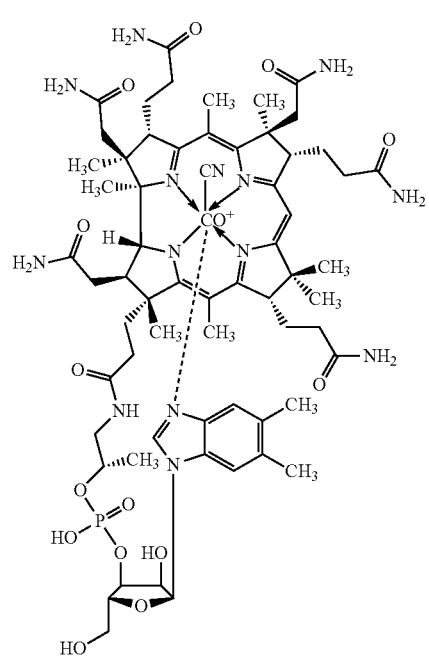 | 4.2 | >40 |

TABLE 1-continued

| Cmpd. No. | Cmpd. Name | Chemical Structure | HEI-OC1 IC$_{50}$ (μM) | HEI-OC1 LD$_{50}$ (μM) |
|---|---|---|---|---|
| 7 | EHT1864 | 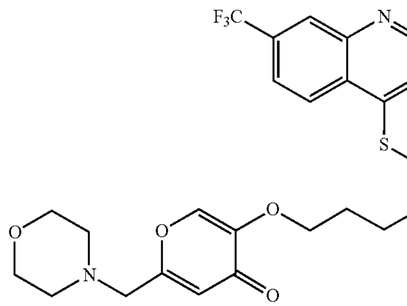 | 2.0 | >20 |
| 8 | Lanatoside C | 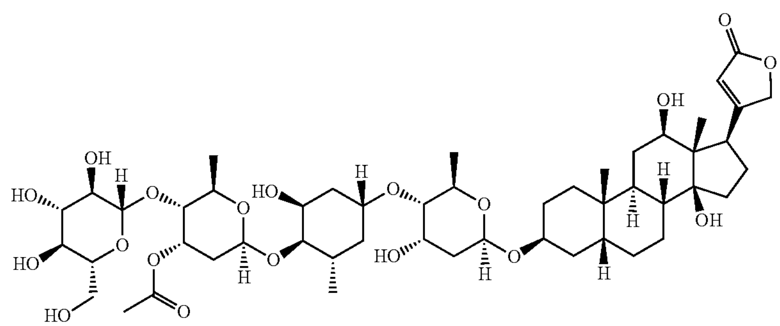 | 7.6 | >40 |
| 9 | Olomoucine II | 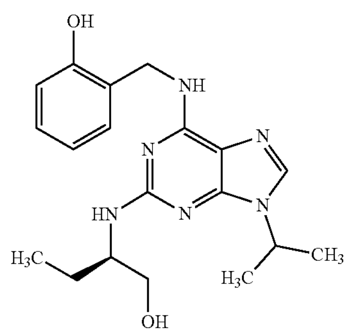 [SMILES: CC[C@H](CO)Nc1nc(NCc2ccccc2O)c2ncn(C(C)C)c2n1] | 0.8 | >40 |
| 10 | 2-Mercaptobenzothiazole | 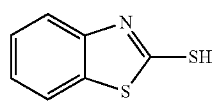 | 7.0 | >10 |
| 11 | Patulin | 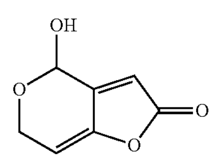 [SMILES: O=C1C=C2C(=CCOC2O)O1] | 0.7 | >10 |
| 12 | CDK2 inhibitor II | 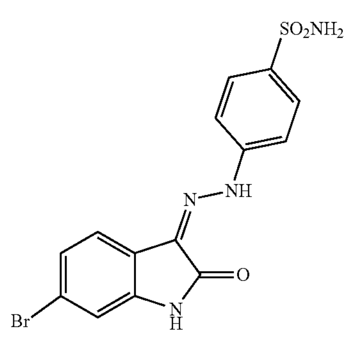 [SMILES: NS(=O)(=O)c1ccc(N/N=C2\C(=O)Nc3cc(Br)ccc32)cc1] | 0.5 | >40 |

TABLE 1-continued

| Cmpd. No. | Cmpd. Name | Chemical Structure | HEI-OC1 IC$_{50}$ (μM) | HEI-OC1 LD$_{50}$ (μM) |
|---|---|---|---|---|
| 13 | D-Ribofuranosylbenzimidazole | 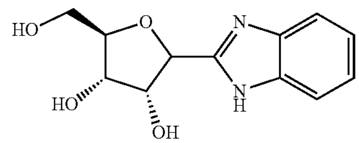 [SMILES: OC[C@H]1OC(c2nc3ccccc3[nH]2)[C@H](O)[C@@H]1O] | 4.0 | >40 |
| 14 | GSK JS 84326-047A1 | 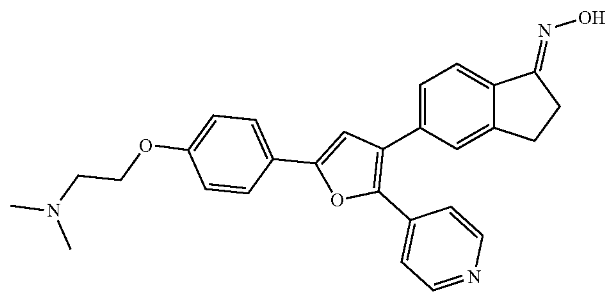 [SMILES: CN(C)CCOc1ccc(-c2cc(-c3ccc4c(c3)CC/C4=N\O)c(-c3ccncc3)o2)cc1] | 1.3 | >10 |
| 15 | Roche (RO02830409-001) | 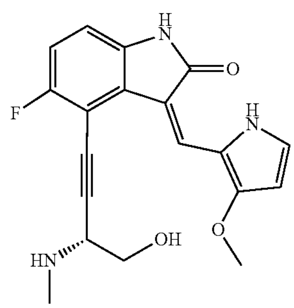 [SMILES: CN[C@H](C#Cc1c(F)ccc2c1/C(=C/c1[nH]ccc1OC)C(=O)N2)CO] | 0.1 | >10 |
| 16 | GSK (AN100368-079A1) | 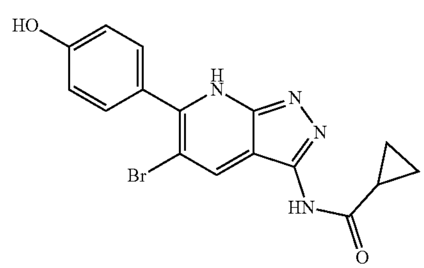 [SMILES: O=C(Nc1nnc2[nH]c(-c3ccc(O)cc3)c(Br)cc1-2)C1CC1] | 0.8 | >40 |
| 17 | GSK (U18675/6/1) | 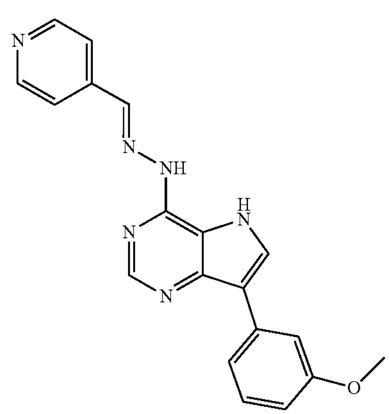 [SMILES: COc1cccc(-c2c[nH]c3c(N/N=C/c4ccncc4)ncnc23)c1] | 2.1 | >40 |

TABLE 1-continued

| Cmpd. No. | Cmpd. Name | Chemical Structure | HEI-OC1 IC$_{50}$ (µM) | HEI-OC1 LD$_{50}$ (µM) |
|---|---|---|---|---|
| 18 | GSK (U11667/23/1) | 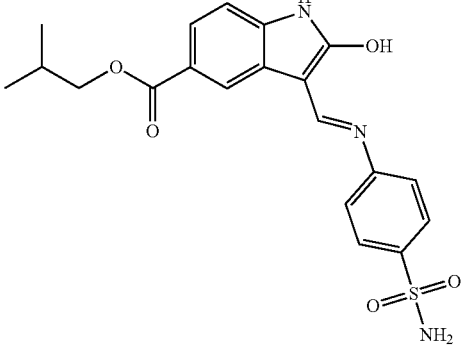 | 3.4 | >40 |

TABLE 2

| Cmpd. No. | Drug Status For Other Diseases | Mechanism of Action in Other Diseases |
|---|---|---|
| 1 | FDA approved for the treatment of active rheumatoid arthritis | Prodrug: pyrimidine synthesis inhibitor for rheumatoid arthritis, inhibitor of JNK, inhibitor of TNF-dependent NF-kB activation, inhibitor of Cox-2, inhibitor of tyrosine kinase phosphorylation, inhibitor of DHODH (de novo pyrimidine synthesis). |
| 2 | FDA approved | Derivative of salicylate: 5-aminosalicyclic acid prodrug used in inflammatory bowel disease, ulcerative colitis, anti-inflammatory and anti-apoptotic regulation. |
| 3 | IND phase | Irreversible inhibitor of epidermal growth factor receptor. |
| 4 | In vivo, Rodent | Inhibitor of CDK1/cyclin B (IC$_{50}$ = 400 nM), CDK2/cyclin A (IC$_{50}$ = 680 nM), CDK5/p25 (IC$_{50}$ = 850 nM), GSK-3β (IC$_{50}$ = 230 nM), and HCK (MAP4K4) kinases (reduction of HGK-Tak1-Mkk4-JNK-c-Jun cell death signaling cascade) |
| 5 | In vivo, Rodent | Antibiotic, inhibitor of mitochondrial electron transport and inducer of apoptosis, toxin |
| 6 | FDA approved | General methyl metabolism, methyl donor for L-methionine synthesis |
| 7 | In vivo, Rodent | Inhibitor of Rac family of GTPases and blocks activation by direct binding to Rac1, Rac1b, Rac2, and Rac3 |
| 8 | IND Phase | Cardiac glycoside, inhibitor of Na$^+$/K$^+$-ATPase |
| 9 | In vitro | Inhibitor of CDKs 2, 5, 7, and 9; inhibitor and substrate of ABCB1 and ABCG2 transporters |
| 10 | In vivo, Rodent | Toxin, multiple mechanisms |
| 11 | In vivo, Rodent | Mycotoxin, antibiotic |
| 12 | In vitro | ATP-competitive, selective inhibitor of CDK2 (IC$_{50}$ = 60 nM) |
| 13 | In vitro | Inhibitor of CDKs 7 and 9, RNA synthesis |
| 14 | — | Potent and selective CNS penetrant furan-based inhibitor of B-Raf kinase |
| 15 | — | Potent oxindole inhibitor of CDK2 |
| 16 | — | Potent and selective inhibitor of GSK3 |
| 17 | — | Heterocyclic inhibitor of GSK3 |
| 18 | — | Oxindole-based inhibitor of CDK2 |

3. Protection Against Cisplatin-Induced Hair Cell Loss in Cochlear Explants

The top 13 compounds were texted ex vivo in neonatal (P3) mouse cochlear explants. P3 wild-type mouse cochleae were dissected and cultured with the aid of matrigel as previously described (Driver and Kelley (2010) Curr. Protoc. Neurosci. Chapter 4, Unit 4 34: 31-10). After one day of culture, cisplatin (50 µM) with or without compounds were added to growth media and incubated for 24 hrs at 37° C. 50 µM cisplatin was chosen because the explant assay consistently showed death at ~40% of outer hair cells (OHCs) in the mouse cochlea at this concentration after 24 hrs co-incubation (FIG. 3A-G). It is known that OHCs are the first cells to be damaged ex vivo and in vivo by cisplatin and noise, while inner hair cells (IHCs) are injured at higher concentrations of cisplatin or higher levels of noise (Oishi and Schacht (2011) Expert Opin. Emerg. Drugs 16: 235-245; Zhang et al. (2003) Neuroscience 120: 191-205). Cochleae were fixed with 4% paraformaldehyde (PFA) and stained against actin with Phalloidin-Alexa Fluor 568 to determine hair cells' viability, which was also assayed by 4',6-diamidino-2-phenylindole (DAPI) staining, FM1-43 dye uptake, and immunohistochemistry with known hair cell markers (Parvalbumin and Myo7a). Cochleae were imaged by confocal microscopy, two 160 µm regions from middle turns were photographed, and the number of intact hair cells was counted. Three to twelve cochleae were tested under each condition.

Referring to FIG. 3A-D, compound 4 protects against cisplatin-induced hair cell loss in mouse cochlear explants. Confocal images of whole mount cochlear explants that have been treated with media (FIG. 3A), cisplatin (FIG. 3B), compound 4 (FIG. 3C), or cisplatin and compound 4 (FIG. 3C) for 24 hrs are shown. Phalloidin labels the hair cells.

Figure 3E:
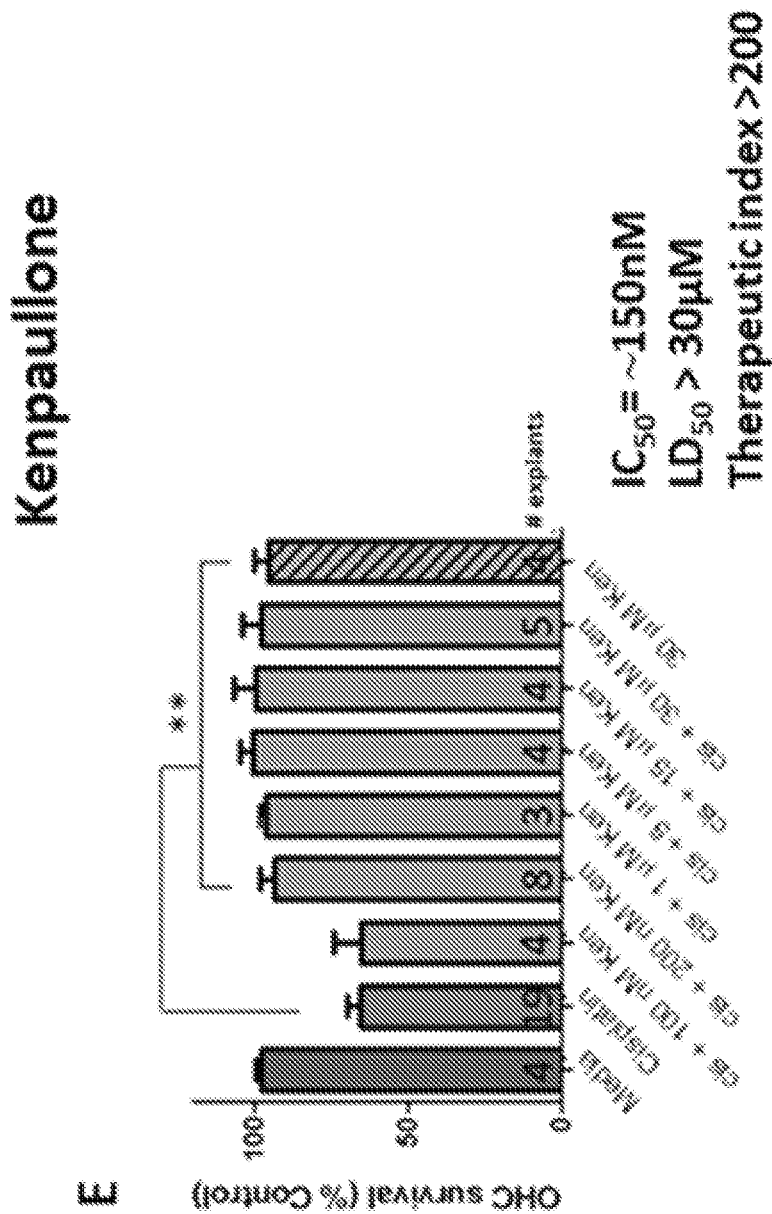
Figure 3F:
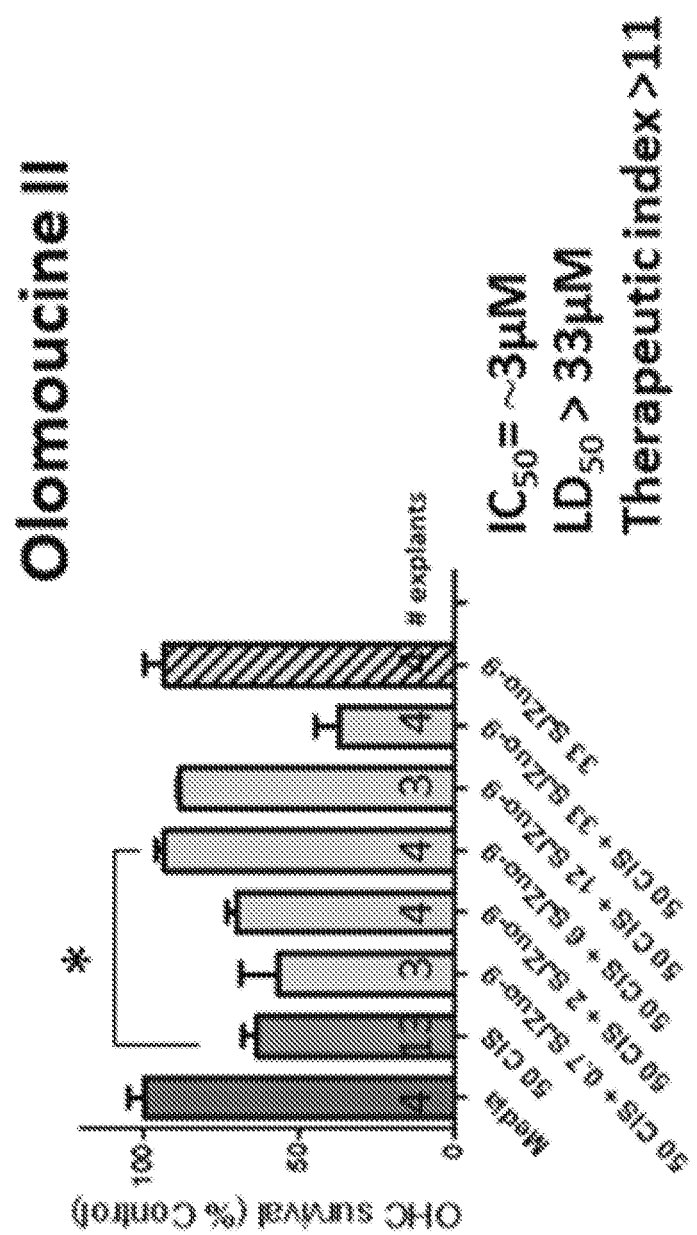
Figure 3G:
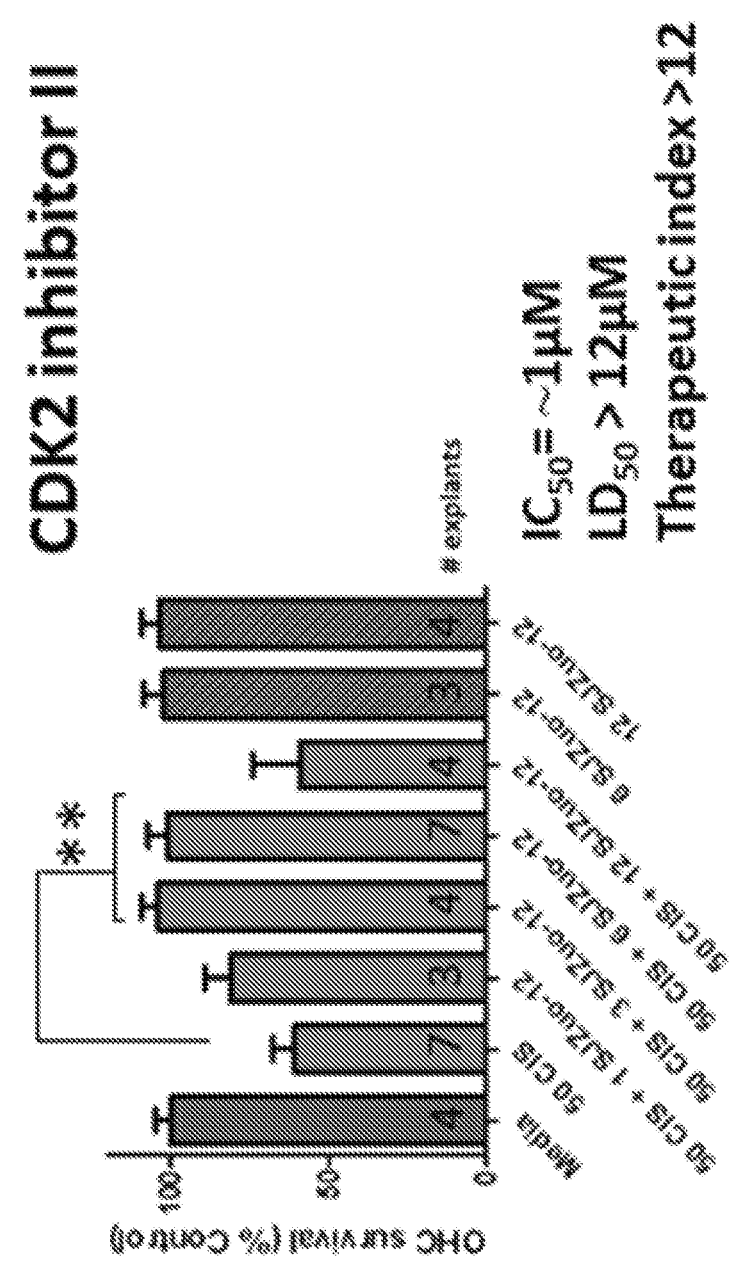

Referring to FIG. 3E-G, outer hair cell survival (%) when treated with various doses (µM) of compounds 4 (FIG. 3E), 9 (FIG. 3F), or 12 (FIG. 3G), and/or cisplatin (CIS) are shown. The number of cochlear explants analyzed is indicated in each bar. ***P<0.001 using one-way ANOVA test followed by Bonferroni comparison.

Ten of these compounds protected the cochlear explants at >2 concentrations, as measured by hair cell viability after 24 hr cisplatin co-treatment. Four compounds (1, 4, 9, and 12) showed excellent protection (100% OHC survival), with IC$_{50}$ values of 0.1 to 25 µM (FIG. 3 shows compound 4; Table 3). The remaining compounds (2, 3, 5-7, and 13) protected 31-76% of the OHCs against cisplatin (Table 3).

TABLE 3

| Cmpd. No. | Mouse Explant IC$_{50}$ (μM) | Mouse Explant LD$_{50}$ (μM) |
|---|---|---|
| 1 | ~25 | >50 |
| 2 | ~30 (For 50%) | >30 |
| 3 | ~6 (For 50%) | <13 |
| 4 | ~0.15 | >30 |
| 5 | ~1.8 (For 31%) | <4 |
| 6 | ~21 (For 53%) | >21 |
| 7 | ~10 (For 58%) | <20 |
| 8 | >12-76 | |
| 9 | ~2.0 | >33 |
| 10 | >49 | |
| 11 | >3-9 | |
| 12 | ~2.0 | >12 |
| 13 | ~8.0 (For 76%) | |

4. Protection Against Cisplatin-Induced Hair Cell Loss in Zebrafish Lateral Lines In Vivo The top ten compounds as determined by the mouse cochlear explants were further tested in the lateral line neuromasts of 5-days post-fertilization (dpf) zebrafish larvae in vivo. Hair cells in the zebrafish lateral line are considered homologous to sensory hair cells in the mammalian inner ear and have similar responses to ototoxic drugs (Ou et al. (2007) Hear. Res. 233: 46-53). Zebrafish are well established in vivo system to test cisplatin damage, as the hair cells are easily accessible to drugs (Coffin et al. (2013) Apoptosis 18: 393-408; Vlasits et al. (2012) Hear. Res. 294: 153-165). The experiments were performed with 5-dpf larval zebrafish of the *AB wild-type strain. Dose-response studies were performed to find the cisplatin concentration at which most of the hair cells in each neuromast were killed in the absence of a protective compound and at the same DMSO concentration (<0.2%). It was determined that 5 μM cisplatin killed 91% of the hair cells without addition of protective compounds in zebrafish treated for 20 hrs (FIG. 4A-E, see the data point of 9% survival with "5.0 CIS"). Next, the cisplatin protection effect of the top ten compounds as determined by the experiments herein above was tested. As positive controls in these experiments, Paroxetine and Benzamil were used at concentrations previously shown to confer cisplatin protection in zebrafish (Vlasits et al. (2012) Hear. Res. 294: 153-165; FIG. 4A-E).

Figures 4A, 4B:
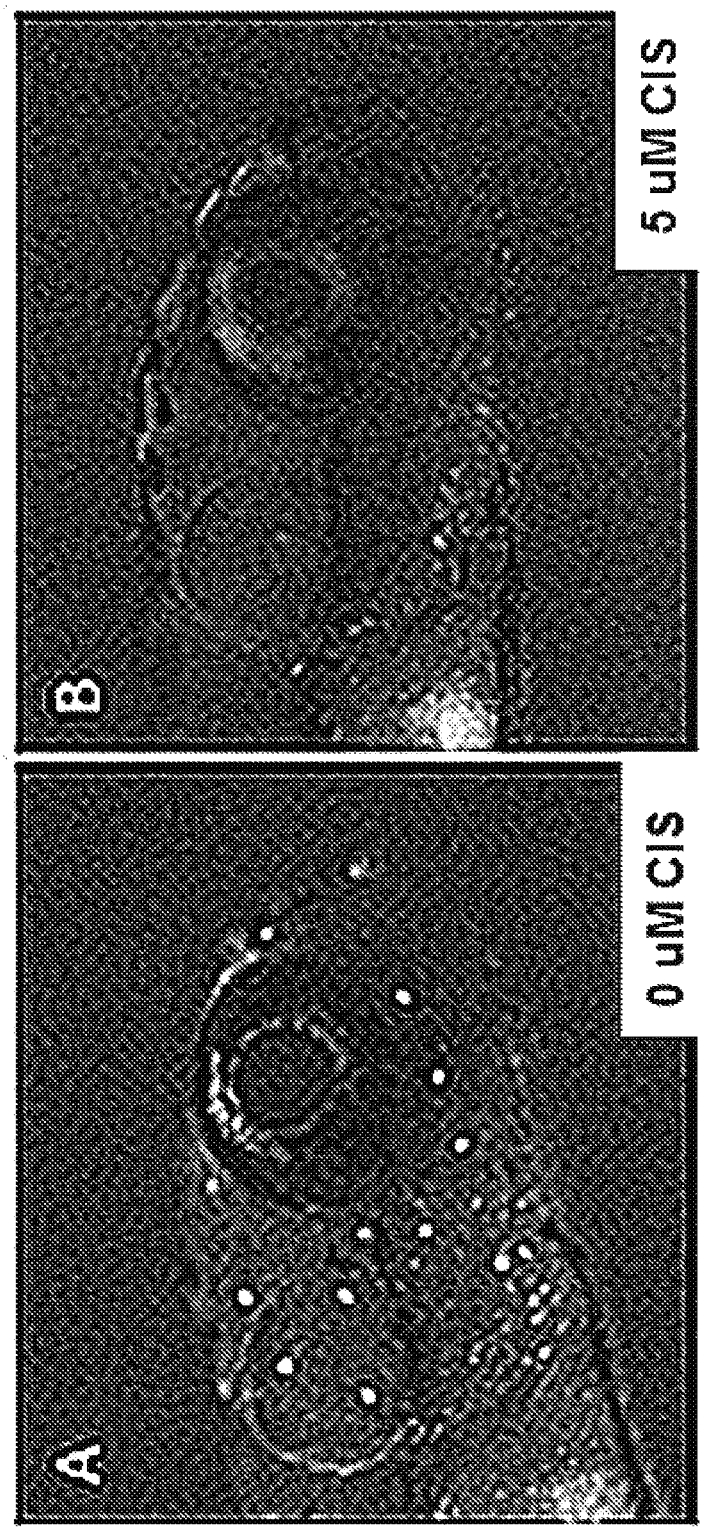
FIG. 4A-E show representative data illustrating that compound 4 protects against cisplatin-induced hair cell loss in zebrafish lateral lines in vivo.
Figures 4C, 4D:
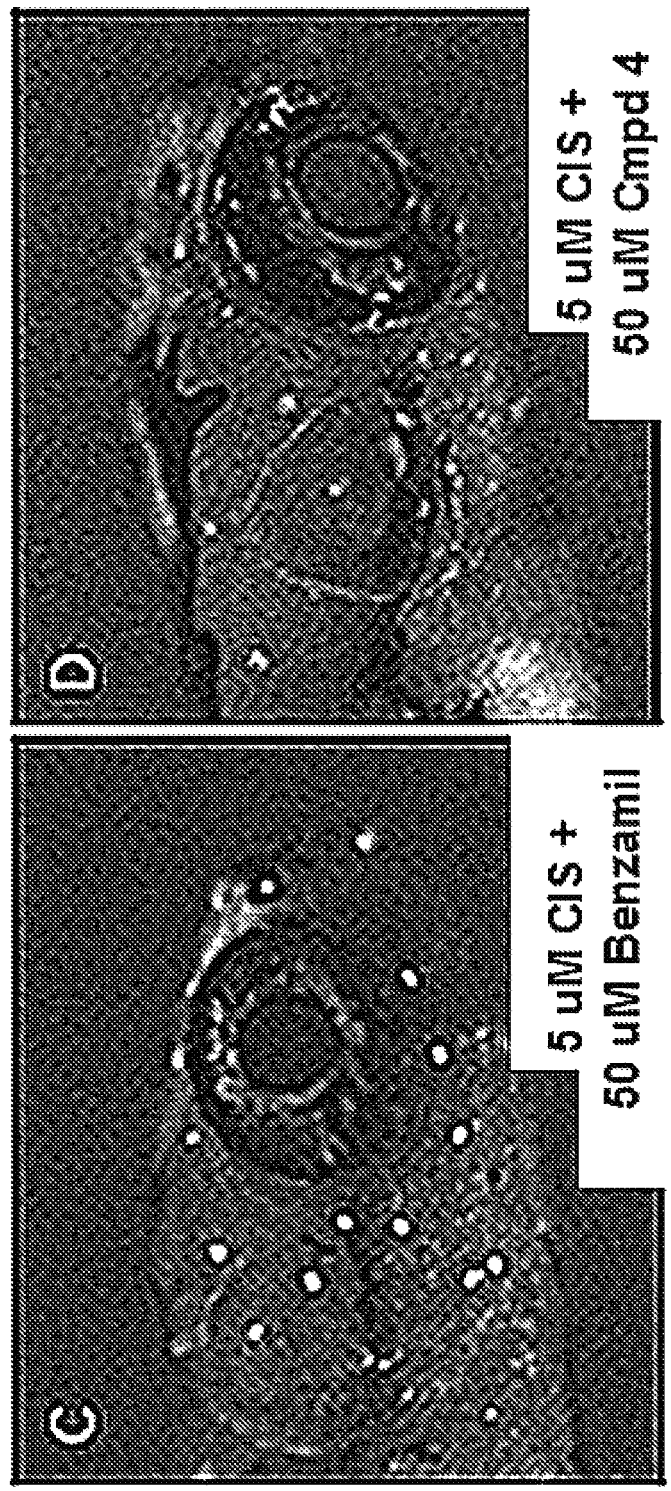

Referring to FIG. 4A-D, compound 4 protects against cisplatin-induced hair cell loss in zebrafish lateral lines in vivo. Lateral line neuromasts (white dots) in the zebrafish head were visualized by staining with 0.005% DASPEI vital dye after treatment with medium (FIG. 4A), cisplatin (FIG. 4B), compound 4 and Benzamil (FIG. 4C), or compound 4 and cisplatin (FIG. 4D). Benzamil and Paroxetine are compounds known to protect against cisplatin-induced hair cell loss in zebrafish (Vlasits et al. (2012) Hear. Res. 294: 153-165).

Figure 4E:
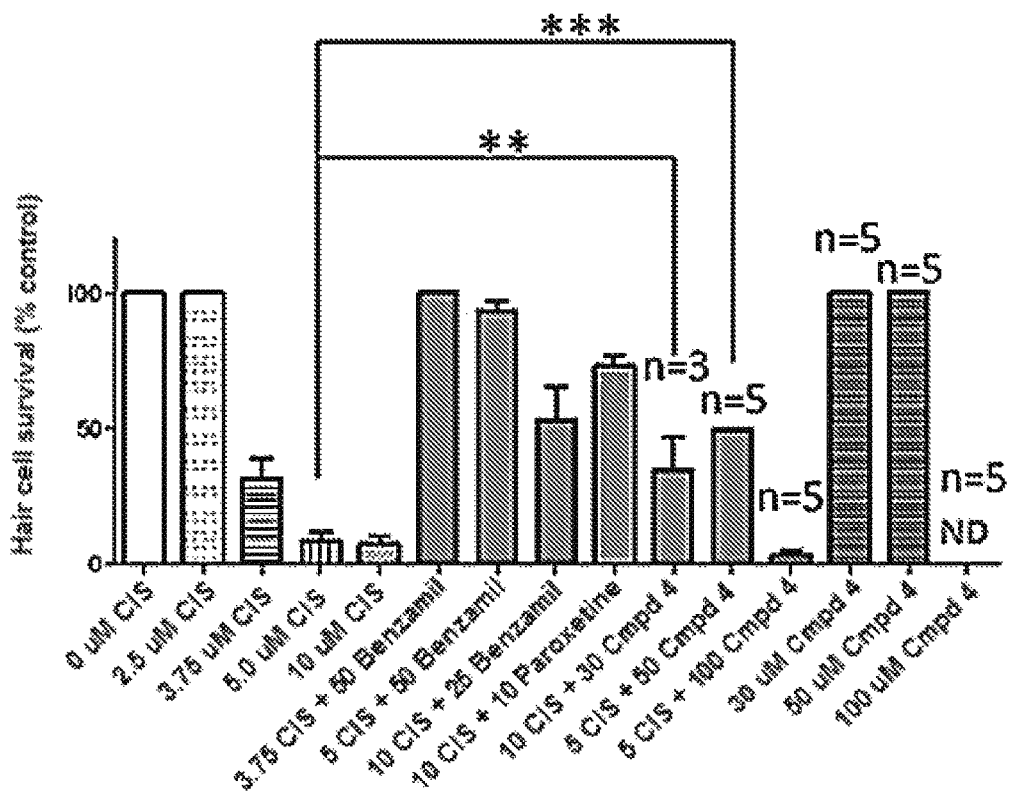

Referring to FIG. 4E, hair cell survival (%) at various doses (μM) of compound 4 and cisplatin are shown. The number of zebrafish tested in each condition was 3-13. Standard errors are shown for each condition. ***P<0.001 using one-way ANOVA followed by Bonferroni comparison. ND: not detected.

Experiments were performed in 24-well plates with 5 fish per well in volumes of 1-2 mL. Fish were incubated with 5 μM and stained with 0.005% DASPEI vital dye for 15 minutes. After two washes with egg water, fish were visualized in an epiflourescence microscope. Ten specific neuromasts in each fish were scored based on their intensity, in a scale from 0 (no labeling) to 2 (high intensity), as described previously (Owens et al. (2009) Hear. Res. 253: 32-41). Results were plotted as percent survival of hair cells in the cisplatin-treated fish relative to the untreated fish (FIG. 4A-E).

Of the ten compounds tested, only compound 4 showed significant protection of zebrafish neuromasts against cisplatin-induced hair cell loss (FIG. 4A-E; Table 4). Without wishing to be bound by theory, these results suggest that most of these compounds protect through molecular mechanisms that are specific and unique to mammalian cells. This observation is consistent with recent work that shows that only a fraction of the compounds that protect zebrafish neuromasts from aminoglycosides and cisplatin also protect mammalian cochlear cells from these drugs (Ou et al. (2007) Hear. Res. 233: 46-53; Ou et al. (2010) Drug Discov. Today 15: 265-271; Vlasits et al. (2012) Hear. Res. 294: 153-165).

TABLE 4

| Cmpd. No. | Zebrafish IC$_{50}$ (μM) | Zebrafish LD$_{50}$ (μM) |
|---|---|---|
| 1 | No | >5.0 |
| 2 | No | >30 |
| 3 | No | <27 |
| 4 | ~30 | <90 |
| 5 | No | <0.6 |
| 7 | No | <1.0 |
| 8 | No | >50 |
| 9 | No | >50 |
| 12 | No | >50 |
| 13 | No | >75 |

Figure 5:
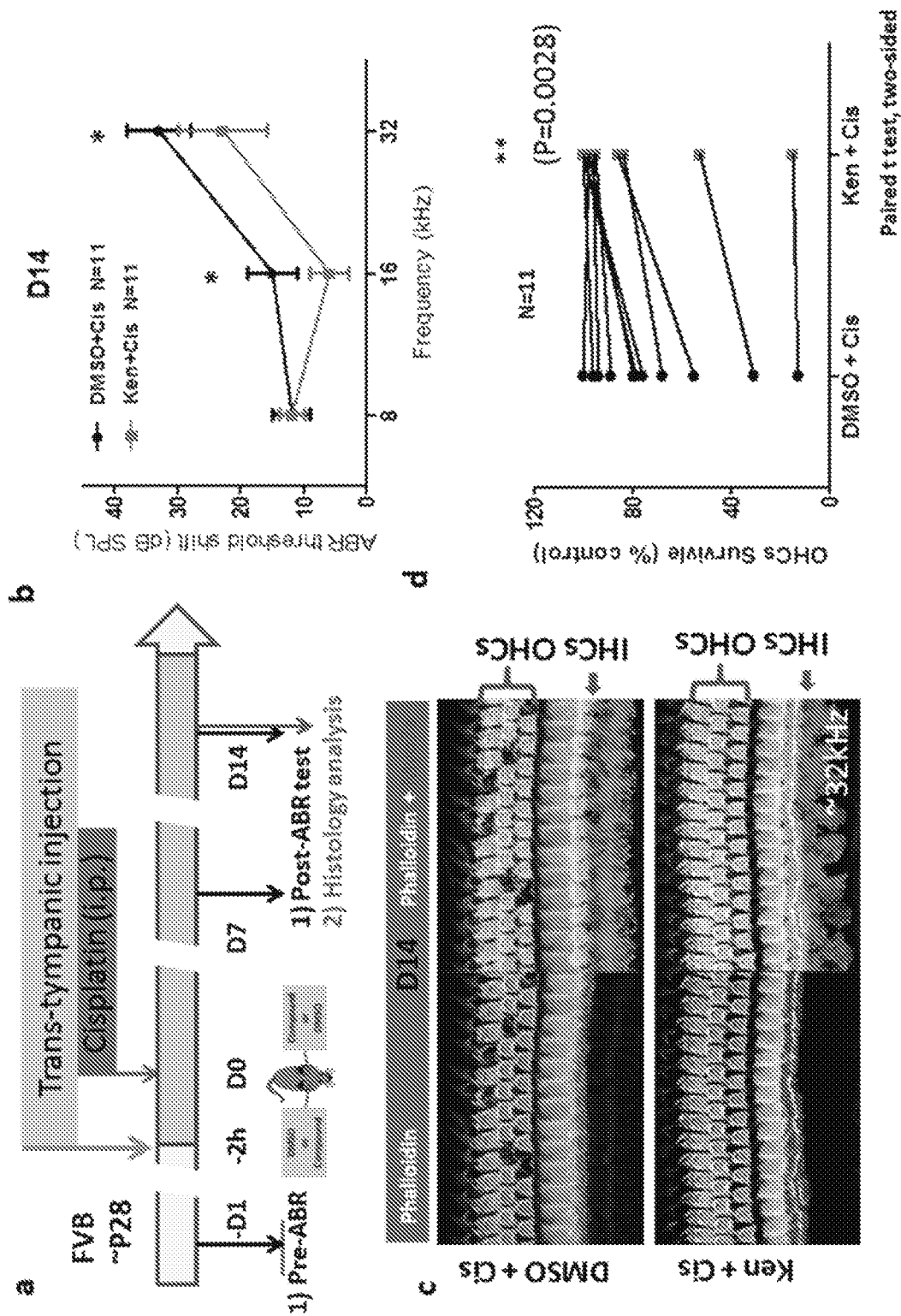
FIG. 5 shows kenpaullone protects against cisplatin-induced hair cell loss in vivo in mouse. Panel 5a shows experimental diagram. Either ear of the same FVB wild-type mouse at P28 was trans-tympanically injected (in a volume of 5 µL) with compound (Kenpaullone 250 µM in 0.5% DMSO) or 0.5% DMSO only, in a double-blinded manner. Two hours later, the mice were treated intraperitoneally (IP) with cisplatin 30 mg/kg body weight, which was expected to damage OHCs equally in both ears. Panel 5b demonstrates that kenpaullone (Ken) significantly reduces cisplatin (Cis)-induced ABR hearing threshold shifts relative to DMSO control at 16 kHz and 32 kHz 14 days post transtympanic injection. Panel 5c shows representative images double stained with phalloidin and myosin 7a which is a hair cell specific marker in the cochlea and illustrates that kenpaullone protects against cisplatin-induced hair cell loss at 32 kHz region 14 days post transtympanic injection. Panel 5d demonstrates kenpaullone significantly increases outer hair cell (OHC) survival in all 11 mice at the 32 kHz region.

5. Protection Against Cisplatin-Induced Hair Cell Loss and Hearing Loss in Adult Mice Treated Locally Via Transtympanic Injection Compound 4 was tested for protection against cisplatin-induced hair cell loss in vivo in adult mice (FIG. 5) after transtympanic injection. Either ear of the same FVB P28 wild-type mouse was trans-tympanically injected (in a volume of 5 μL) with compound 4 (250 μM in 0.5% DMSO) or 0.5% DMSO only, in a double-blinded manner. Two hours later, the mice were treated intraperitoneally (IP) with cisplatin 30 mg/kg body weight, which was expected to damage OHCs equally in both ears (FIG. 5A). At 14 days post-cisplatin treatment, cochlear hair cells were analyzed by phalloidin staining. As expected, many OHCs at basal turns were lost in DMSO-treated ears; however, these OHCs were significantly protected in Compound 4 treated ears (paired t-tests, one-tailed or two-tailed) (FIG. 5C-D). Without wishing to be bound by theory, these results indicate that locally delivered compound 4 protects against cisplatin-induced hair cell loss in vivo.

Referring to FIG. 5C-D, compound 4 protects against cisplatin-induced hair cell loss in adult mice by local delivery in vivo. Either compound 4 (250 μM) or DMSO was delivered to either ear of the same mouse for 2 hrs; cisplatin was injected via i.p. and cochleae were fixed after 24 hrs and analyzed (FIG. 5C). Confocal images of basal turn cochleae with phalloidin staining are shown for DMSO, compound 4, and cisplatin+ compound 4 (FIG. 5C).

Referring to FIG. 5D, outer hair cell survival (%) in eleven mice is shown. Each line links two cochleae of each mouse. Using paired t-test, two-tailed: p=0.0028. Despite variations between animals, compound 4 significantly protects cisplatin-induced hair cell loss in these conditions. Referring to FIG. 5B, Compound 4 was tested for protection against cisplatin-induced hearing loss in vivo in adult mice after transtympanic injection (TT), similar to the procedures described in FIG. 5A and FIG. 6A, followed by intraponeal injection of cisplatin (30 mg/kg) in 2 hrs. Hearing tests (ABR) were performed 7 and 14 days post treatment. Referring to FIG. 5B, hearing loss as measured by ABR threshold shift (dB SPL) is significantly reduced at 16 and 32 kHz in compound 4 treated ears compared to DMSO control ears in 11 mice. (*: p<0.05, paired t-tests, two-sided).

Figure 6:
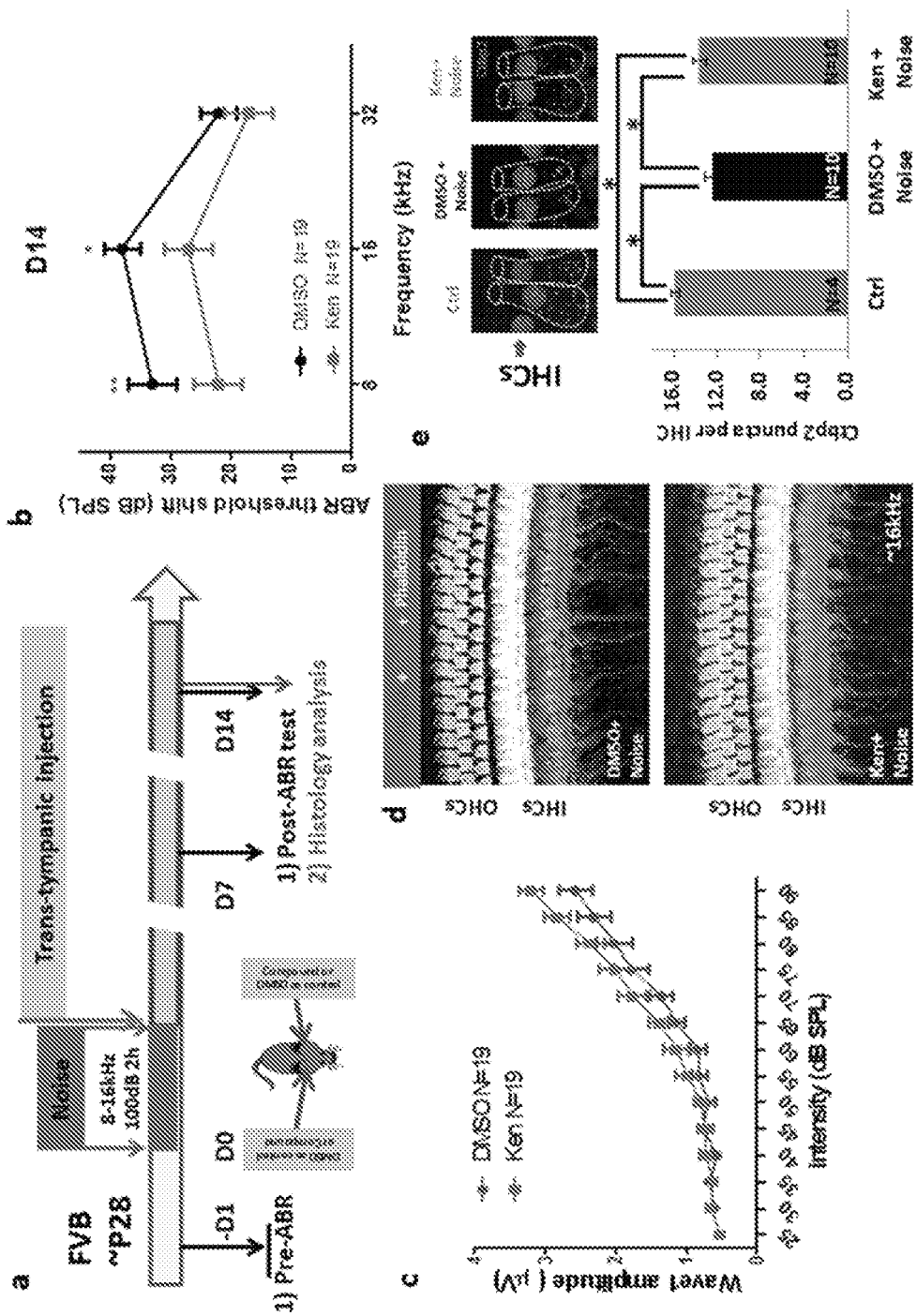
FIG. 6 shows kenpaullone protects against noise-induced hearing loss. Panel 6a is an experimental design in which adult FVB mice at P28 were exposed to noise (8-16 kHz at 100 dB SPL for 2 hours). Immediately afterward, kenpaullone (250 µM in 0.5% DMSO) or 0.5% DMSO was delivered (via trans-tympanic injection) to either ear of the same mouse. ABR thresholds were recorded prior, 7 days, or 14 days post noise exposure. Cochlear histology was examined at 14 days. Panel 6b shows that, in a total of 19 mice, kenpaullone significantly protects noise-induced hearing loss at 8 kHz and 16 kHz 14 days post noise damage. Panel 6c also shows that wave 1 amplitudes of ABRs at 16 kHz displayed significant differences between the kenpaullone and DMSO control ears. Panel 6d shows representative images of triple staining with phalloidin, Tuj 1 and myosin 7a in the organ of Corti. There are no hair cell loss and no detectable spiral ganglion neuron fiber differences at the 16 kHz region. Panel 6e comparison of the ctbp2 puncta staining and qualification in control (Ctrl) without any treatment, noise damage with DMSO transtympanic injection (DMSO+Noise) and noise damage with kenpaullone transtympanic injection (Ken+Noise). Kenpaullone significantly protects ctbp2 puncta loss comparing with DMSO sample. Inner hair cells (IHCs) are traced by dash line in Panel 6e top figure.

6. Protection Against Noise-Induced Hearing Loss in Adult Mice Treated Locally Via Transtympanic Injection To confirm that compound 4 protects against noise-induced hearing loss in vivo, another set of experiments was performed (FIG. 6A). First, auditory brainstem response (ABR) thresholds were recorded at P28 in adult FVB wild-type mice and exposed to 100 dB SPL 8-16 kHz octave band noise for 2 hrs. A few minutes afterward, compound 4 (250 µM in 0.5% DMSO) or 0.5% DMSO only was injected (5 µL, trans-tympanically) in either ear of the same mouse. Next, ABR thresholds were recorded 7 and 14 days post-exposure and cochlear morphology was analyzed after the day-14 ABR measurement (FIG. 6A). The entire experiment was performed in a double-blinded manner.

Referring to FIG. 6A, an experimental design in which adult FVB mice at P28 were exposed to noise or TBI. Immediately afterward, compound 4 (250 µM) or DMSO was delivered (via trans-tympanic injection) to either ear of the same mouse. ABR and DPOAE thresholds were recorded prior, 7 days, or 14 days post noise exposure. Cochlear histology was examined at 14 days.

Referring to FIG. 6A, a double-blinded design for compound versus DMSO injection to either ear of the same mouse is shown.

The results in a total of 19-20 mice indicated that compound 4 significantly protects adult mice from NIHL 7 days after exposure to 8 kHz and 14 days after exposure 8 kHz and 16 kHz of noise (FIG. 6B and FIG. 6C). The mice had a mean of ~12 dB of hearing protection at these frequencies. Moreover, significant differences were detected in a multiple regression longitudinal modeling with time points (pre-, D7 and D14) and frequencies (8, 16 and 32 kHz) as explanatory factors (p<0.01, t test of regression coefficients) (not shown). The wave 1 amplitudes of ABR at 16 kHz were also increased in compound 4 injected ears relative to DMSO-injected ears (FIG. 6C). Without wishing to be bound by theory, these results suggest that compound 4 protects in vivo against NIHL when delivered locally.

Referring to FIG. 6B, the ABR threshold shift at post-exposure day 14 (D14) in DMSO and compound 4 treated ears in 19 mice is shown. Error bars: S.E. **p<0.01; *p<0.05, paired t-test, two-tailed.

Box plots of the intra-mouse ABR threshold difference between the two treated ears ($ABR_4$-$ABR_{DMSO}$) of each mouse is shown at pre- and post-exposure day 7 (D7) and 14 (D14) in 20, 20, and 19 mice, respectively, at 8, 16, and 32 kHz. Significant differences were observed at 8 kHz at D7 and D14 and at 16 kHz at D14. **p<0.01 (paired t-test). Additionally, significant differences were detected in multiple regression longitudinal modeling with time points (pre-, D7, and D14) and frequencies (8, 16, and 32 kHz) as explanatory factors (p<0.01, t-test of regression coefficients).

7. Effect of Compound 4 on Cisplatin Anti-Tumor Activity

Figure 11:
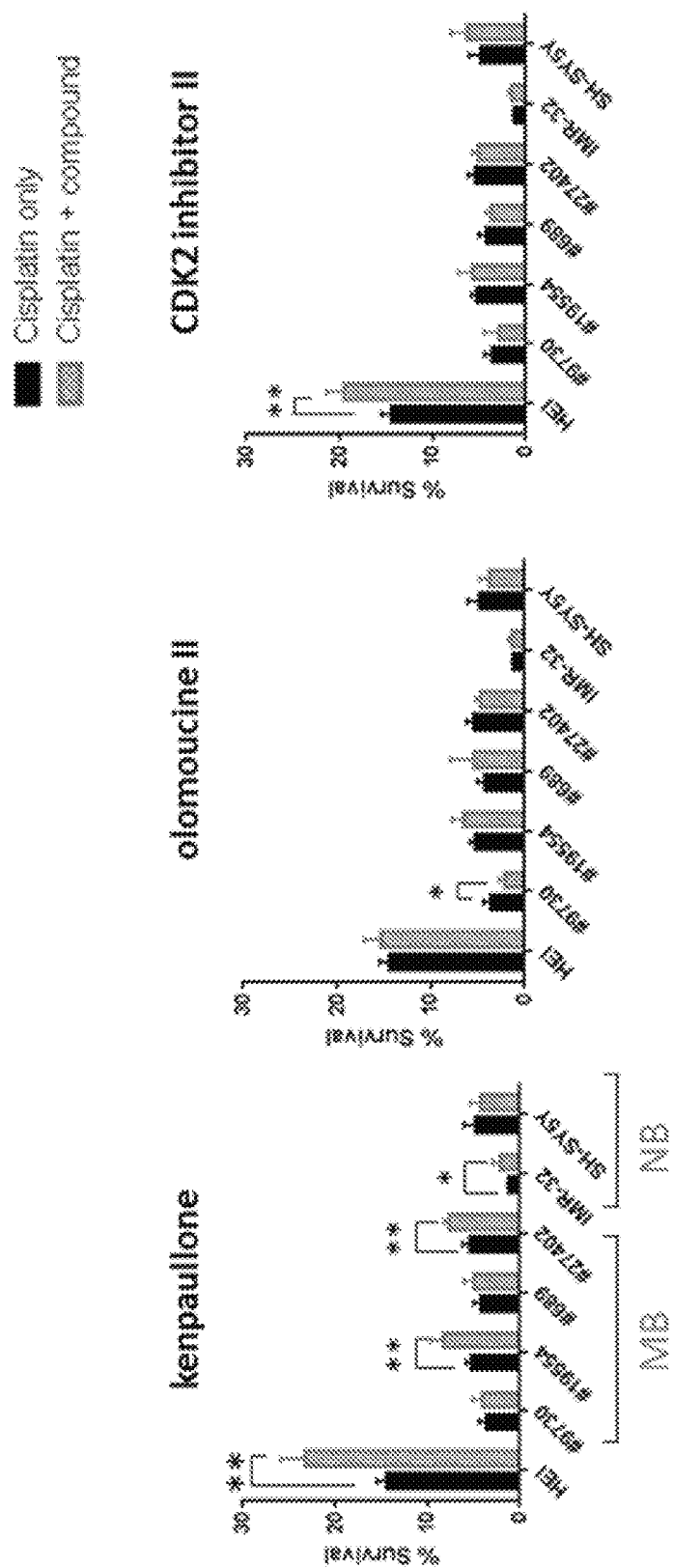
FIG. 11 addresses interference with cisplatin's killing function in tumors. Four neurosphere lines derived from mouse medulloblastoma (MB) and two human neuroblastoma (NB) cell lines were tested. HEI-OC1 cell line was tested as controls. Viability assay (Cell Titer Glo) was used 48 hours post treatment of the cells with or without cisplatin (23 µM, $IC_{90\pm10}$ for all 7 cell lines) and each tested compound (conc. of 3× $IC_{50}$). * and ** indicated $p<0.05$ and 0.01 respectively.

Compound 4 did not interfere with cisplatin anti-tumor activity in three tumor cell lines (two mouse medulloblastoma neurosphere cell lines and one human neuroblastoma cell line) although it did so to certain extent in three other tumor cell lines (two medulloblastoma neurosphere cell lines and one human neuroblastoma cell line) (Morfouace, M. et al. *Cancer cell* 25, 516-529, 2014). FIG. 11 provides strong evidence that our compound 4 is more suitable for local delivery while compounds 7 and 12 exhibited no interference in all tumor cell lines (except one for Compound 7) and therefore were better suitable for both systemic and local delivery.

J. PROPHETIC EXAMPLES

1. Protection Against Cisplatin Ototoxicity Ex Vivo in Neonatal Mouse Cochlear Explant Culture The ability of the top 18 compound hits to protect against cisplatin ototoxicity will be measured in wild-type mouse cochleae harvested from P3 mice and grown in medium for 1-4 days at 37° C. The explants will be isolated and grown with the aid of matrigel (Driver and Kelley (2010) *Curr. Protoc. Neurosci.* Chapter 4, Unit 4 34: 31-10). Cisplatin solution will be added in a final concentration of 50 µM, 1 day after cochleae are placed in medium. For every compound tested, hair cell death will be compared under four conditions: growth medium only, 50 µM cisplatin only, test compound only, and test compound with 50 µM cisplatin. Each compound will be tested at least three concentrations ($IC_{10}$, $IC_{50}$, and $IC_{90}$) based on the dose responses in the HEI-OC1 cell experiments. In addition, each compound's toxicity will be tested at three or more concentrations ($1 \times IC_{90}$, $5 \times IC_{90}$, and $25 \times IC_{90}$). Each compound's $IC_{50}$ (potency of protection) and $LD_{50}$ (toxicity) will be estimated in explants.

After immunostaining with phalloidin, both outer and inner hair cells in the cultured cochleae will be counted after each treatment by confocal microscopy. Co-immunostaining with Myo7a will further confirm that the phalloidin+ cells are viable hair cells. The live hair cells will be enumerated in two separate 160 µm long areas in the cochlear apical, middle, and basal regions, respectively.

Two-sample two-sided t test will be applied to compare the percentage of surviving cells between cells treated by Cisplatin-only (control) vs. cisplatin-plus-compound at a given concentration. Five cochleae will be tested at each concentration of each compound, to adjust for the variability in ex-vivo explant cultures. zVAD-fmk and pifithrin-α will be used as positive control at concentrations reported to confer cisplatin protection in mouse cochlear explants (Atar and Avraham (2010) *Neuroscience* 168: 851-857; Liu et al. (1998) *Neuroreport* 9: 2609-2614; Zhang et al. (2003) *Neuroscience* 120: 191-205).

2. Protection Against Noise- and Blast Injury-Induced Hearing Loss In Vivo in Adult Mouse Models The protective effects of the top 4 compounds, administered locally (transtympanic injection into the middle ear), will be tested against NIHL and blast injury-induced hearing loss in adult mouse models. The local delivery route was chosen for several reasons. First, it is frequently used in mammalian hearing studies, as it offers minimal invasiveness and simple procedures. In fact, drugs are commonly administered via this route by pediatricians and ENT doctors to patients of diverse ages (Banerjee and Parnes (2005) *Otol. Neurotol.* 26: 878-881; Dodson et al. (2004) *Ear Nose Throat J.* 83: 394-398; McCall et al. (2010) *Ear Hear.* 31: 156-165; Muller and Barr-Gillespie (2015) *Nat. Rev. Drug Discov.* 14: 346-365; Rauch (2004) *Otolaryngol. Clin. North Am.* 37: 1061-1074). If the compounds work well in murine models when delivered in this manner, they can be directly tested for prevention of cisplatin-associated hearing loss in patients undergoing cisplatin chemotherapy in clinical trials. Second, transtympanic delivery allows the compounds to diffuse easily across the round window membrane into the endolymphatic fluid (Borkholder (2008) *Curr. Opin. Otolaryngol. Head Neck Surg.* 16: 472-477; Mizutari et al. (2013) *Neuron* 77: 58-69; Swan et al. (2008) *Adv. Drug Deliv. Rev.* 60: 1583-1599; Tamura et al. (2005) *Laryngoscope* 115: 2000-2005), such that their potency and toxicity can be directly tested in vivo with little concern about the blood-labyrinth barrier (BLB). In the future oral and other routes may be considered for further characterization of in vivo properties of these compounds (e.g., solubility, permeability, pharmacokinetics/pharmacodynamics (PK/PD), and absorption, distribution, metabolism, excretion, and toxicology (ADMET)).

The compounds to test in this manner will be chosen on the basis of the following considerations: (1) they exhibit potent $IC_{50}$ values and minimal toxicity (i.e., high $LD_{50}/IC_{50}$ values, preferably >50-100 μM); (2) they target several different biological targets/pathways; and (3) they can be delivered via other routes (e.g., oral).

For tests of noise injury, wild-type FVB mice will be used at age P28, when hearing has matured but long before significant age-related hearing loss (Kermany et al. (2006) *Hear Res.* 220: 76-86; Maison et al. (2002) *J. Neurosci.* 22: 10838-10846; Maison et al. (2007) *J. Neurophysiol.* 97: 2930-2936; Zheng et al. (1999) *Hearing Research* 130: 94-107). The standard noise exposure protocols (94, 100, 106, 116, and 120 dB sound pressure level (SPL) ocaaveband 8-16 kHz noise for 2 hrs) have previously been tested in various transgenic mouse strains from the FVB background (Maison et al. (2002) *J. Neurosci.* 22: 10838-10846; Maison et al. (2007) *J. Neurophysiol.* 97: 2930-2936). These noise injury protocols led to hearing loss (ABR) (see FIG. 6A-D) similar to those previously reported in CBA/CaJ mice (Wang et al. (2002) *J. Assoc. Res. Otolaryngol.* 3: 248-268).

Repeated impulses at 135-155 dB SPL can effectively recapitulate the effects of blast injury in adult mouse cochleae. Previous studies of blast injuries in animal models have demonstrated that 50-160 repeated impulses at 147-160 dB SPL impose physiological and morphological damage to the cochleae of chinchilla, sheep and pigs similar to 3-4 impulses of 14 psi blasts (194 peak dB SPL) in rats (Choi et al. (2008) *Free Radic. Biol. Med.* 44: 1772-1784; Hamernik et al. (1987) *J. Acoust. Soc. Am.* 81: 1118-1129; Henselman et al. (1994) *Hear. Res.* 78: 1-10; Kopke et al. (2005) *Acta Otolaryngol.* 125: 235-243; Roberto et al. (1989) *Ann. Otol. Rhinol. Laryngol. Suppl.* 140: 23-34). More interestingly, 3-4 impulses of 14 psi blasts caused 43% OHC loss and 30-40 dB ABR threshold elevation in rats 21 days post-blast, damage that resembles that caused by 6 hrs of continuous exposure to 105 dB SPL octave-band noise centered at 4 kHz in chinchillas (Choi et al. (2008) *Free Radic. Biol. Med.* 44: 1772-1784; Ewert et al. (2012) *Hear. Res.* 285: 29-39; Kopke et al. (2005) *Acta Otolaryngol.* 125: 235-243). Based on these results, a range of 135-155 dB SPL octave-band 8-16 kHz noise impulses of ~10-ms duration were chosen, which can be repeated 100 times at 1-s intervals in mouse models to mimic traumatic blast injury (Choi et al. (2008) *Free Radic. Biol. Med.* 44: 1772-1784; Ewert et al. (2012) *Hear. Res.* 285: 29-39; Henselman et al. (1994) *Hear. Res.* 78: 1-10; McFadden et al. (2000) *J. Acoust. Soc. Am.* 107: 2162-2168).

FIG. 6A depicts the experimental design. Mice exposed to noise or blast exposure will be immediately treated with the individual compounds in one ear and vehicle control (0.5% DMSO) in the other ear. DMSO or compound will be delivered locally at the highest feasible dose (which should be much higher than the $IC_{50}$ in cochlear explants but not toxic by itself in vivo) by trans-tympanic injection into the adult mouse middle ear at ~54 per ear. The ABR and Distortion Products Otoacoustic Emissions (DPOAE) will be measured pre-noise exposure or TBI and at 1 and 2 weeks post-injection. After hearing tests by ABR and DPOAE, the mice will be cardiac-perfused for fixation and harvesting of the cochleae. The cochleae will be analyzed by using both whole-mount preparations and sections, and immunofluorescence will be used to detect HC/SC markers (i.e., phalloidin, Myo7a, Prestin, and Sox2, etc.) and synaptic markers (Ctbp2, GluR2/3 and Tuj 1) (Liu et al. (2014) *PLoS One* 9: e89377).

The entire procedure will be double-blinded: one person will encode DMSO or compound while the other person will randomly inject the left and right ears of the same mouse, and the person who records ABR and DPOAE will not know which ear was injected with compound until the entire experiment is completed.

a. ABR/DPOAE Measurements in Adult Mice

ABR measurements have been previously described in detail (Dallos et al. (2008) *Neuron* 58: 333-339; Gao et al. (2007) *Mol. Cell Biol.* 27: 4500-4512; Liberman et al. (2002) *Nature* 419: 300-304; Liu et al. (2014) *PLoS One* 9: e89377; Wu et al. (2004) *Brain Res. Mol. Brain Res.* 126: 30-37; Yamashita et al. (2012) *PLoS One* 7: e45453). Briefly, mice will be anesthetized by intraperitoneal injection of Avertin (0.5 mg/kg body weight) and placed on an electric heating pad to maintain body temperature, using a homeothermic blanket system (Harvard Apparatus Ltd). Mice that die or show signs of middle-ear dysfunction during the course of the experiment will be excluded from analysis. All recordings will be conducted in a sound booth (Industrial Acoustic Company). For acoustic stimulation and measurements two speakers (f1 and f2; EC1) and a microphone (ER-10B, Etymotic Research, Elk Grove Village, IL) are connected to a short flexible coupler tube with a tapered plastic tip that is inserted into the external auditory meatus. The microphone will be calibrated in situ, with the coupler in the measuring position. At frequencies higher than 22 kHz, the frequency responses of the measurement microphone (ER10B+) are lower than those of a reference microphone (ACO-7017; ACO Pacific, Inc., Belmont, CA). Therefore, DPOAE 2f1-f2 responses will be recorded at a frequency f1 range of 5454-18180 Hz, using the TDT BioSig III system (TDT). Signal duration is 83.88 ms, with a repetition rate of 11.92/s. The f1 and f2 responses are passed separately through an RX6 MultiFunction Processor (TDT) for digital/analog conversion to PAS programmable attenuators. Stimulus intensity will be reduced from 90 to 0 dB in 5 dB steps to establish thresholds and will be digitally sampled at 200 kHz and averaged from 100 discrete spectra. The signals are delivered through ED1 speaker drivers that feed into the EC1 electrostatic speakers coupled to the ear canal. The resulting ear canal sound pressure will be recorded with an ER10B+ low noise microphone (gain Ox) and probe (Etymotic) housed in the same coupler as the f1 and f2 speakers. The output of the ER10B+ amplifier is routed directly to an RX6 MultiFunction Processor (TDT) for analog/digital conversion for sampling at 200 kHz. Fast-Fourier transforms (FFT) of averaged responses will be generated by using TDT BioSigRP software on the resultant waveform (TDT). Noise floors will be determined by averaging the sound levels of 10 frequency bins above and below the 2f1-f2 frequency bin. No instrumental distortion products have been observed in evaluation of ears postmortem.

b. Noise Injury in Adult Mice

Mice will be placed individually in a cage within a custom-made acrylic chamber in which no two sides are parallel. The sound stimulus will be produced by an RZ6 processor (Tucker-Davis Technologies, Gainesville FL), filtered (Frequency Devices, Inc., Haverhill, MA), amplified (Crown XTi 1000 amplifier; Crown, Elkhart, IN), and delivered to the acrylic chamber via a speaker horn (JBL, Northridge, CA). The sound pressure level will be measured through a ¼-inch freefield microphone (ACO Pacific, Belmont, CA) and calibrated to a 124 dB pistonphone (Bruel and Kjaer, Denmark). Prior to experimental noise exposure, four quadrants of the chamber will be sampled with the ¼-inch microphone to ensure that sound pressure varies by <0.5 dB across the measured positions.

c. Trans-Tympanic Injection of Adult Mice

Mice will be anesthetized by intraperitoneal (i.p.) injection of Avertin or ketamine and xylazine. Body temperature is maintained on a heating pad during the surgical procedure. Lubricant eye ointment is applied to prevent corneal ulcers, as the blinking reflex disappears during surgery. The tympanic membrane is visualized with a surgical stereomicroscope. Using a 33-gauge cannula, 5 µL of compound or DMSO in PBS is gently injected through the tympanic membrane, followed by surgical stereomicroscopic confirmation that the solution is in the middle ear cavity. Mice are then placed in the cage on the heating pad for an additional 30 minutes. After surgery, all mice are allowed to recover on a heating pad before being returned to the animal housing facility.

K. REFERENCES

Abaamrane, L., Raffin, F., Gal, M., Avan, P., and Sendowski, I. (2009). Long-term administration of magnesium after acoustic trauma caused by gunshot noise in guinea pigs. Hear Res 247, 137-145.

Abaamrane, L., Raffin, F., Schmerber, S., and Sendowski, I. (2011). Intracochlear perfusion of leupeptin and z-VAD-FMK: influence of antiapoptotic agents on gunshot-induced hearing loss. Eur Arch Otorhinolaryngol 268, 987-993.

Atar, O., and Avraham, K. B. (2010). Anti-apoptotic factor z-Val-Ala-Asp-fluoromethylketone promotes the survival of cochlear hair cells in a mouse model for human deafness. Neuroscience 168, 851-857.

Attias, J., Weisz, G., Almog, S., Shahar, A., Wiener, M., Joachims, Z., Netzer, A., Ising, H., Rebentisch, E., and Guenther, T. (1994). Oral magnesium intake reduces permanent hearing loss induced by noise exposure. Am J Otolaryngol 15, 26-32.

Banerjee, A., and Parnes, L. S. (2005). Intratympanic corticosteroids for sudden idiopathic sensorineural hearing loss. Otol Neurotol 26, 878-881.

Borkholder, D. A. (2008). State-of-the-art mechanisms of intracochlear drug delivery. Curr Opin Otolaryngol Head Neck Surg 16, 472-477.

Campbell, K., Claussen, A., Meech, R., Verhulst, S., Fox, D., and Hughes, L. (2011). D-methionine (D-met) significantly rescues noise-induced hearing loss: timing studies. Hear Res 282, 138-144.

Campbell, K. C., Meech, R. P., Klemens, J. J., Gerberi, M. T., Dyrstad, S. S., Larsen, D. L., Mitchell, D. L., El-Azizi, M., Verhulst, S. J., and Hughes, L. F. (2007). Prevention of noise- and drug-induced hearing loss with D-methionine. Hear Res 226, 92-103.

Cascella, V., Giordano, P., Hatzopoulos, S., Petruccelli, J., Prosser, S., Simoni, E., Astolfi, L., Fetoni, A. R., Skarzynski, H., and Martini, A. (2012). A new oral otoprotective agent. Part 1: Electrophysiology data from protection against noise-induced hearing loss. Med Sci Monit 18, BR1-8.

Chai, R., Kuo, B., Wang, T., Liaw, E. J., Xia, A., Jan, T. A., Liu, Z., Taketo, M. M., Oghalai, J. S., Nusse, R., et al. (2012). Wnt signaling induces proliferation of sensory precursors in the postnatal mouse cochlea. Proc Natl Acad Sci USA 109, 8167-8172.

Cheng, P. W., Liu, S. H., Young, Y. H., Hsu, C. J., and Lin-Shiau, S. Y. (2008). Protection from noise-induced temporary threshold shift by D-methionine is associated with preservation of ATPase activities. Ear Hear 29, 65-75.

Choi, C. H., Chen, K., Vasquez-Weldon, A., Jackson, R. L., Floyd, R. A., and Kopke, R. D. (2008). Effectiveness of 4-hydroxy phenyl N-tert-butylnitrone (4-OHPBN) alone and in combination with other antioxidant drugs in the treatment of acute acoustic trauma in chinchilla. Free Radic Biol Med 44, 1772-1784.

Coffin, A. B., Williamson, K. L., Mamiya, A., Raible, D. W., and Rubel, E. W. (2013). Profiling drug-induced cell death pathways in the zebrafish lateral line. Apoptosis 18, 393-408.

Dallos, P., Wu, X., Cheatham, M. A., Gao, J., Zheng, J., Anderson, C. T., Jia, S., Wang, X., Cheng, W. H., Sengupta, S., et al. (2008). Prestin-based outer hair cell motility is necessary for mammalian cochlear amplification. Neuron 58, 333-339.

Dodson, K. M., Woodson, E., and Sismanis, A. (2004). Intratympanic steroid perfusion for the treatment of Meniere's disease: a retrospective study. Ear Nose Throat J 83, 394-398.

Driver, E. C., and Kelley, M. W. (2010). Transfection of mouse cochlear explants by electroporation. Curr Protoc Neurosci Chapter 4, Unit 4 34 31-10.

Du, X., Ewert, D. L., Cheng, W., West, M. B., Lu, J., Li, W., Floyd, R. A., and Kopke, R. D. (2013). Effects of antioxidant treatment on blast-induced brain injury. PLoS One 8, e80138.

Ewert, D. L., Lu, J., Li, W., Du, X., Floyd, R., and Kopke, R. (2012). Antioxidant treatment reduces blast-induced cochlear damage and hearing loss. Hear Res 285, 29-39.

Fang, J., Zhang, W. C., Yamashita, T., Gao, J., Zhu, M. S., and Zuo, J. (2012). Outer hair cell-specific prestin-Cre-ERT2 knockin mouse lines. Genesis 50, 124-131.

Forge, A., and Van De Water, T. R. (2008). Protection and repair of inner ear sensory cells. In Hair cell regeneration, repair, and protection, R. J. Salvi, A. N. Popper, and R. R. Fay, eds. (New York: Springer Science), pp. 199-256

Gao, J., Maison, S. F., Wu, X., Hirose, K., Jones, S. M., Bayazitov, I., Tian, Y., Mittleman, G., Matthews, D. B., Zakharenko, S. S., et al. (2007). Orphan glutamate receptor delta1 subunit required for high-frequency hearing. Mol Cell Biol 27, 4500-4512.

Giono, L. E., and Manfredi, J. J. (2007). Mdm2 is required for inhibition of Cdk2 activity by p21, thereby contributing to p53-dependent cell cycle arrest. Mol Cell Biol 27, 4166-4178.

Hamernik, R. P., Patterson, J. H., and Salvi, R. J. (1987). The effect of impulse intensity and the number of impulses on hearing and cochlear pathology in the chinchilla. J Acoust Soc Am 81, 1118-1129.

Henselman, L. W., Henderson, D., Subramaniam, M., and Sallustio, V. (1994). The effect of 'conditioning' exposures on hearing loss from impulse noise. Hear Res 78, 1-10.

Huang, H., Regan, K M., Lou, Z., Chen, J., and Tindall, D. J. (2006). CDK2-dependent phosphorylation of FOXO1 as an apoptotic response to DNA damage. Science 314, 294-297.

Ising, H., Handrock, M., Gunther, T., Fischer, R., and Dombrowski, M. (1982). Increased noise trauma in guinea pigs through magnesium deficiency. Arch Otorhinolaryngol 236, 139-146.

Joachims, Z., Babisch, W., Ising, H., Gunther, T., and Handrock, M. (1983). Dependence of noise-induced hearing loss upon perilymph magnesium concentration. J Acoust Soc Am 74, 104-108.

Joachims, Z., Netzer, A., Ising, H., Rebentisch, E., Attias, J., Weisz, G., and Gunther, T. (1993). Oral magnesium supplementation as prophylaxis for noise-induced hearing loss: results of a double blind field study. Schriftenr Ver Wasser Boden Lufthyg 88, 503-516.

Kalinec, G. M., Webster, P., Lim, D. J., and Kalinec, F. (2003). A cochlear cell line as an in vitro system for drug ototoxicity screening. Audiol Neurootol 8, 177-189.

Kermany, M. H., Parker, L. L., Guo, Y. K., Miller, D., Swanson, D. J., Yoo, T. J., Goldowitz, D., and Zuo, J. (2006). Identification of 17 hearing impaired mouse strains in the TMGC ENU-mutagenesis screen. Hear Res 220, 76-86.

Kim, H. J., Lee, J. H., Kim, S. J., Oh, G. S., Moon, H. D., Kwon, K. B., Park, C., Park, B. H., Lee, H. K., Chung, S. Y., et al. (2010). Roles of NADPH oxidases in cisplatin-induced reactive oxygen species generation and ototoxicity. J Neurosci 30, 3933-3946.

Kim, S. J., Lim, J. Y., Lee, J. N., Choe, S. K., Kim, Y. I., Song, S. R., Cho, M., So, H. S., and Park, R. (2014). Activation of beta-catenin by inhibitors of glycogen synthase kinase-3 ameliorates cisplatin-induced cytotoxicity and pro-inflammatory cytokine expression in HEI-OC1 cells. Toxicology 320, 74-82.

Kopke, R., Bielefeld, E., Liu, J., Zheng, J., Jackson, R., Henderson, D., and Coleman, J. K. (2005). Prevention of impulse noise-induced hearing loss with antioxidants. Acta Otolaryngol 125, 235-243.

Kopke, R. D., Jackson, R. L., Coleman, J. K., Liu, J., Bielefeld, E. C., and Balough, B. J. (2007). NAC for noise: from the bench top to the clinic. Hear Res 226, 114-125.

Latchoumycandane, C., Goh, C. W., Ong, M. M., and Boelsterli, U. A. (2007). Mitochondrial protection by the JNK inhibitor leflunomide rescues mice from acetaminophen-induced liver injury. Hepatology 45, 412-421.

Le Prell, C. G., Dolan, D. F., Bennett, D. C., and Boxer, P. A. (2011a). Nutrient plasma levels achieved during treatment that reduces noise-induced hearing loss. Transl Res 158, 54-70.

Le Prell, C. G., Gagnon, P. M., Bennett, D. C., and Ohlemiller, K. K. (2011b). Nutrient-enhanced diet reduces noise-induced damage to the inner ear and hearing loss. Transl Res 158, 38-53.

Le Prell, C. G., Hughes, L. F., and Miller, J. M. (2007a). Free radical scavengers vitamins A, C, and E plus magnesium reduce noise trauma. Free Radic Biol Med 42, 1454-1463.

Le Prell, C. G., Yamashita, D., Minami, S. B., Yamasoba, T., and Miller, J. M. (2007b). Mechanisms of noise-induced hearing loss indicate multiple methods of prevention. Hear Res 226, 22-43.

Li, E. K., Tam, L. S., and Tomlinson, B. (2004). Leflunomide in the treatment of rheumatoid arthritis. Clin Ther 26, 447-459.

Li, J., Liu, H., Yao, X., Liu, M., Hu, Z., and Fan, B. (2007). Structure-activity relationship study of oxindole-based inhibitors of cyclin-dependent kinases based on least-squares support vector machines. Anal Chim Acta 581, 333-342.

Liberman, M. C., Gao, J., He, D. Z., Wu, X., Jia, S., and Zuo, J. (2002). Prestin is required for electromobility of the outer hair cell and for the cochlear amplifier. Nature 419, 300-304.

Lin, Y., Kashio, A., Sakamoto, T., Suzukawa, K., Kakigi, A., and Yamasoba, T. (2011). Hydrogen in drinking water attenuates noise-induced hearing loss in guinea pigs. Neurosci Lett 487, 12-16.

Liu, W., Staecker, H., Stupak, H., Malgrange, B., Lefebvre, P., and Van De Water, T. R. (1998). Caspase inhibitors prevent cisplatin-induced apoptosis of auditory sensory cells. Neuroreport 9, 2609-2614.

Liu, Z., Fang, J., Dearman, J., Zhang, L., and Zuo, J. (2014). In vivo generation of immature inner hair cells in neonatal mouse cochleae by ectopic Atoh1 expression. PLoS One 9, e89377.

Luk, K. C., Simcox, M. E., Schutt, A., Rowan, K., Thompson, T., Chen, Y., Kammlott, U., DePinto, W., Dunten, P., and Dermatakis, A. (2004). A new series of potent oxindole inhibitors of CDK2. Bioorg Med Chem Lett 14, 913-917.

Lynch, E. D., Gu, R., Pierce, C., and Kil, J. (2004). Ebselen-mediated protection from single and repeated noise exposure in rat. Laryngoscope 114, 333-337.

Lynch, E. D., and Kil, J. (2005). Compounds for the prevention and treatment of noise-induced hearing loss. Drug Discov Today 10, 1291-1298.

Maison, S. F., Luebke, A. E., Liberman, M. C., and Zuo, J. (2002). Efferent protection from acoustic injury is mediated via alpha9 nicotinic acetylcholine receptors on outer hair cells. J Neurosci 22, 10838-10846.

Maison, S. F., Parker, L. L., Young, L., Adelman, J. P., Zuo, J., and Liberman, M. C. (2007). Overexpression of SK2 channels enhances efferent suppression of cochlear responses without enhancing noise resistance. J Neurophysiol 97, 2930-2936.

Marazita, M. C., Ogara, M. F., Sonzogni, S. V., Marti, M., Dusetti, N.J., Pignataro, O. P., and Canepa, E. T. (2012). CDK2 and PKA mediated-sequential phosphorylation is critical for p19INK4d function in the DNA damage response. PLoS One 7, e35638.

McCall, A. A., Swan, E. E., Borenstein, J. T., Sewell, W. F., Kujawa, S. G., and McKenna, M. J. (2010). Drug delivery for treatment of inner ear disease: current state of knowledge. Ear Hear 31, 156-165.

McFadden, S. L., Zheng, X. Y., and Ding, D. L. (2000). Conditioning-induced protection from impulse noise in female and male chinchillas. J Acoust Soc Am 107, 2162-2168.

Meltser, I., Tahera, Y., and Canlon, B. (2010). Differential activation of mitogen-activated protein kinases and brain-derived neurotrophic factor after temporary or permanent damage to a sensory system. Neuroscience 165, 1439-1446.

Mizutari, K., Fujioka, M., Hosoya, M., Bramhall, N., Okano, H. J., Okano, H., and Edge, A. S. (2013). Notch inhibition induces cochlear hair cell regeneration and recovery of hearing after acoustic trauma. Neuron 77, 58-69.

Mukherj ea, D., Rybak, L. P., Sheehan, K. E., Kaur, T., Ramkumar, V., Jajoo, S., and Sheth, S. (2011). The design and screening of drugs to prevent acquired sensorineural hearing loss. Expert Opin Drug Discov 6, 491-505.

Muller, U., and Barr-Gillespie, P. G. (2015). New treatment options for hearing loss. Nat Rev Drug Discov. Oishi, N., and Schacht, J. (2011). Emerging treatments for noise-induced hearing loss. Expert Opin Emerg Drugs 16, 235-245.

Ou, H. C., Raible, D. W., and Rubel, E. W. (2007). Cisplatin-induced hair cell loss in zebrafish (Danio rerio) lateral line. Hear Res 233, 46-53.

Ou, H. C., Santos, F., Raible, D. W., Simon, J. A., and Rubel, E. W. (2010). Drug screening for hearing loss: using the zebrafish lateral line to screen for drugs that prevent and cause hearing loss. Drug Discov Today 15, 265-271.

Owens, K. N., Coffin, A. B., Hong, L. S., Bennett, K. O., Rubel, E. W., and Raible, D. W. (2009). Response of mechanosensory hair cells of the zebrafish lateral line to aminoglycosides reveals distinct cell death pathways. Hear Res 253, 32-41.

Pourbakht, A., and Yamasoba, T. (2003). Ebselen attenuates cochlear damage caused by acoustic trauma. Hear Res 181, 100-108.

Price, P. M., Yu, F., Kaldis, P., Aleem, E., Nowak, G., Safirstein, R. L., and Megyesi, J. (2006). Dependence of cisplatin-induced cell death in vitro and in vivo on cyclin-dependent kinase 2. J Am Soc Nephrol 17, 2434-2442.

Rauch, S. D. (2004). Intratympanic steroids for sensorineural hearing loss. Otolaryngol Clin North Am 37, 1061-1074.

Roberto, M., Hamernik, R. P., and Turrentine, G. A. (1989). Damage of the auditory system associated with acute blast trauma. Ann Otol Rhinol Laryngol Suppl 140, 23-34.

Rohrmeier, C., Koemm, N., Babilas, P., Prahs, P., Strutz, J., and Buettner, R. (2013). Sudden sensorineural hearing loss: systemic steroid therapy and the risk of glucocorticoid-induced hyperglycemia. Eur Arch Otorhinolaryngol 270, 1255-1261.

Rybak, L. P., and Ramkumar, V. (2007). Ototoxicity. Kidney Int 72, 931-935.

Samson, J., Wiktorek-Smagur, A., Politanski, P., Rajkowska, E., Pawlaczyk-Luszczynska, M., Dudarewicz, A., Sha, S. H., Schacht, J., and Sliwinska-Kowalska, M. (2008). Noise-induced time-dependent changes in oxidative stress in the mouse cochlea and attenuation by D-methionine. Neuroscience 152, 146-150.

Satyanarayana, A., and Kaldis, P. (2009). A dual role of Cdk2 in DNA damage response. Cell Div 4, 9.

Schacht, J., Talaska, A. E., and Rybak, L. P. (2012). Cisplatin and aminoglycoside antibiotics: hearing loss and its prevention. Anat Rec (Hoboken) 295, 1837-1850.

Shelat, A. A., and Guy, R. K. (2007). Scaffold composition and biological relevance of screening libraries. Nat Chem Biol 3, 442-446.

Shim, H. J., Kang, H. H., Ahn, J. H., and Chung, J. W. (2009). Retinoic acid applied after noise exposure can recover the noise-induced hearing loss in mice. Acta Otolaryngol 129, 233-238.

Shutes, A., Onesto, C., Picard, V., Leblond, B., Schweighoffer, F., and Der, C. J. (2007). Specificity and mechanism of action of EHT 1864, a novel small molecule inhibitor of Rac family small GTPases. J Biol Chem 282, 35666-35678.

Suckfuell, M., Canis, M., Strieth, S., Scherer, H., and Haisch, A. (2007). Intratympanic treatment of acute acoustic trauma with a cell-permeable JNK ligand: a prospective randomized phase I/II study. Acta Otolaryngol 127, 938-942.

Swan, E. E., Mescher, M. J., Sewell, W. F., Tao, S. L., and Borenstein, J. T. (2008). Inner ear drug delivery for auditory applications. Adv Drug Deliv Rev 60, 1583-1599.

Tamura, T., Kita, T., Nakagawa, T., Endo, T., Kim, T. S., Ishihara, T., Mizushima, Y., Higaki, M., and Ito, J. (2005). Drug delivery to the cochlea using PLGA nanoparticles. Laryngoscope 115, 2000-2005.

Thomas Dickey, D., Muldoon, L. L., Kraemer, D. F., and Neuwelt, E. A. (2004). Protection against cisplatin-induced ototoxicity by N-acetylcysteine in a rat model. Hear Res 193, 25-30.

Thorne, C. A., Wichaidit, C., Coster, A. D., Posner, B. A., Wu, L. F., and Altschuler, S. J. (2015). GSK-3 modulates cellular responses to a broad spectrum of kinase inhibitors. Nat Chem Biol 11, 58-63.

Tieu, C., and Campbell, K. C. (2013). Current pharmacologic otoprotective agents in or approaching clinical trials: how they elucidate mechanisms of noise-induced hearing loss. Otolaryngology 3, 130.

Uemaetomari, I., Tabuchi, K., Hoshino, T., and Hara, A. (2005). Protective effect of calcineurin inhibitors on acoustic injury of the cochlea. Hear Res 209, 86-90.

Vlasits, A. L., Simon, J. A., Raible, D. W., Rubel, E. W., and Owens, K. N. (2012). Screen of FDA-approved drug library reveals compounds that protect hair cells from aminoglycosides and cisplatin. Hear Res 294, 153-165.

Vu, A. A., Nadaraja, G. S., Huth, M. E., Luk, L., Kim, J., Chai, R., Ricci, A. J., and Cheng, A. G. (2013). Integrity and regeneration of mechanotransduction machinery regulate aminoglycoside entry and sensory cell death. PLoS One 8, e54794.

Wang, B., Liu, Y., Chi, F., Zhang, Y., Yang, M., and Zhu, X. (2013). Dexamethasone suppresses cochlear Hes1 expression after noise exposure. Acta Otolaryngol 133, 233-238.

Wang, Y., Hirose, K., and Liberman, M. C. (2002). Dynamics of noise-induced cellular injury and repair in the mouse cochlea. J Assoc Res Otolaryngol 3, 248-268.

Wu, X., Gao, J., Guo, Y., and Zuo, J. (2004). Hearing threshold elevation precedes hair-cell loss in prestin knockout mice. Brain Res Mol Brain Res 126, 30-37.

Yamashita, T., Fang, J., Gao, J., Yu, Y., Lagarde, M. M., and Zuo, J. (2012). Normal hearing sensitivity at low-to-middle frequencies with 34% prestin-charge density. PLoS One 7, e45453.

Yamasoba, T., Pourbakht, A., Sakamoto, T., and Suzuki, M. (2005). Ebselen prevents noise-induced excitotoxicity and temporary threshold shift. Neurosci Lett 380, 234-238.

Yang, H., Gan, J., Xie, X., Deng, M., Feng, L., Chen, X., Gao, Z., and Gan, L. (2010). Gfi1-Cre knock-in mouse line: A tool for inner ear hair cell-specific gene deletion. Genesis 48, 400-406.

Yang, Y. M., Gupta, S. K., Kim, K. J., Powers, B. E., Cerqueira, A., Wainger, B. J., Ngo, H. D., Rosowski, K. A., Schein, P. A., Ackeifi, C. A., et al. (2013). A small molecule screen in stem-cell-derived motor neurons identifies a kinase inhibitor as a candidate therapeutic for ALS. Cell Stem Cell 12, 713-726.

Zaharevitz, D. W., Gussio, R., Leost, M., Senderowicz, A. M., Lahusen, T., Kunick, C., Meijer, L., and Sausville, E. A. (1999). Discovery and initial characterization of the paullones, a novel class of small-molecule inhibitors of cyclin-dependent kinases. Cancer Res 59, 2566-2569.

Zhang, M., Liu, W., Ding, D., and Salvi, R. (2003). Pifithrin-alpha suppresses p53 and protects cochlear and vestibular hair cells from cisplatin-induced apoptosis. Neuroscience 120, 191-205.

Zheng, Q. Y., Johnson, K. R., and Erway, L. C. (1999). Assessment of hearing in 80 inbred strains of mice by ABR threshold analyses. Hearing Research 130, 94-107.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of treating hearing impairment, the method comprising administering to a subject diagnosed with a need for treatment of hearing impairment a therapeutically effective amount of a cyclin-dependent kinase 2 (CDK2) inhibitor, or a pharmaceutically acceptable salt thereof, wherein the cyclin-dependent kinase 2 (CDK2) inhibitor is selected from the group consisting of:

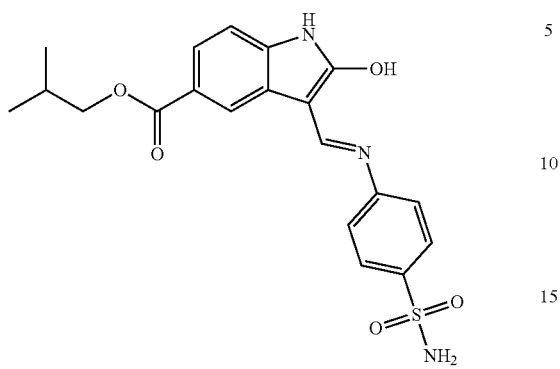

or a pharmaceutically acceptable salt thereof.

2. The method of claim 1, wherein the CDK2 inhibitor is administered in an amount of from about 0.001 µM to about $1.0 \times 10^4$ µM at least once every three weeks.

3. The method of claim 1, wherein the hearing impairment is drug-induced.

4. The method of claim 3, wherein the drug is a chemotherapeutic agent.

5. The method of claim 4, wherein the drug is an antibiotic.

6. The method of claim 5, wherein the antibiotic is selected streptomycin, or a pharmaceutically acceptable salt thereof.

* * * * *